(12) United States Patent
Leyssens et al.

(10) Patent No.: US 11,608,324 B2
(45) Date of Patent: Mar. 21, 2023

(54) SOLID FORMS OF FASORACETAM

(71) Applicant: The Children's Hospital of Philadelphia, Philadelphia, PA (US)

(72) Inventors: Tom Leyssens, Jette (BE); Richard Alan Couch, Bryn Mawr, PA (US); Michael Paul Rene Guillot, Ottignies (BE); Bram Harmsen, GroB-Zimmern (DE); Thomas R. Bailey, Phoenixville, PA (US); Martin Appelmans, Brussels (BE)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 16/963,488

(22) PCT Filed: Jan. 17, 2019

(86) PCT No.: PCT/US2019/014022
§ 371 (c)(1),
(2) Date: Jul. 20, 2020

(87) PCT Pub. No.: WO2019/143824
PCT Pub. Date: Jul. 25, 2019

(65) Prior Publication Data
US 2021/0355102 A1    Nov. 18, 2021

Related U.S. Application Data

(60) Provisional application No. 62/683,325, filed on Jun. 11, 2018, provisional application No. 62/668,092, filed on May 7, 2018, provisional application No. 62/619,062, filed on Jan. 18, 2018.

(51) Int. Cl.
*C07D 401/06* (2006.01)
*C07C 229/60* (2006.01)

(52) U.S. Cl.
CPC .......... *C07D 401/06* (2013.01); *C07C 229/60* (2013.01); *C07B 2200/13* (2013.01)

(58) Field of Classification Search
None
See application file for complete search history.

(56) References Cited

U.S. PATENT DOCUMENTS

| 5,102,882 A | 4/1992 | Kimura et al. |
| 2017/0087139 A1 | 3/2017 | Hakonarson et al. |

FOREIGN PATENT DOCUMENTS

| WO | 2017/044491 A1 | 3/2017 |
| WO | 2017/044503 A1 | 3/2017 |
| WO | 2018/048868 A1 | 3/2018 |

OTHER PUBLICATIONS

International Search Report, dated Jun. 14, 2019, for International Application No. PCT/US2019/014022, filed Jan. 17, 2019.
Harmsen et al., "A Study of Fasoracetam's Solid State Forms: A Potential Anti-Alzheimer Pharmaceutical," Journal of Pharmaceutical Sciences, vol. 106, No. 5, Jan. 19, 2017, pp. 1-5.
Springuel et al., "Cocrystal Formation between Chiral Compounds: How Cocrystals Differ from Salts," Crystal Growth & Design, vol. 14, No. 8, Jun. 27, 2014, pp. 3996-4004.
Extended European Search Report, dated Sep. 7, 2021, issued in corresponding European Patent Application No. 19741128.3.
Sanphui et al., "Pharmaceutical Cocrystals of Niclosamide," Crystal Growth & Design, vol. 12, No. 9, Sep. 5, 2012, pp. 4588-4599.
Maddileti et al., "Soluble Cocrystals of the Xanthine Oxidase Inhibitor Febuxostat," Crystal Growth & Design, vol. 13, No. 7, Jun. 5, 2013, pp. 3188-3196.
Thakuria, Ranjit et al., "Pharmaceutical cocrystals and poorly soluble drugs," International Journal of Pharmaceutics, vol. 453, No. 1, Dec. 1, 2012, pp. 101-125.
Cysewski, Piotr et al., "Exploring the cocrystallization potential of urea and benzamide," Journal of Molecular Modeling, Springer Berlin Heidelberg, Berlin/Heidelberg, vol. 22, No. 5, Apr. 6, 2016, pp. 1-10.
Hirouchi et al., "Role of metabotropic glutamate receptor subclasses in modulation of adenylyl cyclase activity by a nootropic NS-105," European Journal of Pharmacology, vol. 387, No. 1, Nov. 3, 2000, pp. 9-17.
Lee et al., "Pharmaceutical Analysis," Blackwell Publishing Ltd., 2003, pp. 225-257.
Search Report and Written Opinion, dated May 14, 2021, issued in corresponding Singapore Patent Application No. 11202006790X.

*Primary Examiner* — Zinna Northington Davis
(74) *Attorney, Agent, or Firm* — Kathleen D. Rigaut; Howson & Howson LLP

(57) ABSTRACT

The disclosure is directed to cocrystals of fasoracetam, including R-fasoracetam, and various coformers. Crystalline materials comprising fasoracetam, including R-fasoracetam, are also provided. The disclosure further includes pharmaceutical compositions and methods of treatment of the cocrystals and crystalline materials of the disclosure.

18 Claims, 137 Drawing Sheets

ORTEP of R-fasoracetam:PABA cocrystal

ORTEP of R-fasoracetam monohydrate Form II

ORTEP of R-fasoracetam anhydrate

ORTEP of R-fasoracetam monohydrate Form I

ORTEP of R-fasoracetam urea cocrystal Form B

ORTEP of R-fasoracetam phthalic acid cocrystal

ORTEP of a monohydrate cocrystal of R-fasoracetam and phloroglucinol

ORTEP of a monohydrate of R-fasoracetam and methyl-3, 4, 5-trihydroxybenzoate cocrystal ORTEP of a 1:1 cocrystal of R-fasoracetam to ethyl gallate ORTEP of 1:2 R-fasoracetam:ethyl gallate cocrystal ORTEP of dihydrate 1:2 R-fasoracetam to ethyl gallate cocrystal Figure 118. XRPD pattern of R-fasoracetam:urea cocrystal Form A from Example 36

Hydrogen bonding pattern of a R-fasoracetam:4-nitrobenzoic acid cocrystal

Hydrogen bonding pattern of a R-fasoracetam:Urea cocrystal Form B

Hydrogen bonding pattern of a R-fasoracetam:phthalic acid cocrystal

Hydrogen bonding pattern of a monohydrate of R-fasoracetam:phloroglucinol cocrystal Hydrogen bonding pattern of a monohydrate of R-fasoracetam:methyl-3,4,5-trihydroxybenzoate cocrystal Hydrogen bonding pattern of a 1:1 cocrystal of R-fasoracetam:ethyl gallate Hydrogen bonding pattern of a 1:2 cocrystal of R-fasoracetam:ethyl gallate Hydrogen bonding pattern of a dihydrate of a 1:2 cocrystal of R-fasoracetam: ethyl gallate Hydrogen bonding pattern of a R-fasoracetam:R-ibuprofen cocrystal

SOLID FORMS OF FASORACETAM

This application is a § 371 of International Application No. PCT/US2019/014022, filed Jan. 17, 2019, which claims the benefit of priority to U.S. Provisional Application No. 62/619,062, filed Jan. 18, 2018; U.S. Provisional Application No. 62/668,092, filed May 7, 2018; and U.S. Provisional Application No. 62/683,325, filed Jun. 11, 2018; all of which are incorporated by reference in their entirety.

Recently, a precision-medicine-based clinical trial was completed reporting successful treatment of attention deficit hyperactive disorder (ADHD) in subjects having at least one genetic alteration in a metabotropic glutamate receptor (mGluR) network gene. In that study, subjects having a genetic alteration in an mGluR network gene were successfully treated with fasoracetam (NFC-1), which has been shown in vitro to be a nonselective activator against all classes of mGluRs (See Hirouchi M, et al. (2000) European Journal of Pharmacology 387:9-17; see also WO2017/044491). Fasoracetam has also been successful in treating subjects having ADHD and 22q11.2 Deletion Syndrome (see, e.g., WO2017/044491), anxiety (see, e.g., WO2017/044503), conduct disorder (see, e.g., WO2017/044502), Tourette's syndrome (see, e.g., WO2017/044497), and suggested for treatment of anorexia (see, e.g., PCT/US2017/050228). Fasoracetam is orally available and to date has typically been made available as a monohydrate. Fasoracetam has one chiral center and the R-enantiomer has been developed clinically in the form of R-fasoracetam monohydrate Form I. From a manufacturing standpoint, fasoracetam is a challenging product to work with because of its low melting point, which has been measured to range from about 52° C. to about 57° C. It would be advantageous to work with solid forms of fasoracetam where the melting point is higher so as to make manufacturing and storage more convenient and robust.

All references disclosed herein are incorporated by reference in their entirety.

Disclosed herein are crystalline compounds containing fasoracetam and cocrystals of fasoracetam. A cocrystal is a chemical composition of two or more compounds and generally possesses distinct crystallographic and spectroscopic properties when compared to those of its component compounds. Unlike salts, which possess a neutral net charge, but which are comprised of charge-balanced components, cocrystals, while also having a neutral net charge, are comprised of neutral components. Thus, unlike a salt, one cannot determine the stoichiometry of a cocrystal based on charge balance. Indeed, one can often obtain cocrystals having molar ratios of component compounds of greater than or less than 1:1. The molar ratio of the component compounds is a generally unpredictable feature of a cocrystal. Salts and cocrystals are both crystalline compounds that contain more than one component.

Cocrystals have the potential to alter physicochemical properties. More specifically, cocrystals have been reported to alter aqueous solubility and/or dissolution rates, increase stability with respect to relative humidity, and/or improve bioavailability of active pharmaceutical ingredients with respect to other cocrystals of such ingredients. Such properties are generally unpredictable. For example, the melting temperature of a cocrystal is a non-predictable property. The melting point of a cocrystal can be lower, higher or in between that of constituting components. With regards to fasoracetam, and in particular R-fasoracetam monohydrate Form I, the low-lying melting point of R-fasoracetam monohydrate Form I can lead to processing issues of this form during tableting, or packaging, when temperatures can increase. These issues can be avoided by working with solid state forms that are characterized by higher melting temperatures, such as many of the cocrystals of the disclosure.

Cocrystals may also be polymorphic in that a cocrystal may exist in one or more different polymorphs. A compound, such as a cocrystal, is polymorphic if there are two or more crystalline structures of that compound (or cocrystal) with each crystalline structure being a polymorph of the compound (or cocrystal).

Various spectroscopic and crystallographic techniques may be used to characterize cocrystals. These include XRPD, single-crystal x-ray, Raman spectroscopy, infrared spectroscopy, and solid-state NMR spectroscopy, among other techniques. Cocrystals often also exhibit distinct thermal behavior. Thermal behavior may be analyzed by such techniques as capillary melting point, thermogravimetric analysis (TGA), and differential scanning calorimetry (DSC) to name a few. These techniques can be used to identify and characterize the cocrystals.

SUMMARY

In various aspects of the disclosure, cocrystals comprising fasoracetam and a compound containing a moiety selected from —$NH_2$, —$NO_2$, alkyl, or a carbonyl-containing moiety wherein the compound is not tartaric acid; and cocrystals of fasoracetam and an organic coformer wherein the coformer is not tartaric acid are provided.

In other aspects of the disclosure, cocrystals of fasoracetam and an aromatic compound and cocrystals of R-fasoracetam and an aromatic compound are provided.

In further aspects of the disclosure, crystalline compounds comprising fasoracetam and an aromatic compound are provided, as well as crystalline compounds comprising R-fasoracetam and an aromatic compound are provided.

In additional aspects of the disclosure, cocrystals of fasoracetam and urea, cocrystals of fasoracetam and 4-aminobenzoic acid, cocrystals of fasoracetam and trimesic acid, cocrystals of fasoracetam and methyl-3,4,5-trihydroxybenzoate, cocrystals of fasoracetam and ethyl gallate, cocrystals of fasoracetam and phthalic acid, cocrystals of fasoracetam and 6-hydroxy-2-napthoic acid, cocrystals of fasoracetam and 4-nitrobenzoic acid, and cocrystals of fasoracetam and 2-indole-3-acetic acid are provided.

In further aspects of the disclosure, cocrystals R-fasoracetam and urea, including Form A and Form B of cocrystals of R-fasoracetam and urea, cocrystals of R-fasoracetam and 4-aminobenzoic acid, cocrystals of R-fasoracetam and trimesic acid, cocrystals of R-fasoracetam and R-ibuprofen, cocrystals of R-fasoracetam and methyl-3,4,5-trihydroxybenzoate, cocrystals of R-fasoracetam and ethyl gallate, cocrystals of R-fasoracetam and phthalic acid, cocrystals of R-fasoracetam and 6-hydroxy-2-napthoic acid, cocrystals of R-fasoracetam and 4-nitrobenzoic acid, and cocrystals of R-fasoracetam and 2-indole-3-acetic acid are provided.

In yet additional aspects of the disclosure, crystalline compounds comprising fasoracetam and urea, crystalline compounds comprising fasoracetam and 4-aminobenzoic acid, crystalline compounds comprising fasoracetam and trimesic acid, crystalline compounds comprising fasoracetam and methyl-3,4,5-trihydroxybenzoate, crystalline compounds comprising fasoracetam and ethyl gallate, crystalline compounds comprising fasoracetam and phthalic acid, crystalline compounds comprising fasoracetam and 6-hydroxy-2-napthoic acid, crystalline compounds comprising fasoracetam and 4-nitrobenzoic acid, and crystalline compounds comprising fasoracetam and 2-indole-3-acetic acid are provided.

In further aspects of the disclosure, crystalline compounds comprising R-fasoracetam and urea, crystalline compounds comprising R-fasoracetam and 4-aminobenzoic acid, crystalline compounds comprising R-fasoracetam and trimesic acid, crystalline compounds comprising R-fasoracetam and R-ibuprofen, crystalline compounds comprising R-fasoracetam and methyl-3,4,5-trihydroxybenzoate, crystalline compounds comprising R-fasoracetam and ethyl gallate, crystalline compounds comprising R-fasoracetam and phthalic acid, crystalline compounds comprising R-fasoracetam and 6-hydroxy-2-napthoic acid, crystalline compounds comprising R-fasoracetam and 4-nitrobenzoic acid, and crystalline compounds comprising R-fasoracetam and 2-indole-3-acetic acid are provided.

In additional aspects of the disclosure, pharmaceutical compositions containing cocrystals or crystalline compounds of fasoracetam are disclosed.

In further aspects of the disclosure, methods and uses for treating diseases in humans such as ADHD, 22q11.2 deletion syndrome, anxiety, conduct disorder, Tourette's syndrome, and anorexia with effective amount of cocrystals, crystalline compounds, and/or pharmaceutical compositions comprising the cocrystals and/or crystalline compounds of fasoracetam of the disclosure are provided.

In an additional aspect, a process for preparing a R-fasoracetam:urea cocrystal Form B comprising combining R-fasoracetam in a suitable solvent with urea to form a solution wherein the molar amount of urea to R-fasoracetam ranges from about 0.7 to about 1.2 and cooling the solution to form cocrystals of R-fasoracetam:urea Form B is provided.

Definitions

"2-indole-3-acetic acid" means indole-3-acetic acid which is often commonly known as 2-(1H-indol-3-yl)acetic acid or 2-(1H-indol-3-yl)ethanoic acid.

"Anhydrate form" means the anhydrate form of R-fasoracetam.

"Coformer" in a pharmaceutical cocrystal means the compound, or compounds, other than the active ingredient. For example, with respect to the cocrystals of R-fasoracetam made herein, the coformer is the molecule in the cocrystal other than R-fasoracetam. Examples include urea, PABA, R-ibuprofen, etc. The cocrystal may also contain stoichiometric amounts of water compared to the R-fasoracetam and coformers such as with a monohydrate or a dihydrate.

"Fasoracetam" as used herein means R-fasoracetam unless otherwise stated:

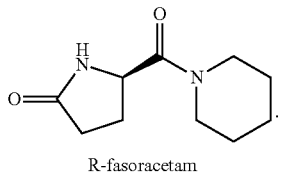 [SMILES: O=C1CC[C@H](C(=O)N2CCCCC2)N1]

R-fasoracetam

"Form A" means Form A of a cocrystal of R-fasoracetam and urea.
"Form B" means Form B of a cocrystal of R-fasoracetam and urea.
"Form I" means R-fasoracetam monohydrate Form I.
"Form II" means R-fasoracetam monohydrate Form II.

"Ground crystalline material" refers to crystalline material that is prepared from the grinding experiments of the disclosure. Such material results, for example, when molar ratios of R-fasoracetam and a coformer are ground according to the various examples. In the examples, the masses of starting materials used corresponds to stoichiometric molar ratios with a variability of on the order of +/−10%. In some cases, a single crystal is prepared and analyzed separately and the simulated diffraction patterns from those single crystals match the x-ray powder diffraction pattern of the ground crystalline material confirming that the ground material is the same crystalline form as the cocrystal made from the single crystal preparation. If a separate pattern emerges, this may be evidence of, for example, a polymorph, a hydrate, or a cocrystal of a different stoichiometry than that made in the single crystal preparation. Even in the absence of single crystal data, a cocrystal may be identified by relying on other techniques such as XRPD and differential scanning calorimetry. When an XRPD pattern of the ground crystalline material differs from a linear combination of the XRPD pattern of the component compounds, that is strong evidence for the formation of a cocrystal. In grinding experiments, $^1$H-NMR experiments are used to determine whether degradation has occurred.

"Match" means that to one of ordinary skill in the art, two analytical responses, typically XRPD patterns, are the same to within normal expected variability. With respect to the matching analysis, x-axis alignment is significantly more important than y-axis alignment in XRPD patterns due to preferred orientation of crystals and particle statistics.

"PABA" means para-aminobenzoic acid also referred to herein as 4-aminobenzoic acid.

"R-Fasoracetam Forms Mixture" means a physical mixture of R-fasoracetam monohydrate Form I, R-fasoracetam monohydrate Form II, and R-fasoracetam anhydrate. This mixture of fasoracetam forms can be prepared, for example in accordance with Example 11.

"Synthon" means an intermolecular construct showing intermolecular bonding, such as hydrogen bonding, between functional moieties of different compounds within the same cocrystal. For example, with respect to fasoracetam, including R-fasoracetam, one or both carbonyls may be hydrogen-bonded to moieties on coformers, such as carboxylic acid, thereby forming a synthon such as shown in Formula II or III.

BRIEF DESCRIPTION OF THE DRAWINGS

FIG. 129 is a hydrogen bonding pattern of a monohydrate of R-fasoracetam:phloroglucinol cocrystal.

FIG. 130 is a hydrogen bonding pattern of a monohydrate of a R-fasoracetam:methyl-3,4,5-trihydroxybenzoate cocrystal.

FIG. 131 is a hydrogen bonding pattern of a 1:1 cocrystal of R-fasoracetam:ethyl gallate.

FIG. 132 is a hydrogen bonding pattern of a 1:2 cocrystal of R-fasoracetam:ethyl gallate.

FIG. 133 is a hydrogen bonding pattern of a dihydrate of a 1:2 cocrystal of R-fasoracetam:ethyl gallate.

FIG. 134 is a hydrogen bonding pattern of a R-fasoracetam:R-ibuprofen cocrystal.

FIG. 135 is a theoretical ternary cocrystal Phase Diagram.

FIG. 136 is an exemplary crystallization process for R-fasoracetam:PABA.

FIG. 137 is a ternary phase diagram for a R-fasoracetam:PABA cocrystal system.

DESCRIPTION

Figure 1:
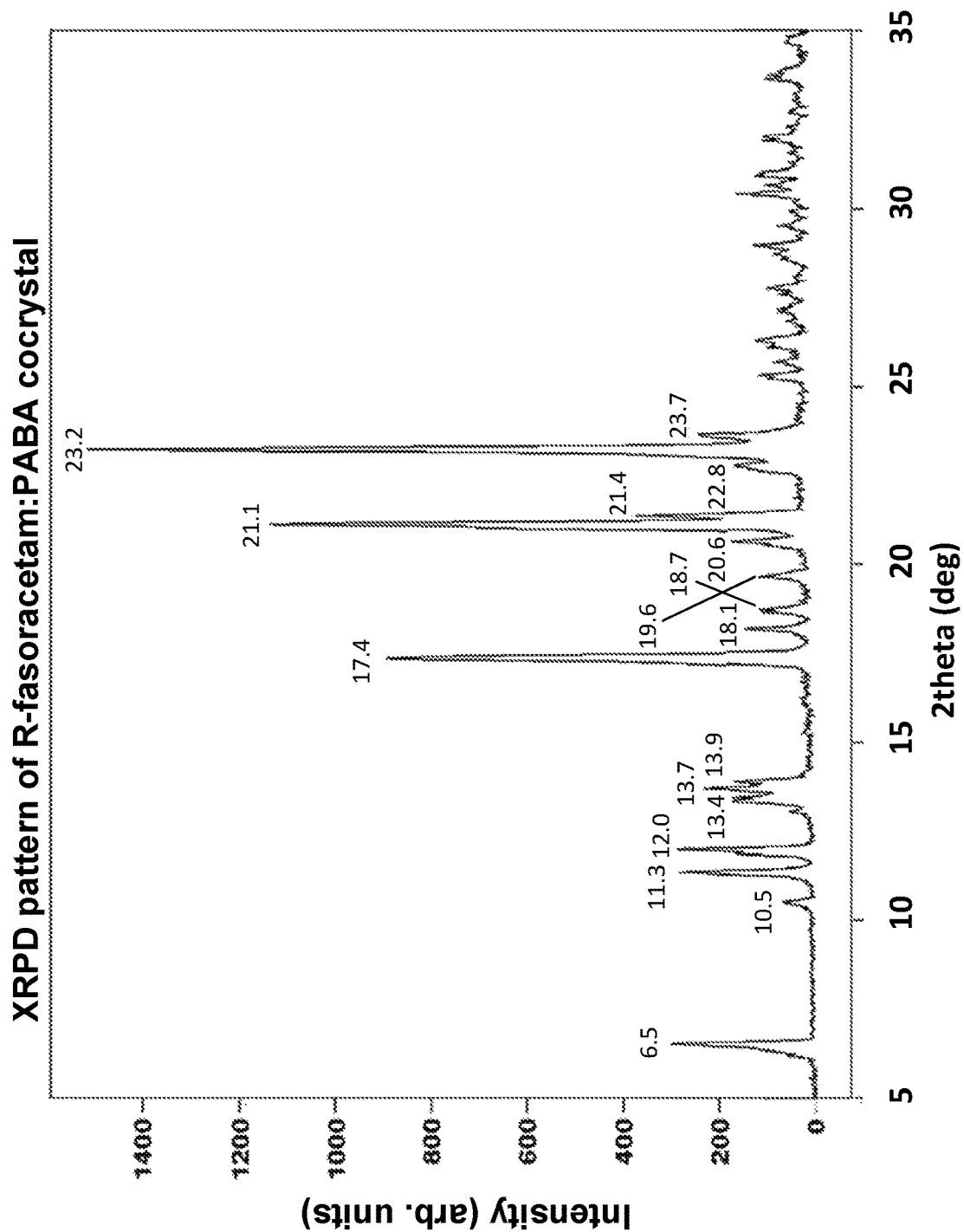
FIG. 1 is an XRPD pattern of R-fasoracetam:PABA cocrystal.

Many embodiments of the disclosure are directed to cocrystals of R-fasoracetam and coformers. The chemical composition of a cocrystal, proof of cocrystal formation, and the molar relationship between the component compounds may be provided by single-crystal x-ray analysis. With a single-crystal x-ray solution, one may also calculate what is called a "simulated" x-ray powder diffraction ("XRPD") pattern using techniques well known in the art. Such a simulated pattern indicates what peaks could be present if the crystal were analyzed in an XRPD instrument. It is not always possible, however, to obtain single crystals of sufficient quality to obtain a single-crystal x-ray solution. In the absence of single-crystal data, other techniques may be used to provide such chemical information about a cocrystal, including proof of formation. For example, by comparing solid-state analytical data of the starting component compounds with corresponding analytical data collected on the cocrystal, one may determine whether a cocrystal has formed. Data from a cocrystal will be represented by an analytical response that is not simply a linear combination of the starting component compounds. For example, XRPD may be used for such comparisons and the XRPD pattern of a cocrystal will differ from that of a physical mixture of the starting materials. The XRPD pattern of a cocrystal will typically have one or more peaks which cannot be obtained by adding the XRPD patterns of the components. Thus, XRPD may be used to distinguish mixtures from cocrystals. Additionally, chemical identity may be obtained from the identity of the starting component compounds and solution-state NMR spectra. Solution-state NMR spectra may also be used to identify molar ratio other than when molar grinding is used to prepare the cocrystal. In molar grinding, the stoichiometric ratios of the component compounds are known and, as a result, NMR spectroscopy is not typically used to verify stoichiometry. However, NMR spectroscopy can be used to determine whether grinding has induced chemical degradation.

The data from a technique may be used in multiple ways to characterize a cocrystal. For example, the entire XRPD pattern output from a diffractometer may be used to characterize a cocrystal. A smaller subset of such data, however, may also be, and typically is, suitable for characterizing a cocrystal. For example, a collection of one or more peaks from such a pattern may be used to characterize a cocrystal. Indeed, often even a single XRPD peak may be used to characterize a cocrystal. When a cocrystal herein is characterized by "one or more peaks" of an XRPD pattern and such peaks are listed, what is meant is that any combination of the peaks listed may be used to characterize the cocrystal. Further, the fact that other peaks are present in the XRPD pattern, does not negate or otherwise limit the characterization.

Similarly, subsets of spectra or diffraction data may be used alone or in combination with other analytical data to prove the presence of or characterize cocrystals. Thermal data may also be used to characterize a cocrystal. For example, DSC measurements may be used to characterize a cocrystal. When the DSC measurements of the purported cocrystal differ from the DSC measurements of the component compounds, the DSC measurement may be used alone, or in combination with other techniques, to characterize the cocrystal. Typically, such measurements are endothermic events.

An XRPD pattern is an x-y graph with °2θ (diffraction angle) on the x-axis and intensity on the y-axis. The pattern contains peaks which may be used to characterize a cocrystal or other solid forms. The peaks are usually represented and referred to by their position on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the pharmaceutical arts to characterize cocrystals or other solid forms.

As with any data measurement, there is variability in x-ray powder diffraction. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline cocrystal. Likewise, different software packages process x-ray data differently and this also leads to variability. These and other sources of variability are known to those of ordinary skill in the pharmaceutical arts.

Due to such sources of variability, it is common to recite x-ray diffraction peaks using the word "about" prior to the peak value in °2θ which presents the data to within 0.1 or 0.2°2θ of the stated peak value depending on the circumstances. All x-ray powder diffraction peaks cited herein have are reported with a variability on the order of 0.2 degree °2θ and are intended to be reported with such a variability whenever disclosed herein whether the word 'about' is present or not.

Variability also exists in thermal measurements, such as DSC, and may also be indicative of sample purity. Melting point, DSC, and hot stage microscopy, alone or in combination with techniques such as x-ray powder diffraction, Raman spectroscopy, infrared spectroscopy or some combination thereof, may be used to characterize cocrystals. With respect to DSC, typical measurement variability is on the order of 1° C. However, with regards to fasoracetam, due to the low melting behavior and interactions with water, DSC measurements are reported herein for fasoracetam-containing materials to within 3° C.

When conducting a cocrystal screen of a compound with various potential coformers, the XRPD pattern of each result of the screen may be compared with the XRPD pattern of the compound and the coformer. If the XRPD pattern of the result can be described by a linear combination of the XRPD patterns of the compound and the coformer, then no cocrystal has formed. If the resulting XRPD pattern on the other hand, cannot be described as a linear combination of the XRPD patterns of the compound and the coformer, such as, for example, due to the presence of one or more additional XRPD peaks, then the XRPD data shows the existence of a new crystalline phase which may be due, for example, to the formation of a cocrystal.

Characterizing a cocrystal does not necessarily use the same data as screening. For example, a cocrystal, like any other compound, is defined by its structure and its structure differs from that of the starting component compounds used to construct it. Thus, for example, a cocrystal of A:B differs from A and differs from B even if all of A, B, and A:B share one or more common XRPD peaks provided that the overall pattern of A:B is not only a linear combination of the A and B patterns.

Often, cocrystals will form when certain intermolecular interactions, such as by hydrogen bonding, form between compounds, such as between R-fasoracetam and a coformer. A common synthon that has been identified, as evidenced from various ORTEP drawings provided herein, is a synthon including the amide moiety in R-fasoracetam (Formula I) and a carboxylic acid moiety from a coformer. The synthon is represented in Formula II where the amide moiety is on the right hand-side of the synthon shows both covalent and hydrogen bonds. The synthon of Formula II is specific to carboxylic acids. In Formula III, another synthon can be seen between either carbonyl of R-fasoracetam (on the left-hand side of the synthon) and a class of moieties where the intermolecular interaction, like with Formula II, is through hydrogen bonding. In this synthon, Y may be oxygen, nitrogen, —NH, or —(O)COR$_5$ where R$_5$ is selected from substituted or unsubstituted alkyl, such as a C$_1$ to C$_5$ alkyl or substituted or unsubstituted aryl. In some embodiments, Y is —(O)COR$_5$ where R$_5$ is selected from substituted or unsubstituted alkyl.

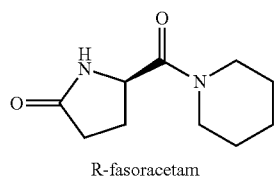

Formula I

R-fasoracetam

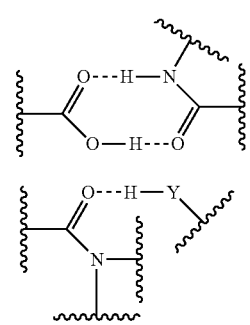

Formula II

Formula III

In other embodiments, cocrystals of fasoracetam, including R-fasoracetam are provided where the coformer has at least one moiety selected from —NH$_2$, —NO$_2$, or a carbonyl containing moiety, provided that the coformer is not tartaric acid. Examples of carbonyl-containing moieties include organic acids, esters, and amides. In other embodiments, cocrystals of fasoracetam, including R-fasoracetam, are provided wherein the coformer is an aromatic coformer, which may be optionally substituted. The aromatic compound may be a six-membered ring or of a different ring size or a polycyclic aromatic compound. One example of a polycyclic aromatic compound is where a six-membered ring is fused with a five-membered ring and another example is two or more six-membered rings. As used herein, aromatic includes heteroaromatic such that the ring atoms may all be carbon or, for example, at least one ring carbon may be a different element such as nitrogen and the fused rings may be substituted or unsubstituted. Furthermore, the aromatic coformer may be fused to a non-aromatic cyclic moiety. Example of such non-aromatic cyclic moieties may be partially saturated when the non-aromatic cyclic moiety shares ring atoms with the aromatic ring or fully-saturated when it does not.

The aromatic compound may be optionally substituted, whether the aromatic coformer has a fused ring structure or not. For example, the aromatic compound may have at least one substituent. Examples of substituents include —OH, —NH$_2$, alkyl, carbonyl-containing moieties, and —NO$_2$ moieties. When the carbonyl-containing moiety is an organic acid moiety, examples of such organic acid moieties include C$_1$-C$_4$ organic acid such as a C$_1$ acid. When the carbonyl containing moiety is an ester moiety, examples include C$_1$-C$_5$ ester moieties.

According to the present disclosure, the aromatic coformer may have two substitutions where each substituent is independently chosen from —OH, —NH$_2$, alkyl, organic acid, ester, and —NO$_2$ moieties. In embodiments with two substituents, a first substituent is an organic acid moiety and a second substituent is chosen from —OH, -an amine, alkyl, organic acid, ester, and —NO$_2$ moieties. The amine may be an —NH$_2$ moiety. The organic acid moiety may be a C$_1$-C$_4$ organic acid moiety such as —COOH. In these and other embodiments, when the first substitution is an organic acid moiety and the second substitution is —NH$_2$ moiety, the organic acid and the —NH$_2$ moieties may be, for example, ortho, metal, or para to each other.

In some embodiments, the second substituent is an —NO$_2$ moiety and the organic acid moiety may be, for example, ortho, meta, or para to the —NO$_2$ moiety. The organic acid moiety in such embodiments may be a C$_1$-C$_4$ organic acid moiety such as —COOH.

In other embodiments, the second substituent is an —OH moiety and the organic acid moiety may be, for example, ortho, meta, or para to the —OH moiety. The organic acid moiety in such embodiments may be a C$_1$-C$_4$ organic acid moiety such as —COOH.

In further embodiments, the second substituent is an alkyl moiety, such as a C$_1$-C$_5$ alkyl moiety and the organic acid moiety may be, for example, ortho, meta, or para to the alkyl moiety. The organic acid moiety in such embodiments may be a C$_1$-C$_4$ organic acid moiety such as —COOH.

In additional embodiments, both substituents are independently organic acid moieties, such as C$_1$-C$_4$ organic acid moiety including, but not limited to —COOH. The organic acids may be, for example, ortho, meta, or para to each other.

In other embodiments, the second substituent is an ester moiety, such as a C$_1$-C$_5$ ester moiety and the organic acid moiety may be, for example, ortho, meta, or para to the ester moiety. The organic acid moiety in such embodiments may be a C$_1$-C$_4$ organic acid such as —COOH.

According to the present disclosure, when aromatic, the coformer may have three substituents where each substituent is independently chosen from —OH, —NH$_2$, alkyl, organic acid, ester, and —NO$_2$ moieties. In some embodiments, each substituent is an —OH moiety and in other embodiments only one or two substituents is an —OH moiety. In some embodiments one, two, or all three substituents are organic acid moieties. The organic acids may be, for example, C$_1$-C$_4$ organic acid moieties such as —COOH.

According to the present disclosure, when aromatic, the coformer may have four substituents wherein each substituent is independently chosen from —OH, —NH$_2$, alkyl, organic acid, ester, and —NO$_2$ moieties. Examples include where one substituent is an ester, such as C$_1$-C$_5$ ester moiety including methyl ester moieties. When one substituent is an ester moiety, in some embodiments, one, or two, or three other substituents are alcohol moieties such as an —OH moiety. In many embodiments, at least one substituent is an organic acid moiety such as —COOH.

According to the present disclosure, the coformer may be non-aromatic and contain at least one moiety selected from —NH$_2$, —NO$_2$, —COOH, —C(=O)—X, —C(=O)—OR$_1$, wherein X is a nitrogen containing radical and R$_1$ is alkyl. In some embodiments, the alkyl is a C$_1$-C$_{11}$ alkyl. In these and other embodiments, the coformer contains at least one —NH$_2$ moiety including embodiments where the coformer contains two —NH$_2$ moieties.

According to the present disclosure, the coformer may be non-aromatic and contain at least one —C(O)NR$_2$R$_3$ moiety where R$_2$ and R$_3$ are independently selected from H, alkyl, substituted alkyl, and a C$_1$-C$_5$ alcohol. In some embodiments, the coformer contains one C(O)NR$_2$R$_3$ moiety. In these and other embodiments, the alkyl and the substituted alkyl may independently contain 1, 2, 3, 4, 5, 6, 7, 8, 9, 10, or 11 carbons. In certain embodiments, the alkyl is a C$_{11}$ alkyl. The substituted alkyl may contain a halogen, a nitrile moiety, or both with bromine as a particular halogen. In certain embodiments, the alcohol is a C$_2$ alcohol.

According to the present disclosure, the coformer may be non-aromatic and contain at least one —C(O)NX moiety where X is =N—R$_4$ where R$_4$ a carbonyl containing moiety such as, for example, an amide.

The disclosure includes multiple cocrystals of fasoracetam. In particular, the disclosure includes examples of cocrystals of R-fasoracetam with 11 different coformers. In some examples, multiple different cocrystals were prepared with R-fasoracetam and the same coformer. Table 1 lists the coformers which formed cocrystals hereunder with R-fasoracetam.

TABLE 1

Cocrystal Structures

| COFORMER | STRUCTURE |
| --- | --- |
| PABA | [structure of 4-aminobenzoic acid] |
| Urea | [structure of urea] |
| Trimesic acid | [structure of trimesic acid] |
| R-ibuprofen | [structure of R-ibuprofen] |
| Phthalic acid | [structure of phthalic acid] |
| Phloroglucinol | [structure of phloroglucinol] |
| Methyl-3,4,5-trihydroxybenzoate | [structure of methyl gallate] |

TABLE 1-continued

Cocrystal Structures

| COFORMER | STRUCTURE |
|---|---|
| Ethyl gallate | HO, HO, HO-substituted benzoate ethyl ester |
| 6-hydroxy-2-naphthoic acid | HO-naphthalene-COOH |
| 4-nitrobenzoic acid | O2N-C6H4-COOH |
| 2-indole-3-acetic acid | indole-CH2-COOH |

Of the 11 coformers exemplified herein, 10 of them are aromatic. The aromatic coformers are substituted with various functional groups including amines, carboxylic acids, alkyls, hydroxides, esters, and nitro groups. Some are multiply substituted. The hydrogen donating side groups (e.g., alcohols, amines, carboxylic acids, etc.) are at a position and distance that may favor cocrystallization with fasoracetam. Table 2 and Table 3 summarize the coformers based on the type of substitution.

TABLE 2

Substitution of Aromatic Coformer

| # OF COFORMERS | # SUBSTITUTIONS |
|---|---|
| 1 | 1 |
| 5 | 2 |
| 2 | 3 |
| 2 | 4 |

TABLE 3

Substitution Type of Aromatic Coformers

| SUBSTITUENT TYPE | # OF COFORMERS |
|---|---|
| —NH2 | 1 |
| —COOH | 6 |
| -alkyl | 1 |
| —OH | 4 |
| -ester | 2 |
| —NO2 | 1 |

Figure 2:
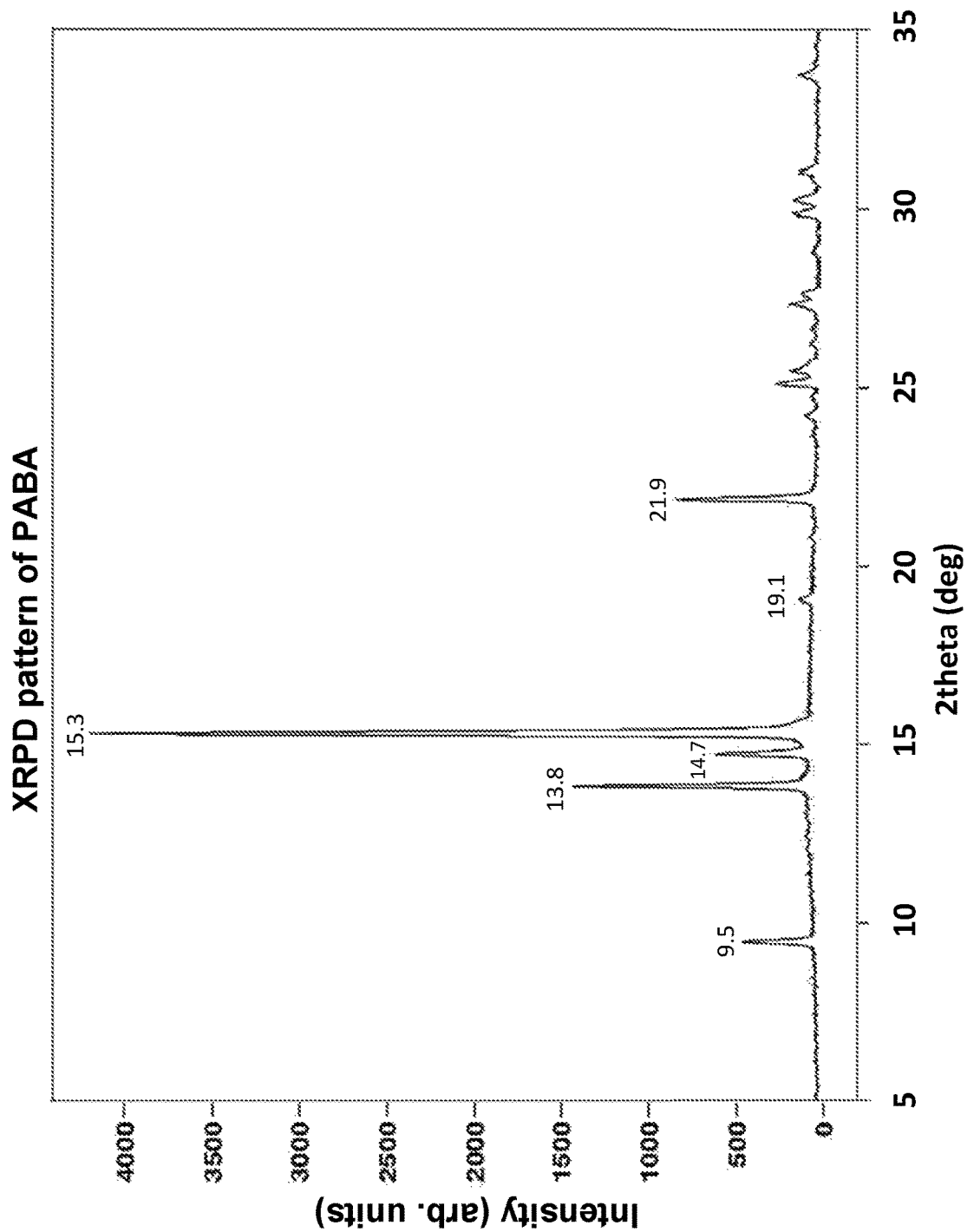
FIG. 2 is an XRPD pattern of PABA.
Figure 7:
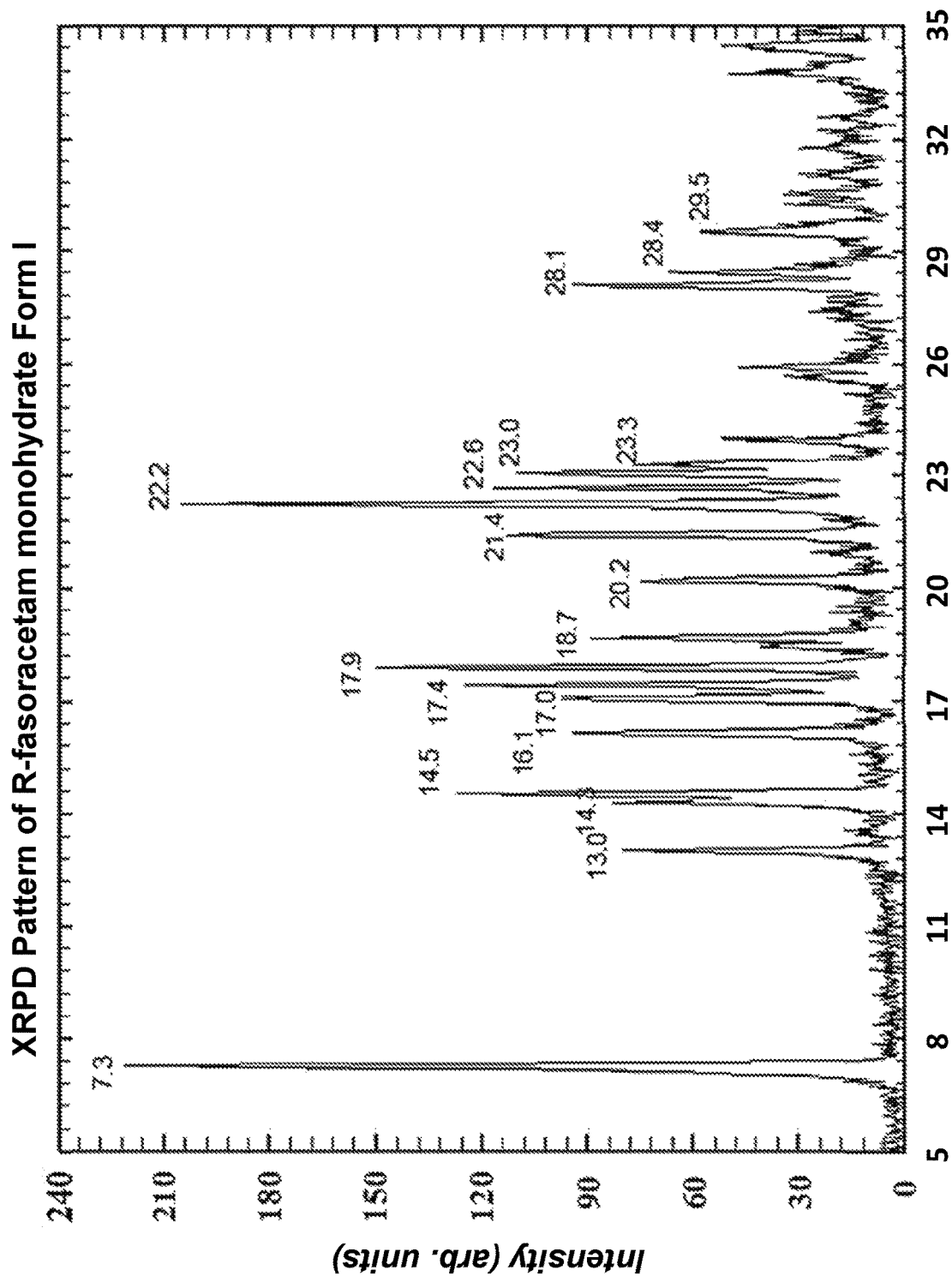
FIG. 7 is an XRPD pattern of R-fasoracetam monohydrate Form I.

In some embodiments of the disclosure, crystalline fasoracetam 4-aminobenzoic acid is provided, such as, for example, cocrystals of fasoracetam and 4-aminobenzoic acid. In many such embodiments, the fasoracetam is R-fasoracetam. FIG. 1 is an XRPD pattern of a 1:1 cocrystal of R-fasoracetam to 4-aminobenzoic acid. The diffraction pattern of FIG. 1 differs from the diffraction patterns of the components of the cocrystal, namely FIGS. 2 and 7. FIG. 2 is an x-ray powder diffraction pattern of 4-aminobenzoic acid and FIG. 7 is the x-ray powder diffraction pattern of R-fasoracetam monohydrate Form I. These two component compounds were used to make the cocrystal whose diffraction pattern is represented in FIG. 1 and the preparation of the cocrystal is set forth in Example 1. The cocrystal exhibits an XRPD peak at about 6.5°2θ. There is no corresponding peak in either FIG. 2 or FIG. 7. The closest peak is a peak in the XRPD pattern of R-fasoracetam monohydrate Form I at about 7.3°2θ, which is 0.8°2θ from the 6.5°2θ in FIG. 1, well outside typical variability for an XRPD peak. Thus, the presence of this peak at about 6.5°2θ confirms that the corresponding crystalline material is not a mixture of R-fasoracetam monohydrate Form I and PABA but rather a distinct crystalline phase. This phase is a cocrystal of R-fasoracetam and PABA. The peak at about 6.5°2θ may also be used to characterize a 1:1 cocrystal of R-fasoracetam and PABA.

Figure 3:
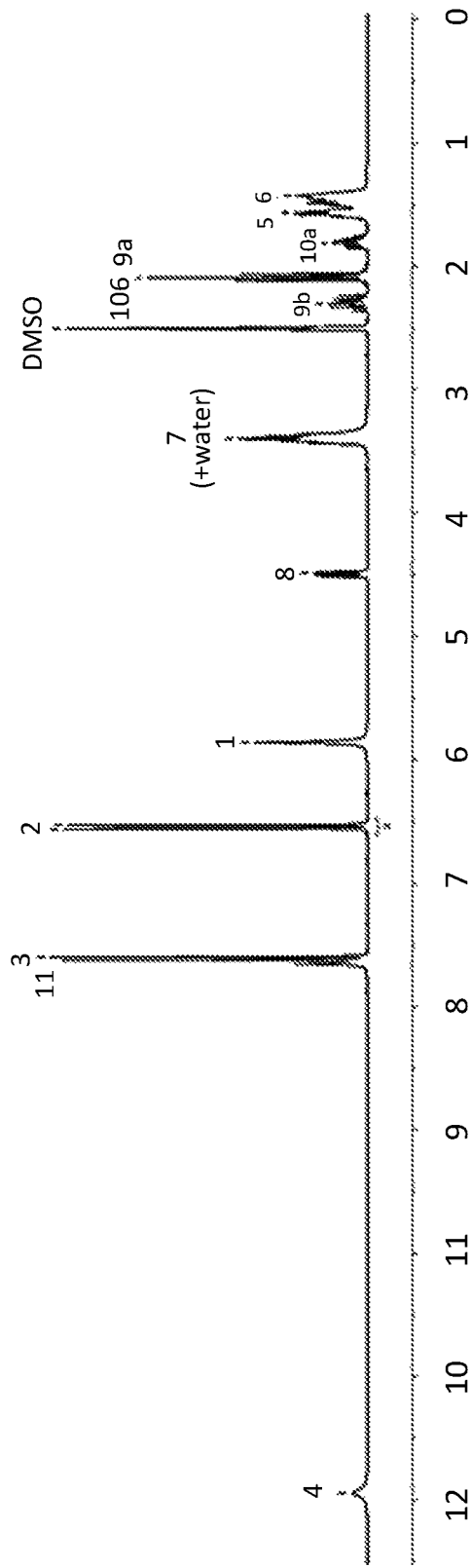
FIG. 3 is a $^1$H-NMR spectrum of R-fasoracetam:PABA cocrystal. The values of the peaks are also provided in Table 3A.

A stoichiometry of 1:1 is shown by the solution-state $^1$H-NMR spectrum of FIG. 3, which may be used to evaluate stoichiometry since it comes from a non-grinding preparation. The chemical shifts in FIG. 3 are shown in Table 3A with corresponding atom numbers identified on the molecular structure of a 1:1 cocrystal of R-fasoracetam to PABA shown below.

TABLE 3A

Chemical shifts of a $^1$H-NMR Spectrum of FIG. 3 of R-fasoracetam: PABA Cocrystal

| Atom Number | δ (ppm) |
|---|---|
| 4 | 11.9 |
| 3 | 7.6 |
| 2 | 6.5 |
| 1 | 5.9 |
| 11 | 7.6 |
| 8 | 4.5 |
| 7 | 3.4 |
| 9b | 2.3 |
| 9a, 10b | 2.1 |
| 10a | 1.8 |
| 5, 6 | 1.4-1.6 |

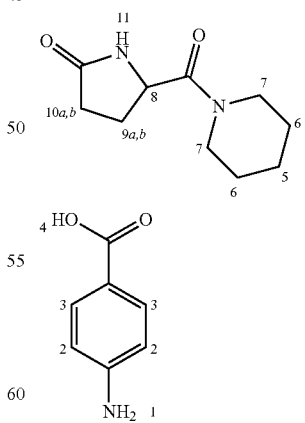

Figure 10:
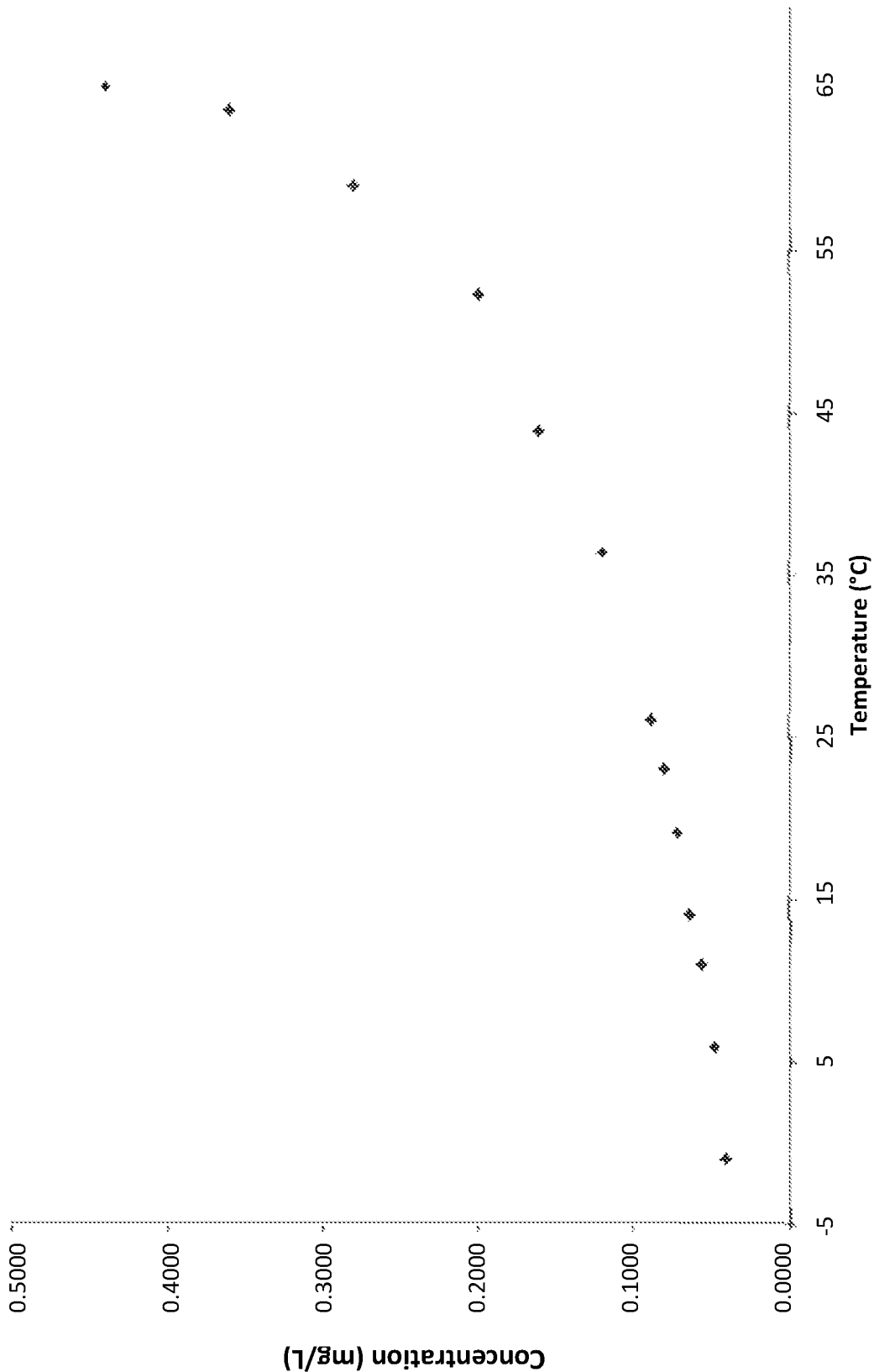
FIG. 10 is a solubility curve of R-fasoracetam:PABA cocrystal.

The stoichiometry of the cocrystal is further confirmed by a single-crystal preparation and x-ray analysis as set forth in Example 3 the stoichiometry is 1:1. A thermal-gravimetric analysis thermogram is provided in FIG. 6 and a solubility curve in ethyl acetate is provided in FIG. 10. As compared with R-fasoracetam monohydrate Form I, the solubility of the cocrystal is approximately three-fold lower. The TGA shows the thermal stability of the cocrystal up to about 200° C.

Likewise, none of the XRPD peaks at about 10.5°2θ, about 11.3°2θ, and about 12.0°2θ have corresponding peaks within the typical variability of such XRPD peaks in either the PABA or R-fasoracetam monohydrate Form I XRPD patterns. Thus, any one of these XRPD peaks is evidence of the formation of a cocrystal as opposed to a mixture of PABA and R-fasoracetam monohydrate Form I. Any one or more of these four peaks, about 6.5°2θ, about 10.5°2θ, about 11.3°2θ, and about 12.0°2θ may be used to characterize a 1:1 cocrystal of R-fasoracetam and PABA. Other peaks may also be used to characterize a cocrystal of R-fasoracetam and PABA. Indeed, one or more of the peaks chosen from peaks at about 6.5°2θ, about 10.5°2θ, about 11.3°2θ, about 12.0°2θ, about 13.4°2θ, about 13.7°2θ, about 17.4°2θ, about 18.1°2θ, about 18.7°2θ, about 19.6°2θ, about 20.6°2θ, about 21.1°2θ, about 21.4°2θ, about 22.8°2θ, about 23.2°2θ, and about 23.7°2θ, may be used to characterize a 1:1 cocrystal of R-fasoracetam to PABA. Although some of these peaks in and of themselves cannot be used to confirm the presence of a cocrystal, such as in the results from a screen, because they have potentially corresponding peaks in the XRPD patterns of R-fasoracetam monohydrate Form I or PABA, they can nevertheless be used to characterize a cocrystal of 1:1 R-fasoracetam to PABA because the chemical composition of the cocrystal differs from each component compound.

Figure 11:
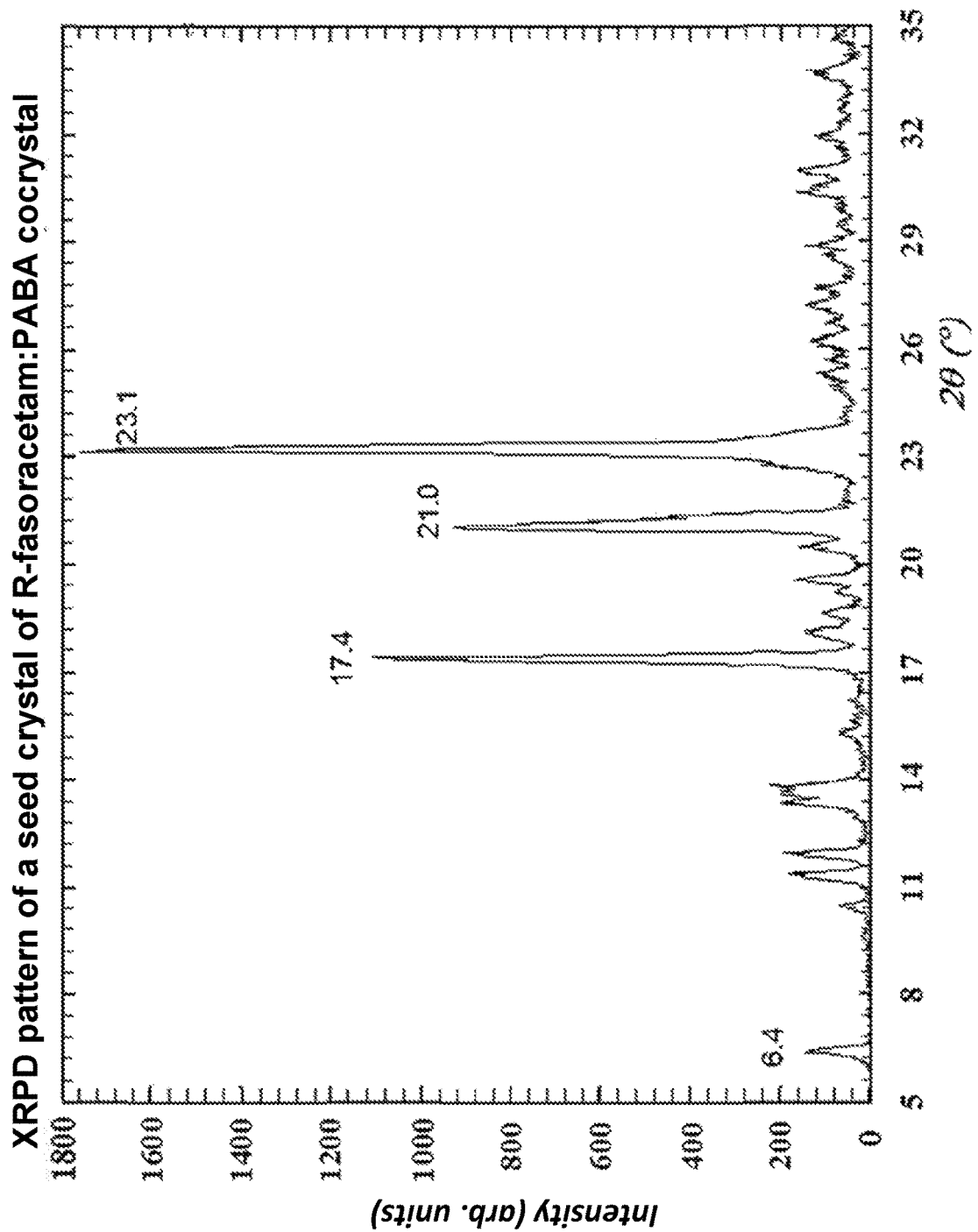
FIG. 11 is an XRPD pattern of a seed crystal of R-fasoracetam:PABA cocrystal.
Figure 13:
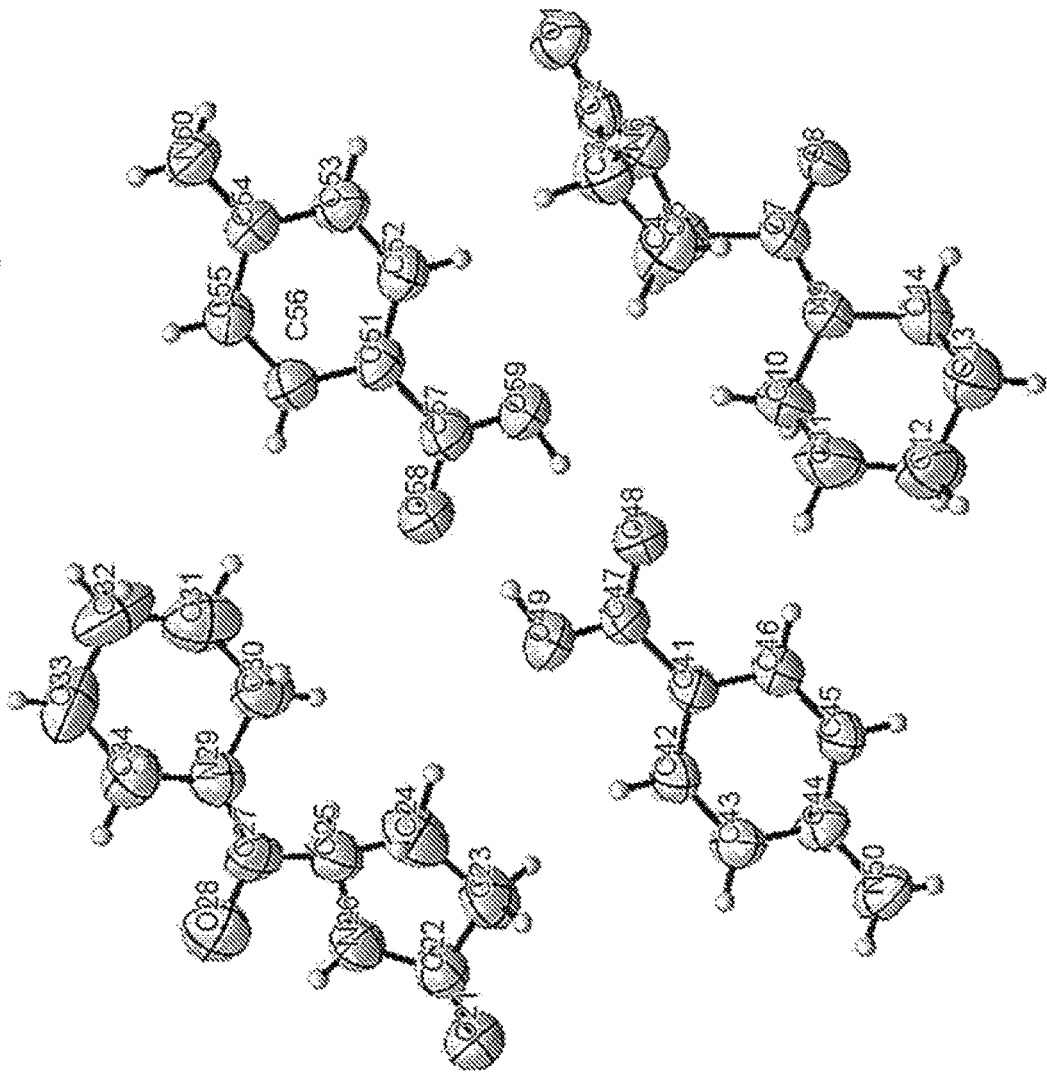
FIG. 13 is the ORTEP drawing of R-fasoracetam:PABA cocrystal.

The preparation of a 1:1 cocrystal of R-fasoracetam and PABA in Example 1 uses a seed cocrystal of a 1:1 cocrystal of R-fasoracetam and PABA made in accordance with Example 2. In some embodiments, such seed crystals are used in batch preparation. FIG. 11 is an XRPD pattern of the seed crystal of Example 2. It matches the XRPD pattern of FIG. 1 which confirms it is a 1:1 cocrystal of R-fasoracetam and PABA. In addition, a single crystal of a 1:1 cocrystal of R-fasoracetam and PABA was prepared as set forth in Example 3. Table 4 of Example 3 lists the corresponding single-crystal data for the solution. It indicates a triclinic unit cell with 2 asymmetric units within the unit cell and showing a molecular stoichiometry of 1:1 of R-fasoracetam to PABA thus confirming a stoichiometry of 1:1. The ORTEP drawing showing the molecules in the unit cell is set forth in FIG. 13 showing molecules of both PABA and R-fasoracetam.

Figure 135:
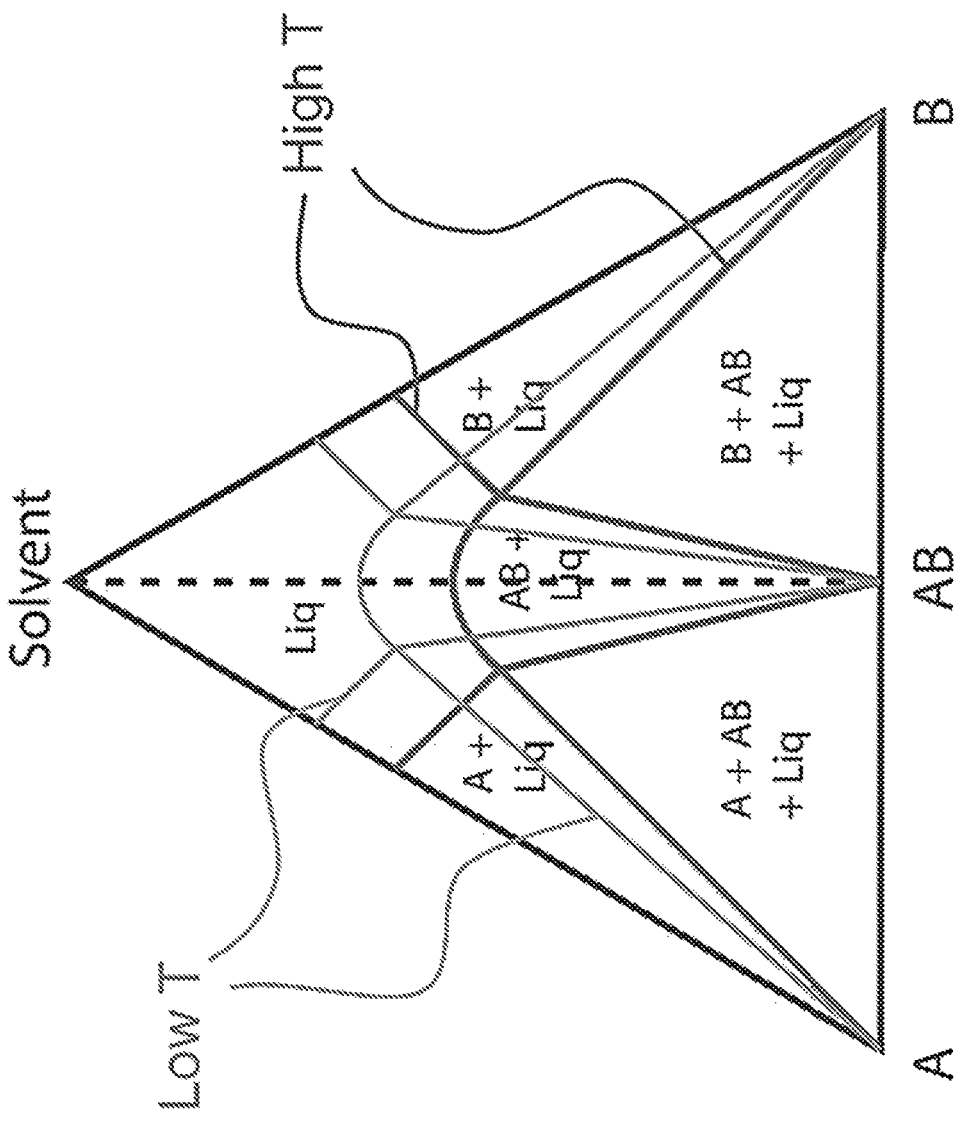

Also provided herein are processes for scaling-up cocrystals of R-fasoracetam and PABA cocrystals. The design of a scaled-up process for this cocrystal is based on the congruency of the R-fasoracetam:PABA cocrystal. As seen in the hypothetical system of FIG. 135, the dashed line shows the 1:1 ratio of both API and co-former, which, in this process, is analogous to the R-fasoracetam:4-aminobenzoic acid cocrystal. In this case when the temperature is lowered no phase boundary is crossed. Thus, the change of temperature does not result in a solid phase transformation.

The single crystal structures in the disclosure are represented both by ORTEP drawings as well as in hydrogen bonded patterns which help illustrate the intermolecular actions of the cocrystal. The thermal ellipsoid represents the probability of the electrons around the atom to be found within its boundaries as a result of vibration. The hydrogen bond pattern shows the molecules in stick representation with dashed lines between hydrogen-bond donors and acceptors. The hydrogen-bond interactions are defined based on the following criteria where "H" is hydrogen, "A" is an acceptor atom; and "Donor" is an atom covalently bound to hydrogen. First, the H-A distances are less than the sum of the Van Der Waals radii of H-A. Second, the Donor-H-A angles are larger than 120°. Third, the Donor must be a nitrogen, oxygen or sulphur with at least 1 covalently bound hydrogen. Fourth, A must be a nitrogen, oxygen, sulphur or halogen with at least 1 available lone pair.

Figure 125:
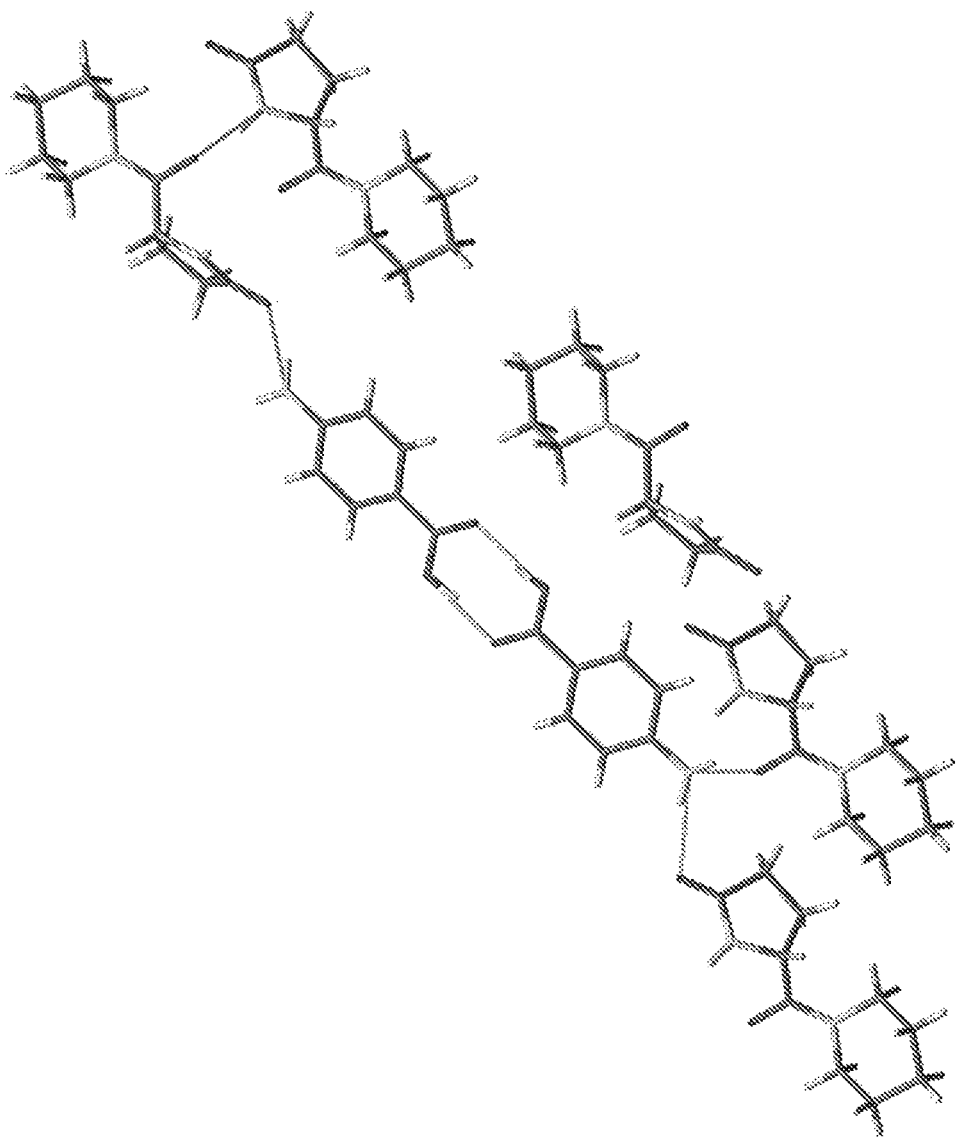
FIG. 125 is a hydrogen bonding pattern of a R-fasoracetam:PABA cocrystal.

In FIG. 125, R-fasoracetam (outer two molecules left, right and three on bottom row) cocrystallizes in a 1:1 manner with 4-aminobenzoic acid (center). The 4-aminobenzoic acid molecules form a homosynthon in a head to head manner, between their carboxylic acid groups.

Without being bound by theory, it is believed that the amine-group of 4-aminobenzoic acid acts as a hydrogen donor towards the carbonyl on R-fasoracetam's five membered ring, and also hydrogen bonds with the bridging carbonyl on another R-fasoracetam molecule, interconnecting different layers in the crystal structure. On the opposite side (top right of FIG. 125), the same interconnectivity happens between two R-fasoracetam molecules, the bridging carbonyl which acts as a hydrogen acceptor and the NH group in the five membered ring acts as a hydrogen donor.

Additional confirmation of structure can be seen from the two XRPD pattern overlays. In the overlay shown in FIG. 12, the XRPD pattern of the single-crystal simulated pattern matches the XRPD pattern of the seed crystal of Example 2. In the overlay shown in FIG. 14, the XRPD pattern of the single-crystal simulated pattern of Example 3 matches the XRPD pattern of the preparation of R-fasoracetam:PABA of Example 1. Thus, each of the Examples 1, 2, and 3 make a 1:1 cocrystal of PABA to R-fasoracetam.

Figure 4:
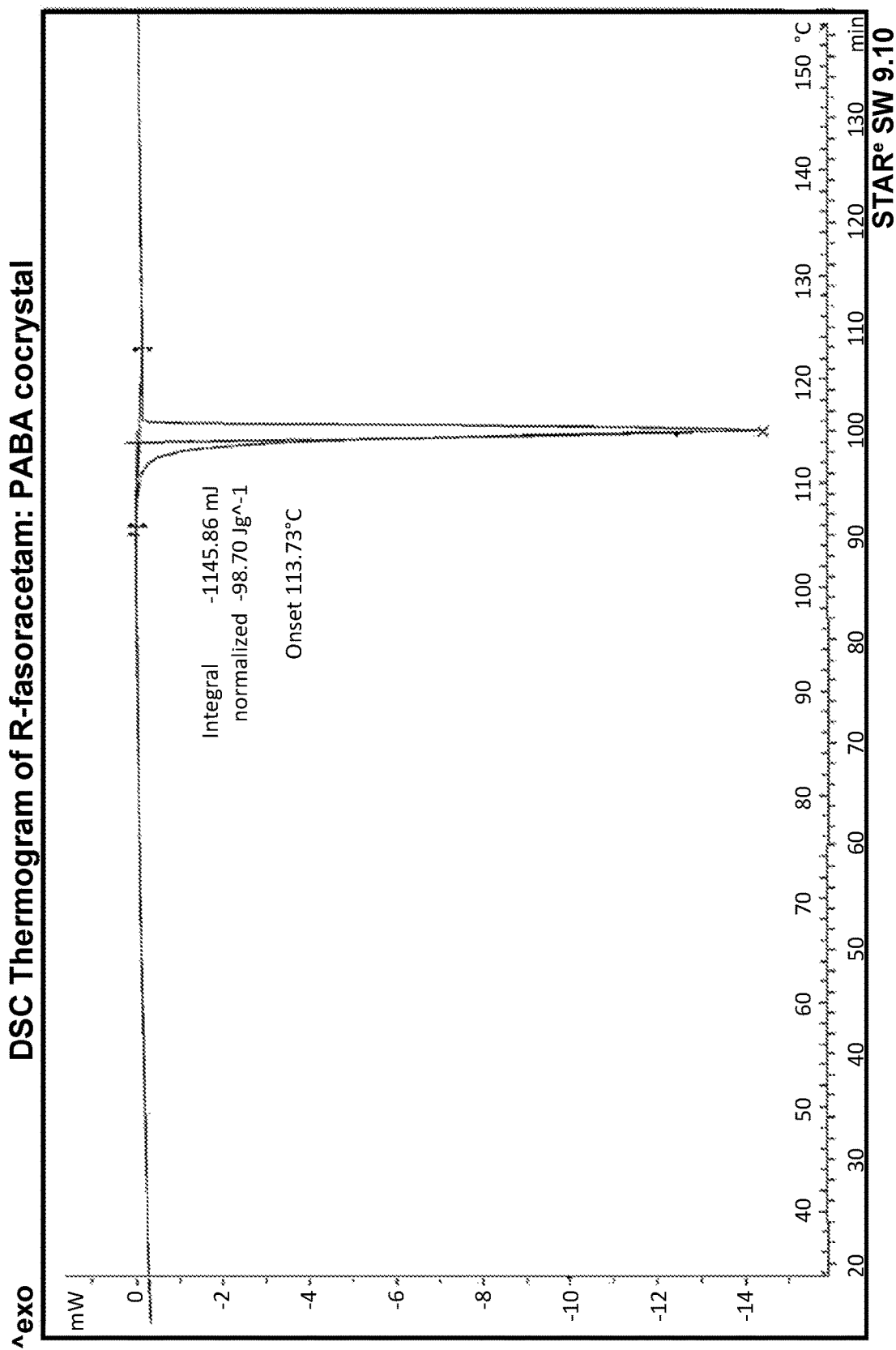
FIG. 4 is a DSC thermogram of a R-fasoracetam:PABA cocrystal.

Thermal data may be used alone, or in combination with other analytical data such as, for example, XRPD data, to characterize a 1:1 cocrystal of R-fasoracetam and PABA. FIG. 4 is a DSC thermogram of the 1:1 cocrystal of R-fasoracetam and PABA prepared in accordance with Example 1. The DSC shows an endotherm at about 114° C. as an onset temperature and this may be used to characterize a 1:1 cocrystal of R-fasoracetam to PABA. The DSC endotherm differs from that of PABA and R-fasoracetam monohydrate Form I. PABA exhibits an onset endotherm at about 187° C. (FIG. 5) and R-fasoracetam monohydrate Form I exhibits an endotherm at about 52° C. (FIG. 8; in FIG. 9, the DSC measurement was performed on a sample of R-fasoracetam monohydrate Form I stored at drier conditions compared to ambient conditions). The DSC also indicates that the cocrystal may have superior handling and storage properties since the endotherm represents melting and the cocrystal melts at about 60° C. higher than the relatively low-melting R-fasoracetam monohydrate Form I.

The DSC onset temperature of about 114° C. may also be used to characterize a 1:1 cocrystal of R-fasoracetam and PABA together with XRPD data. In particular, the DSC onset temperature of about 114° C. may be used with one or more XRPD peaks chosen from peaks at about 6.5°2θ, about 10.5°2θ, about 11.3°2θ, about 12.0°2θ, about 13.4°2θ, about 13.7°2θ, about 17.4°2θ, about 18.1°2θ, about 18.7°2θ, about 19.6°2θ, about 20.6°2θ, about 21.1°2θ, about 21.4°2θ, about 22.8°2θ, about 23.2°2θ, and about 23.7°2θ to characterize a 1:1 cocrystal of R-fasoracetam and PABA.

An XRPD pattern substantially the same as that of FIG. 1 and/or a DSC thermogram substantially the same as FIG. 4 may be used to characterize a cocrystal of fasoracetam and PABA such as the R-fasoracetam and PABA cocrystal.

Figure 23:
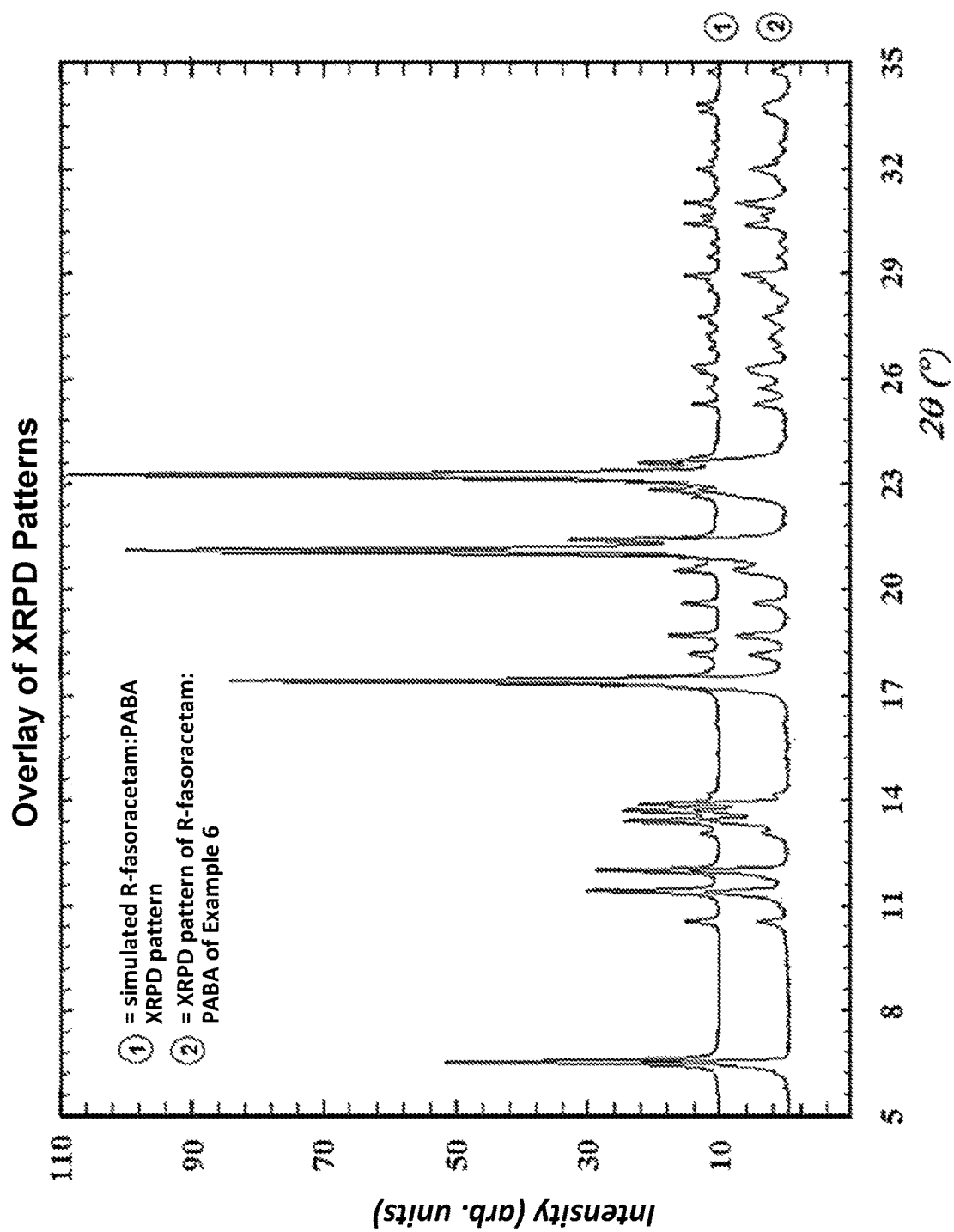
FIG. 23 is an overlay of XRPD patterns: (1) simulated R-fasoracetam:PABA XRPD pattern; (2) XRPD pattern of R-fasoracetam:PABA of Example 6.
Figure 25:
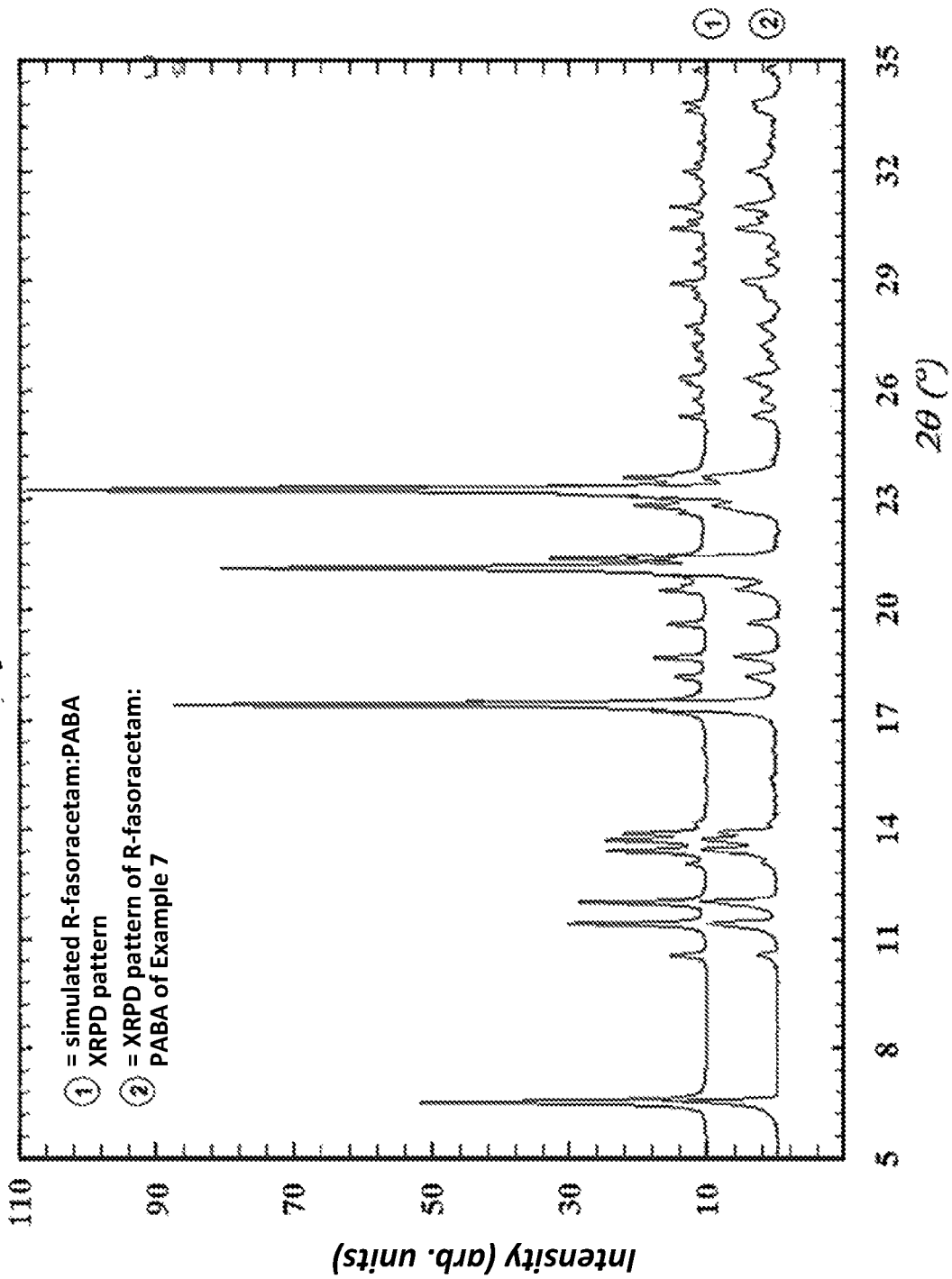
FIG. 25 is an overlay of XRPD patterns: (1) simulated R-fasoracetam:PABA XRPD pattern; (2) XRPD pattern of R-fasoracetam:PABA of Example 7.

The R-fasoracetam PABA cocrystal process may be scaled-up to provide gram or larger-sized quantities of R-fasoracetam PABA cocrystals. For example, a mixture of Form I, Form II, and anhydrate R-fasoracetam may be dissolved in a solvent and both PABA and a seed crystal of an R-fasoracetam PABA cocrystal may be added to the solution. Isolation of resulting solids provides the cocrystal of R-fasoracetam and PABA. Alternatively, a different form of R-fasoracetam, such as R-fasoracetam monohydrate Form I may be used as a starting material. Examples 6 and 7 provide such scale-up examples. FIG. 23 is an XRPD pattern overlay of the simulated XRPD pattern derived from the single-crystal x-ray solution of a 1:1 R-fasoracetam: PABA cocrystal and the cocrystal made in Example 6 showing a match. FIG. 25 likewise shows a match between the simulated pattern and that of Example 7.

Figure 18:
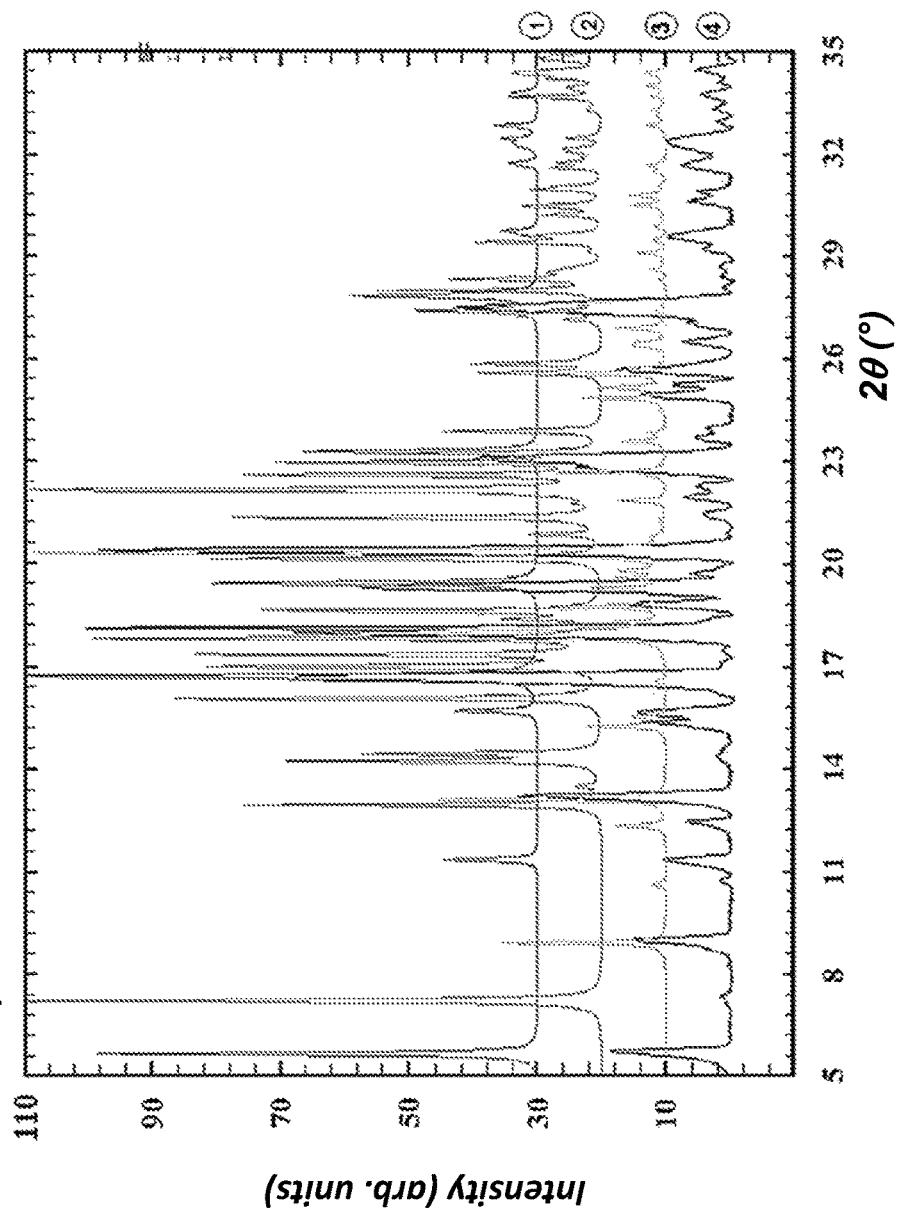
FIG. 18 is an overlay of XRPD patterns: (1) R-fasoracetam monohydrate Form II simulated; (2) R-fasoracetam monohydrate Form I simulated; (3) anhydrate R-fasoracetam simulated; (4) XRPD pattern of a mixture of R-fasoracetam monohydrate Form I, R-fasoracetam monohydrate Form II, anhydrate R-fasoracetam.
Figure 44:
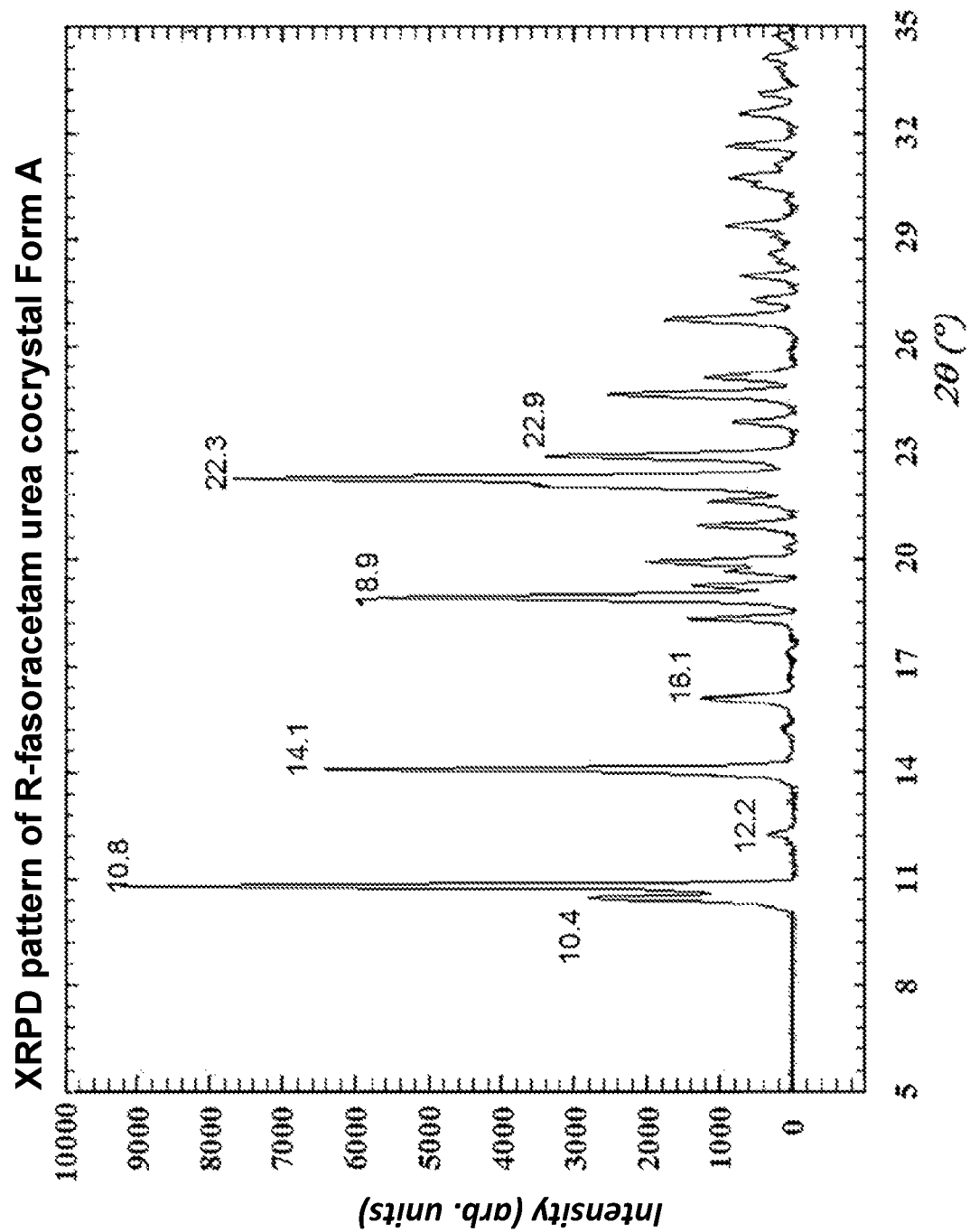
FIG. 44 is an XRPD pattern of a R-fasoracetam:urea cocrystal Form A.

In additional embodiments, the disclosure provides for crystalline fasoracetam urea such, as, for example, cocrystals of fasoracetam and urea. In particular, the fasoracetam may be R-fasoracetam. As set forth herein, cocrystals of R-fasoracetam and urea may be polymorphic (herein designated as Form A and Form B). The crystal structure of Form B reveals it to be a 1:1 cocrystal of R-fasoracetam to urea. While there is no single-crystal structure solution herein for Form A, without being bound by theory, it is believed that Form A is a polymorph of Form B (in that the two forms would have the same stoichiometry) because, for example, the equimolar grinding experiment for making Form A (Example 15) does not show any remaining XRPD signals associated with the starting materials as seen in FIG. 44, which is an XRPD pattern corresponding to a cocrystal of R-fasoracetam and urea Form A. To make that cocrystal, a mixture of R-fasoracetam forms as set forth according to the general procedures of Example 11 and/or Example 16. This mixture contains R-fasoracetam Form I, Form II, and the anhydrate form (R-Fasoracetam Forms Mixture) and FIG. 18 shows the XRPD pattern of that mixture compared with the simulated pattern of the component parts. The XRPD pattern of the mixture is a linear combination of the pure simulated patterns (with varying intensities) which indeed confirms a mixture is present. For example, considering the first 7 peaks of the mixture's diffraction pattern, those peaks each correspond to a peak in one of the simulated patterns. The peaks at about 5.7°2θ and about 11.3°2θ correspond to Form II. The peak at about 7.2°2θ corresponds to Form I, and the peaks at about 8.9°2θ, about 12.3°2θ, and about 13.1°2θ correspond to the anhydrate. The peak at about 12.9°θ corresponds to Form I, but is also close to the 13.1°2θ in the anhydrate. Nevertheless, these two peaks between about 12.8°2θ and about 13.2°2θ are accounted for by Form I and the anhydrate. It is also worth noting that the general intensity of the Form I peaks at angles under about 14°2θ are much weaker than Form II and the anhydrate form. The simulated XRPD patterns can be found at FIGS. 33 (R-fasoracetam Form I), 28 (R-fasoracetam Form II), and 30 (anhydrate R-fasoracetam).

Figure 35:
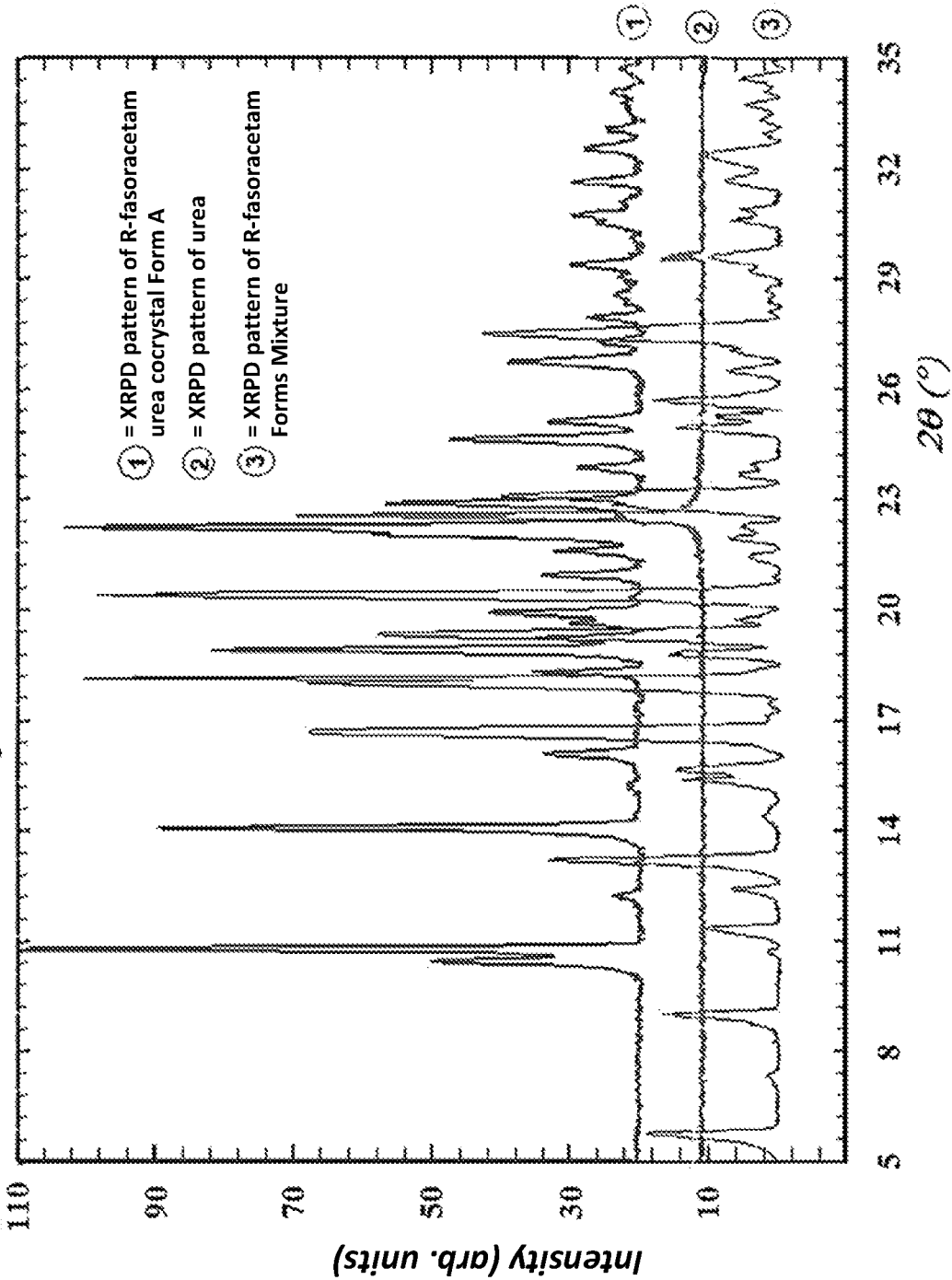
FIG. 35 is an overlay of XRPD patterns: (1) XRPD pattern of R-fasoracetam:urea cocrystal Form A; (2) XRPD pattern of urea; (3) XRPD pattern of R-fasoracetam Forms Mixture.
Figure 45:
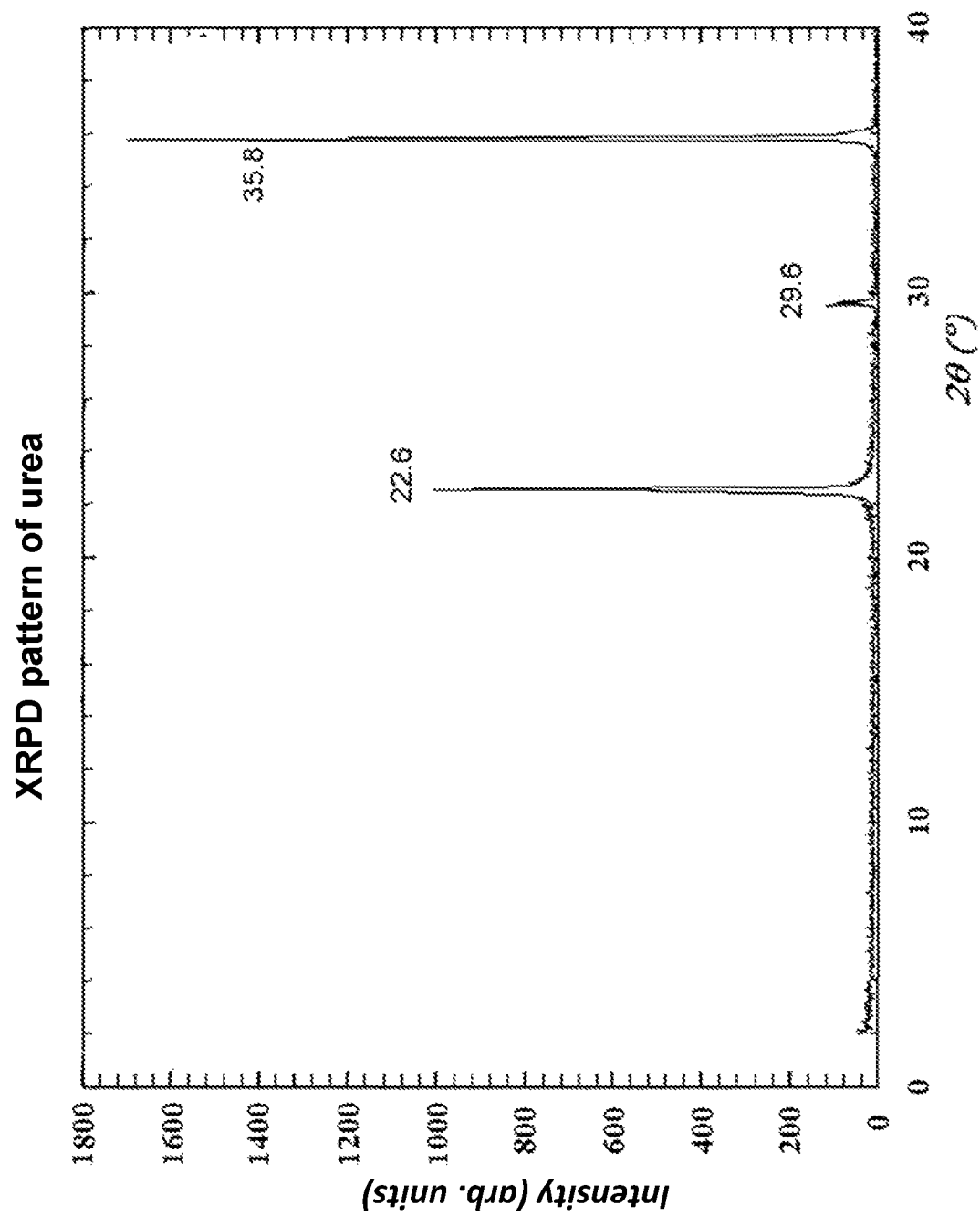
FIG. 45 is an XRPD pattern of urea.
Figure 113:
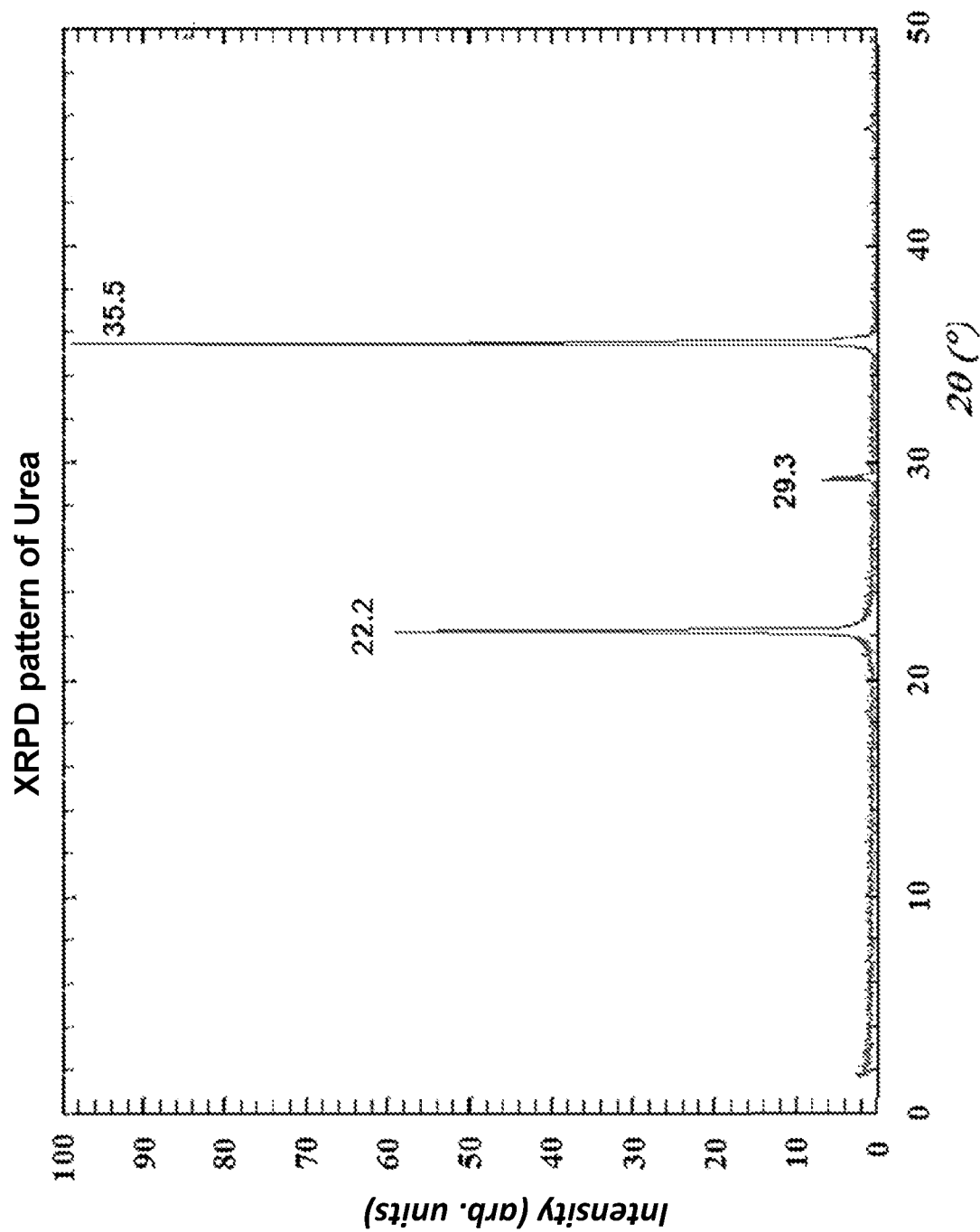
FIG. 113 is an XRPD pattern of urea.
Figure 124:
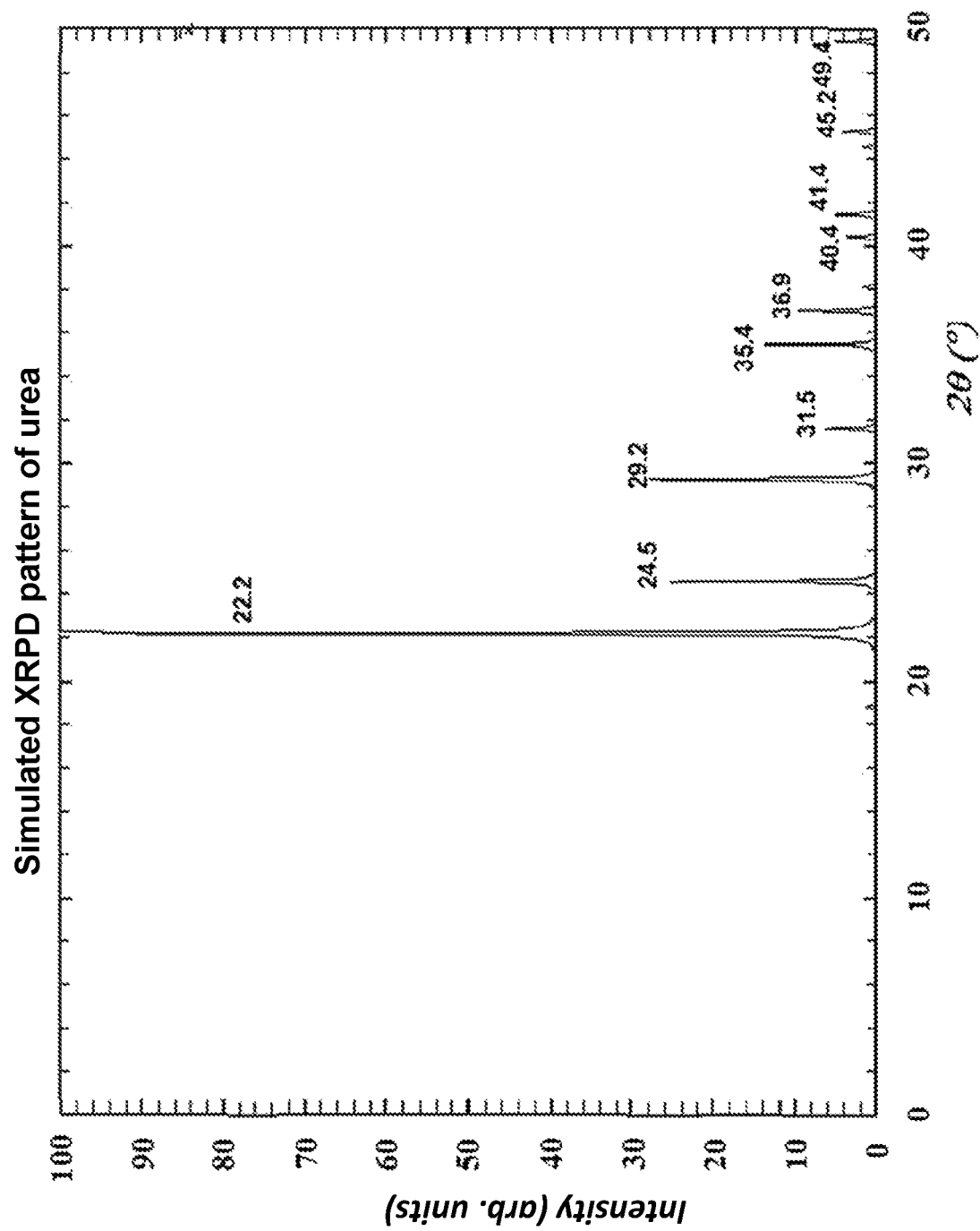
FIG. 124 is a simulated XRPD pattern of urea.

FIG. 35 is an overlay of XRPD patterns of the cocrystal of Form A R-fasoracetam and urea of Example 16 and the XRPD patterns of urea (FIG. 45 and FIG. 113) and that of the R-Fasoracetam Forms Mixture. The XRPD pattern of urea in FIG. 45 is shifted by about 0.3°2θ with respect to the urea XRPD pattern of FIG. 113. The shift in FIG. 45 is due to an experimental error induced by sample holder during the XRPD measurement. The XRPD pattern of FIG. 113 is the more accurate XRPD pattern and no such sample holder error occurred during its measurement. FIG. 124 is the simulated XRPD pattern of urea. Some peaks in the experimental diffraction pattern of urea (FIG. 113), such as the peak at about 24.5°2θ, are not visible due to the preferred orientation of the urea crystals.

Figure 114:
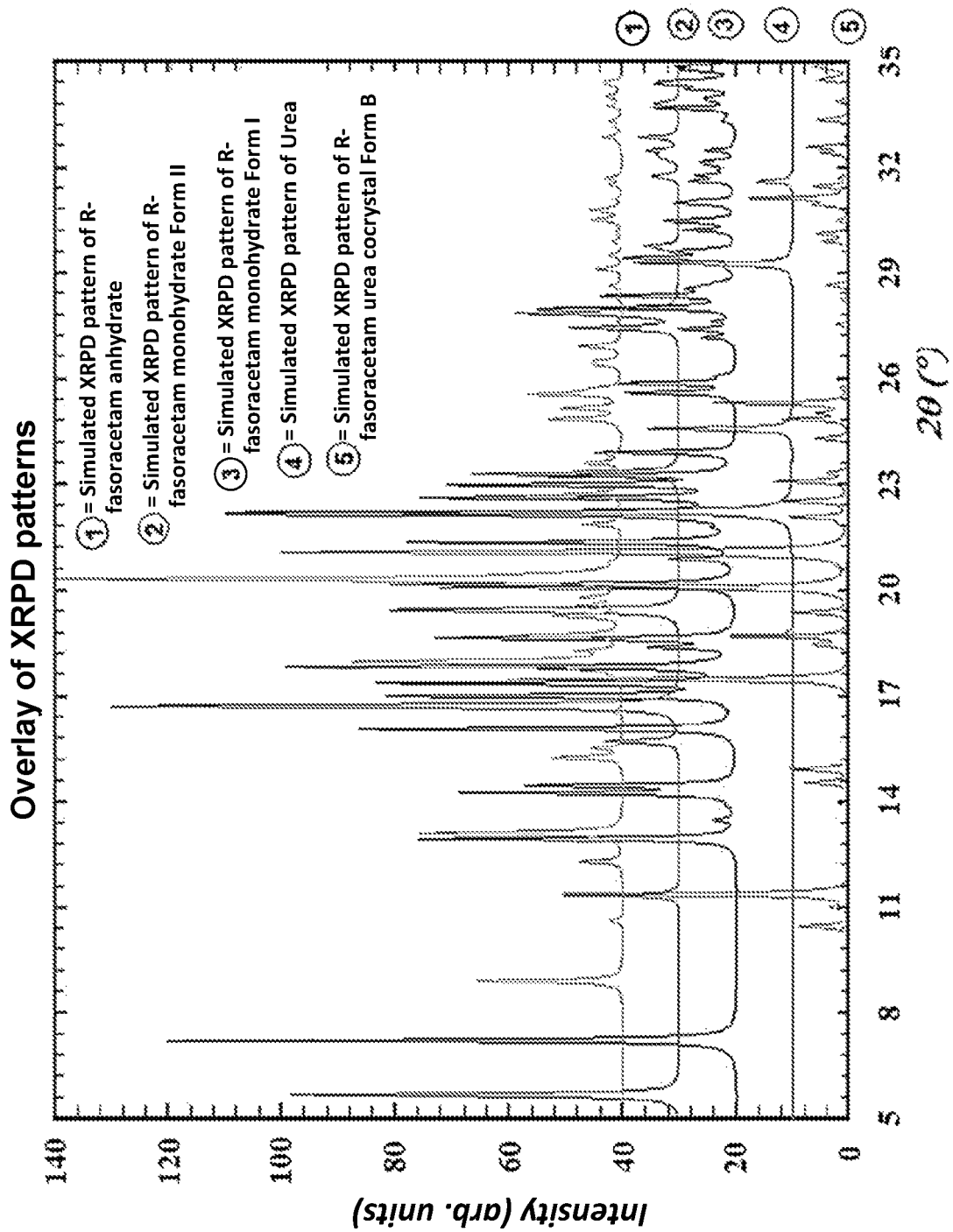
FIG. 114 is an overlay of XRPD patterns: (1) Simulated XRPD pattern of R-fasoracetam anhydrate; (2) Simulated XRPD pattern of R-fasoracetam monohydrate Form II; (3) Simulated XRPD pattern of R-fasoracetam monohydrate Form I; (4) Simulated XRPD pattern of urea; (5) Simulated XRPD pattern of R-fasoracetam:urea cocrystal Form B.
Figure 115:
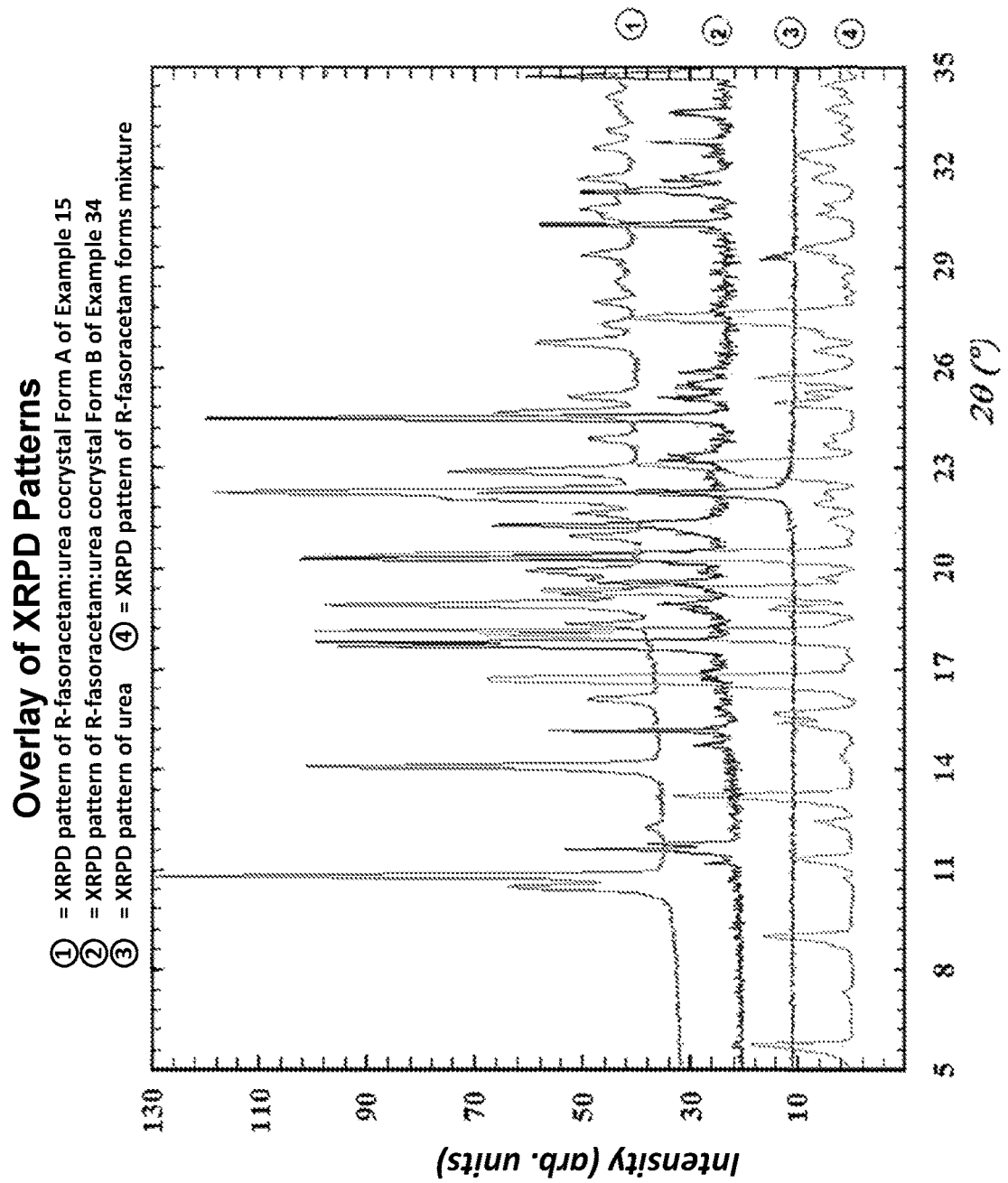
FIG. 115 is an overlay of XRPD patterns: (1) XRPD pattern of R-fasoracetam:urea cocrystal Form A of Example 15; (2) XRPD pattern of R-fasoracetam:urea cocrystal Form B of Example 34; (3) XRPD pattern of urea; (4) XRPD pattern of R-fasoracetam Forms Mixture.

The XRPD pattern of the Form A cocrystal has a unique pattern that is not described as a linear combination of the XRPD patterns from that of urea and the R-Fasoracetam Forms Mixture. For example, the peak at about 10.4°2θ is not in either of urea or the R-Fasoracetam Forms Mixture patterns. Likewise, there is no evidence of Form II or the anhydrate forms in that cocrystal XRPD pattern given the absence of peaks at about 5.7°2θ and at about 8.9°2θ. The XRPD pattern of Form I shows peaks at about 7.2°2θ and 12.9°2θ, neither of which are present in the XRPD pattern of the Form A cocrystal of R-fasoracetam and urea. Thus, the FIG. 44 XRPD pattern of the Example 15 ground crystalline material does not represent a mixture of urea and R-fasoracetam but is a new crystalline phase. It is a Form A cocrystal of R-fasoracetam and urea and the peak at about 10.4°2θ is a characteristic peak which is characteristic of a cocrystal of R-fasoracetam and urea although that peak is susceptible to preferred orientation effects and is not seen in all experimental patterns such as, for example, in FIGS. 115 and 117. That peak is also present in Form B of a cocrystal of R-fasoracetam and urea so while that peak alone does not distinguish Form A from Form B, it does distinguish from the starting materials so it is characteristic of a cocrystal of R-fasoracetam and urea, such as a cocrystal of Form A or Form B. Another peak which is common is a peak at about 14.0°2θ or about 14.1°2θ. The peak at about 14.0°2θ appears in Form B and the peak at about 14.1°2θ appears in Form A. This difference of 0.1°2θ is within the typical variability of XRPD peaks. Thus, like the peak at about 10.4°2θ, such a peak at about 14.0°2θ or about 14.1°2θ can be used to characterize a cocrystal of R-fasoracetam and urea such as Form A or Form B or both. In addition, one or more of the XRPD peaks chosen from about 10.4°2θ, about 10.8°2θ, about 12.2°2θ, about 14.1°2θ, about 16.1°2θ, about 18.9°2θ, about 22.3°2θ, and about 22.9°2θ may be used to characterize a Form A cocrystal of R-fasoracetam to urea. With respect to distinguishing Form A from Form B, the peak at about 16.1°2θ distinguishes Form A from Form B since there is no corresponding peak in Form B. Likewise, a peak at about 12.2°2θ distinguishes Form A from Form B. For example, therefore, a peak at about 12.2°θ or a peak at about 16.1°2θ or both and one or more peaks chosen from peaks at about 10.4°2θ, about 10.8°2θ, about 14.1°2θ, about 18.9°2θ, about 22.3°2θ, and about 22.9°2θ may be used to characterize Form A. FIGS. 114 and 115 illustrate the difference in XRPD patterns between Form A, Form B, urea, the R-fasoracetam Forms Mixture, the Anhydrate, Form I, and Form II.

Figure 20:
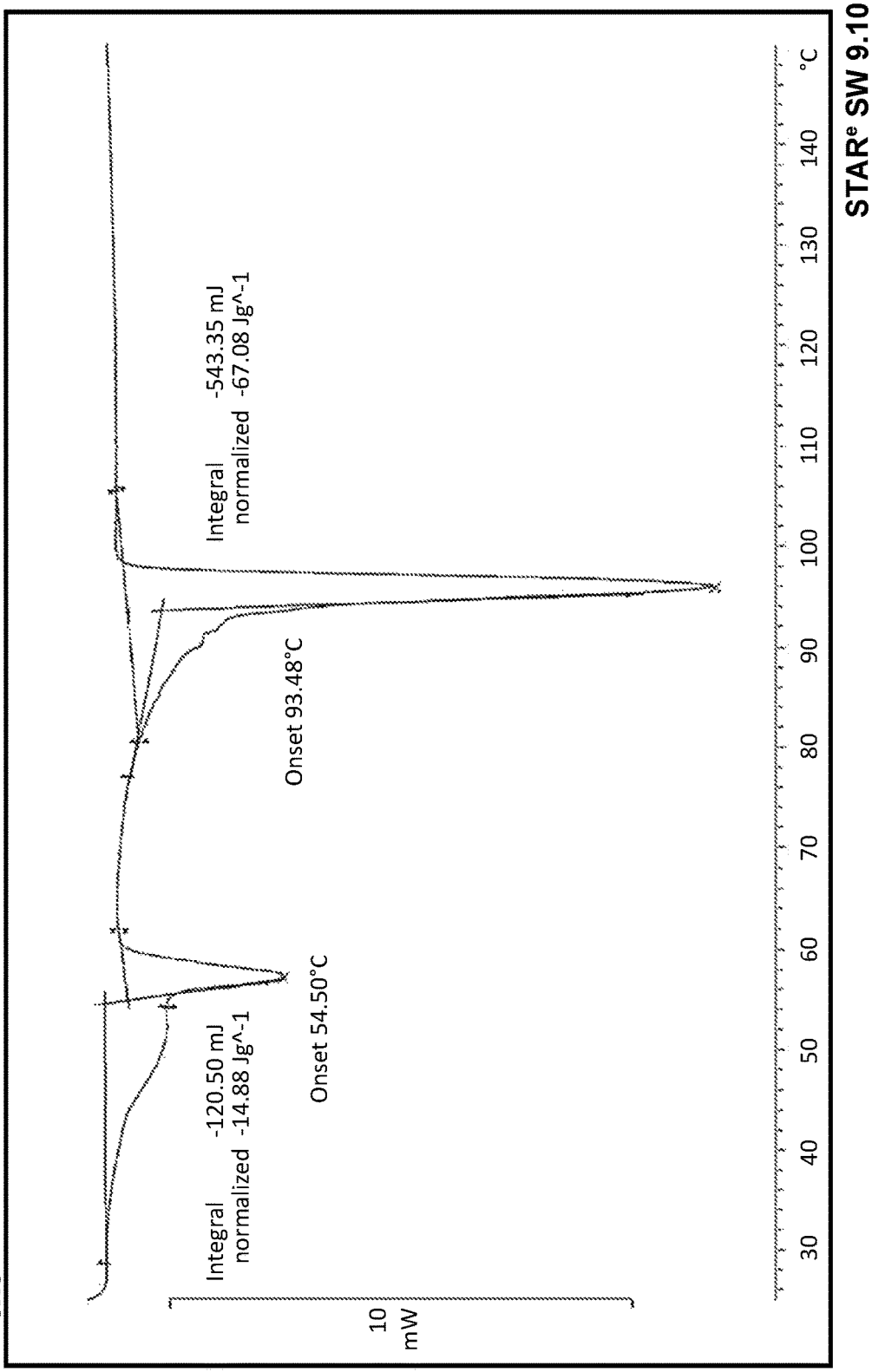
FIG. 20 is a DSC thermogram of the mixture of R-fasoracetam monohydrate Form I, R-fasoracetam monohydrate Form II, and R-fasoracetam anhydrate.
Figure 21:
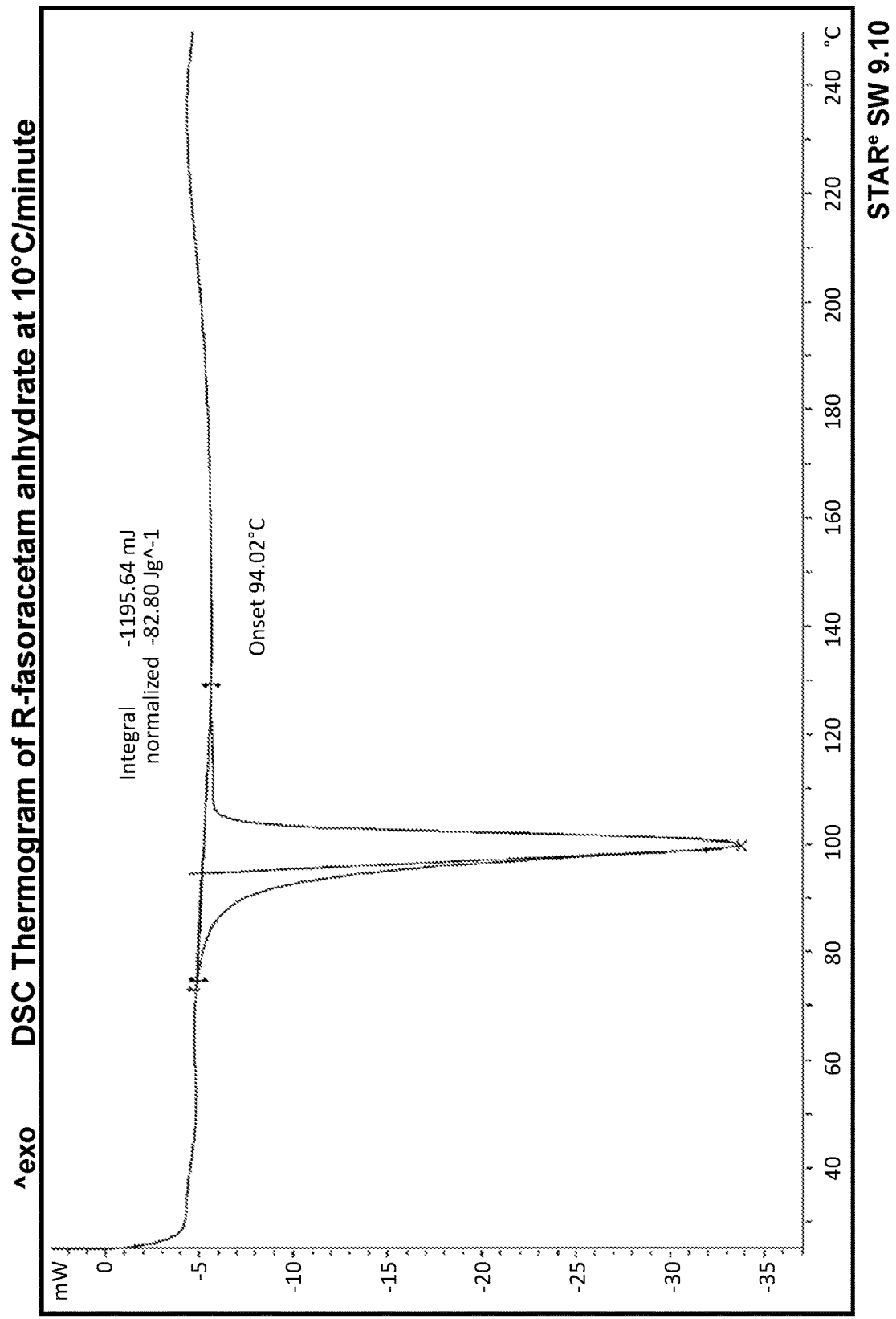
FIG. 21 is a DSC thermogram of R-fasoracetam anhydrate at 10° C./minute.

Melting behavior may also be used to characterize a cocrystal of fasoracetam and urea such as a cocrystal of R-fasoracetam and urea. For example, a sample that was believed to be Form A cocrystal of R-fasoracetam and urea was measured to have an onset melting point of about 103° C. when measured with differential scanning calorimetry as reported in FIG. 47, which is well below the DSC onset melting temperature of urea at about 133° C. and well above the DSC onset melting point temperature of Form I (about 52° C. as set forth in FIG. 8; about 57° C. as set forth in FIG. 9), Form II (about 49° C. as set forth in FIG. 17), or the anhydrate forms of R-fasoracetam (about 93° C. as set forth in FIG. 20 and at about 94° C. as seen in FIG. 21 where the ramp rate was increased to about 10° C./minute). (The Anhydrate being hygroscopic, the sample in FIG. 21 was obtained by keeping R-fasoracetam monohydrate Form I under vacuum for a prolonged period at a temperature of 65° C. to try to limit water uptake.)

However, the 103° C. DSC measurement in FIG. 47 actually corresponds to that of Form B, because it was determined that Form B is the more thermodynamically stable form of the R-fasoracetam:urea cocrystal than Form A, and the Form A material converted to Form B prior to or during the DSC measurement. A more representative DSC of Form A can be found at FIG. 119, where the onset melting point is at about 91° C. Such a cocrystal may also be characterized with a combination of melting onset temperature, such as when measured by DSC, together with one or more characteristic XRPD peaks. Thus, for example, an onset melting temperature of about 91° C. together with one or more peaks chosen from peaks at about 10.4°2θ, about 10.8°2θ, about 12.2°2θ, about 14.1°2θ, about 16.1°2θ, about 18.9°2θ, about 22.3°2θ, or about 22.9°2θ may be used to characterize a cocrystal of fasoracetam and urea such as a Form A cocrystal of R-fasoracetam and urea.

Figure 119:
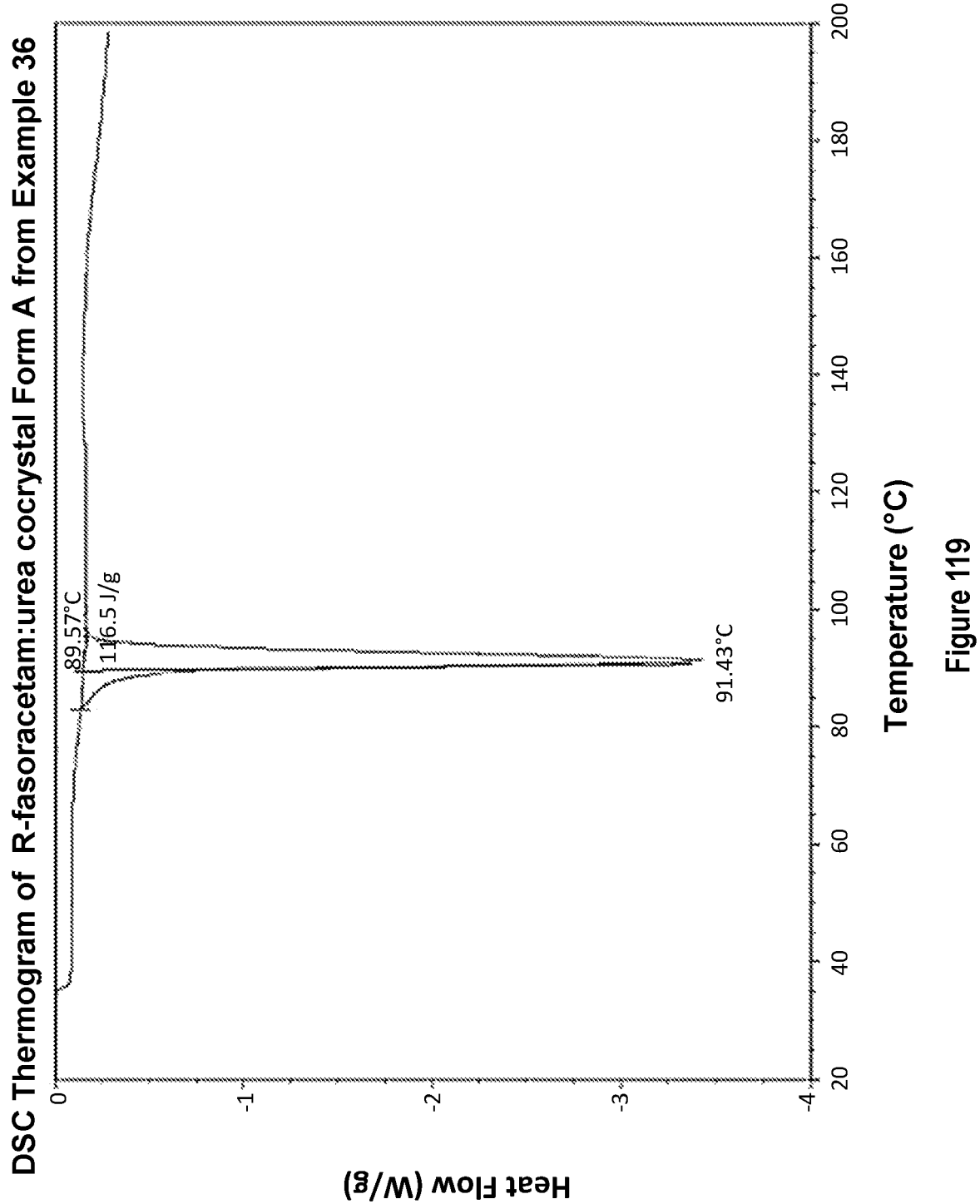
FIG. 119 is a DSC thermogram of R-fasoracetam:urea cocrystal Form A from Example 36.

The XRPD pattern substantially the same as that of FIG. 44 and/or a DSC thermogram substantially the same as FIG. 119 may be used to characterize a Form A cocrystal of R-fasoracetam and urea.

Figure 127:
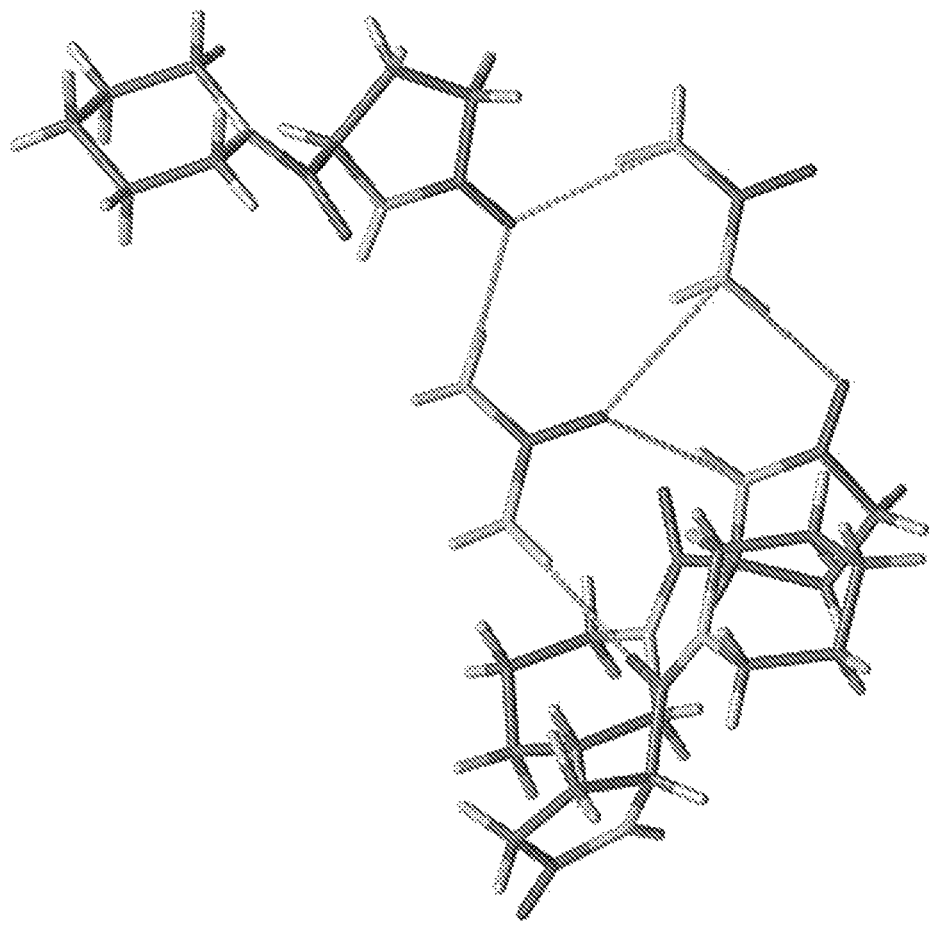
FIG. 127 is a hydrogen bonding pattern of a R-fasoracetam:urea cocrystal Form B.

In various embodiments, the disclosure provides for Form B of a cocrystal of R-fasoracetam and urea. An ORTEP drawing of the cocrystal appears in FIG. 36 which comes from the single crystal solution of Form B in Example 12. As shown in FIG. 127, R-fasoracetam (left, two molecules on top of each other, right) crystallizes in a 1:1 manner with urea (two center molecules).

Without being bound by theory, it is believed that the carbonyl on R-fasoracetam's five membered ring acts as a hydrogen acceptor for urea's hydrogen donating $NH_2$, and the carbonyl of urea acts as an acceptor for the NH hydrogen donor on the five membered ring of R-fasoracetam. It is believed that the other hydrogen bond from the hydrogen donor $NH_2$ on urea to the bridging carbonyl on R-fasoracetam serves to connect the different layers of molecules together, creating a 3D hydrogen bonding pattern.

Figure 37:
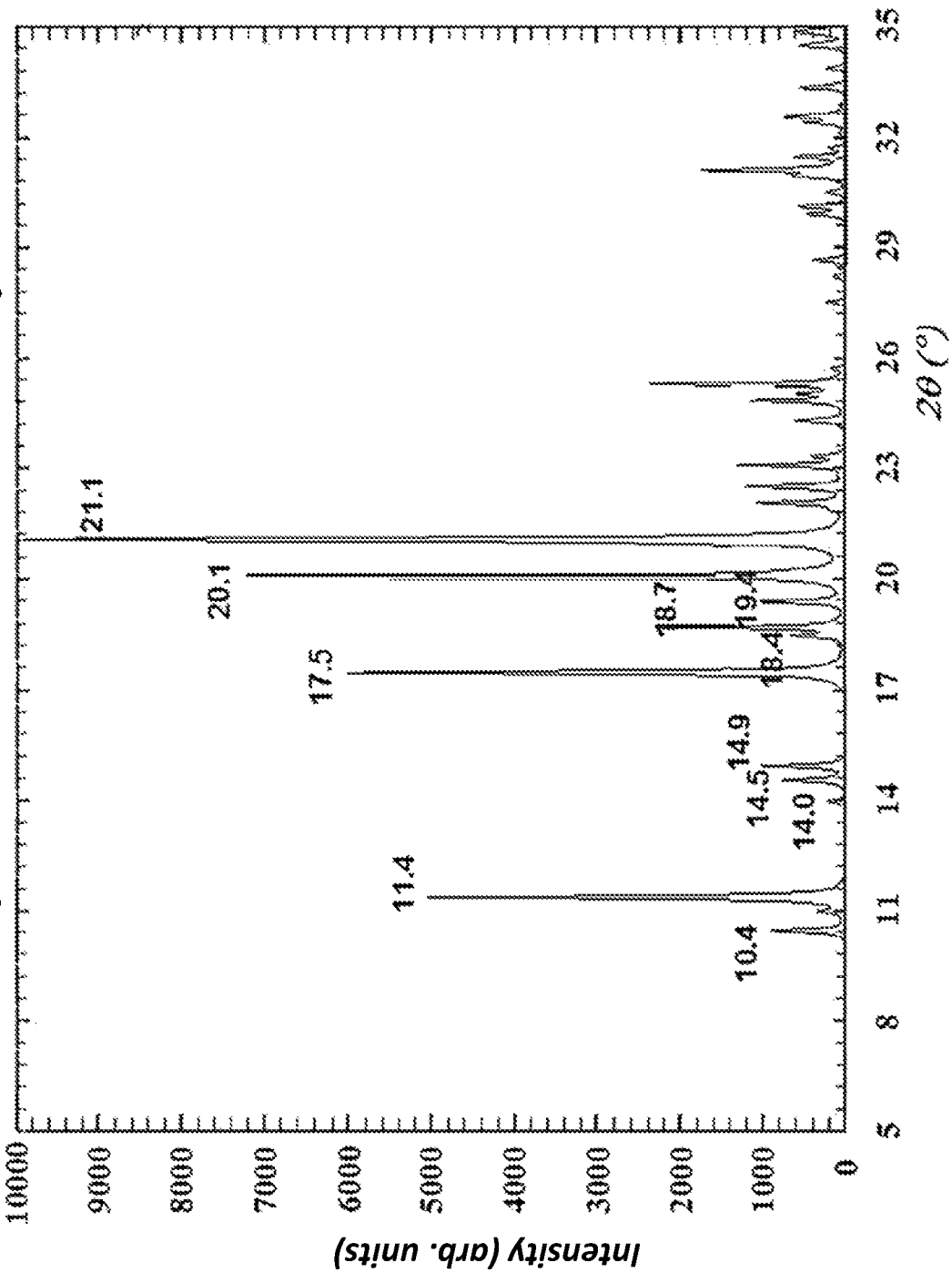
FIG. 37 is a simulated XRPD pattern of a cocrystal of a R-fasoracetam and urea Form B.
Figure 49:
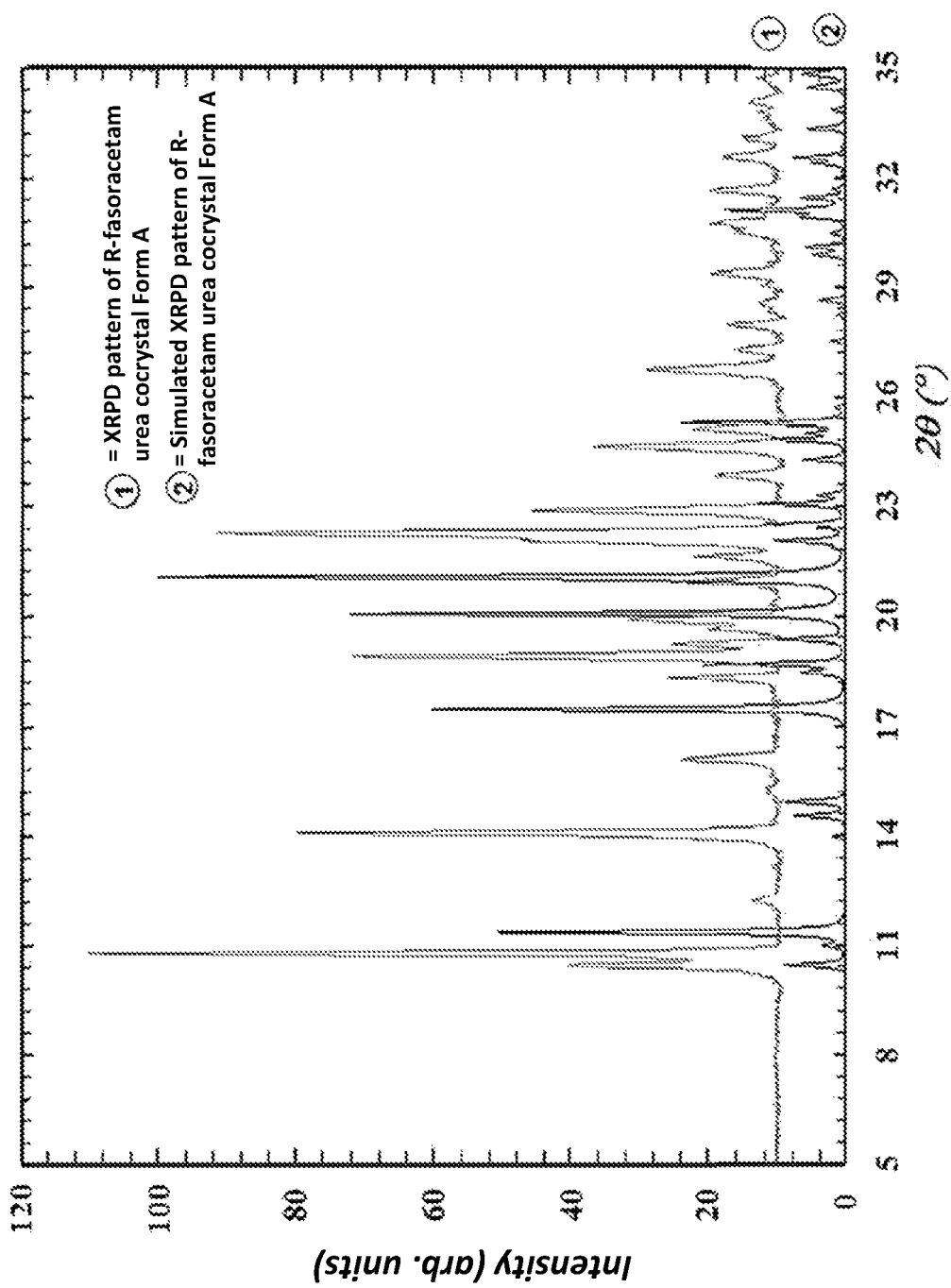
FIG. 49 is an overlay of XRPD patterns: (1) XRPD pattern of R-fasoracetam:urea cocrystal Form A; (2) Simulated XRPD pattern of R-fasoracetam:urea cocrystal Form B.

A simulated pattern of the single crystal solution is in FIG. 37 and when compared with the x-ray powder diffraction pattern of Form A in FIG. 49, there is not a match and there are multiple peaks that are in Form B which are not in Form A. For example, the peak at about 11.4°2θ in Form B is not in Form A so that peak can be used to distinguish and characterize Form B. Likewise, the peak at about 17.5°2θ is not present in Form A and thus it too can be used to distinguish Form B from A and characterize Form B. Form B further possesses three peaks between about 14.0°2θ and about 14.9°2θ—namely, at about 14.0°2θ, about 14.5°2θ and about 14.9°2θ. By comparison, Form A has one peak at about 14.1°2θ. Thus, the presence of two of the three peaks at about 14.0°2θ, about 14.5°2θ, and about 14.9°2θ characterize Form B. For example, the presence of two peaks at about 14.5°2θ, and about 14.9°2θ characterize Form B as do peaks at about 14.0°2θ and about 14.5°2θ. In other embodiments, the peak at about 14.9°2θ characterizes Form B.

In other embodiments, a Form B cocrystal of R-fasoracetam and urea may be characterized by an x-ray powder diffraction pattern comprising one or more peaks chosen from the peaks at about 11.4°2θ, about 14.0°2θ, about 14.5°2θ, about 14.9°2θ, and about 17.5°2θ. Other embodiments may also be used to characterize Form B. For example, Form B may also be characterized by a peak at about 11.4°2θ and one or more peaks chosen from the peaks at about 10.4°2θ, about 14.0°2θ, about 14.5°2θ, about 14.9°2θ, about 17.5°2θ, about 18.4°2θ, about 18.7°2θ, about 19.4°2θ, about 20.1°2θ, and about 21.1°2θ. In addition, the XRPD diffractogram substantially the same as FIG. 37 may be used to characterize Form B.

Form B may further be characterized by an onset melting point of about 102° C. The melting point, such as measured by DSC, may also be combined with the x-ray powder diffraction embodiments for Form B herein to characterize Form B and distinguish Form B over Form A.

Figure 38:
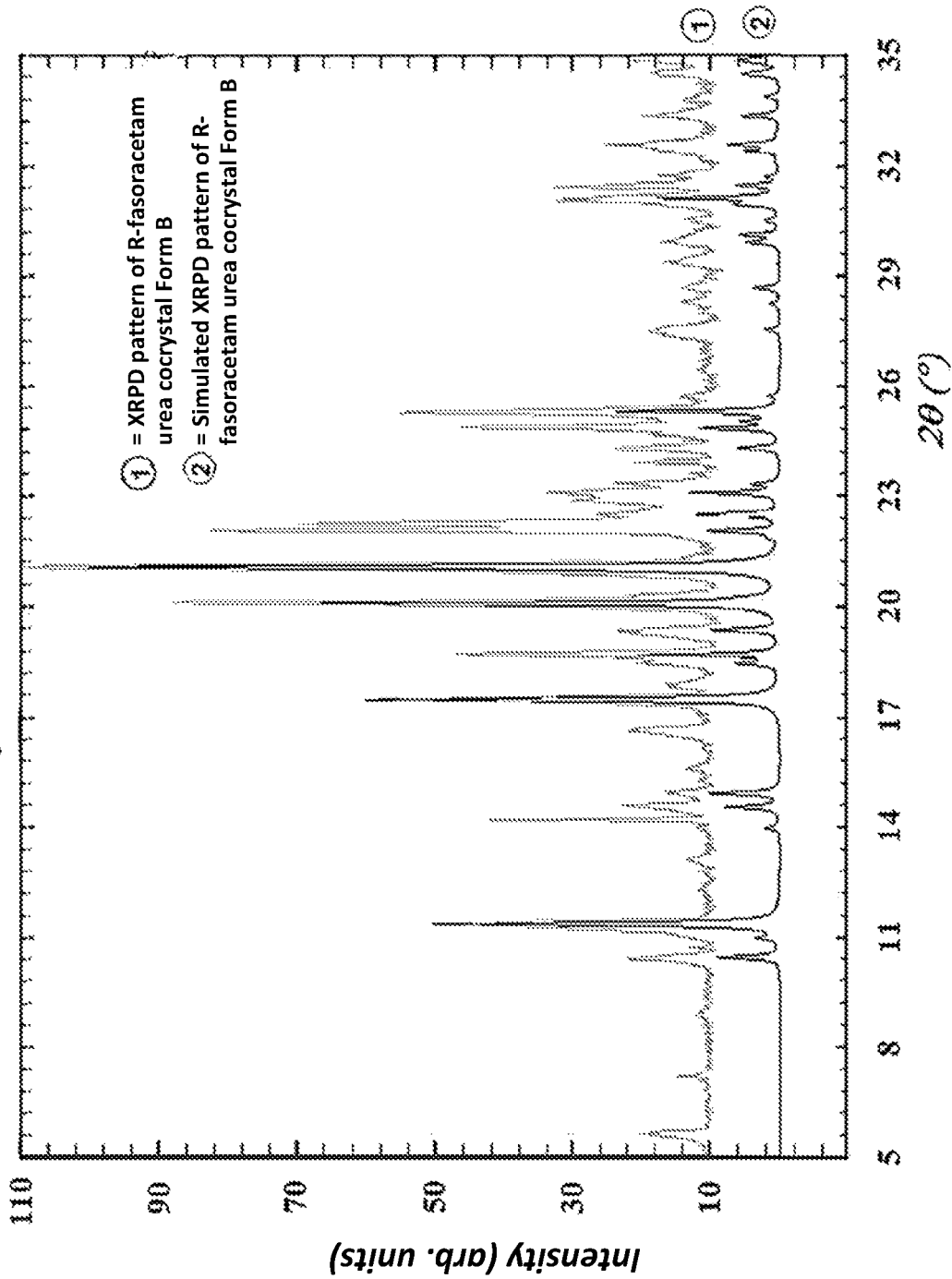
FIG. 38 is an overlay of XRPD patterns: (1) XRPD pattern of R-fasoracetam:urea cocrystal Form B; (2) Simulated XRPD pattern of R-fasoracetam:urea cocrystal Form B.
Figure 39:
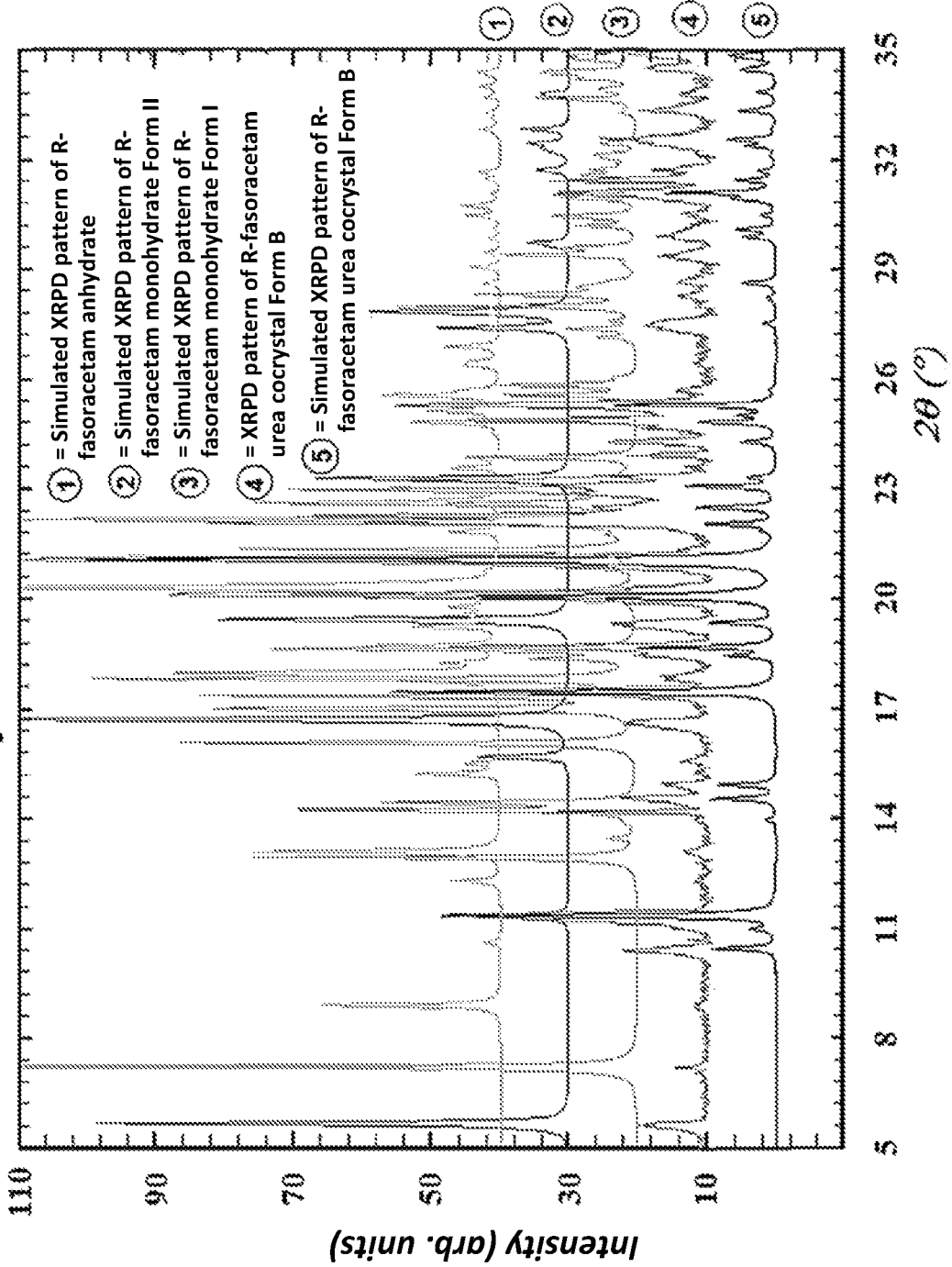
FIG. 39 is an overlay of XRPD patterns: (1) Simulated XRPD pattern of R-fasoracetam anhydrate; (2) Simulated XRPD pattern of R-fasoracetam monohydrate Form II; (3) Simulated XRPD pattern of R-fasoracetam monohydrate Form I; (4) XRPD pattern of R-fasoracetam:urea cocrystal Form B; (5) Simulated XRPD pattern of R-fasoracetam:urea cocrystal Form B.
Figure 40:
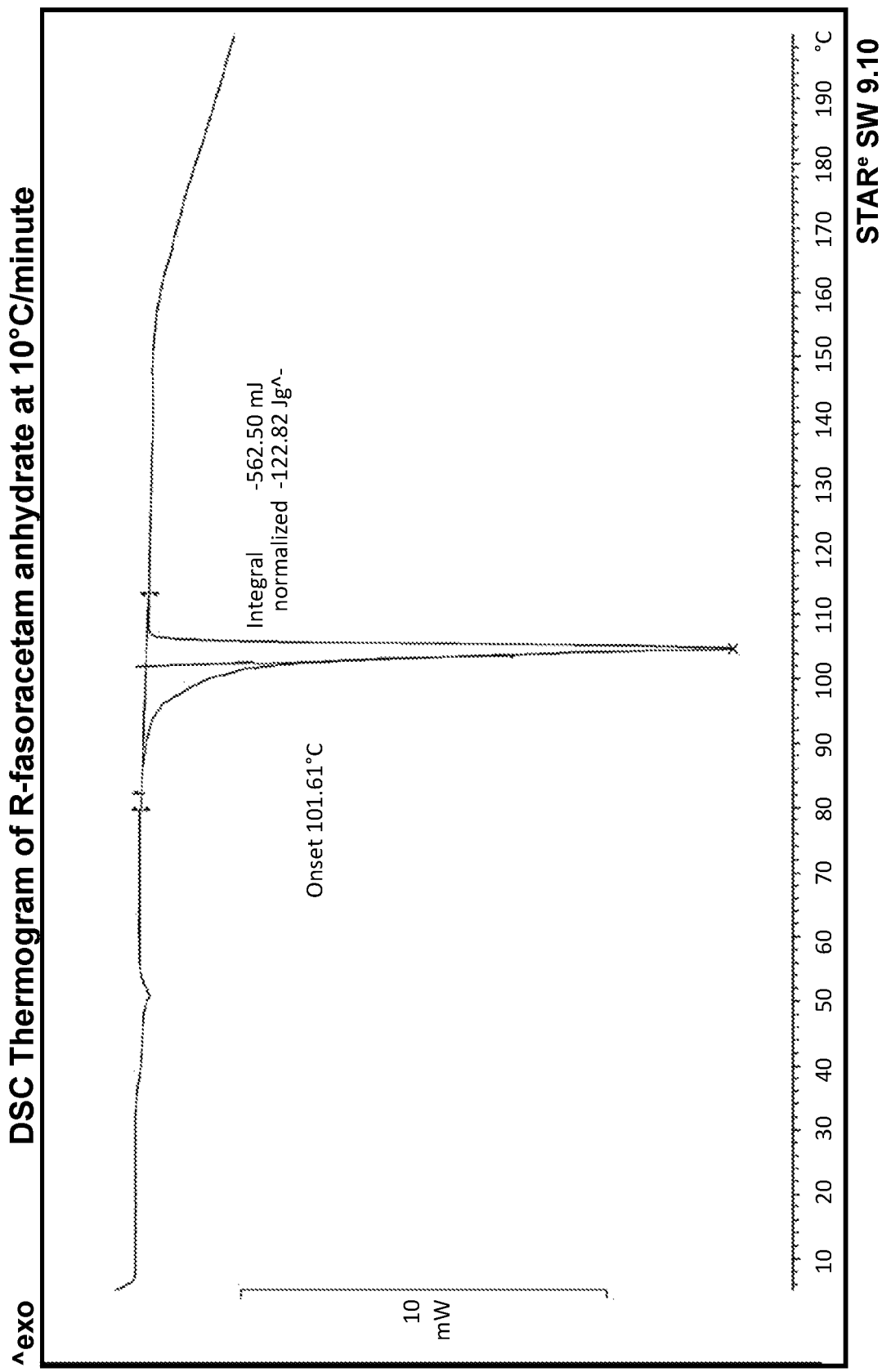
FIG. 40 is a DSC thermogram of an R-fasoracetam cocrystal Form B.

Form B of a cocrystal of R-fasoracetam and urea was also prepared via liquid-assisted grinding as set forth in Example 13 using an R-Fasoracetam Forms Mixture and urea as starting materials. FIG. 38 shows the x-ray powder diffraction pattern obtained from Example 13 overlaid with the simulated x-ray powder diffraction pattern from the single crystal of Example 12. The peaks of the two patterns match, however there are some extra peaks in the Example 13 pattern not found in the simulated pattern. FIG. 39, which is an overlay of the components of the R-Fasoracetam Forms Mixture, shows that these extra peaks are likely due to the presence of unreacted starting materials such as Form I, Form II and R-fasoracetam monohydrate, and the Anhydrate in the Example 13 preparation. FIG. 40 is a DSC thermogram of Form B indicating a melting temperature of about 102° C.

Figure 41:
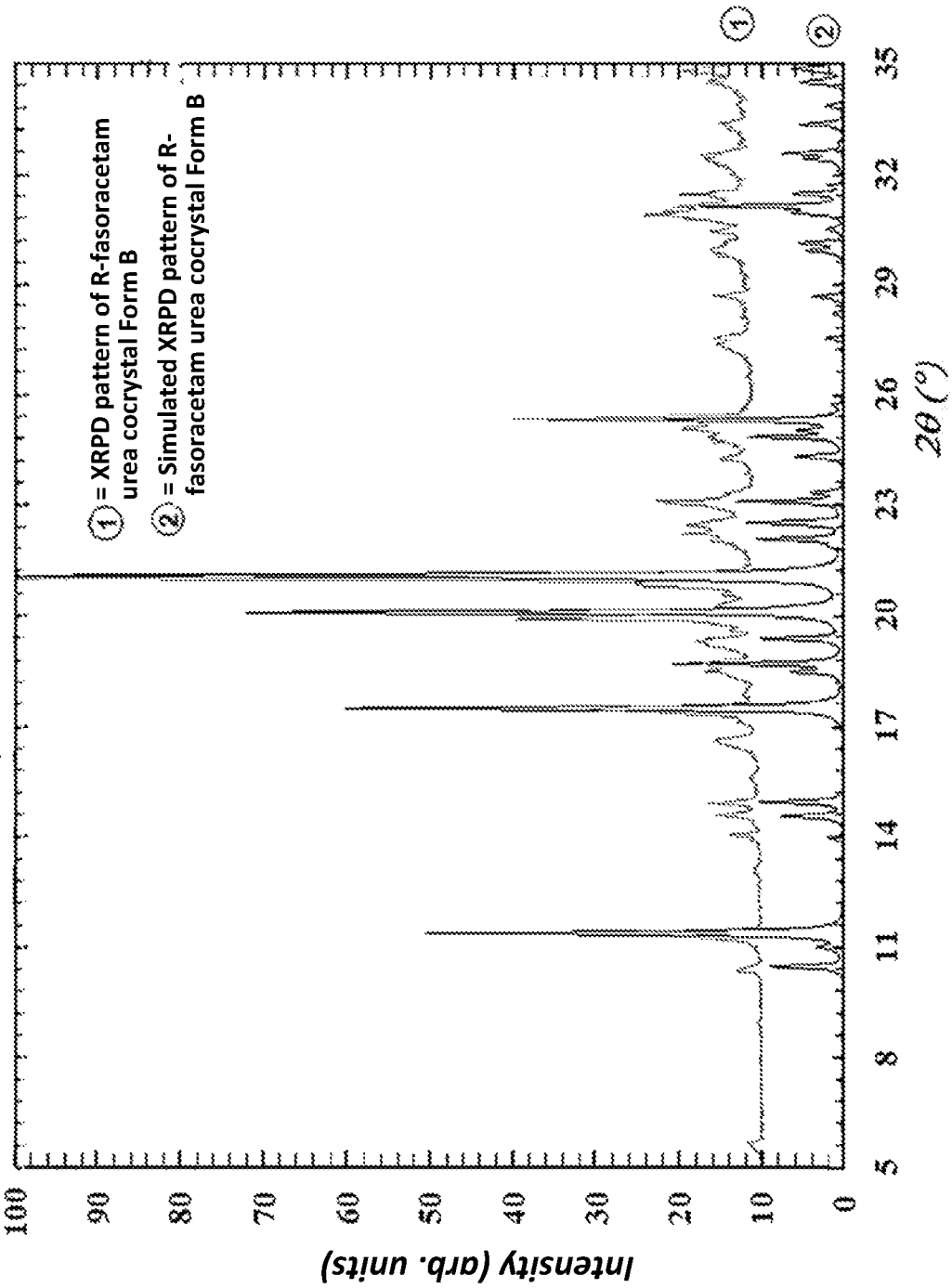
FIG. 41 is an overlay of XRPD patterns: (1) XRPD pattern of R-fasoracetam:urea cocrystal Form B; (2) Simulated XRPD pattern of R-fasoracetam:urea cocrystal Form B.

Form B was also prepared by a rotovapping experiment in Example 14. There, the starting materials were the R-Fasoracetam Form I and urea. In that melt-recrystallization experiment, a cocrystal of Form B R-fasoracetam to urea formed as indicated in FIG. 41 which is an overlay of the resulting diffraction pattern from Example 14 and that of the simulated x-ray powder diffraction pattern of Example 12. As with the liquid-assisted grinding experiment of Example 13, the experimental cocrystal matches that of the simulated pattern, but also contains some R-fasoracetam monohydrate and Anhydrate impurities. Here, that impurity appears to be primarily Form II, but some Form I may be present as seen in the overlay in FIG. 42.

The onset melting points of particular measurements of Form I, Form II, Anhydrate, Urea, and cocrystals Form A and Form B fasoracetam are set forth in Table 3B below. This table illustrates the general differences in melting points between the various materials.

TABLE 3B

| Onset Melting Temperatures of R-fasoracetam forms, urea, and Form A and Form B | |
|---|---|
| Crystal Form | Onset of Melting (° C.) |
| R-fasoracetam monohydrate, Form I | About 57° C. |
| R-fasoracetam monohydrate, Form II | About 49° C. |
| R-fasoracetam anhydrate | About 94° C. |
| Urea | About 133° C. |
| R-fasoracetam:urea cocrystal Form A | About 91° C. |
| R-fasoracetam:urea cocrystal Form B | About 102° C. |

Figure 122:
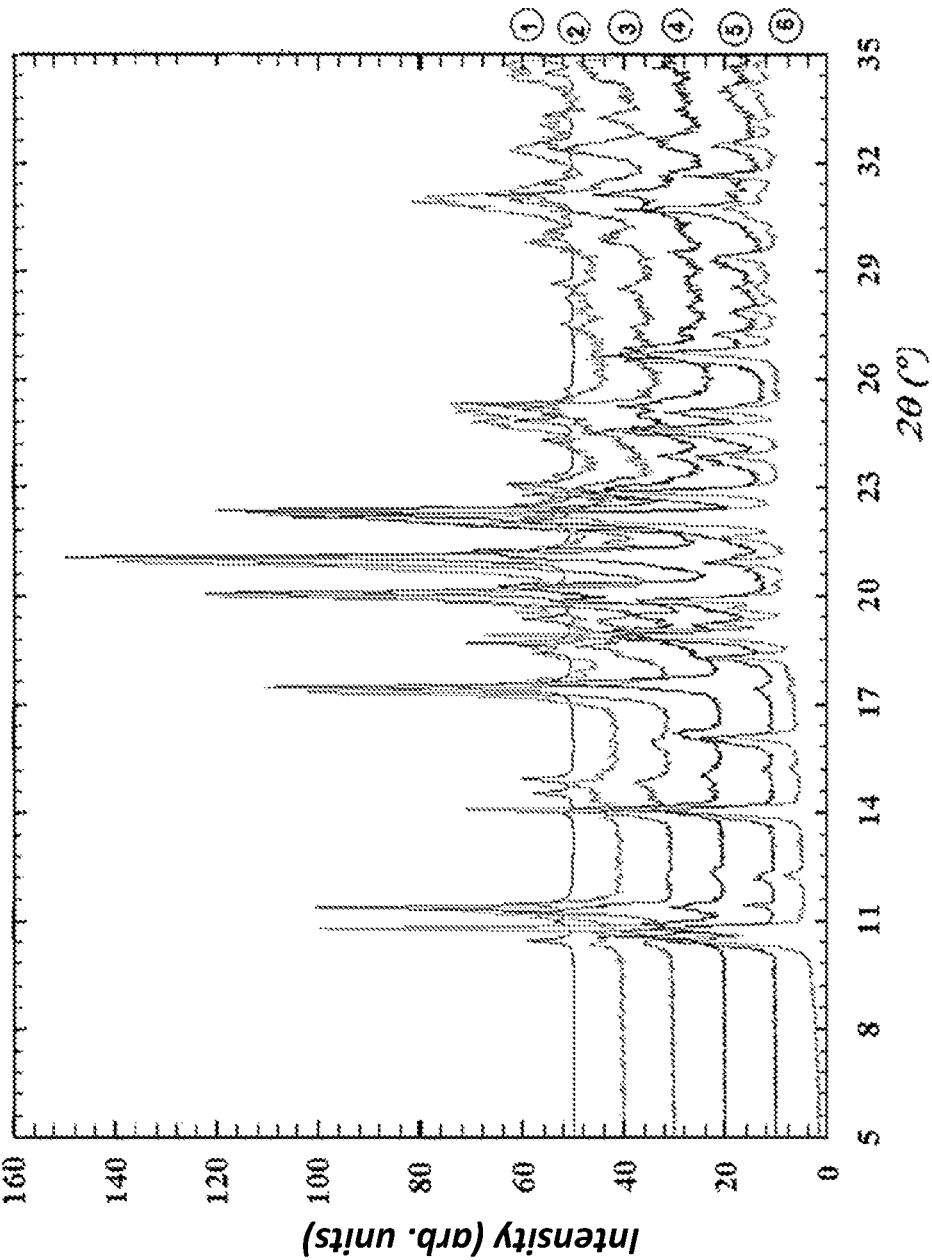
FIG. 122 is an overlay of XRPD patterns: (1) Simulated XRPD pattern of R-fasoracetam:urea cocrystal Form B; (2) XRPD pattern of Example 36 stored at 3 days at room temperature ("RT"); (3) XRPD pattern of Example 36 stored at 2 days at RT; (4) XRPD pattern of Example 36 stored at 1 day at RT; (5) XRPD pattern of Example 36; (6) XRPD pattern of R-fasoracetam:urea cocrytal Form A of Example 15.
Figure 123:
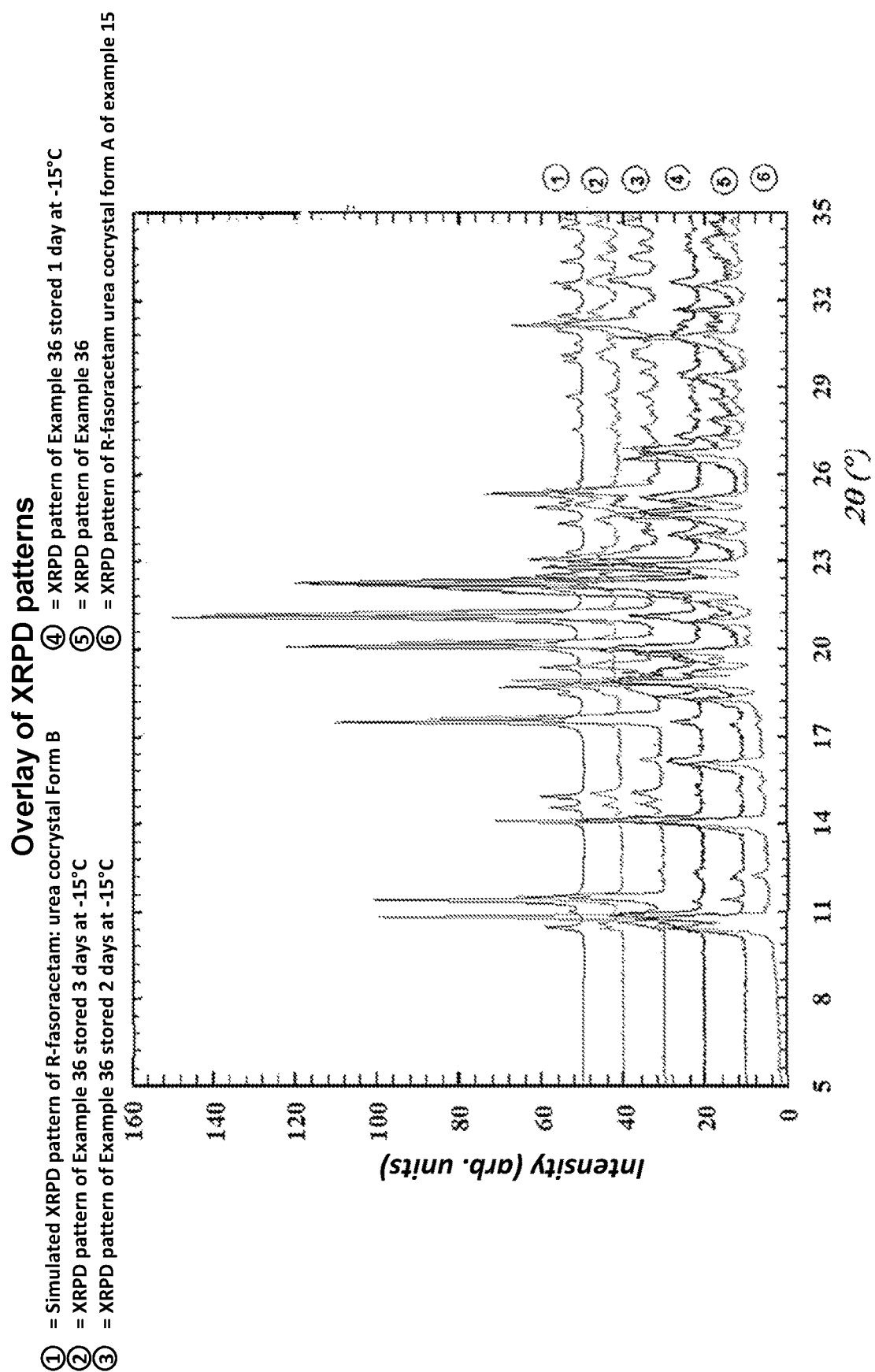
FIG. 123 is an overlay of XRPD patterns: (1) Simulated XRPD pattern of R-fasoracetam:urea cocrystal Form B; (2) XRPD pattern of Example 36 stored 3 days at −15° C.; (3) XRPD pattern of Example 36 stored 2 days at −15° C.; (4) XRPD pattern of Example 36 stored 1 day at −15° C.; (5) XRPD pattern of Example 36; (6) XRPD pattern of R-fasoracetam:urea cocrytal Form A of Example 15.

Initial attempts to make a cocrystal of fasoracetam and urea yielded Form A whereas further attempts resulted in Form B. Indeed, Form A, when in the presence of Form B, converts to Form B, both in suspension as well as solid state, and attempts to make Form A from Form B have failed. FIG. 122 shows the solid state conversion of Form A to Form B over time at room temperature exposed air over three days. Similarly, such conversion occurs in a closed container at −15° C. when the sample was measured daily as seen in FIG. 123.

Various processes may be used to make Form B. For example, Form B can be prepared by grinding, from a melt, or from solution-based chemistry processes. Solution-based processes may be particularly suited for scale-up whereas the melt method is suited for growing single-crystals of Form B.

In solution-state methods, one may typically start with a solution of R-fasoracetam as a starting material in a suitable solvent to which urea is added. A suitable solvent may be used to dissolve the R-fasoracetam. Temperature is controlled to promote crystallization and seeds of the Form B cocrystal prepared previously (and by the same or other processes) may be added. Various parameters may be controlled in order to improve both the quality and the yield of the resulting Form B cocrystal. Such parameters include the identity and amount of the suitable solvent, the identity and amount of the R-fasoracetam starting material, the amount of urea added, the presence of seeds, and the temperature profile of the processes used to make Form B.

A typical starting material is R-fasoracetam Form I, although other starting materials of fasoracetam such as the Forms Mixture, Form II, the amorphous form, or the anhydrate form may also be used as a starting material. When the starting material is R-fasoracetam Form I, the ratio of suitable solvent to the R-fasoracetam Form I in numerous embodiments ranges from about 2.5 ml of suitable solvent to about 6 ml of suitable solvent for every gram of R-fasoracetam Form I used. Other ranges include from about 3.0 ml to 5.0 ml and from about 3.8 ml to about 4.6 ml of suitable solvent. Examples of suitable solvents include isopropyl acetate, ethyl acetate, and mixtures thereof. The solvent range includes solvent initially added to R-fasoracetam as well as any rinses that may be used when combining aliquots as seen, for instance, in Example 42.

When the R-fasoracetam starting material is combined with a solvent, the temperature of that combination may be adjusted to so that it is lower than, at, or higher than room temperature. Examples of temperature ranges include from about 10° C.-15° C., about 15° C.-20° C., about 20° C.-25° C., about 25° C.-30° C., about 30° C.-35° C., about 35° C.-40° C., about 40° C.-45° C., about 45° C.-50° C., about 50° C.-55° C., about 55° C.-60° C., about 60° C.-65° C., or about 65° C.-70° C.

Once the R-fasoracetam and suitable solvent combination is prepared, urea may be added either in steps or all at once. The amount of urea added is related to the amount of R-fasoracetam starting material present. Typically, an amount ranging from about 0.70 to about 1.2 equivalents of urea is used with respect to fasoracetam starting material on a molar basis. Specific equivalents include about 0.70, about 0.71, about 0.72, about 0.73, about 0.74, about 0.75, about 0.76, about 0.77, about 0.78, about 0.79, about 0.80, about 0.81, about 0.82, about 0.83, about 0.84, about 0.85, about 0.86, about 0.87, about 0.88, about 0.89, about 0.90, about 0.91, about 0.92, about 0.93, about 0.94, about 0.95, about 0.96, about 0.97, about 0.98, about 0.99, about 1.0, about 1.1, or about 1.2 or any ranges within such as from about 0.95 to 1.0. Seeds of R-fasoracetam:urea cocrystal Form B previously prepared, such as by grinding or otherwise, may be added together with the urea or afterwards. After addition, the combination is often cooled and then washed to afford R-fasoracetam:urea cocrystal Form B which may also be dried.

Figure 50:
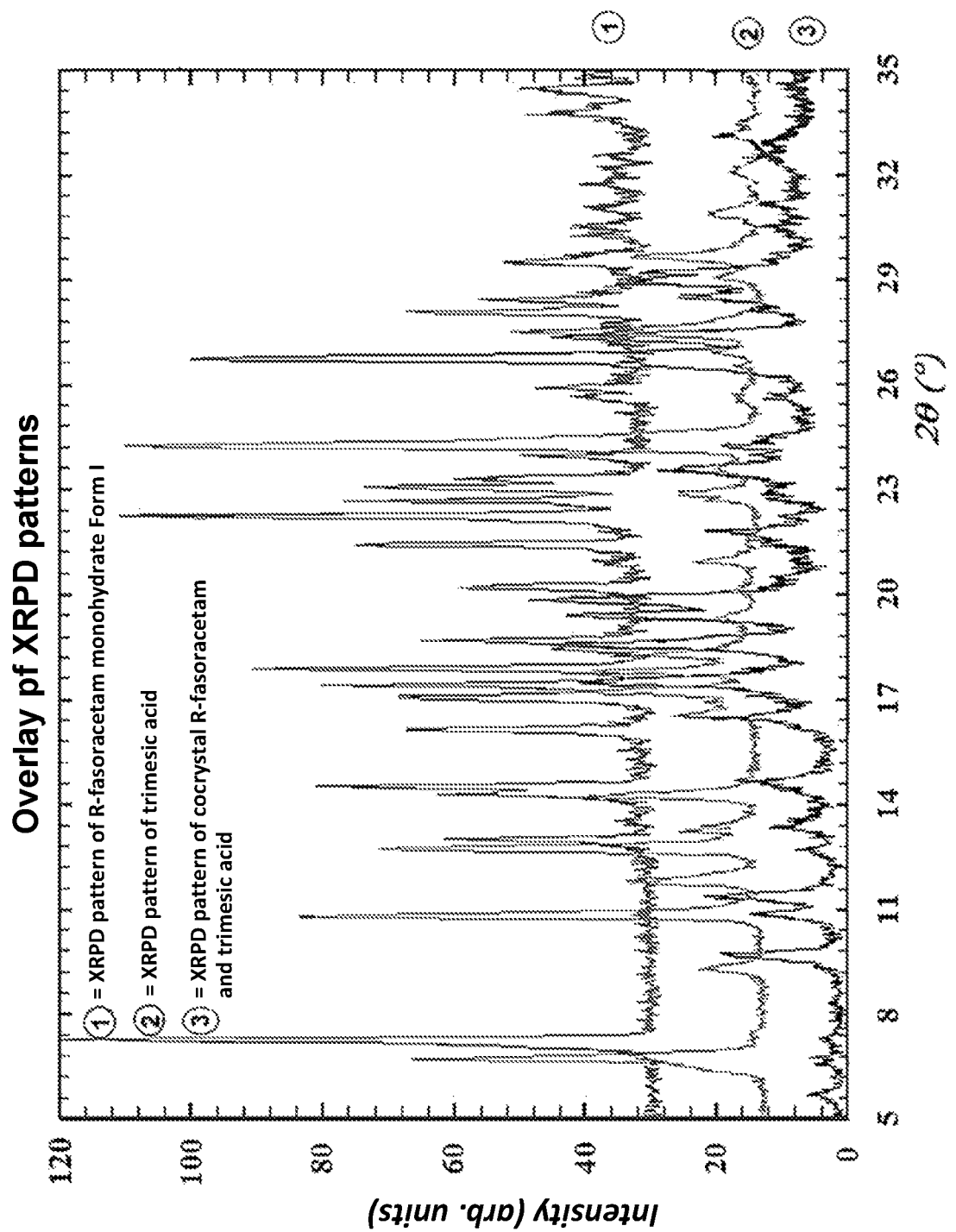
FIG. 50 is an overlay of XRPD patterns: (1) XRPD pattern of R-fasoracetam monohydrate Form I; (2) XRPD pattern of trimesic acid; (3) XRPD pattern of a cocrystal of R-fasoracetam and trimesic acid.
Figure 51:
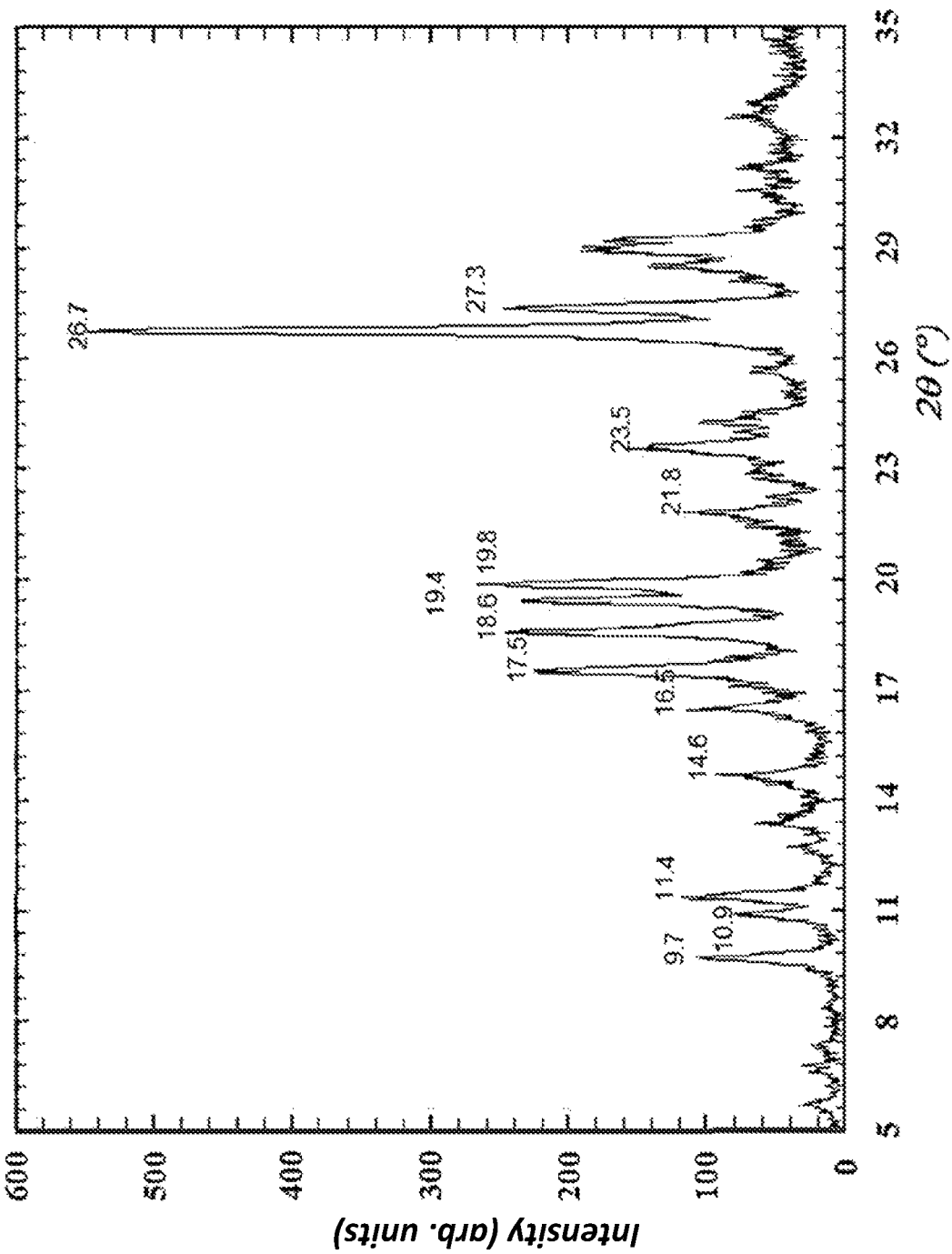
FIG. 51 is an XRPD pattern of R-fasoracetam:trimesic acid cocrystal.

In additional embodiments, the disclosure provides for crystalline fasoracetam trimesic acid such, as, for example, cocrystals of fasoracetam and trimesic acid. In particular, the fasoracetam may be R-fasoracetam. FIG. 51 is an x-ray powder diffractogram corresponding to a cocrystal of R-fasoracetam and trimesic acid. The cocrystal was prepared in accordance with Example 17. The cocrystal was prepared by grinding Form I with trimesic acid. FIG. 50 is an overlay of XRPD patterns showing the patterns of trimesic acid, Form I and the cocrystal. FIG. 50 indicates that the cocrystal pattern is not a linear combination of the component parts and thus is not a physical mixture. For example, the peak at about 9.7°2θ in the cocrystal is not in either of the XRPD patterns of the component parts. Thus, the FIG. 51 XRPD pattern of Example 17 does not represent a mixture of trimesic acid and R-fasoracetam but is a new crystalline phase. It is a cocrystal of R-fasoracetam and trimesic acid.

A cocrystal of fasoracetam and trimesic acid, such as R-fasoracetam and trimesic acid may be characterized by a peak at about 9.7°2θ. In addition, one or more peaks chosen from peaks at about 10.9°2θ, about 11.4°2θ, about 14.6°2θ, about 16.5°2θ, about 17.5°2θ, about 18.6°2θ, about 19.4°2θ, about 19.8°2θ, about 21.8°2θ, about 23.5°2θ, about 26.7°2θ, and about 27.3°2θ may be used to characterize such a cocrystal with or without the peak at about 9.7°2θ. Further, an onset melting point at about 96° C., such as one measured with DSC, may be used to characterize such a cocrystal. This melting point may be used alone or in connection with XRPD peaks to characterize such a cocrystal. That is, an onset melting point of about 96° C. (as set forth in FIG. 54) together with one or more peaks chosen from peaks at about 9.7°2θ, 10.9°2θ, about 11.4°2θ, about 14.6°2θ, about 16.5°2θ, about 17.5°2θ, about 18.6°2θ, about 19.4°2θ, about 19.8°2θ, about 21.8°2θ, about 23.5°2θ, about 26.7°2θ, and about 27.3°2θ may be used to characterize such a cocrystal.

Figure 54:
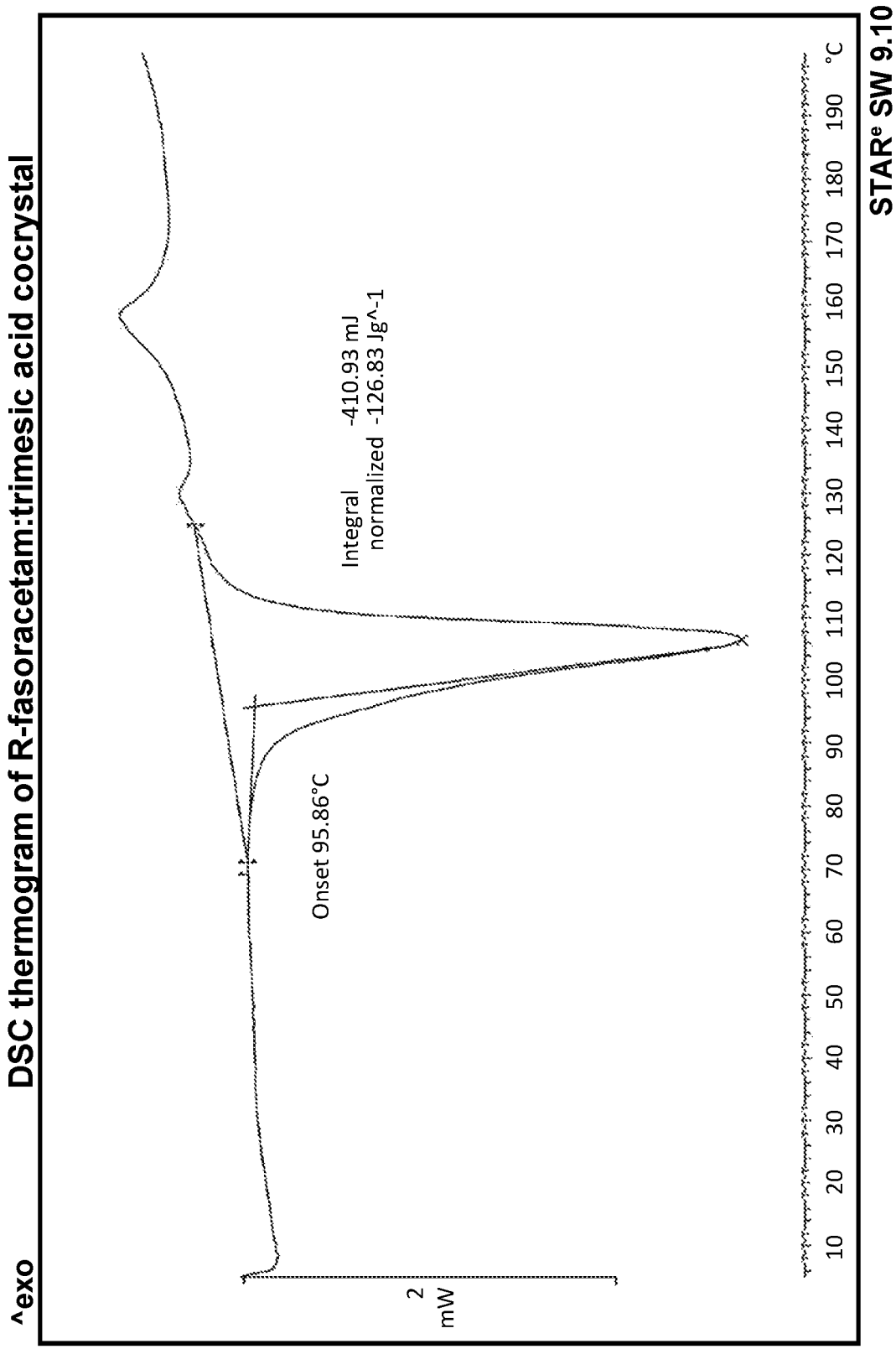
FIG. 54 is a DSC thermogram of R-fasoracetam:trimesic acid cocrystal.

The XRPD pattern substantially the same as that of FIG. 51 and/or a DSC thermogram substantially the same as FIG. 54 may be used to characterize a cocrystal of R-fasoracetam and trimesic acid.

Figure 134:
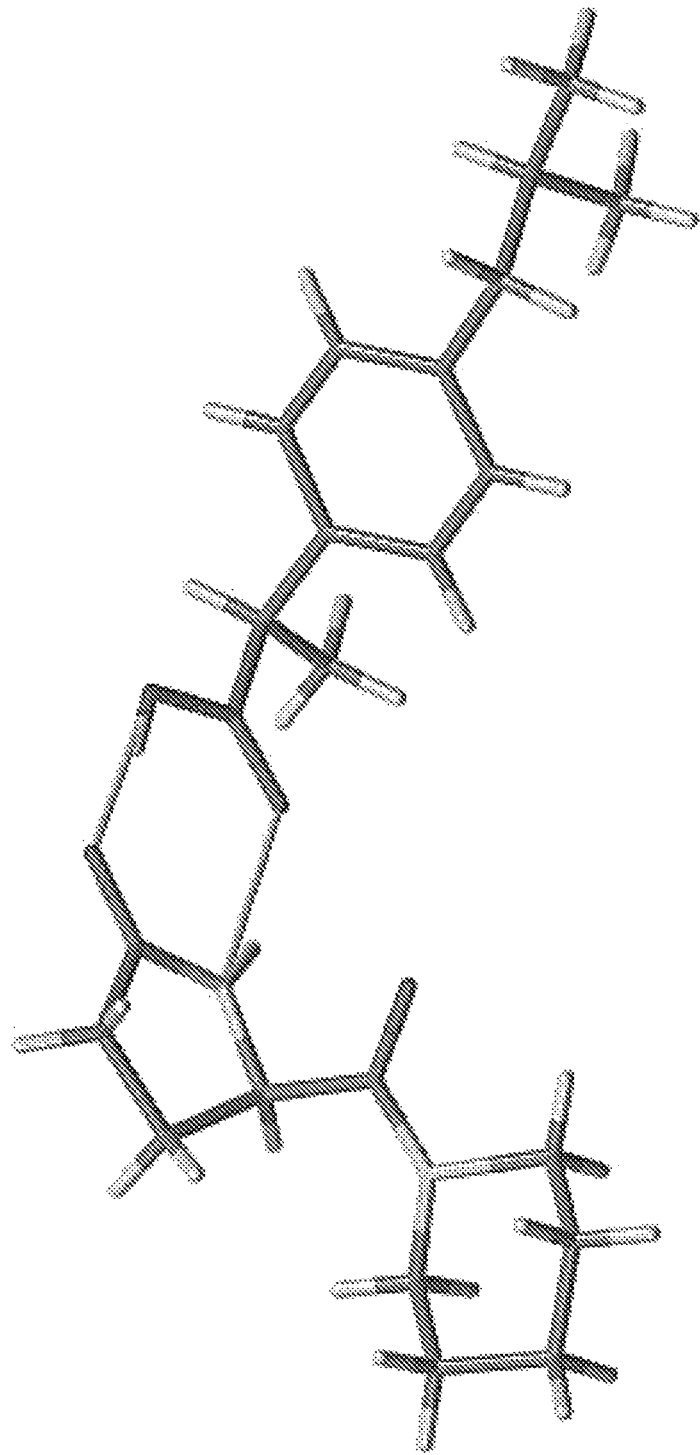

Additional embodiments of the disclosure are directed to cocrystals of R-fasoracetam and R-ibuprofen. A single crystal of a cocrystal of 1:1 R-fasoracetam and R-Ibuprofen was prepared in Example 18 and the structure was solved. An ORTEP drawing illustrating the solution is set forth in FIG. 56 and single data parameters in Table 8 indicating a 1:1 stoichiometry. In FIG. 134, the cocrystal of R-fasoracetam and (R)-ibuprofen is presented as a hydrogen bonding pattern. An acid-amide heterosynthon between R-fasoracetam and ibuprofen is seen.

Without being bound by theory, it is believed that the NH on R-fasoracetam's five membered ring acts as a hydrogen donor, where the carbonyl of the carboxylic acid on ibuprofen acts as a hydrogen acceptor, and the hydroxy-part of the carboxylic acid for ibuprofen acts as a hydrogen donor, forming a hydrogen bond back towards the carbonyl on R-fasoracetam's five membered ring.

Figure 57:
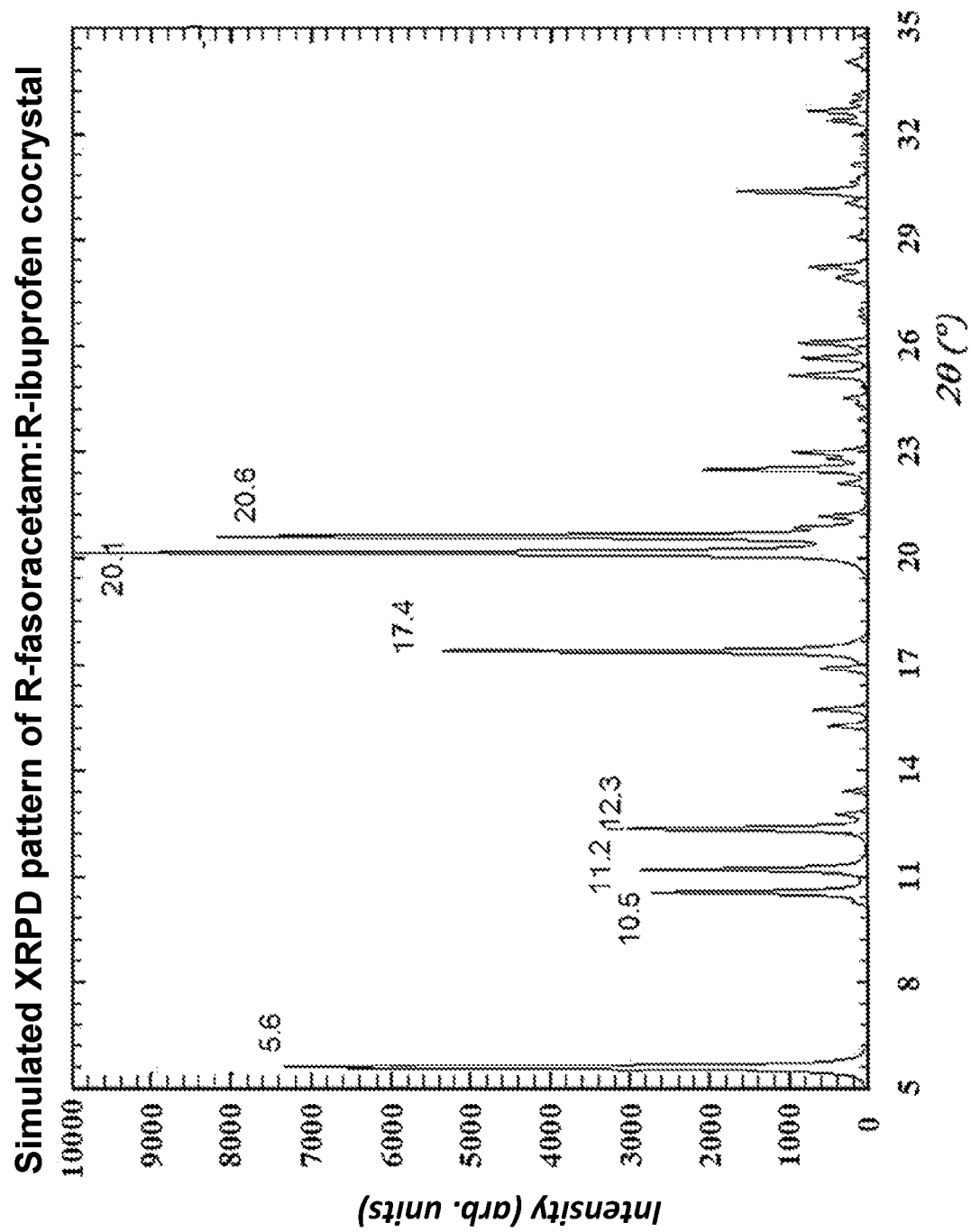
FIG. 57 is a simulated XRPD pattern of R-fasoracetam: R-ibuprofen cocrystal.
Figure 59:
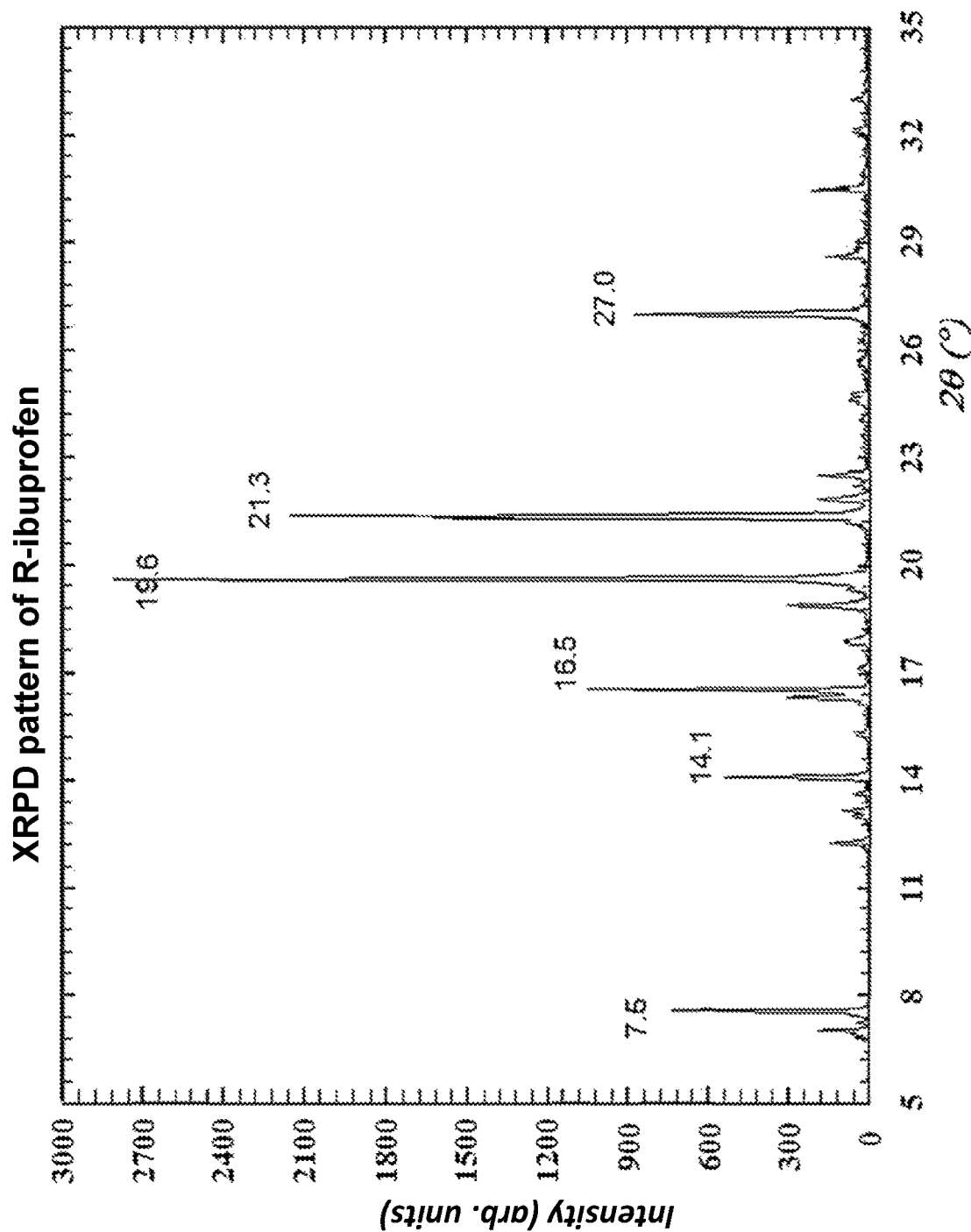
FIG. 59 is an XRPD pattern of R-ibuprofen.

The simulated XRPD pattern for the single crystal is set forth in FIG. 57 based upon the single crystal solution. FIG. 59 is the XRPD pattern of R-ibuprofen. Various peaks may be used to characterize a cocrystal of R-fasoracetam and R-ibuprofen based on the single crystal simulated XRPD pattern. For example, any one or more of the peaks chosen from peaks at about 5.6°2θ, about 10.5°2θ, about 11.2°2θ, about 12.3°2θ, about 17.4°2θ, about 20.1°2θ, and about 20.6°2θ may be used to characterize such a cocrystal.

Figure 58:
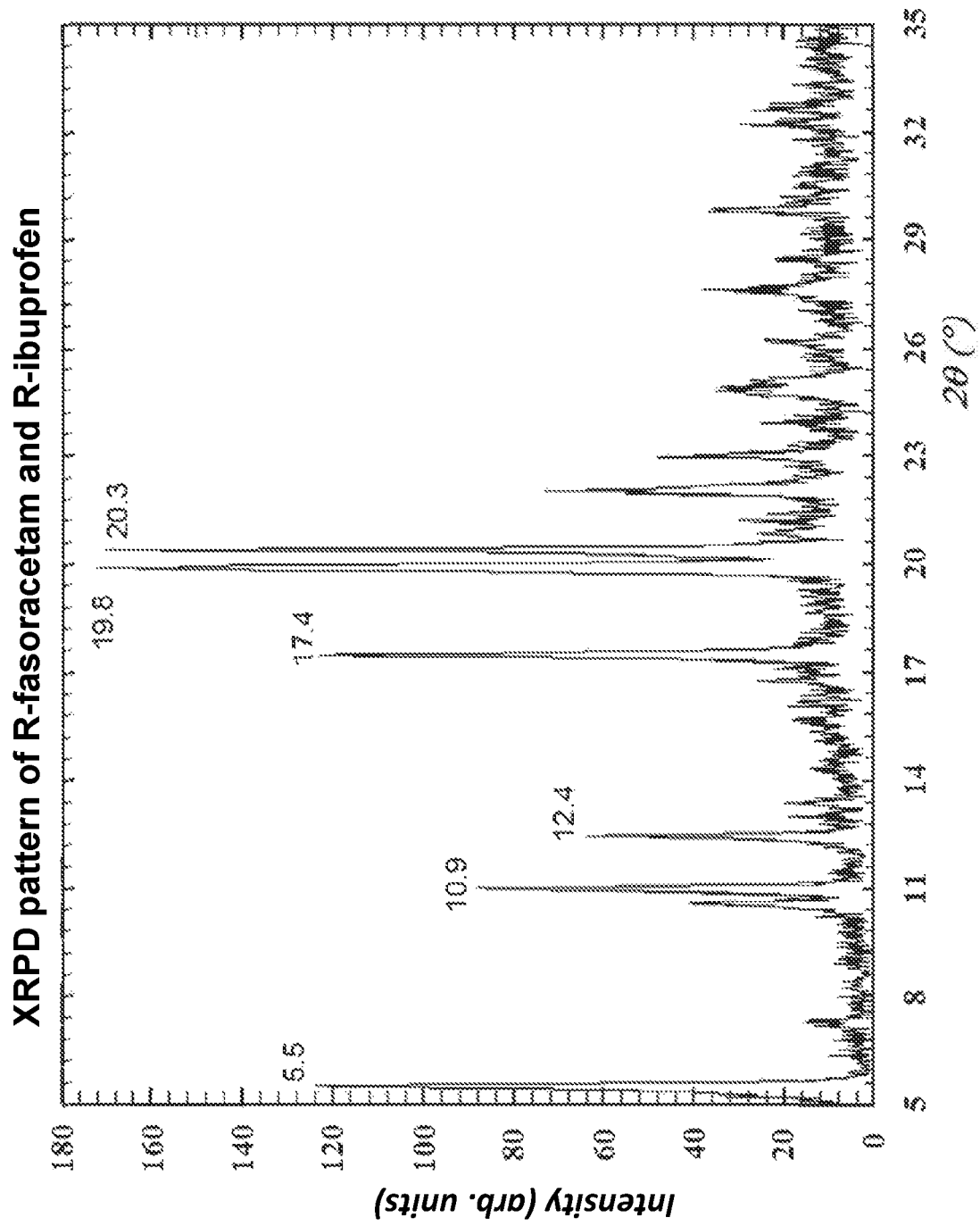
FIG. 58 is an XRPD pattern of ground R-fasoracetam and R-ibuprofen.

A ground crystalline material of R-ibuprofen and R-fasoracetam was prepared in Example 19 with an XRPD pattern in FIG. 58. The XRPD patterns of the component compounds, R-fasoracetam monohydrate Form I and R-ibuprofen, are found at FIG. 7 and FIG. 59 respectively. A comparison between FIG. 58 and FIGS. 7 and 59 reveal that the ground crystalline material is not a mixture of R-ibuprofen and R-fasoracetam monohydrate Form I. For example, the XRPD pattern of the ground crystalline material has peaks at about 5.5°2θ and about 10.9°2θ not in either component compound XRPD pattern. Thus, the ground crystalline material of R-fasoracetam and R-ibuprofen is a new crystalline phase. It is a cocrystal of R-fasoracetam and R-ibuprofen. In comparing the XRPD patterns of the ground cocrystal of Example 19 with the simulated XRPD pattern taken from the single-crystal x-ray solution of Example 18, there are some discrepancies with the peaks such as a 0.3° shift in peaks at about 20.1°2θ and about 20.6°2θ among others. Thus, the cocrystal of Example 19 may be the same cocrystal of Example 18 or a polymorph or hydrate thereof, for example. The melting onset temperature of R-fasoracetam:R-ibuprofen cocrystal of Example 19 is about 115° C., which lies about 63° C. above the melting point of R-fasoracetam monohydrate Form I, as well as about 63° C. above the melting temperature of R-ibuprofen.

Figure 128:
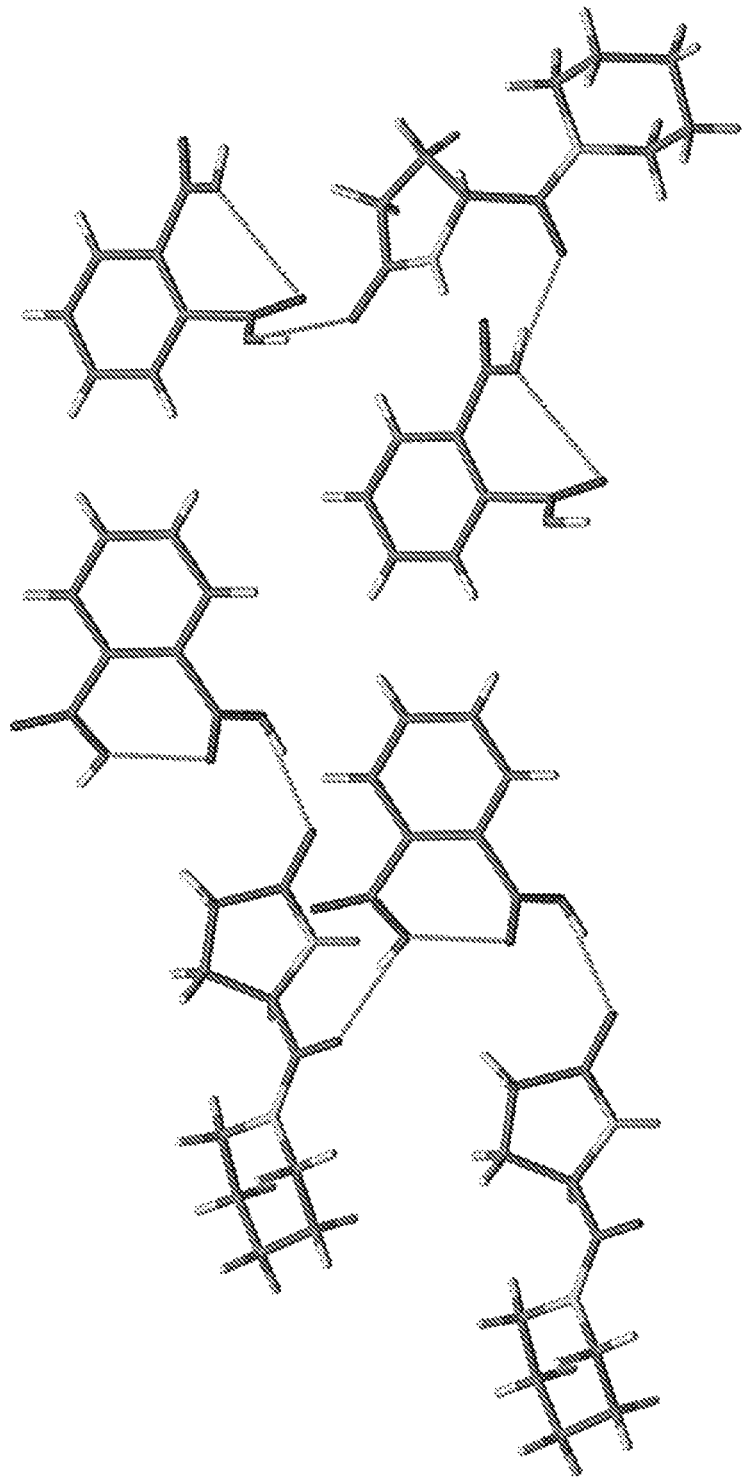
FIG. 128 is a hydrogen bonding pattern of a R-fasoracetam:phthalic acid cocrystal.

Further embodiments of the disclosure are directed to crystalline fasoracetam phthalic acid such, as, for example, cocrystals of fasoracetam and phthalic acid. In particular, the fasoracetam may be R-fasoracetam. In Example 20, a cocrystal of R-fasoracetam phthalic acid was prepared and a single crystal x-ray solution was analyzed with a data table of parameters set forth in Table 9 and an ORTEP drawing in FIG. 63 indicating a 1:1 stoichiometry. FIG. 128 depicts phthalic acid (center 4 molecules) with R-fasoracetam (outer molecules, two on the left, one on the right) in a 1:1 manner as a hydrogen bonding pattern.

Without being bound by theory, it is believed that there is one intramolecular hydrogen bond for phthalic acid, between the two carboxylic acids next to each other, and the other hydrogen bond is between a carboxylic acid (donor) of phthalic acid and the carbonyl moiety (acceptor) on R-fasoracetam's five membered ring. It is further believed, that the two carboxylic acid moieties of phthalic acid create a ribbon-like hydrogen bond network, where each carboxylic acid moiety forms a hydrogen bond with an R-fasoracetam molecule. A simulated XRPD pattern appears in FIG. 64 and the experimental XRPD patterns of the starting materials appear in FIG. 7 for Form I and in FIG. 65 for phthalic acid. Various peaks may be used to characterize a cocrystal of R-fasoracetam phthalic acid based on the single crystal simulated XRPD pattern. For example, any one or more of the peaks chosen from peaks at about 6.1°2θ, about 12.4°2θ, about 15.1°2θ, about 15.8°2θ, about 18.1°2θ, about 19.9°2θ, and about 23.3°2θ may be used to characterize such a cocrystal.

Figure 129:
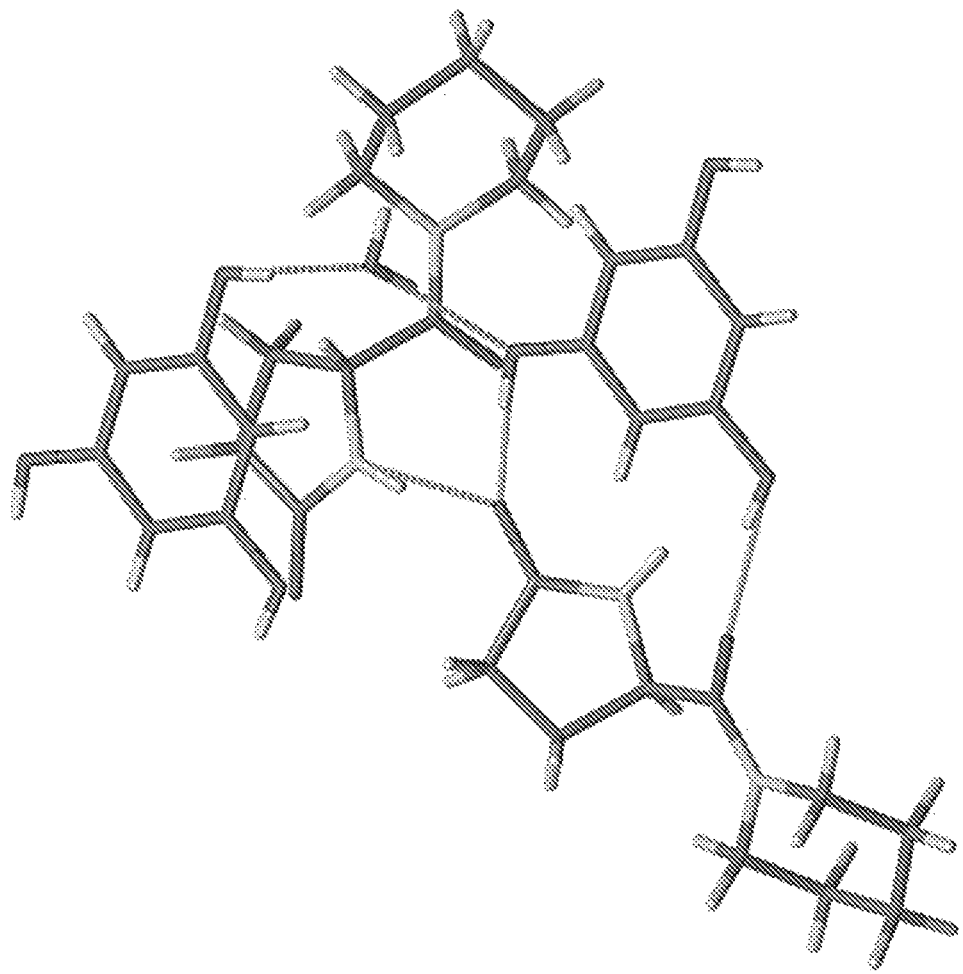

Additional embodiments of the disclosure are directed to crystalline fasoracetam phloroglucinol such, as, for example, cocrystals of fasoracetam and phloroglucinol. In particular, the fasoracetam may be R-fasoracetam. In Example 22, a cocrystal of R-fasoracetam phloroglucinol was prepared and a single crystal x-ray solution was analyzed with a data table of parameters set forth in Table 10 and an ORTEP drawing in FIG. 71 indicating a 1:1:1 stoichiometry of R-fasoracetam to phloroglucinol to water, making the cocrystal a monohydrate. In FIG. 129, phloroglucinol (center, top) and R-fasoracetam (left, right) form a cocrystal monohydrate in a hydrogen bonding pattern.

Without being bound by theory, it is believed that two of the three carboxylic acids on phloroglucinol act as hydrogen donors, where the carbonyl on the bridging atom and on the five membered ring of R-fasoracetam act as hydrogen acceptors. Furthermore, it is believed that water acts as a hydrogen donor to one of phloroglucinol's carboxylic acids, connecting it to another phloroglucinol molecule to create a chain in this alternating manner (not shown). It is further believed that the last hydrogen bond comes from the —NH moiety on R-fasoracetam's five membered ring, which acts as a hydrogen donor with the carbonyl serving as hydrogen acceptor on the five membered ring of another R-fasoracetam molecule.

Figure 67:
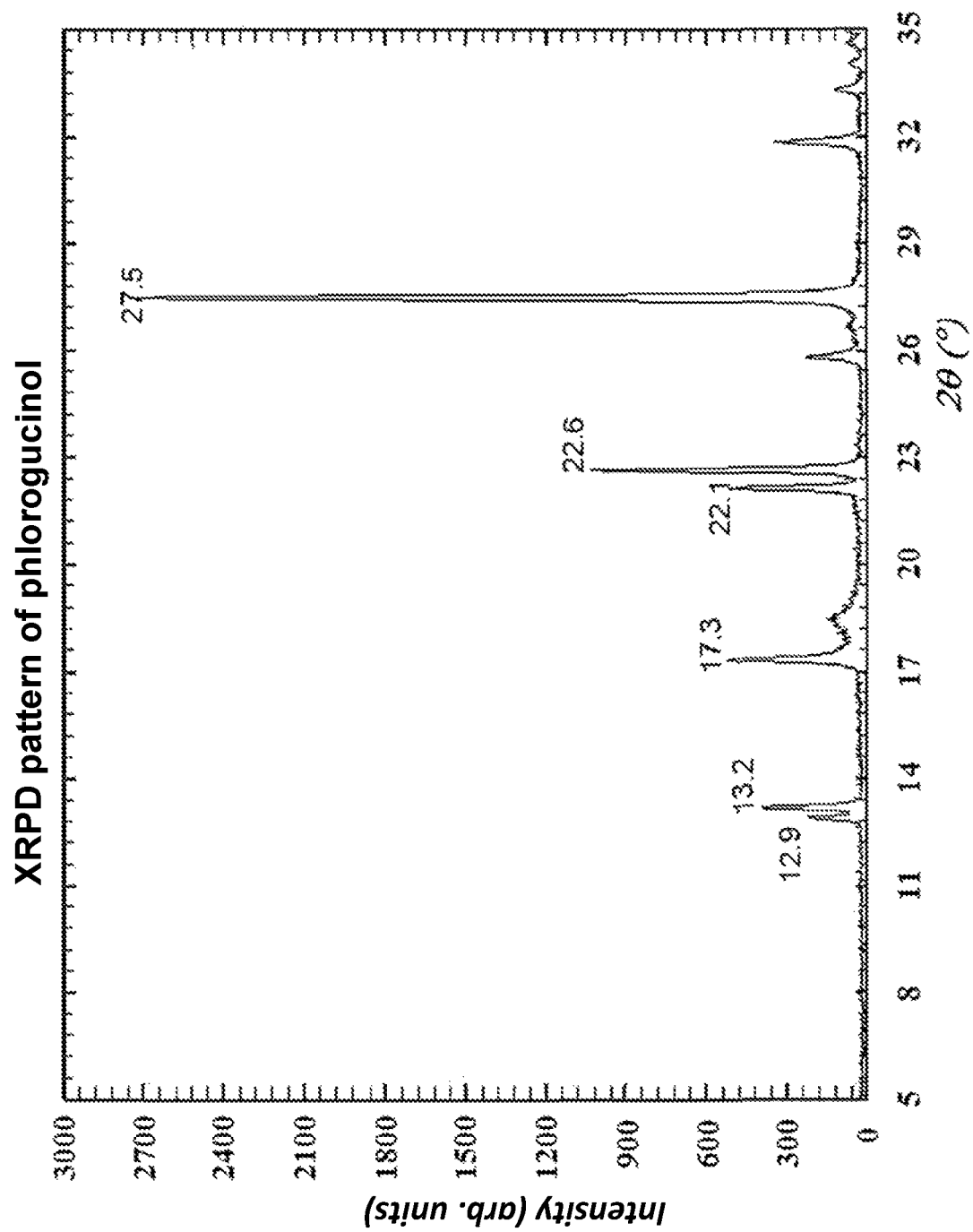
FIG. 67 is an XRPD pattern of phloroglucinol.
Figure 72:
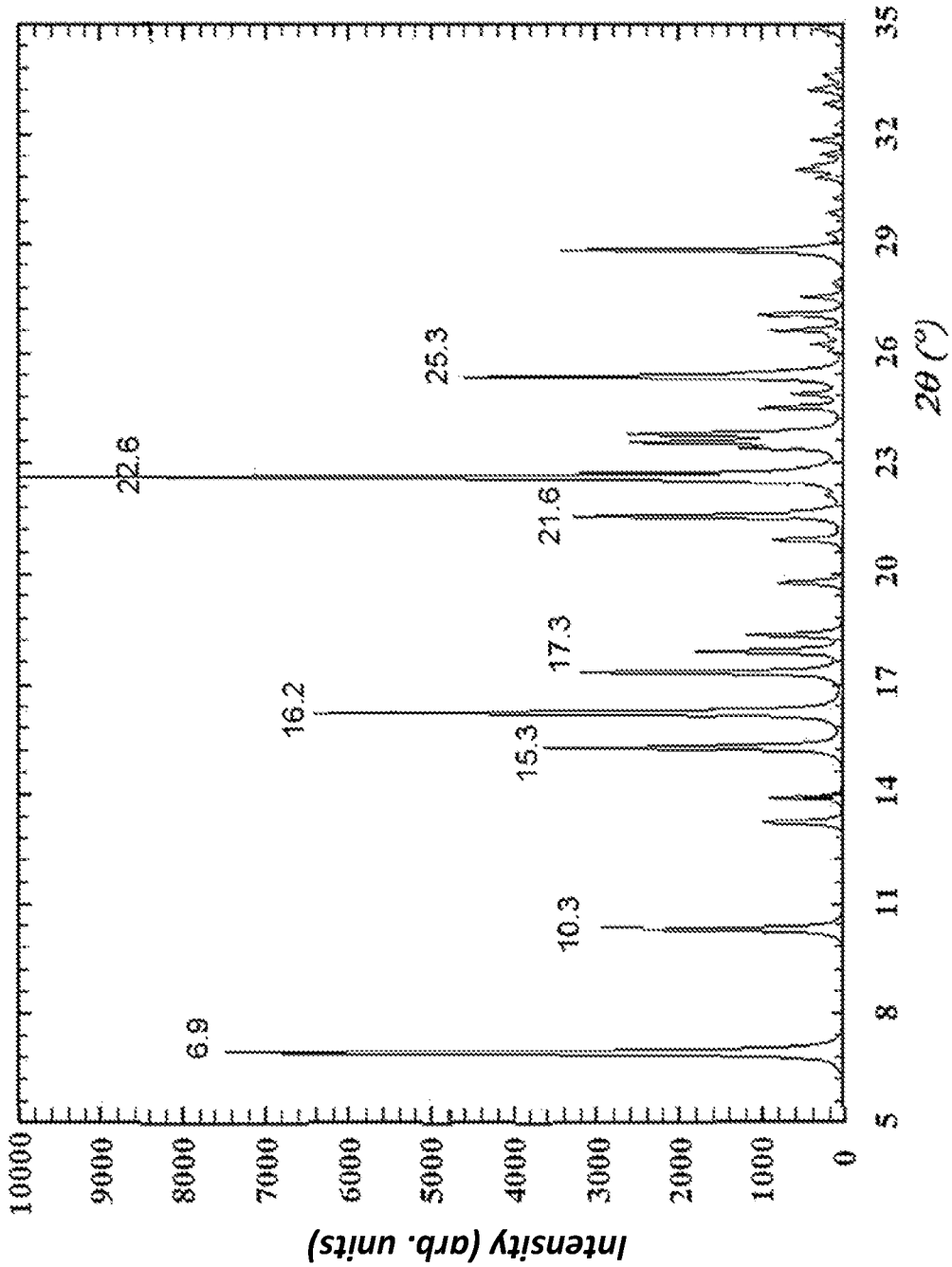
FIG. 72 is a simulated XRPD pattern of a monohydrate cocrystal of R-fasoracetam and phloroglucinol.

A simulated XRPD pattern appears in FIG. 72 and the experimental patterns of the starting materials appear in FIG. 7 for Form I and in FIG. 67 for phloroglucinol. Various peaks may be used to characterize a cocrystal of R-fasoracetam and phloroglucinol based on the single crystal simulated XRPD pattern. For example, any one or more of the peaks chosen from peaks at about 6.9°2θ, about 10.3°2θ, about 15.3°2θ, about 16.2°2θ, about 17.3°2θ, about 21.6°2θ, about 22.6°2θ, and about 25.3°2θ may be used to characterize such a cocrystal. A monohydrate cocrystal of R-fasoracetam and phloroglucinol was further characterized by grinding Form I R-fasoracetam and phloroglucinol in Example 21. The resulting XRPD matches that of the simulated pattern as set forth in FIG. 73.

Figure 130:
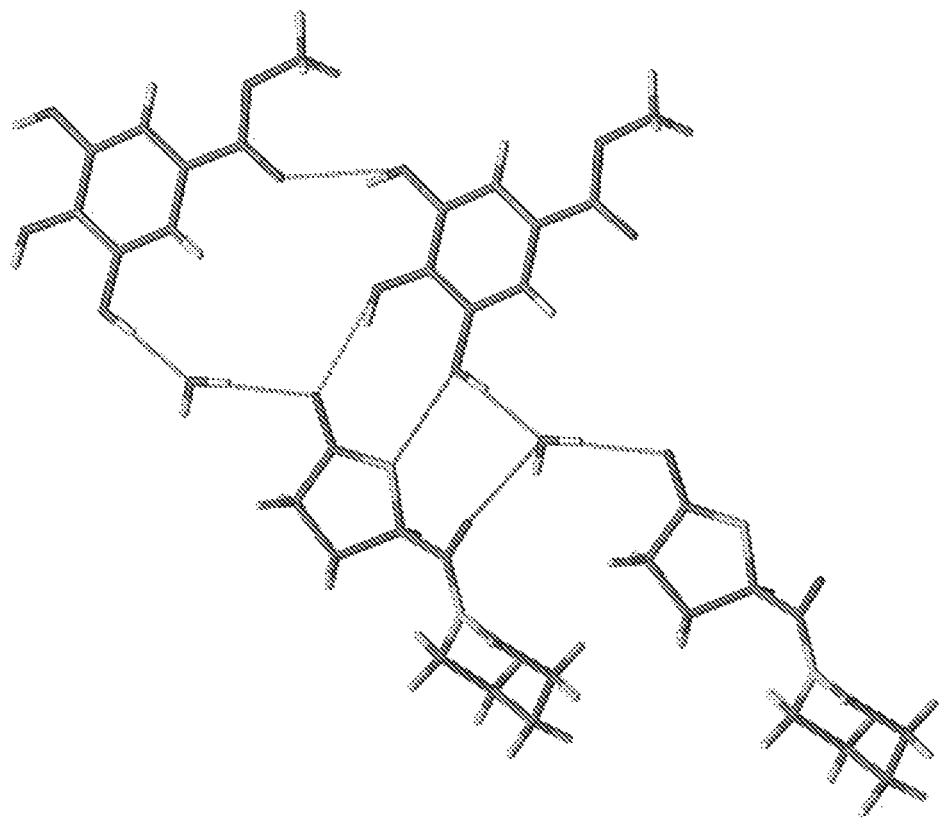

Still further embodiments of the disclosure are directed to crystalline fasoracetam methyl-3,4,5-trihydroxybenzoate such, as, for example, cocrystals of fasoracetam and methyl-3,4,5-trihydroxybenzoate. In particular, the fasoracetam may be R-fasoracetam. In Example 23, a cocrystal of R-fasoracetam and methyl-3,4,5-trihydroxybenzoate was prepared and a single crystal x-ray solution was analyzed with a data table of parameters set forth in Table 11 and an ORTEP drawing in FIG. 74 indicating a 1:1:1 stoichiometry of R-fasoracetam to methyl-3,4,5-trihydroxybenzoate to water, making the cocrystal a monohydrate. In FIG. 130 (R-fasoracetam is on the left, methyl-3,4,5-trihydroxybenzoate right) is shown in a hydrogen bonding network.

Without being bound by theory, it is believed that there are two hydrogen bonds directly between the two different compounds, one from the hydrogen donating hydroxy-group of methyl-3,4,5-trihydroxybenzoate at position 4 on the benzene ring, to the five membered ring of R-fasoracetam (carbonyl) and the donating hydrogen on the nitrogen atom in R-fasoracetam's five membered ring towards the hydroxy-group on the 3 position on the benzene ring of methyl-3,4,5-trihydroxybenzoate. It is believed that the hydrogen bond between R-fasoracetam's bridging carbonyl (acceptor) and the water molecule (donor) is linked back to methyl-3,4,5-trihydroxybenzoate, from the water molecule which is the hydrogen acceptor, to the hydroxy-group on the three position of the benzene ring (donor). It is further believed that the same water molecule also acts as a hydrogen donor in a third hydrogen bond, where a second R-fasoracetam molecule acts as a hydrogen acceptor via its carbonyl on the five membered ring.

Figure 75:
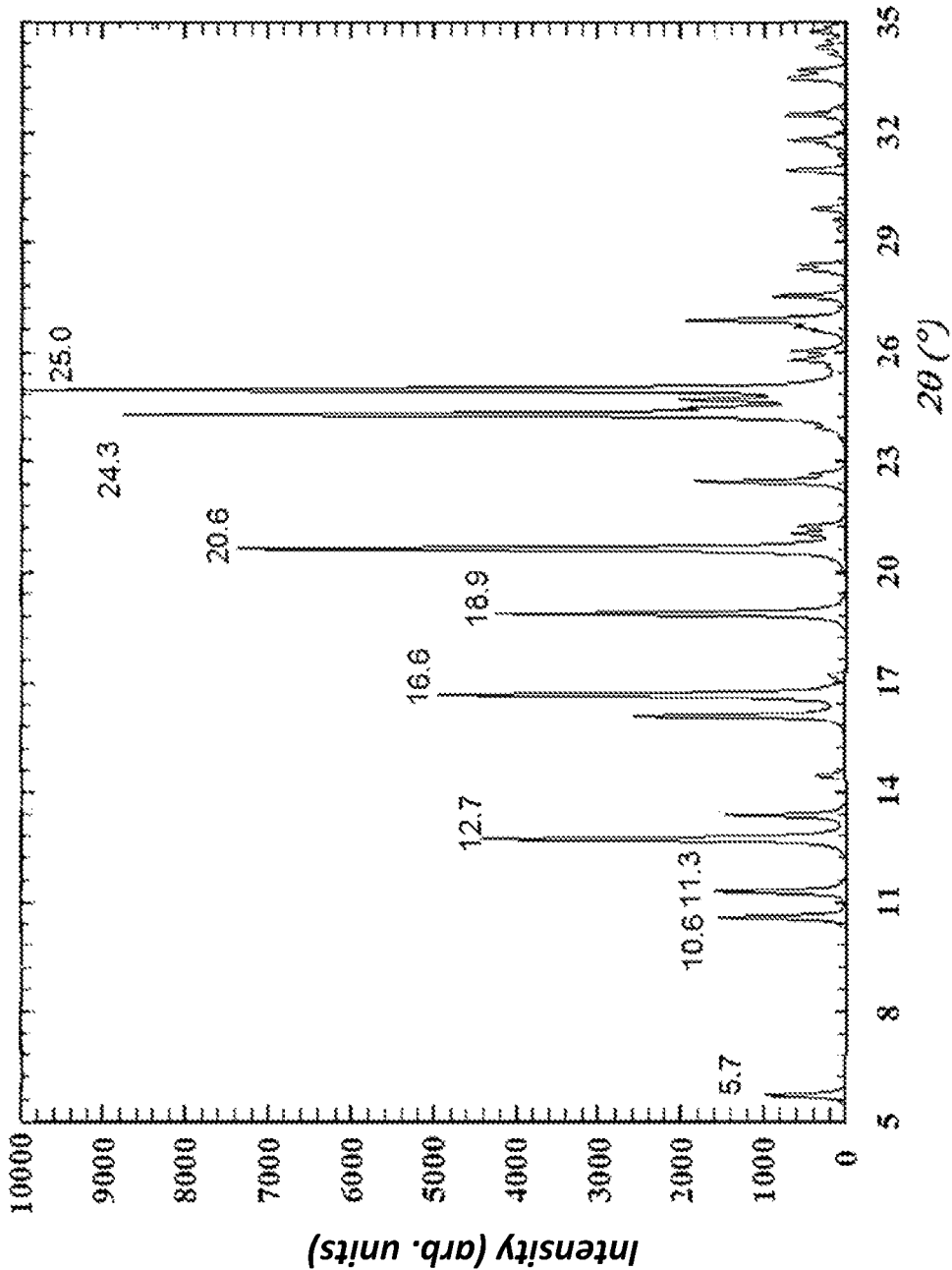
FIG. 75 is a simulated XRPD pattern of a monohydrate of R-fasoracetam and methyl-3,4,5-trihydroxybenzoate cocrystal.
Figure 77:
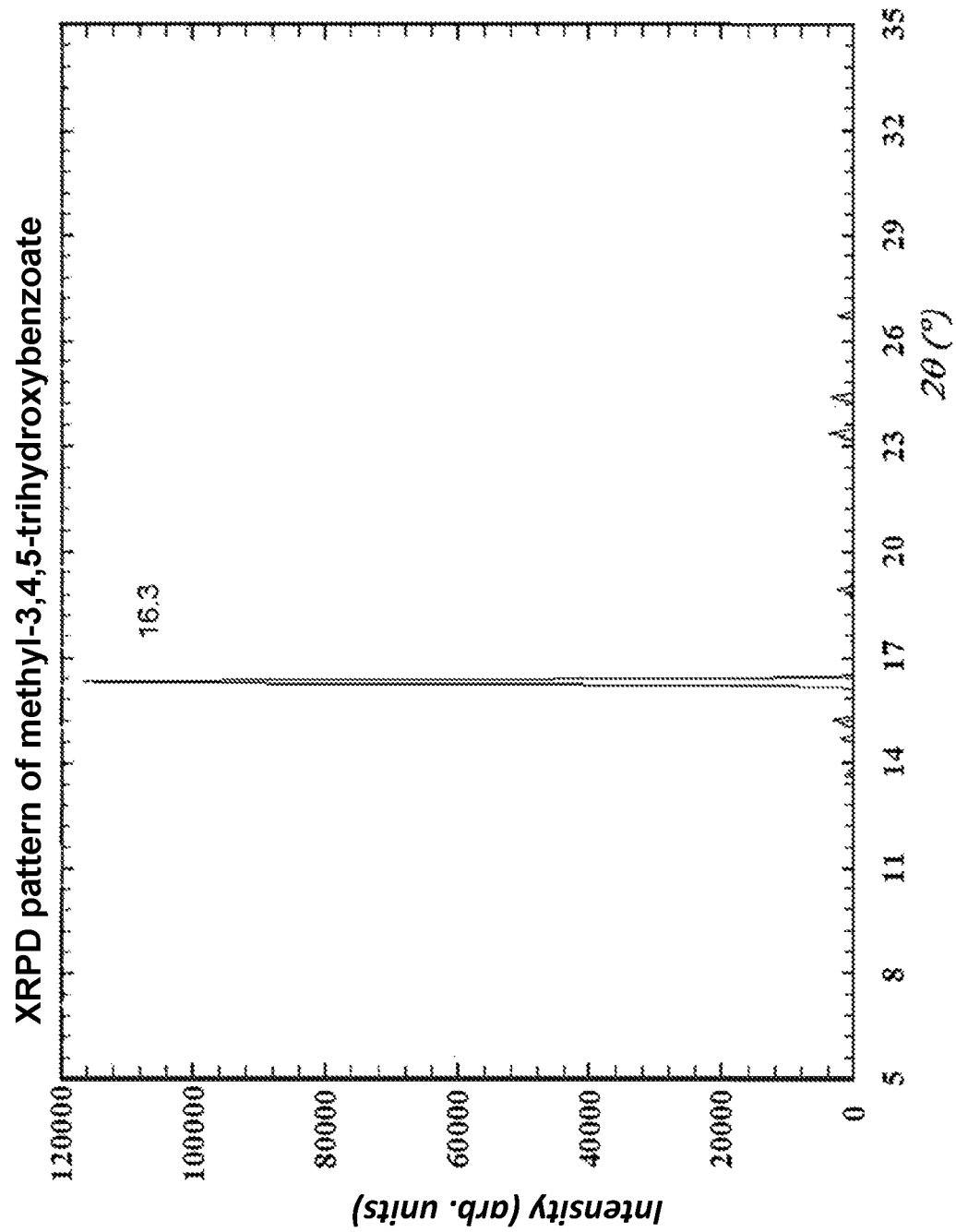
FIG. 77 is an XRPD pattern of methyl-3,4,5-trihydroxybenzoate.

A simulated XRPD pattern appears in FIG. 75 and the experimental patterns of the starting materials appear in FIG. 7 for Form I and in FIG. 77 for methyl-3,4,5-trihydroxybenzoate. Various peaks may be used to characterize a cocrystal of R-fasoracetam and methyl-3,4,5-trihydroxybenzoate based on the single crystal simulated XRPD pattern. For example, any one or more of the peaks chosen from peaks at about 5.7°2θ, about 10.6°2θ, about 11.3°2θ, about 12.7°2θ, about 16.6°2θ, about 18.9°2θ, about 20.6°2θ, about 24.3°2θ, and about 25.0°2θ may be used to characterize such a cocrystal.

Figure 131:
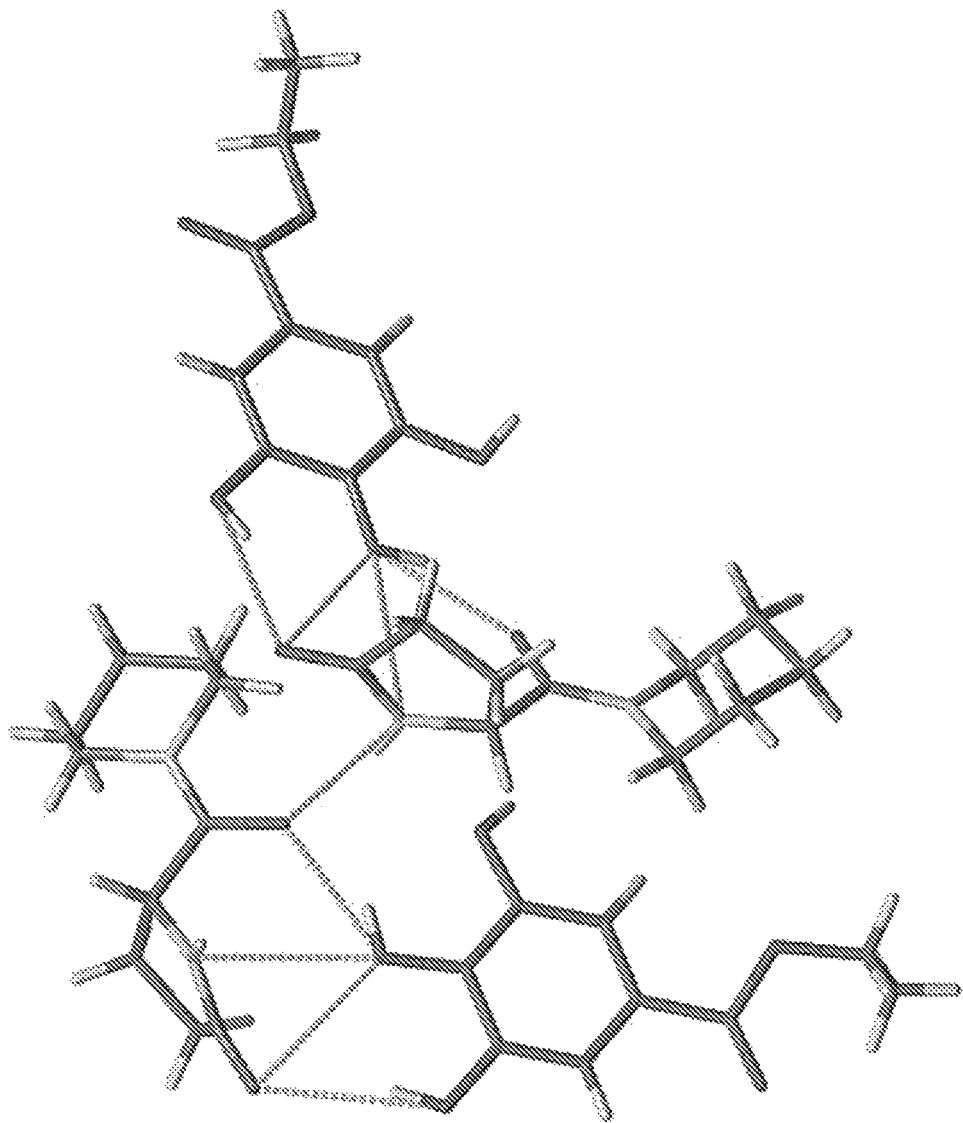

In additional embodiments of the disclosure, crystalline fasoracetam ethyl gallate is provided such, as, for example, cocrystals of fasoracetam and ethyl gallate. In particular, the fasoracetam may be R-fasoracetam. In certain of these embodiments, a 1:1 cocrystal of R-fasoracetam and ethyl gallate is provided. In Example 24, a cocrystal of R-fasoracetam and ethyl gallate was prepared and a single crystal x-ray solution was analyzed with a data table of parameters set forth in Table 12 and an ORTEP drawing in FIG. 78 indicating a 1:1 stoichiometry of R-fasoracetam to ethyl gallate. FIG. 131 shows the asymmetric unit of the 1:1 R-fasoracetam:ethyl gallate cocrystal and its hydrogen bonding pattern where the R-fasoracetam molecules are on the top left and in the center, whereas the ethyl gallate molecules are on the bottom left and right.

Without being bound by theory, it is believed that there are five unique intermolecular hydrogen bonds present. The carbonyl on the five membered ring of R-fasoracetam acts as a hydrogen acceptor for the hydrogen donor from the 3-position hydroxy-group of ethyl gallate. The same carbonyl also is an acceptor for the hydrogen bond originating from ethyl gallate's 4 position hydroxy-group. However, it seems this hydrogen bond is shared with the hydrogen accepting carbonyl on the bridging carbon atom of R-fasoracetam. The hydrogen donor on the NH of R-fasoracetam's five membered ring forms a hydrogen bond with the oxygen of the hydroxy-group on the 4 position of ethyl gallate, which acts as an acceptor. Lastly, the —NH in the five membered ring of another R-fasoracetam molecule acts as a hydrogen donor, connecting it together with the initial R-fasoracetam molecule via the bridging carbonyl which acts as a hydrogen acceptor.

Figure 79:
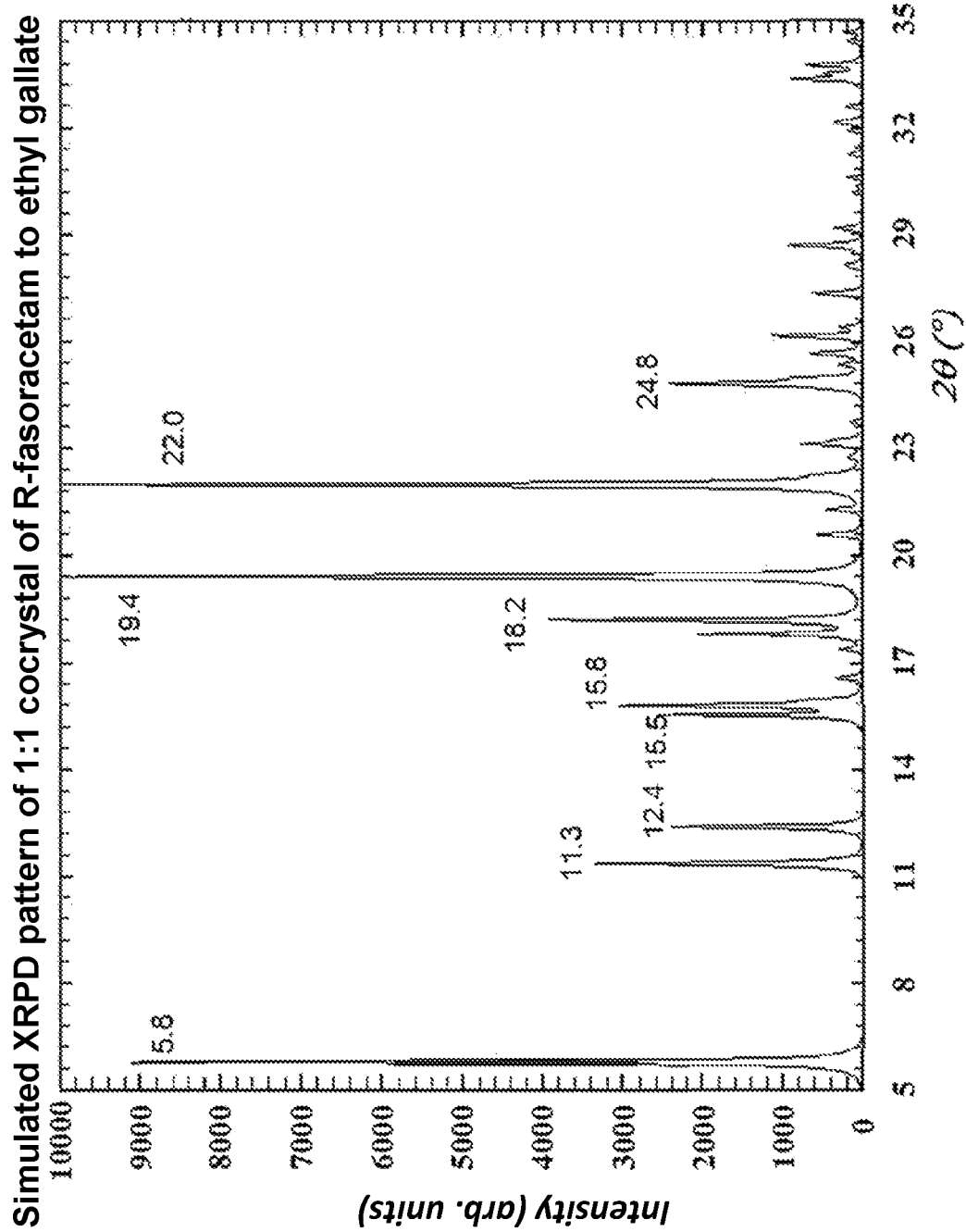
FIG. 79 is a simulated XRPD pattern of a 1:1 cocrystal of R-fasoracetam:ethyl gallate.
Figure 81:
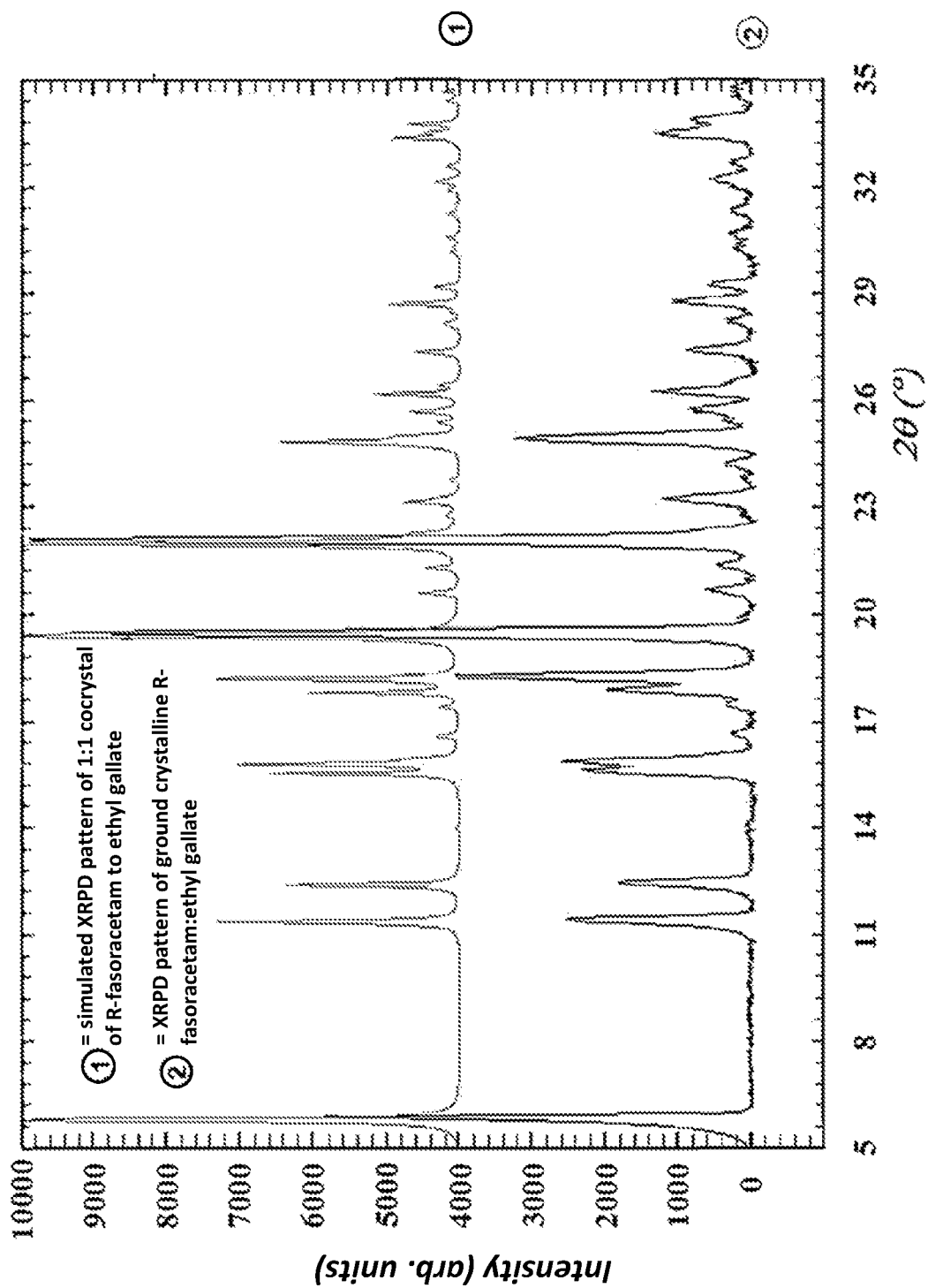
FIG. 81 is an overlay of XRPD patterns: (1) simulated XRPD pattern of a 1:1 cocrystal of R-fasoracetam:ethyl gallate; (2) XRPD pattern of ground crystalline R-fasoracetam:ethyl gallate.
Figure 82:
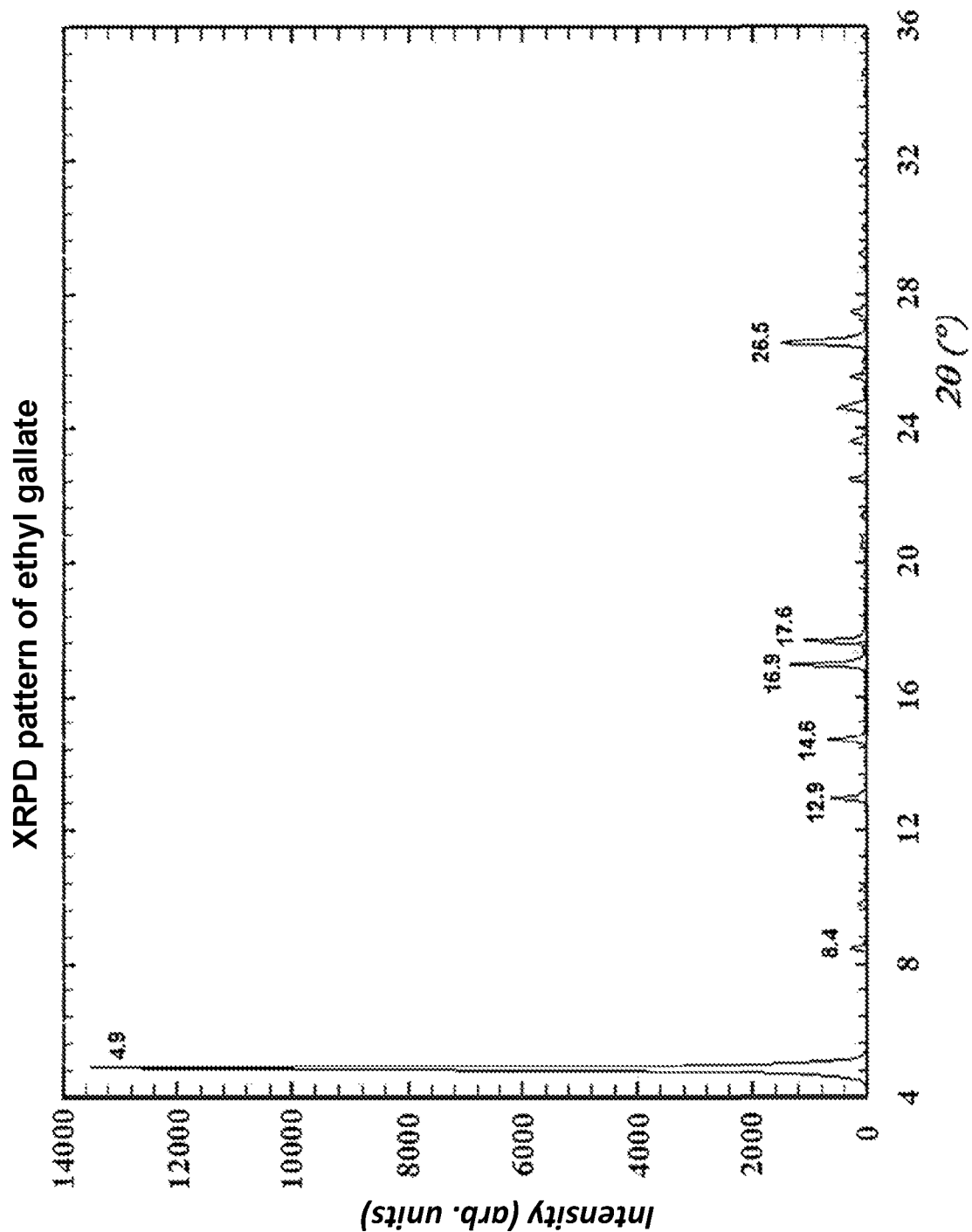
FIG. 82 is an XRPD pattern of ethyl gallate.

A simulated XRPD pattern appears in FIG. 79 and the experimental patterns of the starting materials appear in FIG. 7 for Form I and in FIG. 82 for ethyl gallate. Various peaks may be used to characterize a cocrystal of R-fasoracetam ethyl gallate based on the single crystal simulated XRPD pattern. For example, any one or more of the peaks chosen from peaks at about 5.8°2θ, about 11.3°2θ, about 12.4°2θ, about 15.5°2θ, about 15.8°2θ, about 18.2°2θ, about 19.4°2θ, about 22.0°2θ, or about 24.8°2θ may be used to characterize such a cocrystal. A cocrystal of R-fasoracetam and ethyl gallate was further characterized by grinding Form I R-fasoracetam and ethyl gallate in Example 25. The resulting XRPD matches that of the simulated pattern as set forth in FIG. 81.

Figure 83:
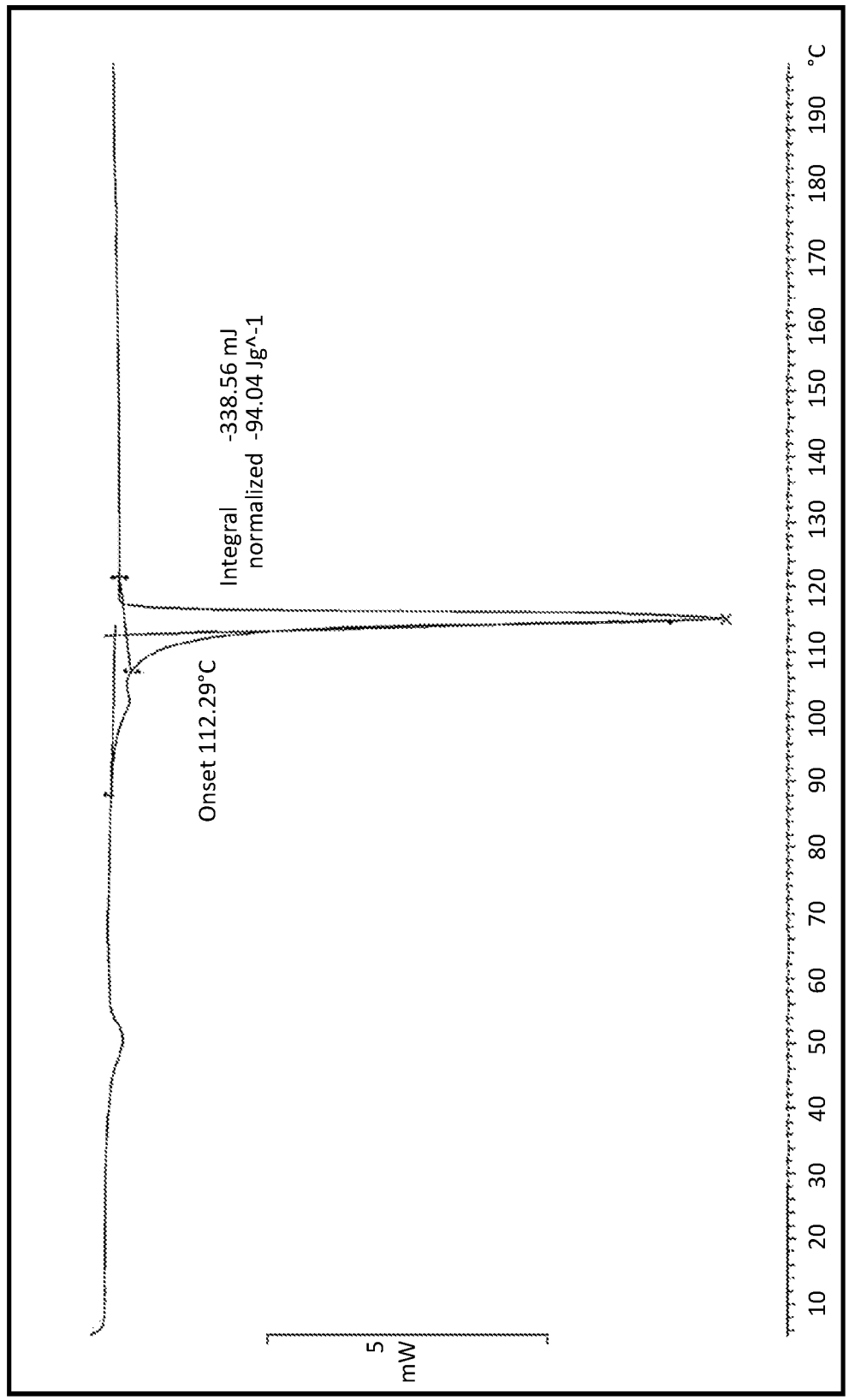
FIG. 83 is DSC thermogram of ground crystalline R-fasoracetam:ethyl gallate.

A melting point temperature onset was measured at about 112° C. as set forth in FIG. 83 for the 1:1 R-fasoracetam to ethyl gallate cocrystal of Example 25. The melting point onset of 112° C. may be used to characterize such a cocrystal of R-fasoracetam and ethyl gallate. In other embodiments, both the DSC onset melting temperature and the XRPD peaks may be used to characterize such a cocrystal of R-fasoracetam and ethyl gallate. Thus, the DSC melting point onset temperature of about 112° C. may be used together with one or more peaks chosen from 5.8°2θ, about 11.3°2θ, about 12.4°2θ, about 15.5°2θ, about 15.8°2θ, about 18.2°2θ, about 19.4°2θ, about 22.0°2θ, and about 24.8°2θ may be used to characterize such a cocrystal. In addition, the XRPD pattern in FIG. 79 and/or the DSC thermogram in FIG. 83 may be used to characterize a 1:1 cocrystal of R-fasoracetam and ethyl gallate.

Figure 132:
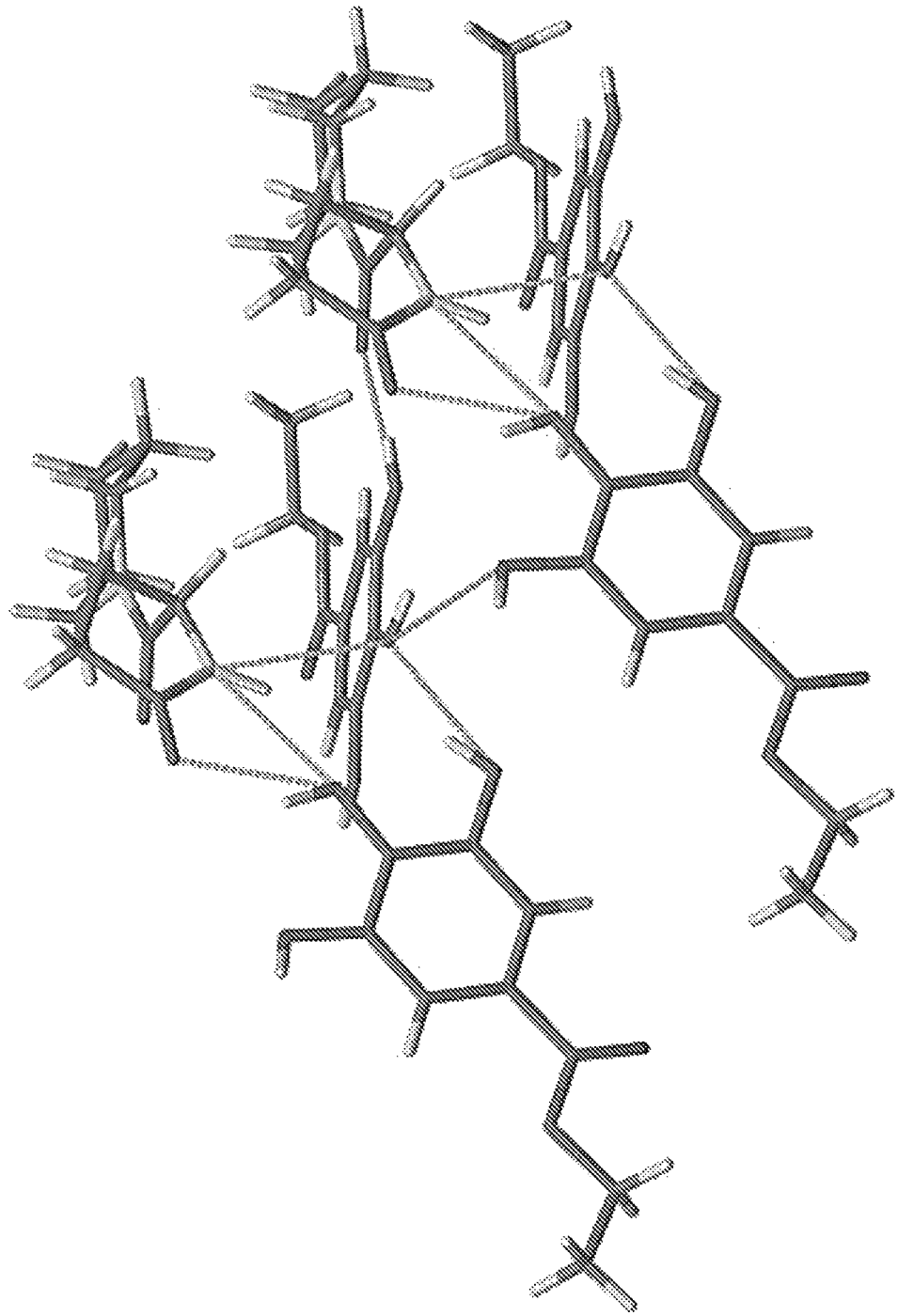

In other embodiments, 1:2 cocrystals of R-fasoracetam and ethyl gallate are provided. In Example 27, a cocrystal of R-fasoracetam ethyl gallate was prepared and a single crystal x-ray solution was analyzed with a data table of parameters set forth in Table 13 and an ORTEP drawing in FIG. 85 indicating a 1:2 stoichiometry of R-fasoracetam to ethyl gallate. FIG. 132 shows the hydrogen bonding pattern of a second cocrystal of R-fasoracetam (top right, center) with ethyl gallate (two bottom left, two lying flat oriented into the paper).

Without being bound by theory, it is believed that all three hydroxy-groups of ethyl gallate act as both hydrogen donors and acceptors where the hydroxy-groups on positions 3 and 5 form a hydrogen bond with a 4-position hydroxy-group on a neighboring molecule of ethyl gallate that lies flat and points into the plane. It is also believed that the 4-position hydroxy-group on both ethyl gallate molecules also form hydrogen bonds with the —NH and carbonyl on R-fasoracetam's five membered ring and the carbonyl is strictly a hydrogen acceptor, but the —NH serves as both hydrogen donor and acceptor. The reason for this is believed to be due to the 3D hydrogen bond pattern which is connected to such an extent that every hydroxyl group participates in two different intermolecular hydrogen bonds. The ethyl ester of ethyl gallate points away from the interaction sites.

Figure 86:
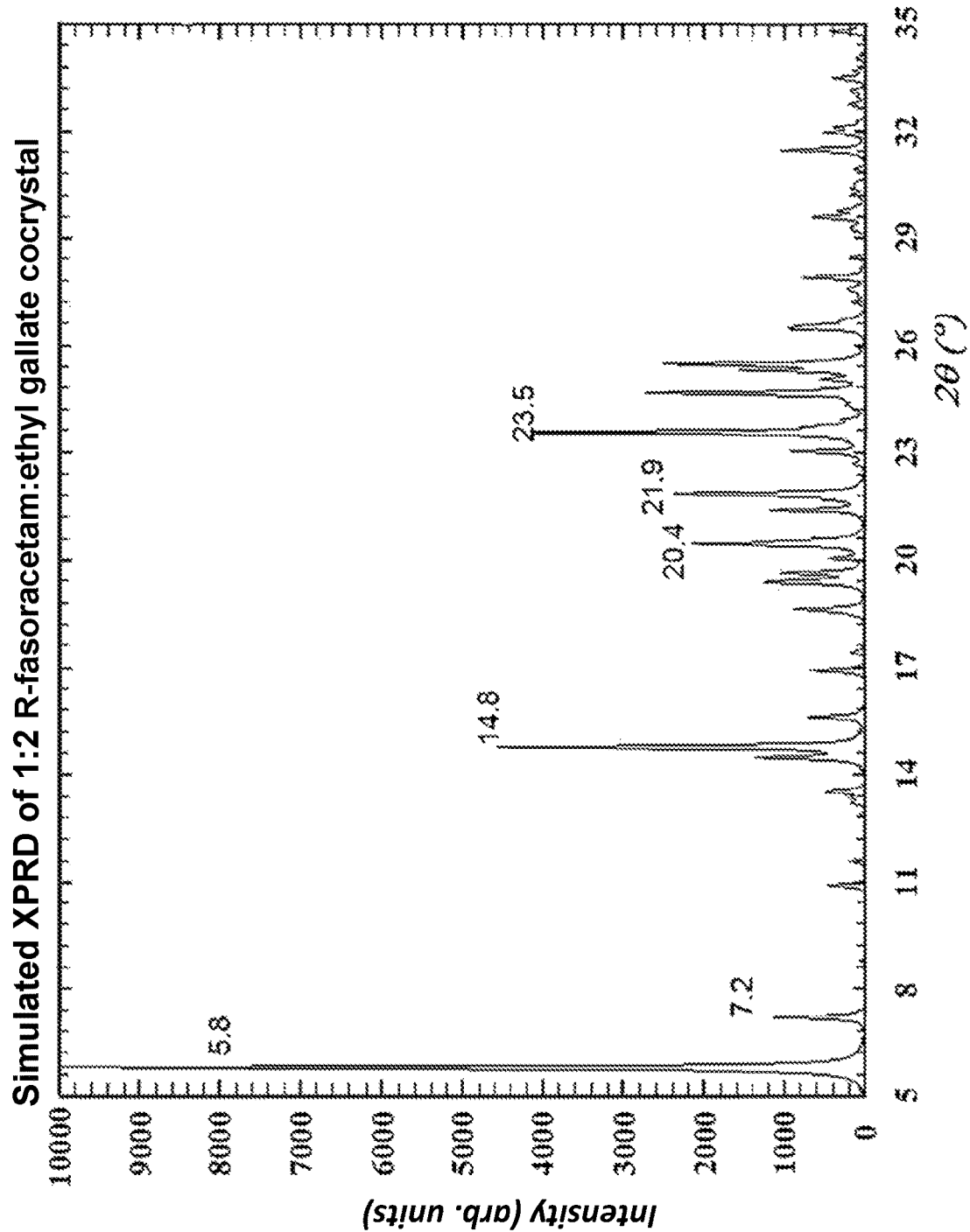
FIG. 86 is a simulated XRPD of 1:2 R-fasoracetam:ethyl gallate cocrystal.

A simulated XRPD pattern appears in FIG. 86 and the experimental patterns of the starting materials appear in FIG. 7 for Form I and in FIG. 82 for ethyl gallate. Various peaks may be used to characterize a cocrystal of R-fasoracetam to ethyl gallate acid based on the single crystal simulated XRPD pattern. For example, any one or more of the peaks chosen from peaks at about 5.8°2θ, about 7.2°2θ, about 14.8°2θ, about 20.4°2θ, about 21.9°2θ, or about 23.5°2θ may be used to characterize such a 1:2 cocrystal of R-fasoracetam and ethyl gallate.

Figure 133:
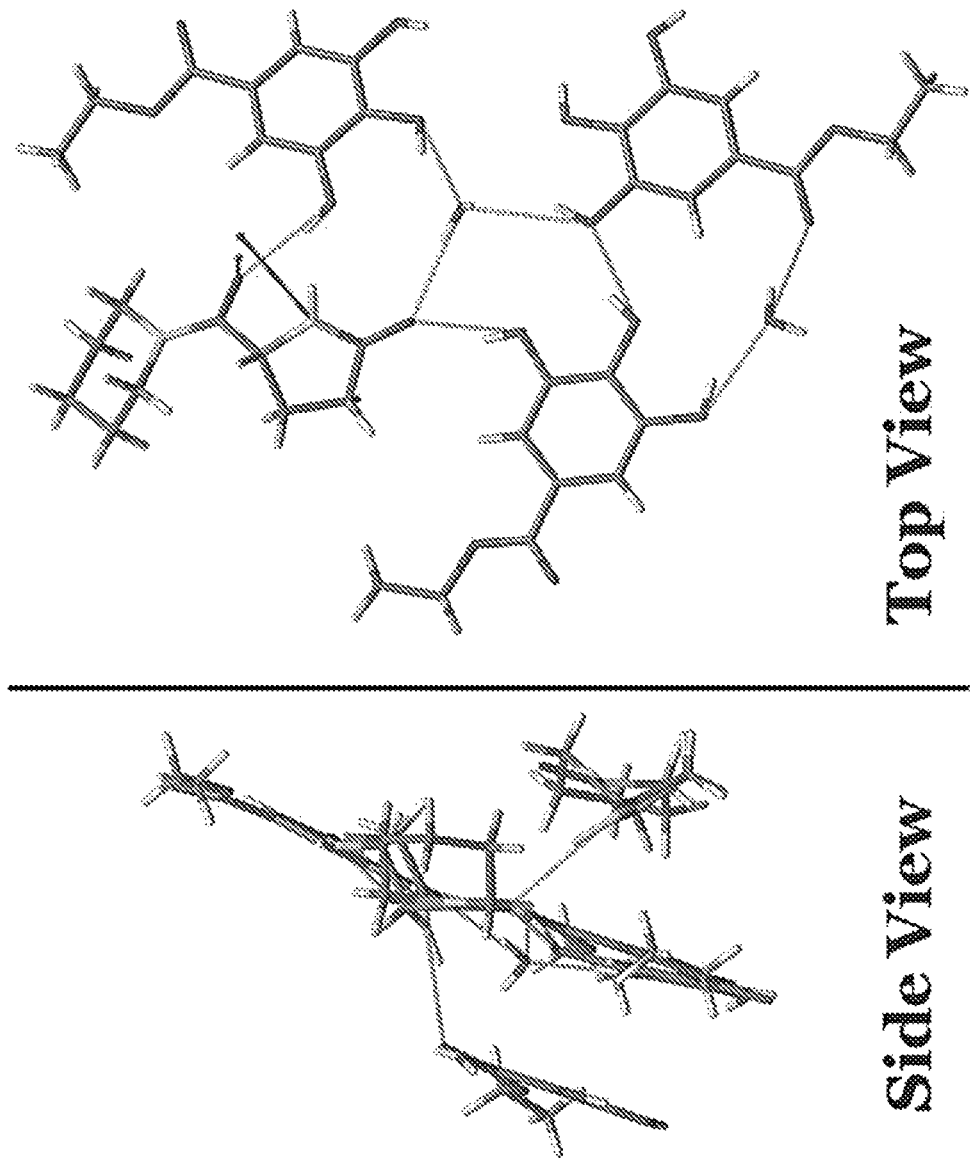

In further embodiments of the disclosure, R-fasoracetam:ethyl gallate:water cocrystals are provided in a 1:1:2 stoichiometry. Crystals suitable for single crystal analysis for such 1:2 R-fasoracetam to ethyl gallate dihydrates were prepared in Example 28. A single crystal x-ray solution was analyzed with a data table of parameters set forth in Table 14 and an ORTEP drawing in FIG. 87 indicating a 1:2:2 stoichiometry of R-fasoracetam to ethyl gallate to water. The hydrogen bonding pattern of a third cocrystal of R-fasoracetam with ethyl gallate, a 1:2:2 cocrystal dihydrate, appears in FIG. 133, with a side view on the left showing the interplanar hydrogen bonds.

Without being bound by theory, it is believed that ethyl gallate on the left acts as a hydrogen acceptor, where the donor is the —NH on R-fasoracetam's five membered ring. In the side view R-fasoracetam's bridging carbonyl acts as a hydrogen acceptor, and the —NH in the five membered ring of R-fasoracetam on the right acts as a hydrogen donor. In the plane itself (top view) the 2D hydrogen bond network consists of two ethyl gallate molecules, two water molecules and one R-fasoracetam molecule. It is believed that the water molecules serve as a bridge between the larger molecules, in the bottom between ethyl gallate's 3-position hydroxy-group (on the left) and the carbonyl of the ester of another ethyl gallate molecule (on the right).

It is further believed that the same ethyl gallate molecule on the left has both of the hydroxy-groups on positions 4 and 5 act as hydrogen donors, forming hydrogen bonds with ethyl gallate on the right (with 3-position hydroxy-group functioning as a hydrogen acceptor) and R-fasoracetam on the top left, where the carbonyl on the five membered ring acts as a hydrogen acceptor. It is believed that this same carbonyl also acts as an acceptor for the hydrogen donor of water, which in turn also acts as a hydrogen acceptor for the hydrogen donating 3-position hydroxy-group of ethyl gallate (bottom right) and hydrogen donating 4-position hydroxy-group of ethyl gallate on the top right. It is further believed that the 3-position of the top-right ethyl gallate's hydroxy-group acts as a hydrogen donor where the bridging carbonyl on R-fasoracetam is the hydrogen acceptor.

Figure 88:
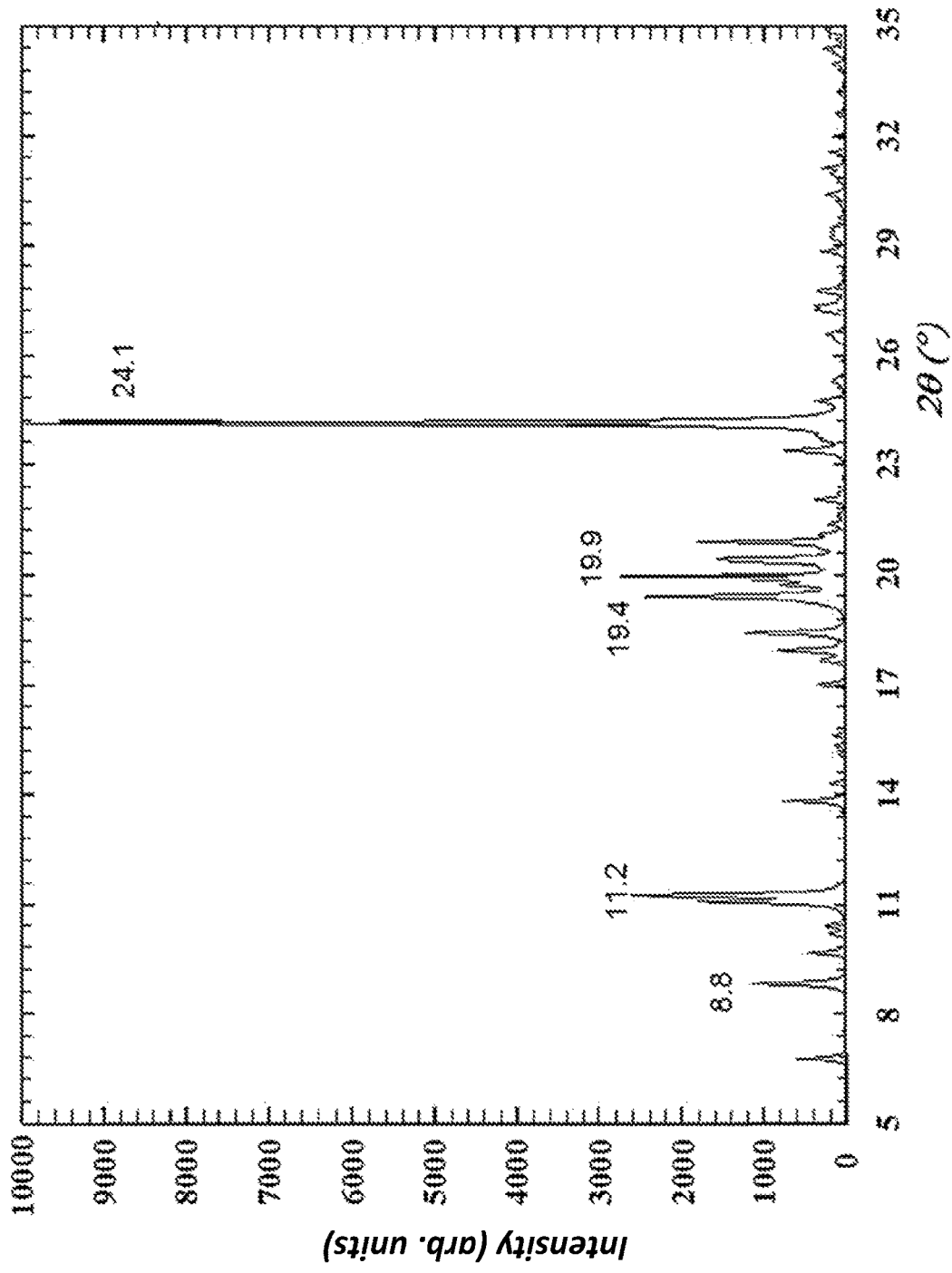
FIG. 88 is a simulated XRPD pattern of dihydrate of 1:2 R-fasoracetam:ethyl gallate cocrystal.

A simulated XRPD pattern appears in FIG. 88 and the experimental XRPD patterns of the starting materials appear in FIG. 7 for Form I and in FIG. 82 for ethyl gallate. Various peaks may be used to characterize a cocrystal of R-fasoracetam ethyl gallate based on the single crystal simulated XRPD pattern. For example, any one or more of the peaks chosen from peaks at about 8.8°2θ, about 11.2°2θ, about 19.4°2θ, about 19.9°2θ, or about 24.1°2θ may be used to characterize such a cocrystal. A cocrystal of R-fasoracetam and ethyl gallate was further characterized by slurrying Form I R-fasoracetam and 2 equivalents ethyl gallate in water set forth in Example 29. The resulting XRPD patterns match that of the simulated pattern as set forth in FIG. 90.

Figure 93:
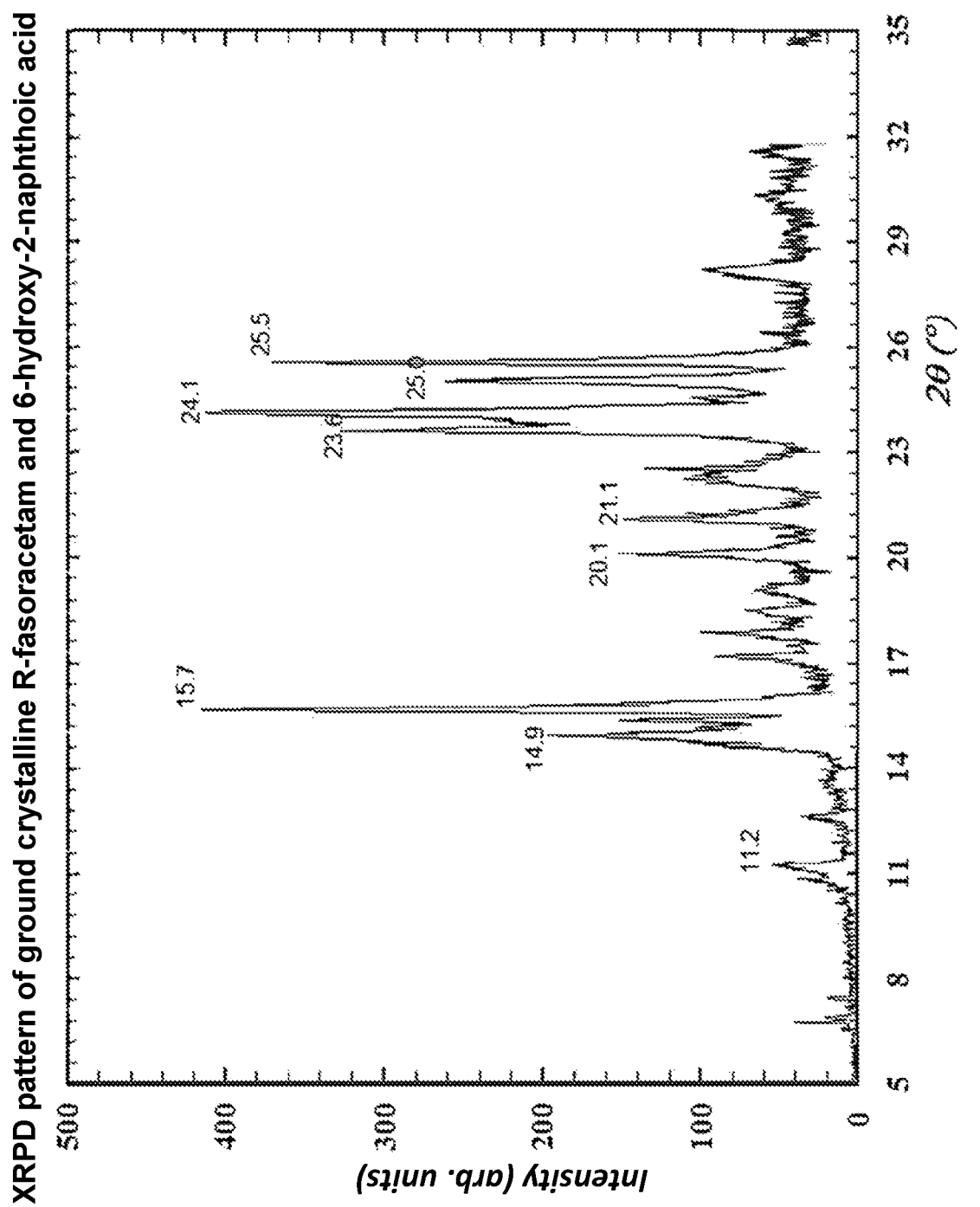
FIG. 93 is an XRPD pattern of ground crystalline R-fasoracetam and 6-hydroxy-2-naphthoic acid.
Figure 94:
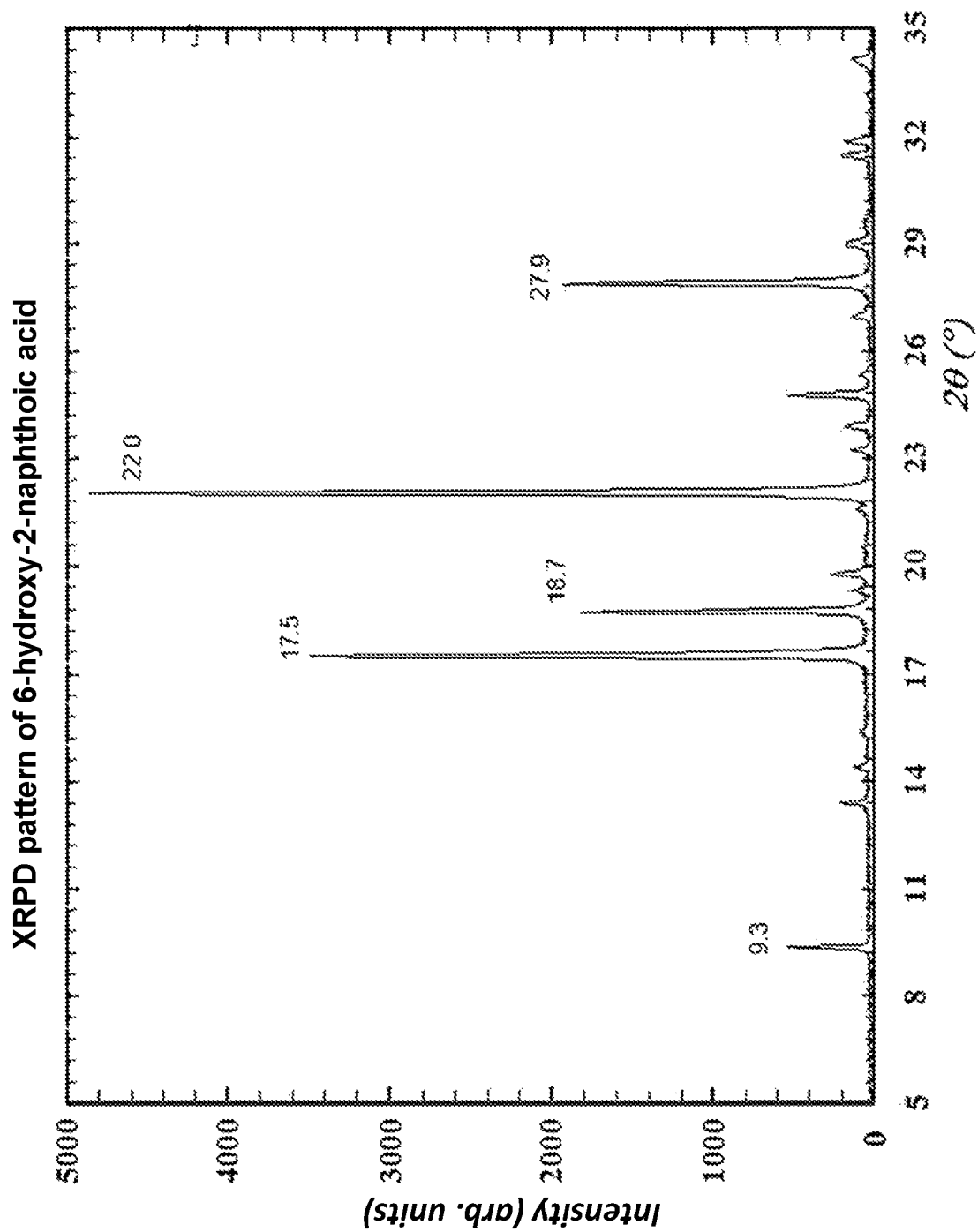
FIG. 94 is an XRPD pattern of 6-hydroxy-2-naphthoic acid.
Figure 95:
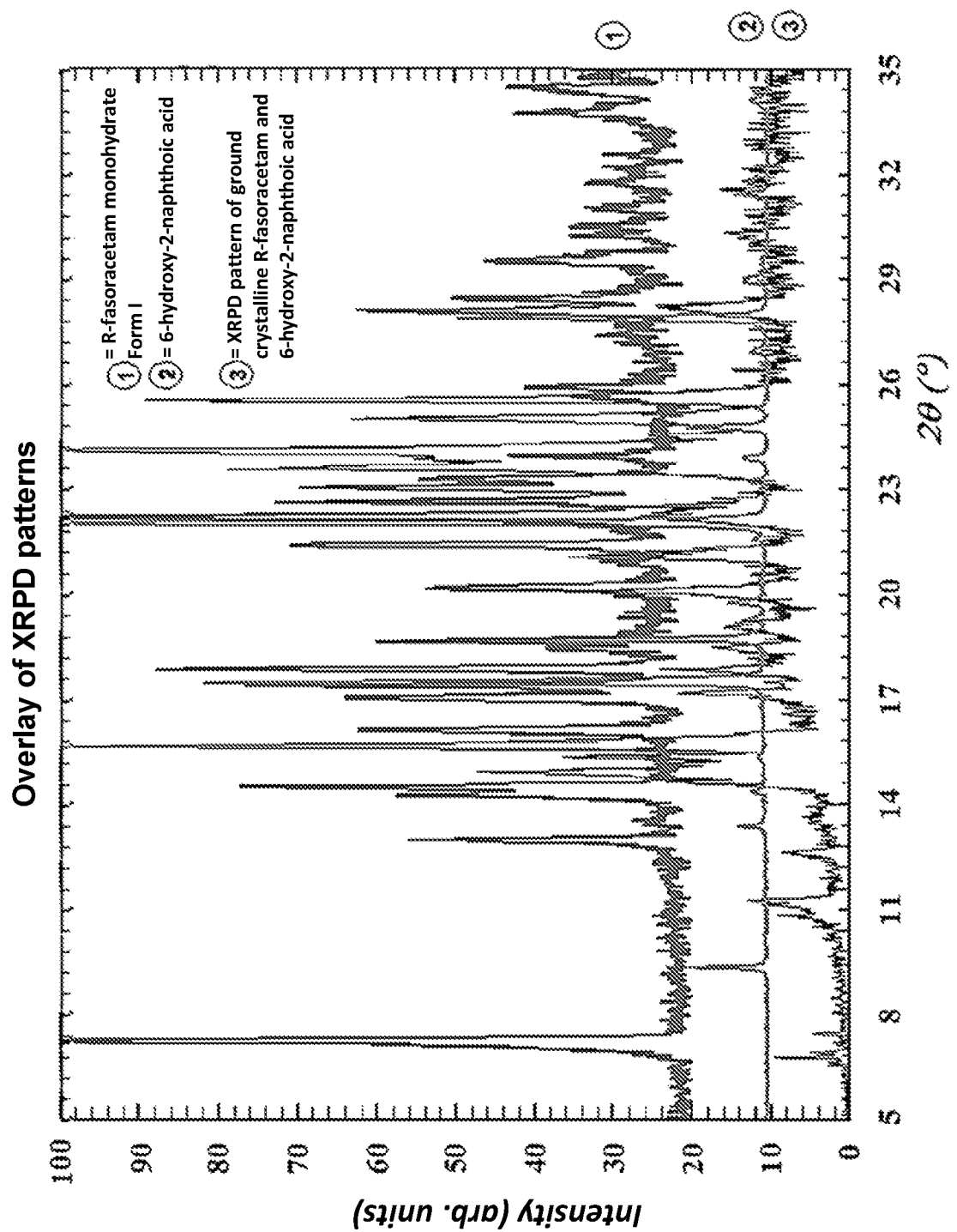
FIG. 95 is an overlay of XRPD patterns: (1) XRPD pattern of R-fasoracetam monohydrate Form I; (2) XRPD pattern of 6-hydroxy-2-naphthoic acid; (3) XRPD pattern of ground crystalline R-fasoracetam and 6-hydroxy-2-naphthoic acid.

In additional embodiments, the disclosure provides for crystalline fasoracetam 6-hydroxy-2-naphthoic acid such as, for example, a cocrystal of fasoracetam and 6-hydroxy-2-naphthoic acid. In particular, the fasoracetam may be R-fasoracetam. FIG. 93 is an XRPD pattern corresponding to a cocrystal of R-fasoracetam and 6-hydroxy-2-naphthoic acid. The cocrystal was prepared in accordance with Example 30. The cocrystal was prepared by grinding Form I with 6-hydroxy-2-naphthoic acid. FIG. 94 is the XRPD pattern of 6-hydroxy-2-naphthoic acid and FIG. 95 is an overlay pattern showing the patterns of 6-hydroxy-2-naphthoic acid, R-fasoracetam Form I monohydrate and the cocrystal of R-fasoracetam and 6-hydroxy-2-naphthoic acid. FIG. 95 indicates that the cocrystal pattern is not a linear combination of the component parts and thus is not a physical mixture. For example, the peak at about 11.2°2θ in the cocrystal is not in either of the XRPD patterns of the component parts.

A cocrystal of fasoracetam and 6-hydroxy-2-naphthoic acid, such as R-fasoracetam and 6-hydroxy-2-naphthoic acid may be characterized by one or more peaks at about 11.2°2θ, about 14.9°2θ, about 15.7°2θ, about 20.1°2θ, about 21.1°2θ, about 23.6°2θ, about 24.1°2θ, about 25.0°2θ and about 25.5°2θ. Further, an onset melting point at about 120° C., such as one measured with DSC, may be used to characterize such a cocrystal. This melting point may be used along or in connection with XRPD peaks to characterize such a cocrystal. That is, an onset melting point of about 120° C. (as set forth in FIG. 97) together with one or more peaks chosen from peaks at about 11.2°2θ, about 14.9°2θ, about 15.7°2θ, about 20.1°2θ, about 21.1°2θ, about 23.6°2θ, about 24.1°2θ, about 25.0°2θ and about 25.5°2θ may be used to characterize such a cocrystal.

Figure 97:
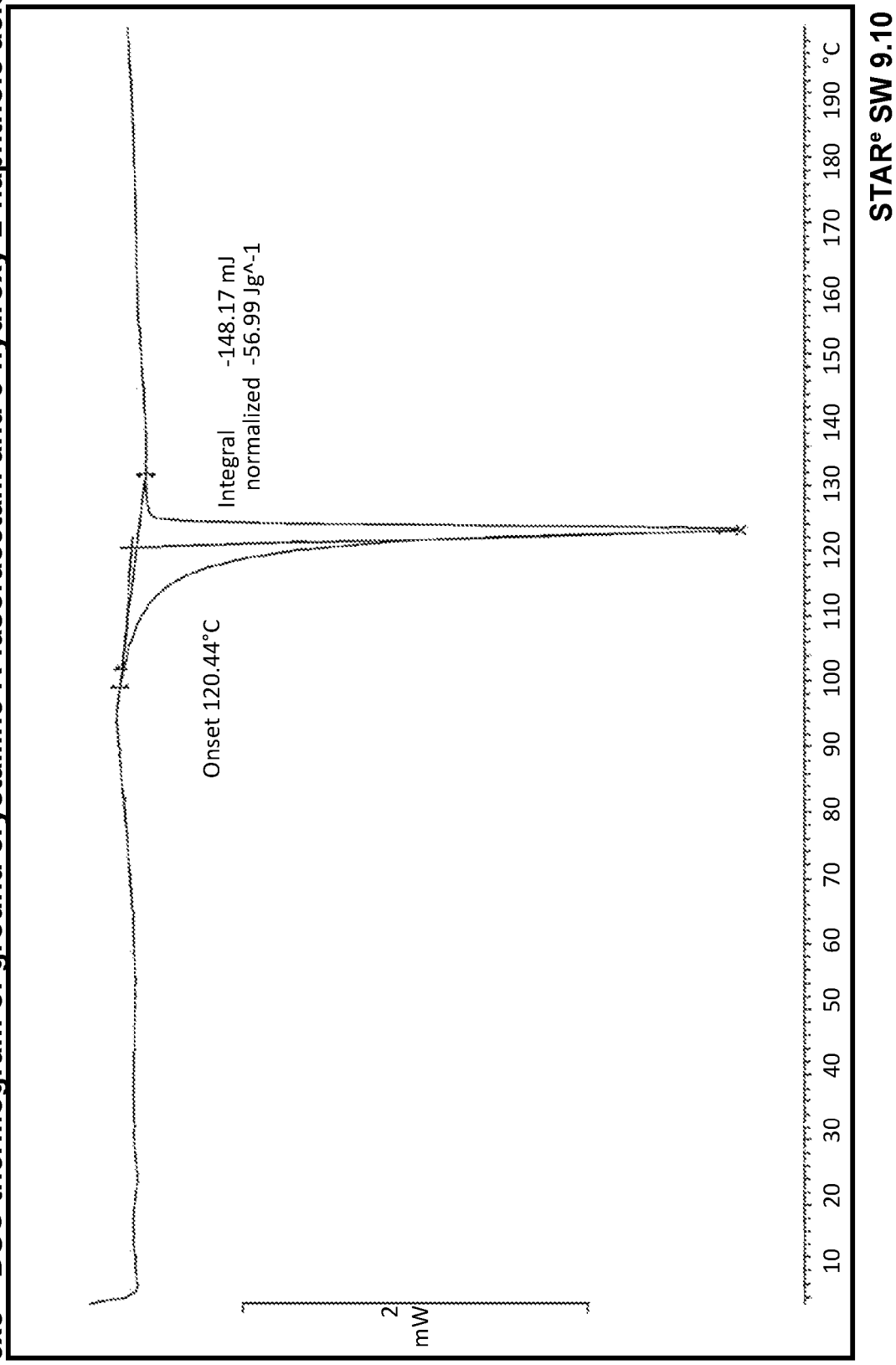
FIG. 97 is a DSC thermogram of ground crystalline R-fasoracetam and 6-hydroxy-2-naphthoic acid.

The XRPD pattern substantially the same as that of FIG. 93 and/or a DSC thermogram substantially the same as FIG. 97 may be used to characterize a cocrystal of fasoracetam and 6-hydroxy-2-naphthoic acid cocrystal such as the R-fasoracetam and 6-hydroxy-2-naphthoic acid cocrystal.

Figure 126:
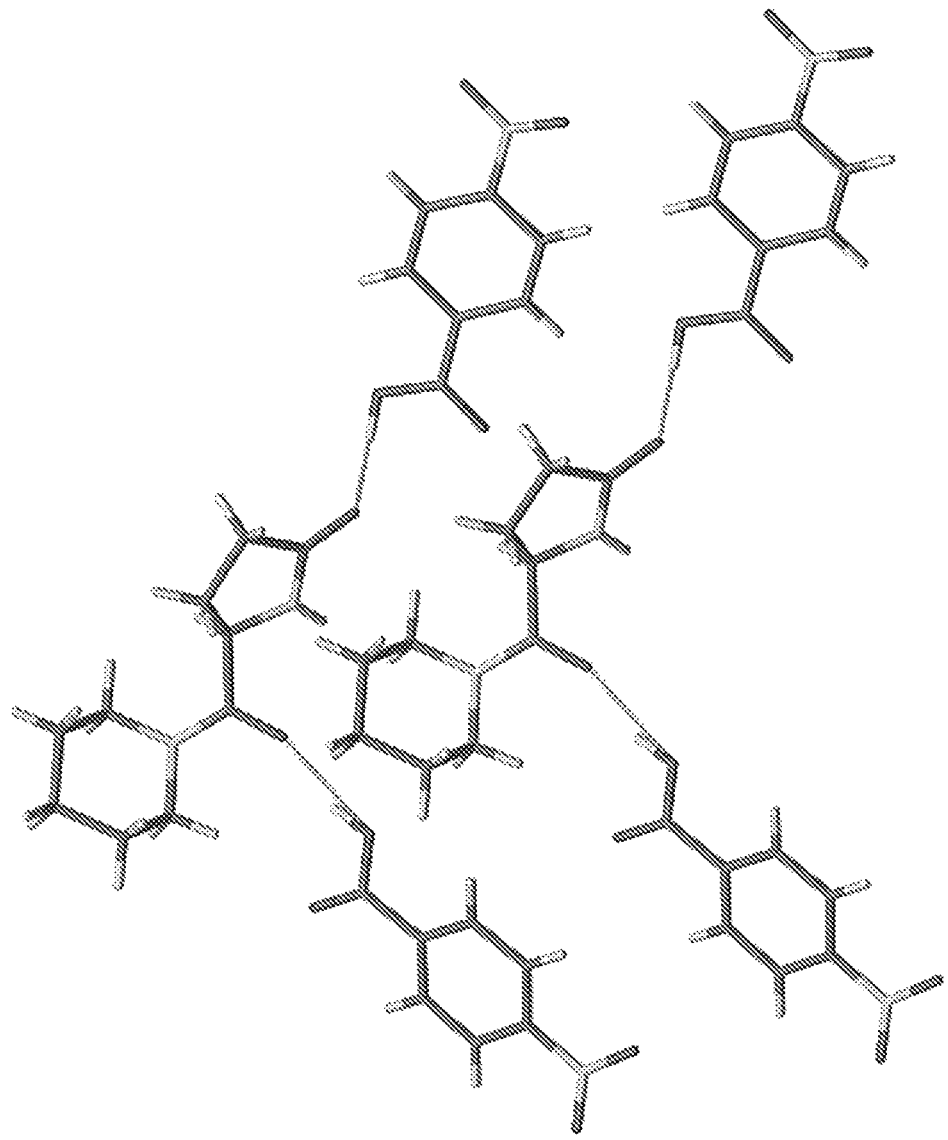
FIG. 126 is a hydrogen bonding pattern of a R-fasoracetam:4-nitrobenzoic acid cocrystal.

In additional embodiments of the disclosure, crystalline fasoracetam 4-nitrobenzoic acid is provided such, as, for example, cocrystals of fasoracetam and 4-nitrobenzoic acid. In particular, the fasoracetam may be R-fasoracetam. In certain of these embodiments, a 1:2 cocrystal of R-fasoracetam and 4-nitrobenzoic acid is provided. In Example 31, a cocrystal of R-fasoracetam 4-nitrobenzoic acid was prepared and a single crystal x-ray solution was analyzed with a data table of parameters set forth in Table 15 and an ORTEP drawing in FIG. 99 indicating a 1:2 stoichiometry of R-fasoracetam to 4-nitrobenzoic acid. FIG. 126 shows 4-nitrobenzoic acid (left and right) with R-fasoracetam (center).

Without being bound by theory, it is believed that both carbonyl groups on R-fasoracetam act as hydrogen acceptors with the hydrogen donating carboxylic acid group of 4-nitrobenzoic acid, and the aromatic ring of the 4-nitrobenzoic acid molecules is oriented such that there is a stabilizing pi-pi interaction. The different molecules appear in an alternating manner forming sheets.

Figure 100:
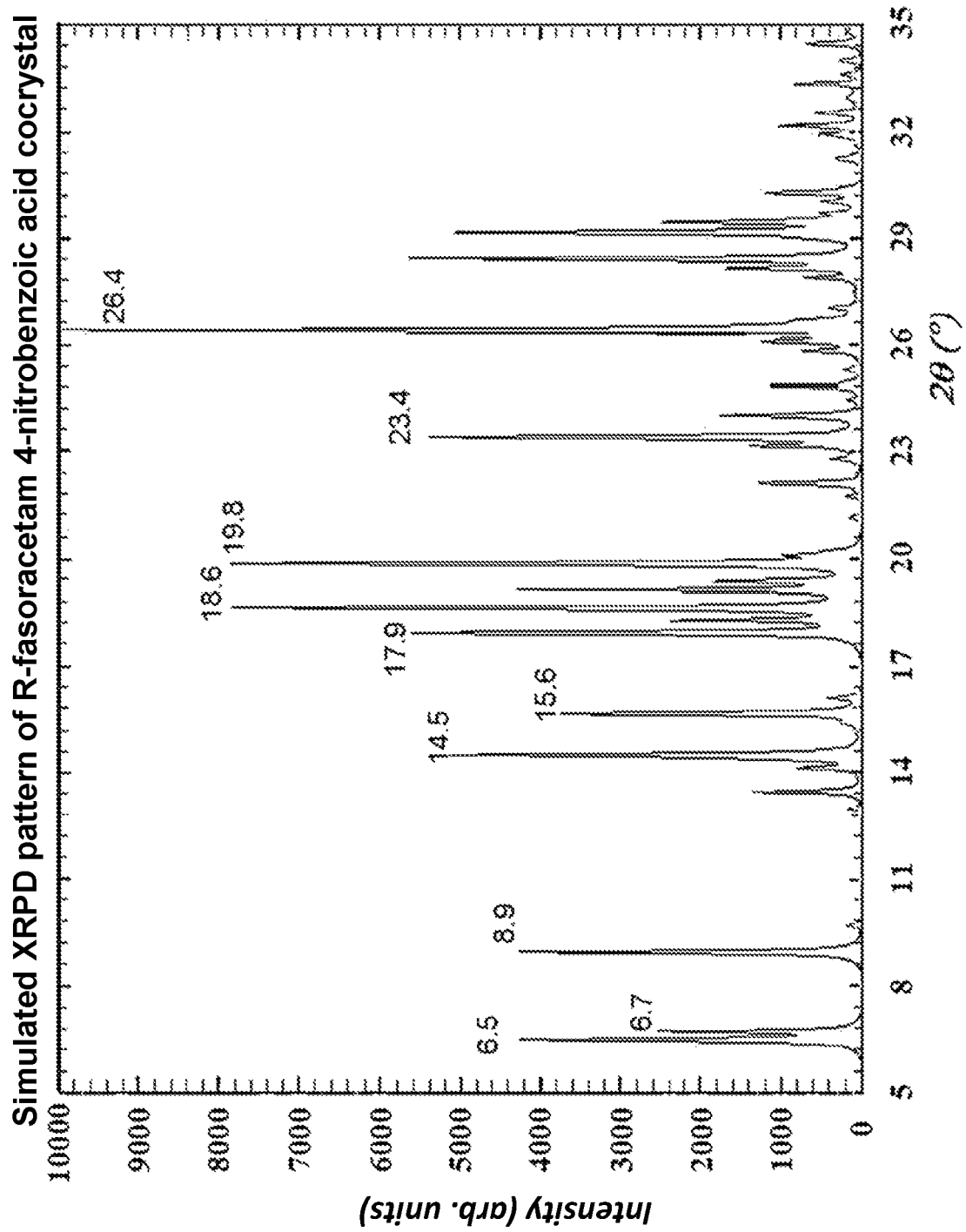
FIG. 100 is a simulated XRPD pattern of R-fasoracetam:4-nitrobenzoic acid cocrystal.
Figure 102:
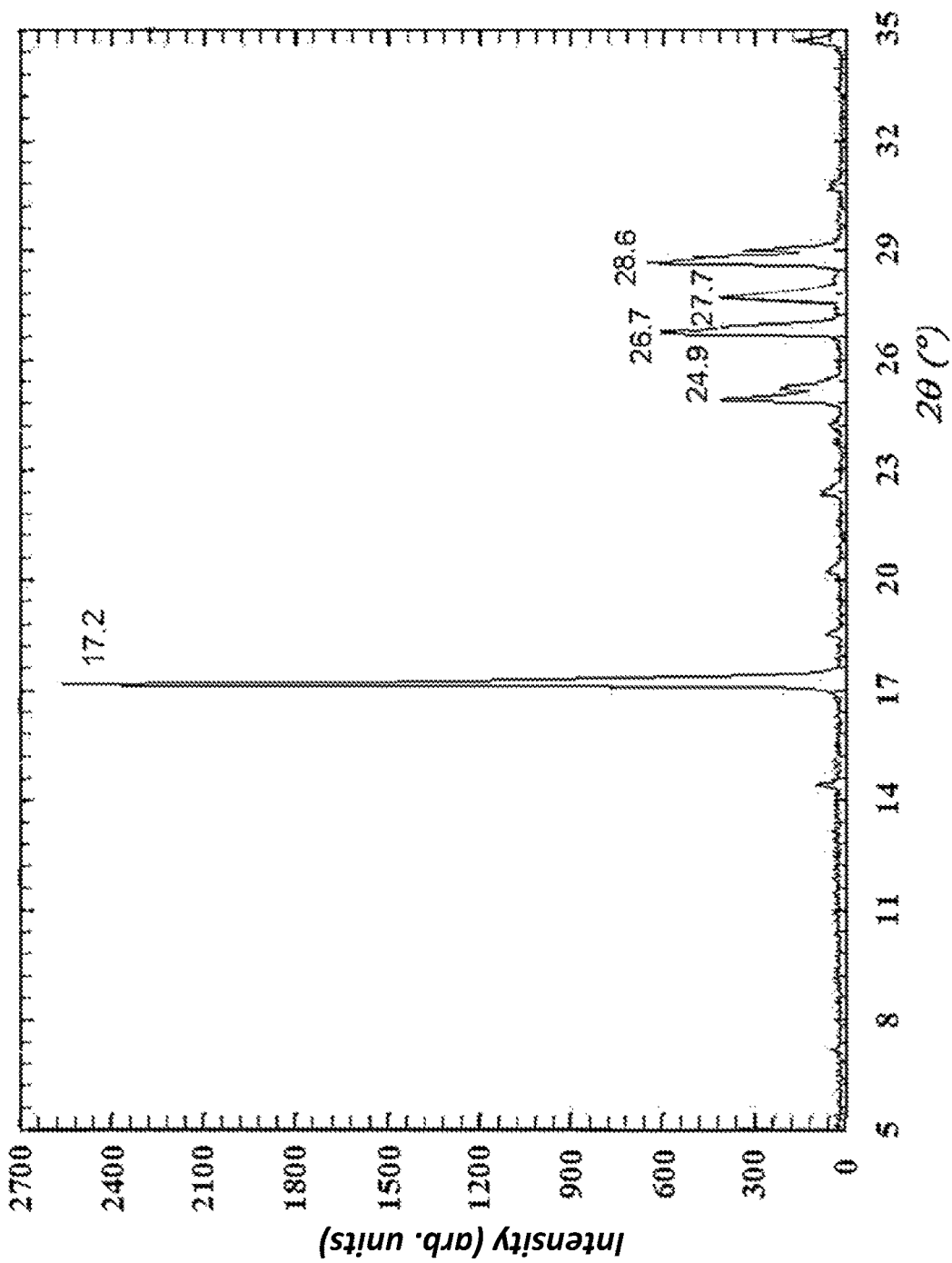
FIG. 102 is an XRPD pattern of 4-nitrobenzoic acid.

A simulated XRPD pattern appears in FIG. 100 and the experimental patterns of the starting materials appear in FIG. 7 for Form I and in FIG. 102 for 4-nitrobenzoic acid. Various peaks may be used to characterize a cocrystal of R-fasoracetam 4-nitrobenzoic acid based on the single crystal simulated XRPD pattern. For example, any one or more of the peaks chosen from peaks at about 6.5°2θ, about 6.7°2θ, about 8.9°2θ, about 14.5°2θ, about 15.6°2θ, about 17.9°2θ, about 18.6°2θ, about 19.8°2θ, about 23.4°2θ or about 26.4°2θ may be used to characterize such a cocrystal. A cocrystal of R-fasoracetam and 4-nitrobenzoic acid was further characterized by grinding Form I R-fasoracetam and 4-nitrobenzoic acid in Example 32. The resulting XRPD matches that of the simulated pattern as set forth in the overlay of patterns in FIG. 104.

Figure 107:
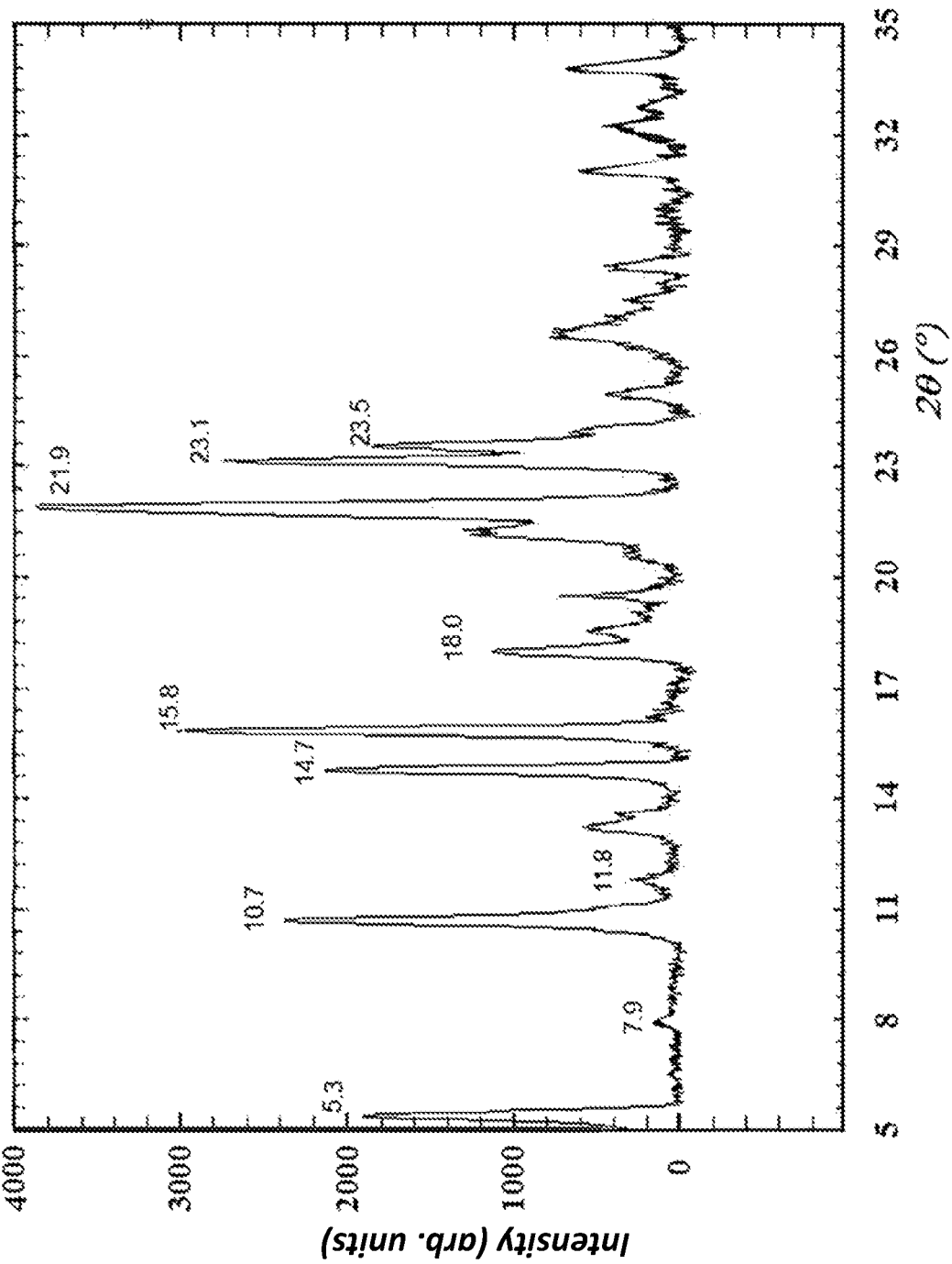
FIG. 107 is an XRPD pattern of ground crystalline R-fasoracetam and 2-indole-3-acetic acid.
Figure 108:
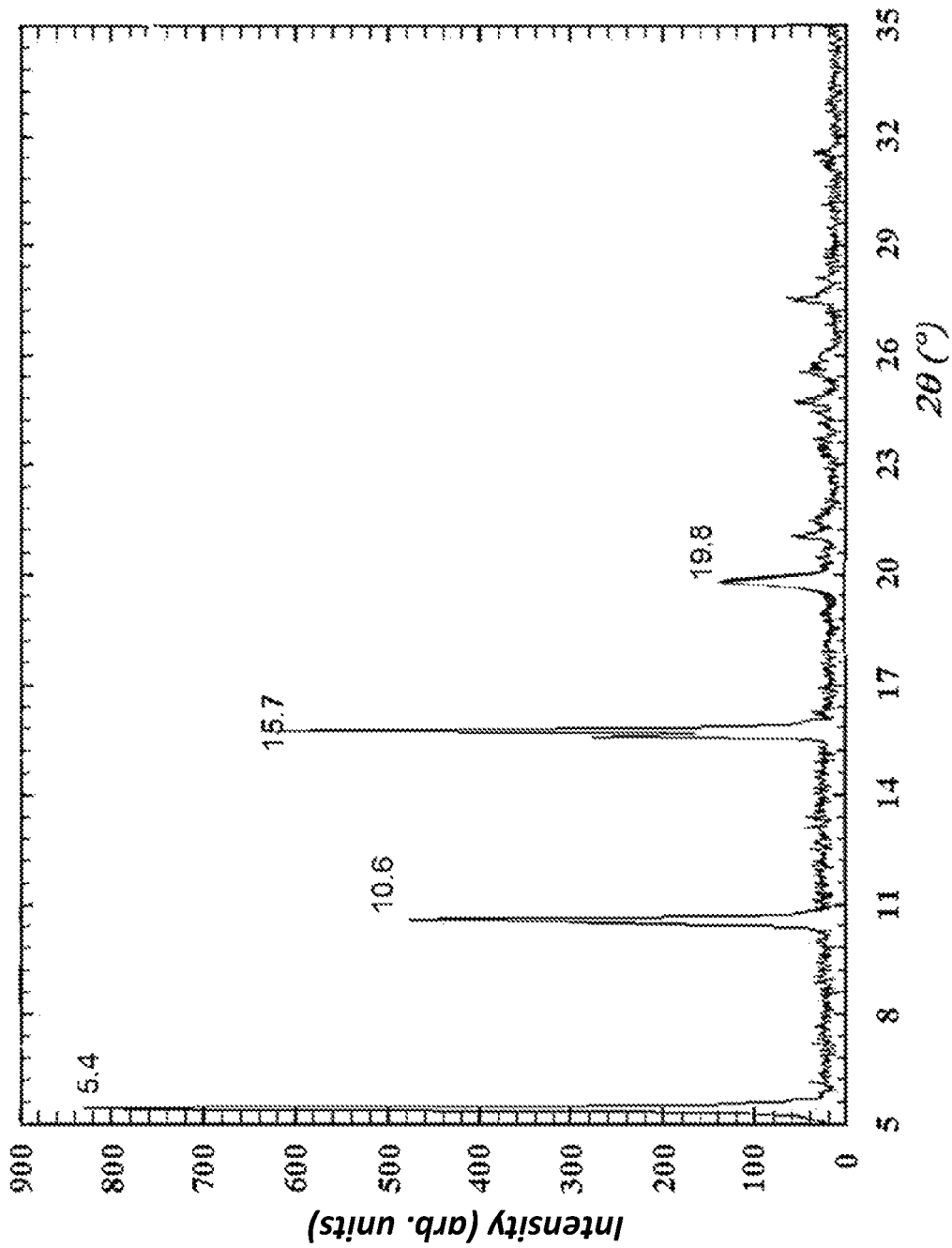
FIG. 108 is XRPD pattern of 2-indole-3-acetic acid.
Figure 109:
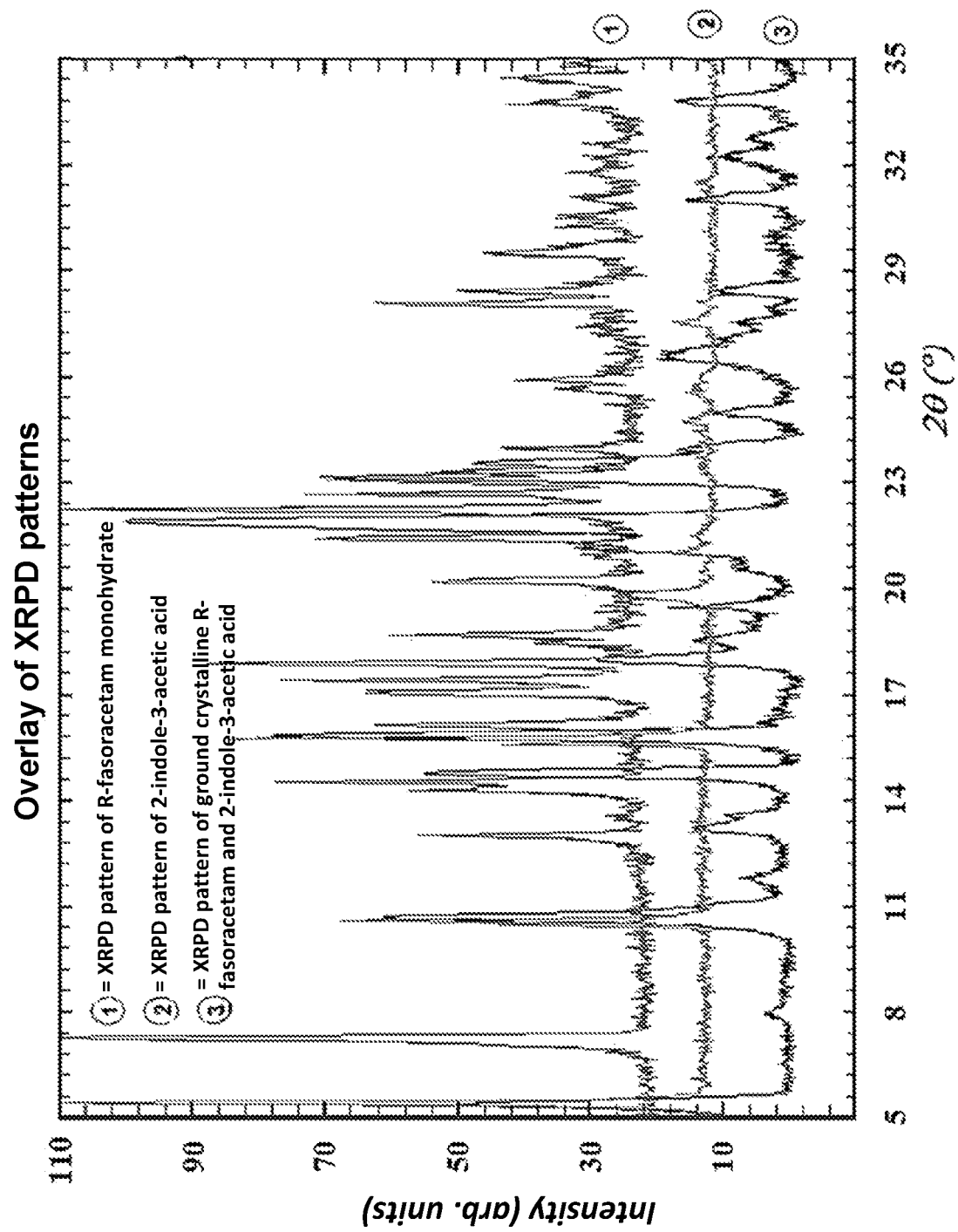
FIG. 109 is an overlay of XRPD patterns: (1) XRPD pattern of R-fasoracetam monohydrate Form I; (2) XRPD pattern of 2-indole-3-acetic acid; (3) XRPD pattern of ground crystalline R-fasoracetam and 2-indole-3-acetic acid.

In additional embodiments, the disclosure provides for crystalline fasoracetam 2-indole-3-acetic acid such, as, for example, a cocrystal of fasoracetam and 2-indole-3-acetic acid. In particular, the fasoracetam may be R-fasoracetam. FIG. 107 is an XRPD pattern corresponding to a cocrystal of R-fasoracetam and 2-indole-3-acetic acid. The cocrystal was prepared in accordance with Example 33. The cocrystal was prepared by grinding Form I with 2-indole-3-acetic acid. FIG. 108 is the XRPD pattern of 2-indole-3-acetic acid and FIG. 109 is an overlay pattern showing the patterns of 2-indole-3-acetic acid, Form I R-fasoracetam monohydrate and the cocrystal of R-fasoracetam and 2-indole-3-acetic acid. The overlay of patterns in FIG. 109 indicates that the cocrystal pattern is not a linear combination of the component parts and thus is not a physical mixture. For example, the peak at about 11.8°2θ in the cocrystal is not in either of the XRPD patterns of the component parts.

A cocrystal of fasoracetam and 2-indole-3-acetic acid, such as R-fasoracetam and 2-indole-3-acetic acid may be characterized by one or more peaks chosen from peaks at about 5.3°2θ, about 7.9°2θ, about 10.7°2θ, about 14.7°2θ, about 15.8°2θ, about 18.0°2θ, about 21.9°2θ, about 23.1°2θ, and about 23.5°2θ. Further, an onset melting point at about 69° C., such as one measured with DSC, may be used to characterize such a cocrystal. In addition, the cocrystal may be characterized by a combination of the onset melting temperature and XRPD peaks. For example, a melting onset temperature of about 69° C. together with one or more peaks chosen from peaks at about 5.3°2θ, about 7.9°2θ, about 10.7°2θ, about 14.7°2θ, about 15.8°2θ, about 18.0°2θ, about 21.9°2θ, about 23.1°2θ, and about 23.5°2θ may be used to characterize a cocrystal of R-fasoracetam and 2-indole-3-acetic acid. The XRPD pattern substantially the same as that of FIG. 107 and/or a DSC thermogram substantially the same as FIG. 111 may be used to characterize a cocrystal of fasoracetam and 2-indole-3-acetic acid such as the R-fasoracetam and 2-indole-3-acetic acid.

The experimental data presented for cocrystals of fasoracetam originate from experiments conducted with the R-enantiomer of fasoracetam. Thus, all cocrystals were prepared with R-fasoracetam and R-fasoracetam is the enantiomer of fasoracetam present in each cocrystal. It is expected that the S-enantiomer would also form cocrystals with each achiral coformer as the R-enantiomer. The S-enantiomer would not be expected to necessarily form a cocrystal with a chiral coformer such as, for example, R-ibuprofen. With achiral coformers, however, one would expect the S-fasoracetam cocrystal to have similar structural and property characteristics such as melting point behavior and dissolution characteristics as the R-enantiomer. The same is not necessarily the case with racemic fasoracetam. It may form cocrystals with the same achiral coformers, but any cocrystals so made may have different structural and property characteristics as the R-fasoracetam cocrystals.

This disclosure also relates to pharmaceutical compositions containing cocrystals or crystalline compounds of fasoracetam as disclosed herein. Such pharmaceutical compositions are comprised of one or more pharmaceutically acceptable excipients and a cocrystal or crystalline material of the disclosure. Such pharmaceutical compositions may be administered orally or configured to be delivered as any effective conventional dosage unit forms, including immediate, slow and timed release oral preparations, parenterally, topically, nasally, ophthalmically, optically, sublingually, rectally, vaginally, and the like.

The disclosure further includes methods and uses for treating diseases in humans such as ADHD, 22q11.2 deletion syndrome, anxiety, conduct disorder, Tourette's syndrome, and anorexia with effective amount of cocrystals, crystalline compounds, and/or pharmaceutical compositions comprising the cocrystals and/or crystalline compounds of fasoracetam of the disclosure. In some embodiments, the subject with ADHD, 22q11.2 deletion syndrome, anxiety, conduct disorder, Tourette's syndrome, or anorexia has at least one has at least one copy number variation (CNV) in a metabotropic glutamate receptor (mGluR) network gene (see, e.g., FIGS. 1-3 of WO2017/044491). In some embodiments, the mGluR network gene selected from GRM5, GRM8, GRM7, GRM1, NEGR1, SGTB/NLN, USP24, CNTN4, CTNNA2, LARP7, MC4R, SNCA, CA8.

The following clauses provide numerous embodiments and are non-limiting:

Clause 1. A cocrystal of fasoracetam and a coformer wherein the coformer is not tartaric acid.

Clause 2. The cocrystal of clause 1, wherein the coformer is an organic compound and contains at least one moiety selected from —$NH_2$, —$NO_2$, alkyl, or a carbonyl-containing moiety.

Clause 3. The cocrystal as in clause 1 or clause 2, wherein the fasoracetam is R-fasoracetam.

Clause 4. A crystalline compound comprising fasoracetam and a coformer wherein the coformer is an aromatic compound.

Clause 5. A crystalline compound comprising R-fasoracetam and a coformer wherein the coformer is an aromatic compound.

Clause 6. The crystalline compound as in clause 4 or clause 5, wherein the crystalline compound is a cocrystal.

Clause 7. A cocrystal of fasoracetam and a coformer wherein the coformer is an aromatic compound.

Clause 8. A cocrystal of R-fasoracetam and a coformer wherein the coformer is an aromatic compound.

Clause 9. The cocrystal as in clause 7 or clause 8, wherein the aromatic compound has at least one substituent.

Clause 10. The cocrystal of clause 9, wherein the at least one substituent is chosen from —OH, —$NH_2$, alkyl, —$NO_2$, and carbonyl-containing moieties.

Clause 11. The cocrystal of clause 10, wherein the carbonyl-containing moiety is an organic acid moiety.

Clause 12. The cocrystal of clause 11, wherein the organic acid moiety is chosen from $C_1$-$C_4$ organic acids.

Clause 13. The cocrystal of clause 12, wherein the organic acid moiety is —COOH.

Clause 14. The cocrystal of clause 10, wherein the at least one substituent is an —OH moiety.

Clause 15. The cocrystal of clause 10, wherein the at least one substituent is chosen from ester and alkyl moieties.

Clause 16. The cocrystal of clause 15, wherein the ester is chosen from $C_1$-$C_5$ esters.

Clause 17. The cocrystal of any one of clauses 9-16, wherein the aromatic compound has two substituents.

Clause 18. The cocrystal of any one of clauses 9-16, wherein the aromatic compound has three substituents.

Clause 19. The cocrystal of any one of clauses 9-16, wherein the aromatic compound has four substituents.

Clause 20. The cocrystal of clause 17, wherein there are two substituents and each substituent is independently chosen from —OH, —$NH_2$, alkyl, organic acid, ester, and —$NO_2$ moieties.

Clause 21. The cocrystal of clause 20, wherein a first substituent is an organic acid and a second substituent is chosen from —OH, —$NH_2$, alkyl, organic acid, ester, and —$NO_2$ moieties.

Clause 22. The cocrystal of clause 21, wherein the second substituent is an —$NH_2$ moiety.

Clause 23. The cocrystal of clause 22, wherein the —$NH_2$ moiety and the organic acid moiety are ortho to one another.

Clause 24. The cocrystal of clause 22, wherein the —$NH_2$ moiety and the organic acid moiety are meta to one another.

Clause 25. The cocrystal of clause 22, wherein the —$NH_2$ moiety and the organic acid moiety are para to one another.

Clause 26. The cocrystal of clause 21, wherein the second substituent is an —$NO_2$ moiety.

Clause 27. The cocrystal of clause 26, wherein the —$NO_2$ moiety and the organic acid moiety are ortho to one another.

Clause 28. The cocrystal of clause 26, wherein the —$NO_2$ moiety and the organic acid moiety are meta to one another.

Clause 29. The cocrystal of clause 26, wherein the —$NO_2$ moiety and the organic acid moiety are para to one another.

Clause 30. The cocrystal of clause 21, wherein the second substituent is an —OH moiety.

Clause 31. The cocrystal of clause 30, wherein the —OH moiety and the organic acid moiety are ortho to one another.

Clause 32. The cocrystal of clause 30, wherein the —OH moiety and the organic acid moiety are meta to one another.

Clause 33. The cocrystal of clause 30, wherein the —OH moiety and the organic acid moiety are para to one another.

Clause 34. The cocrystal of clause 21, wherein the second substituent is an alkyl moiety.

Clause 35. The cocrystal of clause 34, wherein the alkyl moiety and the organic acid moiety are ortho to one another.

Clause 36. The cocrystal of clause 34, wherein the alkyl moiety and the organic acid moiety are meta to one another.

Clause 37. The cocrystal of clause 34, wherein the alkyl moiety and the organic acid moiety are para to one another.

Clause 38. The cocrystal of clause 21, wherein the second substituent is an organic acid moiety.

Clause 39. The cocrystal of clause 38, wherein the two organic acid substituents are ortho to one another.

Clause 40. The cocrystal of clause 38, wherein the two organic acid moieties are meta to one another.

Clause 41. The cocrystal of clause 38, wherein the two organic acid moieties are para to one another.

Clause 42. The cocrystal of clause 21, wherein the second substituent is an ester moiety.

Clause 43. The cocrystal of clause 42, wherein the ester moiety and the organic acid moiety are ortho to one another.

Clause 44. The cocrystal of clause 42, wherein the ester moiety and the organic acid moiety are meta to one another.

Clause 45. The cocrystal of clause 42, wherein the ester moiety and the organic acid moiety are para to one another.

Clause 46. The cocrystal of clause 18, wherein there are three substituents and each substituent is independently chosen from —OH, —$NH_2$, alkyl, organic acid, ester, and —$NO_2$ moieties.

Clause 47. The cocrystal of clause 46, wherein a first substituent is —OH.

Clause 48. The cocrystal of clause 47, wherein a second and third substituents are —OH.

Clause 49. The cocrystal of clause 46, wherein a first substituent is an organic acid moiety.

Clause 50. The cocrystal of clause 49, wherein a second and third substituents are organic acids moieties.

Clause 51. The cocrystal of any one of clauses 49-50, wherein the organic acid moiety is —COOH.

Clause 52. The cocrystal of clause 19, wherein there are four substituents and each substituent is independently chosen from —OH, —$NH_2$, alkyl, organic acid, ester, and —$NO_2$ moieties.

Clause 53. The cocrystal of clause 52, wherein a first substituent is an ester moiety or an organic acid moiety.

Clause 54. The cocrystal of clause 53, wherein the ester is a methyl ester.

Clause 55. The cocrystal of clause 53, wherein the ester is an ethyl ester.

Clause 56. The cocrystal of any one of clauses 53-55, wherein a second substituent is an —OH moiety.

Clause 57. The cocrystal of any one of clauses 53-55, wherein a second, a third and a fourth substituent are each an —OH moiety.

Clause 58. The cocrystal of any one of clauses 7-22, wherein the aromatic compound is polycyclic.

Clause 59. The cocrystal of any one of clauses 26, 30, 34, 42, 46, and 49-57, wherein the aromatic compound is polycyclic.

Clause 60. The cocrystal of any one of clauses 58-59, wherein the polycyclic aromatic compound is two six-member rings.

Clause 61. The cocrystal of any one of clauses 58-59, wherein the polycyclic aromatic compound is a six-member ring and a five-member ring.

Clause 62. The cocrystal of any one of clauses 7-61, wherein the ring atoms of the aromatic compound are all carbon.

Clause 63. The cocrystal of any one of clauses 7-61, wherein at least one ring atom of the aromatic compound is not carbon.

Clause 64. The cocrystal of clause 63, wherein at least one ring atom is nitrogen.

Clause 65. The cocrystal of any one of clauses 58-59, wherein there is one substituent on the polycyclic aromatic compound.

Clause 66. The cocrystal of clause 65, wherein the substituent is chosen from $C_1$-$C_4$ organic acid moieties.

Clause 67. The cocrystal of clause 66, wherein the acid is a $C_2$ acid moiety.

Clause 68. The crystalline compound of any one of clauses 4-5, wherein the aromatic compound is substituted.

Clause 69. The crystalline compound of clause 68, wherein there is at least one substituent.

Clause 70. The crystalline compound of clause 69, wherein the at least one substituent is chosen from —OH, —$NH_2$, alkyl, —$NO_2$, and a carbonyl-containing moiety.

Clause 71. The crystalline compound of clause 70, wherein the at least one substituent is an organic acid moiety.

Clause 72. The crystalline compound of clause 71, wherein the organic acid is chosen from $C_1$-$C_4$ organic acid moiety.

Clause 73. The crystalline compound of clause 72, wherein the organic acid moiety is —COOH.

Clause 74. The crystalline compound of clause 70, wherein the at least one substituent is an —OH moiety.

Clause 75. The crystalline compound of clause 70, wherein the at least one substituent is chosen from ester and alkyl moieties.

Clause 76. The crystalline compound of clause 75, wherein the ester is chosen from $C_1$-$C_4$ esters.

Clause 77. The crystalline compound of any one of clauses 69-76, wherein the aromatic compound has two substituents.

Clause 78. The crystalline compound of any one of clauses 69-76, wherein the aromatic compound has three substituents.

Clause 79. The crystalline compound of any one of clauses 69-76, therein the aromatic compound has four substituents.

Clause 80. The crystalline compound of clause 77, wherein there are two substituents and each substituent is independently chosen from —OH, —$NH_2$, alkyl, organic acid, ester, and —$NO_2$ moieties.

Clause 81. The crystalline compound of clause 80, wherein a first substituent is an organic acid and a second substituent is chosen from —OH, —$NH_2$, alkyl, organic acid, ester, and —$NO_2$ moieties.

Clause 82. The crystalline compound of clause 81, wherein the second substituent is an —$NH_2$ moiety.

Clause 83. The crystalline compound of clause 80, wherein the —$NH_2$ moiety and the organic acid moiety are ortho to one another.

Clause 84. The crystalline compound of clause 80, wherein the —$NH_2$ moiety and the organic acid moiety are meta to one another.

Clause 85. The crystalline compound of clause 80, wherein the —$NH_2$ moiety and the organic acid moiety are para to one another.

Clause 86. The crystalline compound of clause 81, wherein the second substituent is an —$NO_2$ moiety.

Clause 87. The crystalline compound of clause 86, wherein the —$NO_2$ moiety and the organic acid moiety are ortho to one another.

Clause 88. The crystalline compound of clause 86, wherein the —$NO_2$ moiety and the organic acid moiety are meta to one another.

Clause 89. The crystalline compound of clause 86, wherein the —$NO_2$ moiety and the organic acid moiety are para to one another.

Clause 90. The crystalline compound of clause 81, wherein the second substituent is an —OH moiety.

Clause 91. The crystalline compound of clause 90, wherein the —OH moiety and the organic acid moiety are ortho to one another.

Clause 92. The crystalline compound of clause 90, wherein the —OH moiety and the organic acid moiety are meta to one another.

Clause 93. The crystalline compound of clause 90, wherein the —OH moiety and the organic acid moiety are para to one another.

Clause 94. The crystalline compound of clause 81, wherein the second substituent is an alkyl moiety.

Clause 95. The crystalline compound of clause 94, wherein the alkyl moiety and the organic acid moiety are ortho to one another.

Clause 96. The crystalline compound of clause 94, wherein the alkyl moiety and the organic acid moiety are meta to one another.

Clause 97. The crystalline compound of clause 94, wherein the alkyl moiety and the organic acid moiety are para to one another.

Clause 98. The crystalline compound of clause 81, wherein the second substituent is an organic acid moiety.

Clause 99. The crystalline compound of clause 98, wherein the two organic acid moieties are ortho to one another.

Clause 100. The crystalline compound of clause 98, wherein the two organic acid moieties are meta to one another.

Clause 101. The crystalline compound of clause 98, wherein the two organic acid moieties are para to one another.

Clause 102. The crystalline compound of clause 81, wherein the second substituent is an ester moiety.

Clause 103. The crystalline compound of clause 102, wherein the ester moiety and the organic acid moiety are ortho to one another.

Clause 104. The crystalline compound of clause 102, wherein the ester moiety and the organic acid moiety are meta to one another.

Clause 105. The crystalline compound of clause 102, wherein the ester moiety and the organic acid moiety are para to one another.

Clause 106. The crystalline compound of any one of clauses 77-78, wherein there are three substituents and each substituent is independently chosen from —OH, —NH$_2$, alkyl, organic acid, ester, and —NO$_2$ moieties.

Clause 107. The crystalline compound of clause 106, wherein a first substituent is an —OH moiety.

Clause 108. The crystalline compound of clause 107, wherein a second and third substituents are —OH moieties.

Clause 109. The crystalline compound of clause 106, wherein a first substituent is an organic acid moiety.

Clause 110. The crystalline compound of clause 106, wherein a second and third substituents are organic acid moieties.

Clause 111. The crystalline compound of any one of clauses 109-110, wherein the organic acid moiety is —COOH.

Clause 112. The crystalline compound of any one of clauses 77-79, wherein there are four substituents and each substituent is independently chosen from —OH, —NH$_2$, alkyl, organic acid, ester, and —NO$_2$ moieties.

Clause 113. The crystalline compound of clause 112, wherein a first substituent is an ester.

Clause 114. The crystalline compound of clause 113, wherein the ester is a methyl ester.

Clause 115. The crystalline compound of clause 113, wherein the ester is an ethyl ester.

Clause 116. The crystalline compound of any one of clauses 113-115, wherein a second substituent is an —OH moiety.

Clause 117. The crystalline compound of any one of clauses 113-115, wherein a second, a third and a fourth substituent are each an —OH moiety.

Clause 118. The crystalline compound of any one of clauses 4-5, wherein the aromatic compound is polycyclic.

Clause 119. The crystalline compound of any one of clauses 68-90, wherein the aromatic compound is polycyclic.

Clause 120. The crystalline compound of any one of clauses 118-119, wherein the polycyclic aromatic is two six-member rings.

Clause 121. The crystalline compound of any one of clauses 118-119, wherein the polycyclic aromatic is a six-member ring and a five-member ring.

Clause 122. The crystalline compound of any one of clauses 4-5, or 68-121, wherein the ring atoms of the aromatic compound are all carbon.

Clause 123. The crystalline compound of any one of clauses 4-5, or 68-121, wherein at least one ring atom is not carbon.

Clause 124. The crystalline compound of clause 123, wherein at least one ring atom is nitrogen.

Clause 125. The crystalline compound of any one of clauses 118-124 wherein there is one substituent on the polycyclic aromatic compound.

Clause 126. The crystalline compound of clause 125, wherein the substituent is chosen from $C_1$-$C_4$ organic acid moieties.

Clause 127. The crystalline compound of clause 126, wherein the organic acid moiety is a $C_2$ acid.

Clause 128. A crystalline compound comprising fasoracetam and 4-aminobenzoic acid.

Clause 129. The crystalline compound of clause 128, wherein the fasoracetam is R-fasoracetam.

Clause 130. A cocrystal of fasoracetam and 4-aminobenzoic acid.

Clause 131. A cocrystal of R-fasoracetam and 4-aminobenzoic acid.

Clause 132. The cocrystal of clause 130, wherein the stoichiometric ratio of fasoracetam to 4-aminobenzoic acid is about 1:1.

Clause 133. The cocrystal of clause 130, wherein the molar ratio of fasoracetam to 4-aminobenzoic acid in a unit cell of the cocrystal is 1:1.

Clause 134. The cocrystal of clause 131, wherein the stoichiometric ratio of R-fasoracetam to 4-aminobenzoic acid is about 1:1.

Clause 135. The cocrystal of clause 131, wherein the molar ratio of R-fasoracetam to 4-aminobenzoic acid in a unit cell of the cocrystal is 1:1.

Clause 136. The cocrystal of any one of clauses 131, or 134-135, wherein the cocrystal has an x-ray powder diffraction pattern comprising a peak at about 6.5°2θ.

Clause 137. The cocrystal of any one of clauses 131, or 134-135, wherein the cocrystal has an x-ray powder diffraction pattern comprising a peak at about 10.5°2θ.

Clause 138. The cocrystal of any one of clauses 131, or 134-135, wherein the cocrystal has an x-ray powder diffraction pattern comprising a peak at about 11.3°2θ.

Clause 139. The cocrystal of any one of clauses 131, or 134-135, wherein the cocrystal has an x-ray powder diffraction pattern comprising a peak at about 12.0°2θ.

Clause 140. The cocrystal of any one of clauses 131, or 134-135, wherein the cocrystal has an x-ray powder diffraction comprising one or more peaks chosen from peaks at about 6.5°2θ, about 10.5°2θ, about 11.3°2θ, and about 12.0°2θ.

Clause 141. The cocrystal of any one of clauses 131, or 134-135, wherein the cocrystal has an x-ray powder diffraction pattern comprising one or more peaks chosen from peaks at about 6.5°2θ, about 10.5°2θ, about 11.3°2θ, about 12.0°2θ, about 13.4°2θ, about 13.7°2θ, about 17.4°2θ, about 18.1°2θ, about 18.7°2θ, about 19.6°2θ, about 20.6°2θ, about 21.1°2θ, about 21.4°2θ, about 22.8°2θ, about 23.2°2θ, and about 23.7°2θ.

Clause 142. The cocrystal of any one of clauses 131, or 134-135, wherein the cocrystal has a melting temperature of about 114° C.

Clause 143. The cocrystal of clause 142, wherein the onset melting temperature is measured by differential scanning calorimetry.

Clause 144. The cocrystal of any one of clauses 131, or 134-135, wherein the cocrystal has an x-ray powder diffraction pattern comprising a peak at about 6.5°2θ and an onset melting temperature of about 114° C.

Clause 145. The cocrystal of any one of clauses 131, or 134-135, wherein the cocrystal has an x-ray powder diffraction pattern comprising a peak at about 10.5°2θ and an onset melting temperature of about 114° C.

Clause 146. The cocrystal of any one of clauses 131, or 134-135, wherein the cocrystal has an x-ray powder diffraction pattern comprising a peak at about 11.3°2θ and an onset melting temperature of about 114° C.

Clause 147. The cocrystal of any one of clauses 131, or 134-135, wherein the cocrystal has an x-ray powder diffraction pattern comprising a peak at about 12.0°2θ and an onset melting temperature of about 114° C.

Clause 148. The cocrystal of any one of clauses 131, or 134-135, wherein the cocrystal has an x-ray powder diffraction pattern comprising one or more peaks at 6.5°2θ, about 10.5°2θ, about 11.3°2θ, or about 12.0°2θ and has an onset melting point temperature of about 114° C.

Clause 149. The cocrystal of any one of clauses 131, or 134-135, wherein the cocrystal has an x-ray powder diffraction pattern comprising one or more peaks chosen from peaks at about 6.5°2θ, about 10.5°2θ, about 11.3°2θ, about 12.0°2θ, about 13.4°2θ, about 13.7°2θ, about 17.4°2θ, about 18.1°2θ, about 18.7°2θ, about 19.6°2θ, about 20.6°2θ, about 21.1°2θ, about 21.4°2θ, about 22.8°2θ, about 23.2°2θ, and about 23.7°2θ and has an onset melting point temperature of about 114° C.

Clause 150. The cocrystal of any one of clauses 131, or 134-135, wherein the cocrystal has an x-ray powder diffractogram substantially the same as that of FIG. 1.

Clause 151. The cocrystal of any one of clauses 131, or 134-135, wherein the differential scanning calorimetry thermogram is substantially the same as that of FIG. 4.

Clause 152. The cocrystal of clause 130, wherein the fasoracetam is S-fasoracetam.

Clause 153. A pharmaceutical composition comprising a cocrystal of fasoracetam and 4-aminobenzoic acid and one or more pharmaceutically acceptable excipients.

Clause 154. The pharmaceutical composition of clause 153, wherein the fasoracetam is R-fasoracetam.

Clause 155. The pharmaceutical composition of clause 153, wherein the pharmaceutical composition has an x-ray powder diffraction pattern peak at about 6.5°2θ.

Clause 156. The pharmaceutical composition of clause 154, wherein the x-ray powder diffraction pattern comprises one or more peaks chosen from peaks at about 6.5°2θ, about 10.5°2θ, about 11.3°2θ, about 12.0°2θ, about 13.4°2θ, about 13.7°2θ, about 17.4°2θ, about 18.1°2θ, about 18.7°2θ, about 19.6°2θ, about 20.6°2θ, about 21.1°2θ, about 21.4°2θ, about 22.8°2θ, about 23.2°2θ, and about 23.7°2θ.

Clause 157. The pharmaceutical composition of clause 154, wherein the R-fasoracetam cocrystal has an onset melting point temperature of about 114° C.

Clause 158. A crystalline compound comprising fasoracetam and trimesic acid.

Clause 159. The crystalline compound of clause 158, wherein the fasoracetam is R-fasoracetam.

Clause 160. A cocrystal of fasoracetam and trimesic acid.

Clause 161. A cocrystal of R-fasoracetam and trimesic acid.

Clause 162. The cocrystal of clause 160, wherein the stoichiometric ratio of fasoracetam to trimesic acid is about 1:1.

Clause 163. The cocrystal of clause 160, wherein the molar ratio of fasoracetam to trimesic acid in a unit cell of the cocrystal is 1:1.

Clause 164. The cocrystal of clause 161, wherein the stoichiometric ratio of R-fasoracetam to trimesic acid is about 1:1.

Clause 165. The cocrystal of clause 161, wherein the molar ratio of R-fasoracetam to trimesic acid in a unit cell of the cocrystal is 1:1.

Clause 166. The cocrystal of any one of clauses 161, or 164-165, wherein the cocrystal has an x-ray powder diffraction pattern comprising a peak at about 9.7°2θ.

Clause 167. The cocrystal of any one of clauses 161, or 164-165, wherein the cocrystal has an x-ray powder diffraction pattern comprising one or more peaks chosen from peaks at about 9.7°2θ, about 10.9°2θ, about 11.4°2θ, about 14.6°2θ, about 16.5°2θ, about 17.5°2θ, about 18.6°2θ, about 19.4°2θ, about 19.8°2θ, about 21.8°2θ, about 23.5°2θ, about 26.7°2θ, and about 27.3°2θ.

Clause 168. The cocrystal of any one of clauses 161, or 164-165, wherein the cocrystal has an onset melting temperature of about 96° C.

Clause 169. The cocrystal of clause 168, wherein the cocrystal has an x-ray powder diffraction pattern comprising one or more peaks chosen from peaks at about 9.7°2θ, about 10.9°2θ, about 11.4°2θ, about 14.6°2θ, about 16.5°2θ, about 17.5°2θ, about 18.6°2θ, about 19.4°2θ, about 19.8°2θ, about 21.8°2θ, about 23.5°2θ, about 26.7°2θ, and about 27.3°2θ.

Clause 170. The cocrystal of any one of clauses 161, or 164-165, wherein the cocrystal has substantially the same x-ray powder diffraction pattern as FIG. 51.

Clause 171. The cocrystal of any one of clauses 161, or 164-165, wherein the cocrystal has substantially the same DSC thermogram as FIG. 54.

Clause 172. A crystalline compound comprising R-fasoracetam and R-ibuprofen.

Clause 173. A cocrystal of R-fasoracetam and R-ibuprofen.

Clause 174. The cocrystal of clause 173, wherein the stoichiometric ratio of R-fasoracetam to R-ibuprofen is about 1:1.

Clause 175. The cocrystal of clause 173, wherein the molar ratio of R-fasoracetam to R-ibuprofen in a unit cell of the cocrystal is 1:1.

Clause 176. The cocrystal of any one of clauses 173-175, wherein the cocrystal has an x-ray powder diffraction pattern comprising one or more peaks chosen from peaks at about 5.6°2θ, about 10.5°2θ, about 11.2°2θ, about 12.3°2θ, about 17.4°2θ, about 20.1°2θ, and about 20.6°2θ.

Clause 177. The cocrystal of any one of clauses 173-175, wherein the cocrystal has an onset melting temperature of about 115° C.

Clause 178. The cocrystal of clause 176, wherein the cocrystal has an onset melting temperature of about 115° C.

Clause 179. The cocrystal of any one of clauses 173-175, having substantially the same x-ray powder diffraction pattern as FIG. 57.

Clause 180. The cocrystal of any one of clauses 173-175, having substantially the same DSC thermogram as FIG. 61.

Clause 181. A crystalline compound comprising fasoracetam and phloroglucinol.

Clause 182. The crystalline compound of clause 181, wherein the fasoracetam is R-fasoracetam.

Clause 183. A monohydrate cocrystal of fasoracetam and phloroglucinol.

Clause 184. A monohydrate cocrystal of R-fasoracetam and phloroglucinol.

Clause 185. The cocrystal of clause 183, wherein the stoichiometric ratio of fasoracetam to phloroglucinol to water is about 1:1:1.

Clause 186. The cocrystal of clause 183, wherein the molar ratio of fasoracetam to phloroglucinol to water in a unit cell of the cocrystal is 1:1:1.

Clause 187. The cocrystal of clause 184, wherein the stoichiometric ratio of R-fasoracetam to phloroglucinol is about 1:1.

Clause 188. The cocrystal of clause 184, wherein the molar ratio of R-fasoracetam to phloroglucinol in a unit cell of the cocrystal is 1:1.

Clause 189. The cocrystal of any one of clauses 184, or 187-188, wherein the cocrystal has an x-ray powder diffraction pattern having one or more peaks chosen from peaks at about 6.9°2θ, about 10.3°2θ, about 15.3°2θ, about 16.2°2θ, about 17.3°2θ, about 21.6°2θ, about 22.6°2θ, and about 25.3°2θ.

Clause 190. The cocrystal of any one of clauses 184, or 187-188, having an onset melting temperature of about 58° C.

Clause 191. The cocrystal of clause 189, having an onset melting temperature of about 58° C.

Clause 192. The cocrystal of any one of clauses 184, or 187-188, having substantially the same x-ray powder diffraction pattern as FIG. 72.

Clause 193. A crystalline compound comprising fasoracetam and methyl-3,4,5-trihydroxybenzoate.

Clause 194. The crystalline compound of clause 193, wherein the fasoracetam is R-fasoracetam.

Clause 195. A monohydrate cocrystal of fasoracetam and methyl-3,4,5-trihydroxybenzoate.

Clause 196. A monohydrate cocrystal of R-fasoracetam and methyl-3,4,5-trihydroxybenzoate.

Clause 197. The cocrystal of clause 195, wherein the stoichiometric ratio of fasoracetam to methyl-3,4,5-trihydroxybenzoate is about 1:1.

Clause 198. The cocrystal of clause 195, wherein the molar ratio of fasoracetam to methyl-3,4,5-trihydroxybenzoate in a unit cell of the cocrystal is 1:1.

Clause 199. The cocrystal of clause 196, wherein the stoichiometric ratio of R-fasoracetam to methyl-3,4,5-trihydroxybenzoate is about 1:1.

Clause 200. The cocrystal of clause 196, wherein the molar ratio of R-fasoracetam to methyl-3,4,5-trihydroxybenzoate in a unit cell of the cocrystal is 1:1.

Clause 201. The cocrystal of any one of clauses 196, or 199-200, wherein the cocrystal has an x-ray powder diffraction pattern comprising one or more peaks chosen from peaks at about 5.7°2θ, about 10.6°2θ, about 11.3°2θ, about 12.7°2θ, about 16.6°2θ, about 18.9°2θ, about 20.6°2θ, about 24.3°2θ, and about 25.0°2θ.

Clause 202. The cocrystal of any one of clauses 196, or 199-200, wherein the cocrystal has substantially the same x-ray powder diffraction pattern as FIG. 75.

Clause 203. A crystalline compound comprising fasoracetam and ethyl gallate.

Clause 204. The crystalline compound of clause 203, wherein the fasoracetam is R-fasoracetam.

Clause 205. A cocrystal of fasoracetam and ethyl gallate.

Clause 206. A cocrystal of R-fasoracetam and ethyl gallate.

Clause 207. The cocrystal of clause 205, wherein the stoichiometric ratio of fasoracetam to ethyl gallate is about 1:1 or about 1:2.

Clause 208. The cocrystal of clause 205, wherein the molar ratio of fasoracetam to ethyl gallate in a unit cell of the cocrystal is 1:1 or 1:2.

Clause 209. The cocrystal of clause 206, wherein the stoichiometric ratio of R-fasoracetam to ethyl gallate is about 1:1 or about 1:2.

Clause 210. The cocrystal of clause 206, wherein the molar ratio of R-fasoracetam to ethyl gallate in a unit cell of the cocrystal is 1:1 or 1:2.

Clause 211. The cocrystal of any one of clauses 206, or 209-210, wherein the cocrystal has an x-ray powder diffraction pattern comprising one or more peaks chosen from peaks at about 5.8°2θ, about 11.3°2θ, about 12.4°2θ, about 15.5°2θ, about 15.8°2θ, about 18.2°2θ, about 19.4°2θ, about 22.0°2θ, and about 24.8°2θ wherein the molar ratio of R-fasoracetam to ethyl gallate in a unit cell is 1:1 or the stoichiometric ratio of fasoracetam to ethyl gallate is about 1:1.

Clause 212. The cocrystal of clause 211, wherein the molar ratio of R-fasoracetam to ethyl gallate in a unit cell is 1:1.

Clause 213. The cocrystal of clause 211, wherein the cocrystal has an onset melting temperature of about 112° C.

Clause 214. The cocrystal of clause 212, wherein the cocrystal has an onset melting point temperature of about 112° C.

Clause 215. The cocrystal of clause 206, wherein the cocrystal has an x-ray powder diffraction pattern comprising one or more peaks chosen from peaks at about 5.8°2θ, about 7.2°2θ, about 14.8°2θ, about 20.4°2θ, about 21.9°2θ, and about 23.5°2θ wherein the molar ratio of R-fasoracetam to ethyl gallate in a unit cell of the cocrystal is 1:2.

Clause 216. The cocrystal of clause 206, wherein the cocrystal has an x-ray powder diffraction pattern comprising one or more peaks chosen from peaks at about 5.8°2θ, about 7.2°2θ, about 14.8°2θ, about 20.4°2θ, about 21.9°2θ, and about 23.5°2θ wherein the stoichiometric ratio of R-fasoracetam to ethyl gallate is about 1:2.

Clause 217. A dihydrate cocrystal wherein the stoichiometric ratio of fasoracetam to ethyl gallate is about 1:2.

Clause 218. A dihydrate cocrystal wherein the molar ratio of fasoracetam to ethyl gallate in a unit cell of the cocrystal is 1:2.

Clause 219. The dihydrate cocrystal of any one of clauses 217-218, wherein the cocrystal has an x-ray powder diffraction pattern comprising one or more peaks chosen from peaks at about 8.8°2θ, about 11.2°2θ, about 19.4°2θ, about 19.9°2θ, and about 24.1°2θ.

Clause 220. The cocrystal of any one of clauses 217-219, wherein the cocrystal has an onset melting temperature of about 106° C. as measured by DSC.

Clause 221. The cocrystal of any one of clauses 206, or 209-210, wherein the cocrystal has substantially the same x-ray powder diffraction pattern as FIG. 79.

Clause 222. The cocrystal of any one of clauses 206, or 209-210, wherein the cocrystal has substantially the same x-ray powder diffraction pattern as FIG. 86.

Clause 223. The cocrystal of any one of clauses 217-218, wherein the cocrystal has substantially the same x-ray powder diffraction pattern as FIG. 88.

Clause 224. The cocrystal of any one of clauses 217-218, wherein the fasoracetam is R-fasoracetam.

Clause 225. A crystalline compound comprising fasoracetam and phthalic acid.

Clause 226. The crystalline compound of clause 225, wherein the fasoracetam is R-fasoracetam.

Clause 227. A cocrystal of fasoracetam and phthalic acid.

Clause 228. A cocrystal of R-fasoracetam and phthalic acid.

Clause 229. The cocrystal of clause 227, wherein the stoichiometric ratio of fasoracetam to phthalic acid is about 1:1.

Clause 230. The cocrystal of clause 227, wherein the molar ratio of fasoracetam to phthalic acid in a unit cell of the cocrystal is 1:1.

Clause 231. The cocrystal of clause 228, wherein the stoichiometric ratio of R-fasoracetam to phthalic acid is about 1:1.

Clause 232. The cocrystal of clause 228, wherein the molar ratio of R-fasoracetam to phthalic acid in a unit cell of the cocrystal is 1:1.

Clause 233. The cocrystal of any one of clauses 228, or 231-232, wherein the cocrystal has an x-ray powder diffraction pattern comprising one or more peaks chosen from peaks at about 6.1°2θ, about 12.4°2θ, about 15.1°2θ, about 15.8°2θ, about 18.1°2θ, about 19.9°2θ, and about 23.3°2θ.

Clause 234. The cocrystal of any one of clauses 228, or 231-232, wherein the cocrystal has an x-ray powder diffraction pattern substantially the same as that of FIG. 64.

Clause 235. A crystalline compound comprising fasoracetam and 6-hydroxy-2-napthoic acid.

Clause 236. The crystalline compound of clause 235, wherein the fasoracetam is R-fasoracetam.

Clause 237. A cocrystal of fasoracetam and 6-hydroxy-2-napthoic acid.

Clause 238. A cocrystal of R-fasoracetam and 6-hydroxy-2-napthoic acid.

Clause 239. The cocrystal of clause 238, wherein the cocrystal has an x-ray powder diffraction pattern comprising a peak at about 11.2°2θ.

Clause 240. The cocrystal of clause 238, wherein the cocrystal has an x-ray powder diffraction pattern comprising one or more peaks chosen from peaks at about 11.2°2θ, about 14.9°2θ, about 15.7°2θ, about 20.1°2θ, about 21.1°2θ, about 23.6°2θ, about 24.1°2θ, about 25.0°2θ, and about 25.5°2θ.

Clause 241. The cocrystal of any one of clauses 238-240, wherein the cocrystal has an onset melting temperature of about 120° C.

Clause 242. The cocrystal of clauses 238 or 241, wherein the cocrystal has substantially the same x-ray powder diffraction pattern as FIG. 93.

Clause 243. The cocrystal of any one of clauses 238-240, or 242, wherein the cocrystal has substantially the same DSC thermogram as FIG. 97.

Clause 244. A crystalline compound comprising fasoracetam and 4-nitrobenzoic acid.

Clause 245. The crystalline compound of clause 244, wherein the fasoracetam is R-fasoracetam.

Clause 246. A cocrystal of fasoracetam and 4-nitrobenzoic acid.

Clause 247. A cocrystal of R-fasoracetam and 4-nitrobenzoic acid.

Clause 248. The cocrystal of clause 246, wherein the stoichiometric ratio of fasoracetam to 4-nitrobenzoic acid is about 1:2.

Clause 249. The cocrystal of clause 246, wherein the molar ratio of fasoracetam to 4-nitrobenzoic acid in a unit cell of the cocrystal is 1:2.

Clause 250. The cocrystal of clause 247, wherein the stoichiometric ratio of R-fasoracetam to 4-nitrobenzoic acid is about 1:2.

Clause 251. The cocrystal of clause 247, wherein the molar ratio of R-fasoracetam to 4-nitrobenzoic acid in a unit cell of the cocrystal is 1:2.

Clause 252. The cocrystal of any one of clauses 247, or 250-251, wherein the cocrystal has an x-ray powder diffraction pattern comprising one or more peaks chosen from peaks at about 6.5°2θ, about 6.7°2θ, about 8.9°2θ, about 14.5°2θ, about 15.6°2θ, about 17.9°2θ, about 18.6°2θ, about 19.8°2θ, about 23.4°2θ, and about 26.4°2θ.

Clause 253. The cocrystal of any one of clauses 247, or 250-251, wherein the cocrystal has an x-ray powder diffraction pattern substantially the same as FIG. 100.

Clause 254. The cocrystal of any one of clauses 247, or 250-253, wherein the cocrystal has an onset melting temperature of about 146° C.

Clause 255. The cocrystal of any one of clauses 247, or 250-253, wherein the cocrystal has a DSC thermogram substantially the same as FIG. 105.

Clause 256. A crystalline compound comprising fasoracetam and 2-indole-3-acetic acid.

Clause 257. The crystalline compound of clause 256, wherein the fasoracetam is R-fasoracetam.

Clause 258. A cocrystal of fasoracetam and 2-indole-3-acetic acid.

Clause 259. A cocrystal of R-fasoracetam and 2-indole-3-acetic acid.

Clause 260. The cocrystal of clause 259, wherein the cocrystal has an x-ray powder diffraction pattern comprising a peak at about 11.8°2θ.

Clause 261. The cocrystal of clause 259, wherein the cocrystal has an x-ray powder diffraction pattern comprising one or more peaks chosen from peaks at about 5.3°2θ, about 7.9°2θ, about 10.7°2θ, about 11.8°2θ, about 14.7°2θ, about 15.8°2θ, about 18.0°2θ, about 21.9°2θ, about 23.1°2θ, and about 23.5°2θ.

Clause 262. The cocrystal of any one of clauses 259-261, wherein the cocrystal has an onset melting temperature of about 69° C.

Clause 263. The cocrystal of clause 259, wherein the cocrystal has an x-ray powder diffraction pattern substantially the same as FIG. 107.

Clause 264. The cocrystal of any one of clauses 259-261, or 263, wherein the cocrystal has a DSC thermogram substantially the same as FIG. 111.

Clause 265. The cocrystal of clause 1, wherein the coformer is non-aromatic and contains at least one moiety selected from —$NH_2$, —$NO_2$, organic acids such as —COOH, —C(=O)—X, —C(=O)—$OR_1$, wherein $R_1$ is alkyl and X is a nitrogen containing moiety.

Clause 266. The cocrystal of clause 265, wherein $R_1$ is a $C_1$ to $C_{12}$ alkyl.

Clause 267. The cocrystal of clauses 265 or 266, wherein the non-aromatic coformer contains at least one $NH_2$.

Clause 268. The cocrystal of any one of clauses 265-267, wherein the non-aromatic coformer contains two $NH_2$ moieties.

Clause 269. The cocrystal of any one of clauses 265-268, wherein the fasoracetam is R-fasoracetam.

Clause 270. The cocrystal of clause 1, wherein the coformer is non-aromatic and contains at least one —C(O)$NR_2R_3$ moiety where $R_2$ and $R_3$ are independently selected from H, alkyl, substituted alkyl, and a $C_1$ to $C_5$ alcohol.

Clause 271. The cocrystal of clause 270, wherein the coformer contains one —C(O)$NR_2R_3$ moiety.

Clause 272. The cocrystal of any one of clauses 270-271, wherein the alkyl and the substituted alkyl each contain independently 1, 2, 3, 4, 5, 6, 7, 8, 9, 10, 11, or 12 carbons.

Clause 273. The cocrystal of clause 272, wherein the substituted alkyl is substituted with at least one of halogen or nitrile.

Clause 274. The cocrystal of clause 273, wherein the halogen is bromine.

Clause 275. The cocrystal of any one of clauses 270-274, wherein the alcohol is a $C_2$ alcohol.

Clause 276. The cocrystal of any one of clauses 270-274, wherein the alkyl is a $C_{11}$ alkyl.

Clause 277. The cocrystal of clause 1, wherein the coformer is non-aromatic and contains at least one —C(O)NX moiety where X is =N—$R_4$ where $R_4$ a carbonyl containing moiety.

Clause 278. The cocrystal of clause 277, wherein the carbonyl-containing moiety is an amide.

Clause 279. The cocrystal of any one of clauses 270-278, wherein the fasoracetam is R-fasoracetam.

Clause 280. A crystalline compound comprising fasoracetam and urea.

Clause 281. The crystalline compound of clause 280, wherein the fasoracetam is R-fasoracetam.

Clause 282. A cocrystal of fasoracetam and urea.

Clause 283. A cocrystal of R-fasoracetam and urea.

Clause 284. The cocrystal of clause 282, wherein the stoichiometric ratio of fasoracetam to urea is about 1:1.

Clause 285. The cocrystal of clause 282, wherein the molar ratio of fasoracetam to urea in a unit cell of the cocrystal is 1:1.

Clause 286. The cocrystal of clause 283, wherein the stoichiometric ratio of R-fasoracetam to urea is about 1:1.

Clause 287. The cocrystal of clause 283, wherein the molar ratio of R-fasoracetam to urea in a unit cell of the cocrystal is 1:1.

Clause 288. The cocrystal of any one of clauses 283, or 286-287, wherein the cocrystal has an x-ray powder diffraction pattern comprising a peak at about 10.4°2θ.

Clause 289. The cocrystal of any one of clauses 283, or 286-287, wherein the cocrystal has an x-ray powder diffraction pattern comprising a peak at about 14.0°2θ or about 14.1°2θ.

Clause 290. The cocrystal of any one of clauses 283, or 286-287, wherein the cocrystal has an x-ray powder diffraction pattern comprising a peak at about 10.8°2θ.

Clause 291. Form A of a cocrystal of R-fasoracetam and urea.

Clause 292. The Form A cocrystal of R-fasoracetam and urea of any one of clauses 282-290.

Clause 293. The cocrystal of clause 291, wherein the cocrystal has an x-ray powder diffraction pattern comprising a peak at about 12.2°2θ.

Clause 294. The cocrystal of clause 291, wherein the cocrystal has an x-ray powder diffraction pattern comprising a peak at about 16.1°2θ.

Clause 295. The cocrystal of clause 291, wherein the cocrystal has an x-ray powder diffraction pattern comprising a peak at about 12.2°θ and one or more peaks chosen from peaks at about 10.4°2θ, about 10.8°2θ, about 14.1°2θ, about 16.1°2θ, about 18.9°2θ, about 22.3°2θ, and about 22.9°2θ.

Clause 296. The cocrystal of clause 291, wherein the cocrystal has an x-ray powder diffraction pattern comprising a peak at about 16.1°2θ, and one or more peaks chosen from peaks at about 10.4°2θ, about 10.8°2θ, about 12.2°2θ, about 14.1°2θ, about 18.9°2θ, about 22.3°2θ, and about 22.9°2θ.

Clause 297. The cocrystal of clause 291, having an x-ray powder diffraction pattern substantially the same as that of FIG. 44.

Clause 298. The cocrystal of any one of clauses 291, or 293-297 wherein the cocrystal has a melting onset temperature of about 91° C., Clause 299. The cocrystal of clause 298, wherein the melting temperature is measured with DSC.

Clause 300. The cocrystal of clause 299, wherein the DSC thermogram of the cocrystal is substantially the same as that of FIG. 47.

Clause 301. The cocrystal of clause 282, wherein the fasoracetam is S-fasoracetam.

Clause 302. A pharmaceutical composition comprising a cocrystal of fasoracetam and urea and one or more pharmaceutically acceptable excipients.

Clause 303. The pharmaceutical composition of clause 302, wherein the fasoracetam is R-fasoracetam.

Clause 304. The pharmaceutical composition of any one of clauses 302-303, wherein the pharmaceutical composition has an x-ray powder diffraction pattern peak at about 10.4°2θ.

Clause 305. The pharmaceutical composition of any one of clauses 302-304, wherein the composition comprises a cocrystal of any one of clauses 295 or 296.

Clause 306. The pharmaceutical composition of any one of clauses 302-305, wherein the R-fasoracetam cocrystal has an onset melting point temperature of about 91° C.

Clause 307. Form B of a cocrystal of R-fasoracetam and urea.

Clause 308. The cocrystal of clause 307, wherein the stoichiometry of R-fasoracetam to urea is about 1:1.

Clause 309. The cocrystal of clause 307, wherein the molar ratio of R-fasoracetam to urea in a unit cell of the cocrystal is 1:1.

Clause 310. The cocrystal of any one of clauses 307-309, wherein the cocrystal has an x-ray powder diffraction pattern comprising a peak at about 11.4°2θ.

Clause 311. The cocrystal of any one of clauses 307-309, wherein the cocrystal has an x-ray powder diffraction pattern comprising a peak at about 17.5°2θ.

Clause 312. The cocrystal of any one of clauses 307-309, wherein the cocrystal has an x-ray powder diffraction pattern comprising at least two peaks chosen from the peaks at about 14.0°2θ, about 14.5°2θ, and about 14.9°2θ.

Clause 313. The cocrystal of any one of clauses 307-309, wherein the cocrystal has an x-ray powder diffraction pattern comprising peaks at about 14.5°2θ and about 14.9°2θ.

Clause 314. The cocrystal of any one of clauses 307-309, wherein the cocrystal has an x-ray powder diffraction pattern comprising a peak at about 14.5°2θ.

Clause 315. The cocrystal of any one of clauses 307-309, wherein the cocrystal has an x-ray powder diffraction pattern comprising a peak at about 14.9°2θ.

Clause 316. The cocrystal of any one of clauses 307-309, wherein the cocrystal has an x-ray powder diffraction pattern comprising one or more peaks chosen from the peaks at about 11.4°2θ, about 14.0°2θ, about 14.5°2θ, about 14.9°2θ, and about 17.5°2θ.

Clause 317. The cocrystal of any one of clauses 307-309, wherein the cocrystal has an x-ray powder diffraction pattern comprising a peak at about 11.4°2θ and one or more peaks chosen from the peaks at about 10.4°2θ, about 14.0°2θ, about 14.5°2θ, about 14.9°2θ, about 17.5°2θ, about 18.4°2θ, about 18.7°2θ, about 19.4°2θ, about 20.1°2θ, and about 21.1°2θ.

Clause 318. The cocrystal of any one of clauses 307-317 wherein the cocrystal has an onset melting point of about 102° C.

Clause 319. The cocrystal of clause 318, wherein the onset melting point is determined by DSC.

Clause 320. The cocrystal of any one of clauses 307-309 or 318-319 wherein the cocrystal has an x-ray powder diffraction pattern substantially the same as that of FIG. 37.

Clause 321. The cocrystal of any one of clauses 307 to 317, or 320, wherein the cocrystal has a differential scanning calorimetry thermogram substantially the same as that of FIG. 40.

Clause 322. A pharmaceutical composition comprising a Form B cocrystal of fasoracetam and urea and one or more pharmaceutically acceptable excipients.

Clause 323. The pharmaceutical composition of clause 322, wherein the fasoracetam is R-fasoracetam.

Clause 324. The pharmaceutical composition of any one of clauses 322-323, wherein the pharmaceutical composition has an x-ray powder diffraction pattern peak at about 11.4°2θ.

Clause 325. The pharmaceutical composition of any one of clauses 322-323, wherein the composition has an x-ray powder diffraction pattern comprising one or more peaks wherein the cocrystal has an x-ray powder diffraction pattern comprising a peak at about 11.4°2θ and one or more peaks chosen from the peaks at about 10.4°2θ, about 14.0°2θ, about 14.5°2θ, about 14.9°2θ, about 17.5°2θ, about 18.4°2θ, about 18.7°2θ, about 19.4°2θ, about 20.1°2θ, and about 21.1°2θ.

Clause 326. The pharmaceutical composition of any one of clauses 322-325, wherein the R-fasoracetam cocrystal has an onset melting point temperature of about 102° C.

Clause 327. A cocrystal of clause 1, wherein the coformer contains at least one carboxylic acid functionality.

Clause 328. The cocrystal of clause 327, wherein the fasoracetam forms a synthon of Formula II with a carboxylic acid functionality of the coformer.

Clause 329. The cocrystal of clause 1, wherein the coformer contains at least one functionality chosen from oxygen, nitrogen, —NH, alkyl, and —(O)COR$_5$ where R$_5$ is selected from hydrogen or alkyl, such as a C$_1$ to C$_5$ alkyl.

Clause 330. The cocrystal of clause 329, wherein the fasoracetam forms a synthon of Formula III with the coformer.

Clause 331. The cocrystal of clause 330 wherein Y is selected from oxygen, nitrogen, —NH, and —(O)COR$_5$ where R$_5$ is selected from substituted or unsubstituted alkyl, and substituted or unsubstituted aryl.

Clause 332. The cocrystal of clause 331, wherein Y is —(O)COR$_5$ where R$_5$ is substituted or unsubstituted alkyl.

Clause 333. The cocrystal of any one of clauses 7-22, 26, 30, 34, 42, 46, or 49-57, wherein the aromatic compound contains an aromatic ring fused to a non-aromatic cyclic moiety.

Clause 334. The cocrystal of clause 333, wherein the at least one non-aromatic cyclic moiety is partially saturated.

Clause 335. The cocrystal of clause 333, wherein there are at least two non-aromatic cyclic moieties.

Clause 336. The cocrystal of clause 333, wherein at least one non-aromatic cyclic moiety does not share ring atoms with the aromatic moiety.

Clause 337. A pharmaceutical composition comprising a crystalline compound of any one of clauses 4-6, 68-129, 158-159, 172, 181-182, 193-194, 203-204, 225-226, 235-236, 244-245, 256-257, or 280-281, or a cocrystal of any one of clauses 1-3, 7-67, 130-152, 160-171, 173-180, 183-192, 195-202, 205-224, 227-234, 237-243, 246-255, 258-279, 282-301, 307-321, or 327-336, and one or more pharmaceutically acceptable excipients.

Clause 338. Use of a crystalline compound of any of clauses 4-6, 68-129, 158-159, 172, 181-182, 193-194, 203-204, 225-226, 235-236, 244-245, 256-257, or 280-281, a cocrystal of any of clauses 1-3, 7-67, 130-152, 160-171, 173-180, 183-192, 195-202, 205-224, 227-234, 237-243, 246-255, 258-279, 282-301, 307-321, or 327-336, or a pharmaceutical composition of any of clauses 153-157, 302-306, 322-326, or 337, for treatment of attention-deficit hyperactive disorder in human subject in need thereof.

Clause 339. The use according to clause 338, wherein the subject has at least one copy number variation (CNV) in a metabotropic glutamate receptor (mGluR) network gene.

Clause 340. The cocrystal of any one of clauses 52-57, wherein at least one substituent is an organic acid moiety.

Clause 341. The cocrystal of clause 340, wherein the organic acid is a —COOH moiety.

Clause 342. The pharmaceutical composition according to clause 302, wherein the cocrystal of R-fasoracetam and urea is chosen from any one of clause 283-300 or 307-321.

Clause 343. A process for preparing a R-fasoracetam:urea cocrystal Form B comprising: combining R-fasoracetam in a suitable solvent with urea to form a solution wherein the molar amount of urea to R-fasoracetam ranges from about 0.7 to about 1.2; cooling the solution to form cocrystals of R-fasoracetam:urea cocrystal Form B.

Clause 344. The process of clause 343, wherein the R-fasoracetam is selected from the group consisting of R-fasoracetam Form I, R-fasoracetam Form II, he amorphous form of R-fasoracetam, anhydrate R-fasoracetam, and the Forms Mixture of R-fasoracetam.

Clause 345. The process of clause 344, wherein the R-fasoracetam is Form I.

Clause 346. The process of clause 343-345, wherein the suitable solvent is selected from ethyl acetate and isopropyl acetate.

Clause 347. The process of clause 346, wherein the suitable solvent is ethyl acetate.

Clause 348. The process of clause 345, wherein the ratio of suitable solvent to each gram of R-fasoracetam Form I ranges from about 2.5 ml to about 6 ml.

Clause 349. The process of clause 348, wherein the ratio of suitable solvent to each gram of R-fasoracetam Form I ranges from about 3.0 ml to about 5.0 ml.

Clause 350. The process of clause 348, wherein the ratio of suitable solvent to each gram of R-fasoracetam Form I ranges from about 3.8 ml to about 4.6 ml.

Clause 351. The process of clauses 348-350 wherein the suitable solvent comprises ethyl acetate.

Clause 352. The process of clauses 343-351, wherein the temperature of the solution ranges from about 10° C.-15° C.

Clause 353. The process of clauses 343-351, wherein the temperature of the solution ranges from about 15° C.-20° C.

Clause 354. The process of clauses 343-351, wherein the temperature of the solution ranges from about 20° C.-25° C.

Clause 355. The process of clauses 343-351, wherein the temperature of the solution ranges from about 25° C.-30° C.

Clause 356. The process of clauses 343-351, wherein the temperature of the solution ranges from about 30° C.-35° C.

Clause 357. The process of clauses 343-351, wherein the temperature of the solution ranges from about 35° C.-40° C.

Clause 358. The process of clauses 343-351, wherein the temperature of the solution ranges from about 40° C.-45° C.

Clause 359. The process of clauses 343-351, wherein the temperature of the solution ranges from about 45° C.-50° C.

Clause 360. The process of clauses 343-351, wherein the temperature of the solution ranges from about 50° C.-55° C.

Clause 361. The process of clauses 343-351, wherein the temperature of the solution ranges from about 55° C.-60° C.

Clause 362. The process of clauses 343-351, wherein the temperature of the solution ranges from about 60° C.-65° C.

Clause 363. The process of clauses 343-351, wherein the temperature of the solution ranges from about 65° C.-70° C.

Clause 364. The process of clauses 343-363, wherein the urea is added stepwise.

Clause 365. The process of clauses 343-363, wherein the urea is added all at once.

Clause 366. The process of clauses 343-365, wherein the molar amount of urea to R-fasoracetam is about 0.70, about 0.71, about 0.72, about 0.73, about 0.74, about 0.75, about 0.76, about 0.77, about 0.78, about 0.79, about 0.80, about 0.81, about 0.82, about 0.83, about 0.84, about 0.85, about 0.86, about 0.87, about 0.88, about 0.89, about 0.90, about 0.91, about 0.92, about 0.93, about 0.94, about 0.95, about 0.96, about 0.97, about 0.98, about 0.99, about 1.0, about 1.1, or about 1.2.

Clause 367. The process of clauses 343-365, wherein the molar amount of urea to R-fasoracetam ranges from about 0.95 to about 1.0.

Clause 368. The process of clauses 343-367, wherein seeds of a cocrystal of R-fasoracetam:urea cocrystal Form B is added to the solution.

Clause 369. The process of clauses 343-368, wherein resulting cocrystal of R-fasoracetam:urea cocrystal Form B is washed after cooling.

Clause 370. The process of claim 343-369, wherein the resulting cocrystal of R-fasoracetam:urea cocrystal Form B is dried.

Clause 371. An R-fasoracetam:urea cocrystal Form B produced by the process of any of clauses 343-370.

EXAMPLES

Instrument Settings

Two X-ray powder diffraction (XRPD) devices were used to analyze the samples reported herein. Some samples were measured with a Siemens D5000 diffractometer equipped with a Cu X-ray source operating at 40 kV and 40 mA and a secondary monochromator allowing to select the Kα radiation of Cu ($\lambda$=1.5418 Å). A scanning range of 2θ values from 2° to 50°.

Other samples were analyzed with a PANalytical Bragg-Brentano-geometry diffractometer, using Ni-filtered Cu Kα radiation ($\lambda$=1.54179 Å) at 40 kV and 40 mA with a X'Celerator detector. On this instrument, samples were analyzed between 4 and 50° in 2θ.

Peak picking was performed using the WinPLOTR tool available in the commercially available crystallographic tool software known as "FullProf Suite." Most peak picking was performed using the automatic peak search option with its predefined defaults while some peaks were selected manually.

DSC measurements were performed on a DSC 821 METTLER TOLEDO under continuous nitrogen flow. Perforated aluminium crucibles were used for analysis. Onsets were determined by manually constructing a tangent to the peak and a prolongation of the baseline. Total enthalpies were calculated by manual peak integration using a linear interpolation between the initial and final temperatures of integration. To obtain the normalized enthalpy, the total enthalpy was divided by the total sample mass. Ramp rates were typically done at 5° C./minute TGA measurements were carried out on a METTLER TOLEDO TGA/SDTA 851e. Samples were placed in open aluminum oxide crucible. All experiments were performed under nitrogen flow.

$^1$H-NMR spectra were recorded on Bruker-300. $^1$H-NMR chemical shifts are reported relative to $(CD_3)_2SO$ (2.5 ppm) or $CD_3OD$ (3.3 ppm). Single crystal X-ray diffraction was performed on a MAR345 detector using monochromated Mo Kα radiation ($\lambda$=0.71073 Å)(Xenocs Fox3D mirror) produced by a Rigaku UltraX 18 generator or on an Oxford Diffraction Xcalibur, Ruby, Gemini ultra diffractometer using monochromated Cu Kα radiation ($\lambda$=1.54184 Å). The data images were integrated by CrysAlisPRO and the implemented multiscan absorption applied. In some cases, an analytical numeric absorption correction was also applied. The structures were solved with SHELXT and then refined on $|F^2|$ using SHELXL-2014/7 or SHELXL-2018/1. Non-hydrogen atoms were anisotropically refined. Hydrogen atoms were typically placed in the riding mode with isotropic temperature factors fixed at 1.2 times U(eq) of the parent atoms (1.5 times for methyl groups). In some cases, hydrogens involved in hydrogen bonds were refined freely, with isotropic temperature factors fixed at 1.2 or 1.5 times U(eq) of the parent atoms. Simulated XRPD patterns were calculated from the single crystal structures using the Mercury 3.3 program.

Cocrystal Screening

R-fasoracetam was screened against over 60 potential coformers. Screening was done by dry grinding. Typically, unless otherwise provided for herein, equimolar mixture of R-fasoracetam monohydrate Form I (which is commercially available) and the appropriate amount of coformer were ground in a RETSCH Mixer Mill MM 400 for 90 min with a beating frequency of 30 Hz and using stainless steel grinding beads. The resulting powders were characterized using XRPD. A common sample size was about 30 mg of R-fasoracetam monohydrate Form I. Cocrystal formation was verified by comparing the resulting XRPD pattern with that of R-fasoracetam monohydrate Form I and the coformer. In most cases, cocrystals did not result. Where cocrystals did form, further investigations were done to analyze the cocrystals.

Example 1—Preparation of a Cocrystal of PABA and R-Fasoracetam (Slurrying)

A PABA:R-fasoracetam 1:1 cocrystal was prepared as follows. To 15 ml of ethyl acetate were added 5.03 g of R-fasoracetam monohydrate Form I which was sourced from Jinan Haouhua Co., Ltd. and 1 equivalent of 4-aminobenzoic acid (3.21 g) at 25° C. in a closed 50 ml round bottom flask. The suspension was left to stir for 4 days under magnetic stirring. After day one, the slurry was seeded with a cocrystal of R-fasoracetam-PABA prepared in accordance with Example 2, and again after 3 days. The suspension was filtered after day 4 and washed 10 times with 1 mL of ethyl acetate that was previously cooled to −15° C. The resulting cocrystal powder was left to dry on the filter. 5.63 g of material was recovered and analyzed by single-crystal x-ray diffraction, x-ray powder diffraction, solution-state $^1$H-NMR, DSC, and TGA.

The XRPD pattern of the cocrystal is provided in FIG. 1. FIG. 2 is an XRPD pattern of PABA. The PABA was sourced from Acros Organics. FIG. 3 is a solution-state $^1$H-NMR spectrum of the cocrystal. The spectrum shows a 1:1 ratio of R-fasoracetam and PABA and the protons are accounted for in the spectrum.

Figure 5:
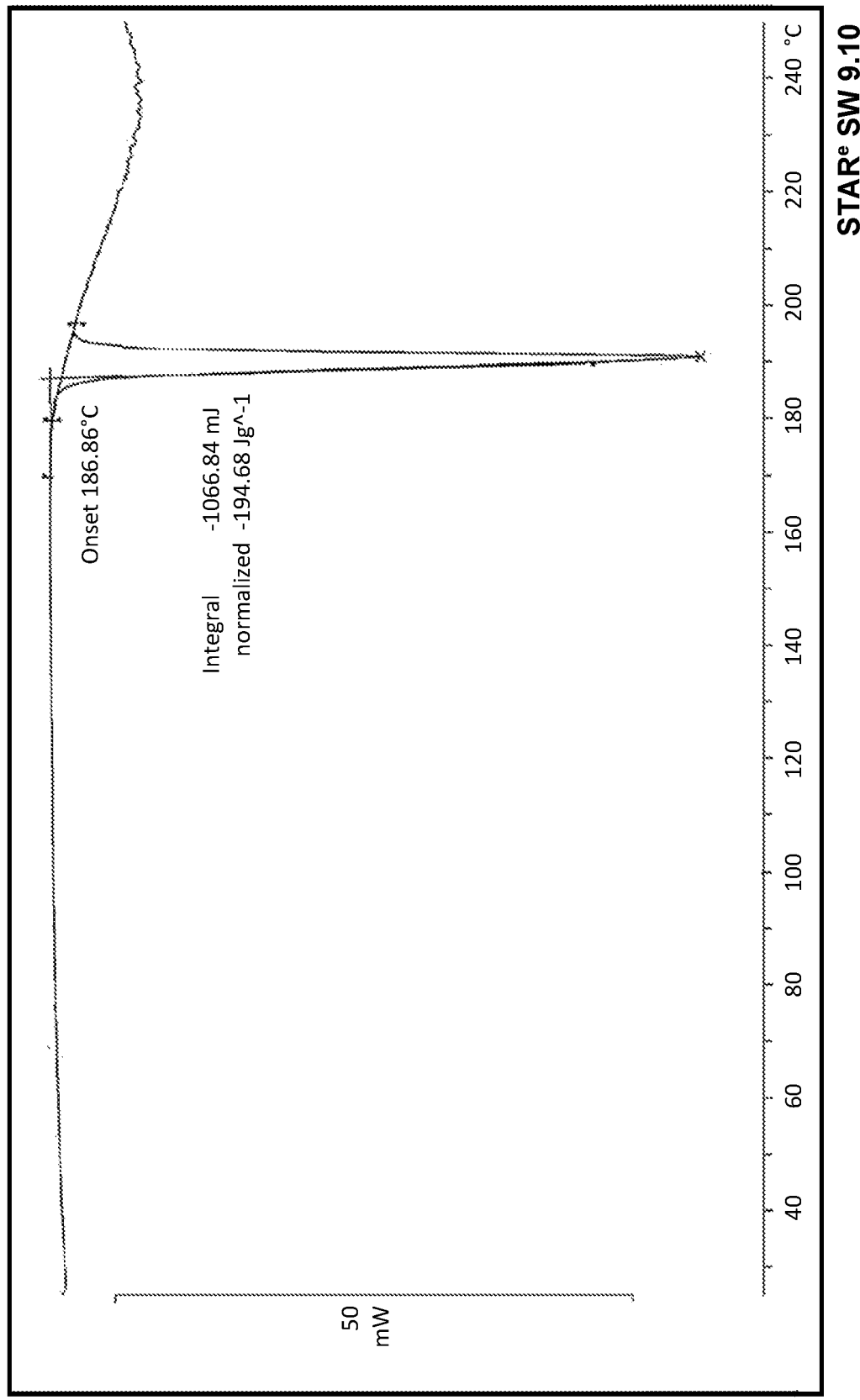
FIG. 5 is a DSC thermogram of PABA.

FIG. 4 is a DSC thermogram of the cocrystal. The sample was equilibrated at 25.0° C. for ten minutes prior to ramping. The ramp heating rate was 1° C. per minute and had an onset of 113.73° C. FIG. 5 is the DSC thermogram of PABA.

Figure 6:
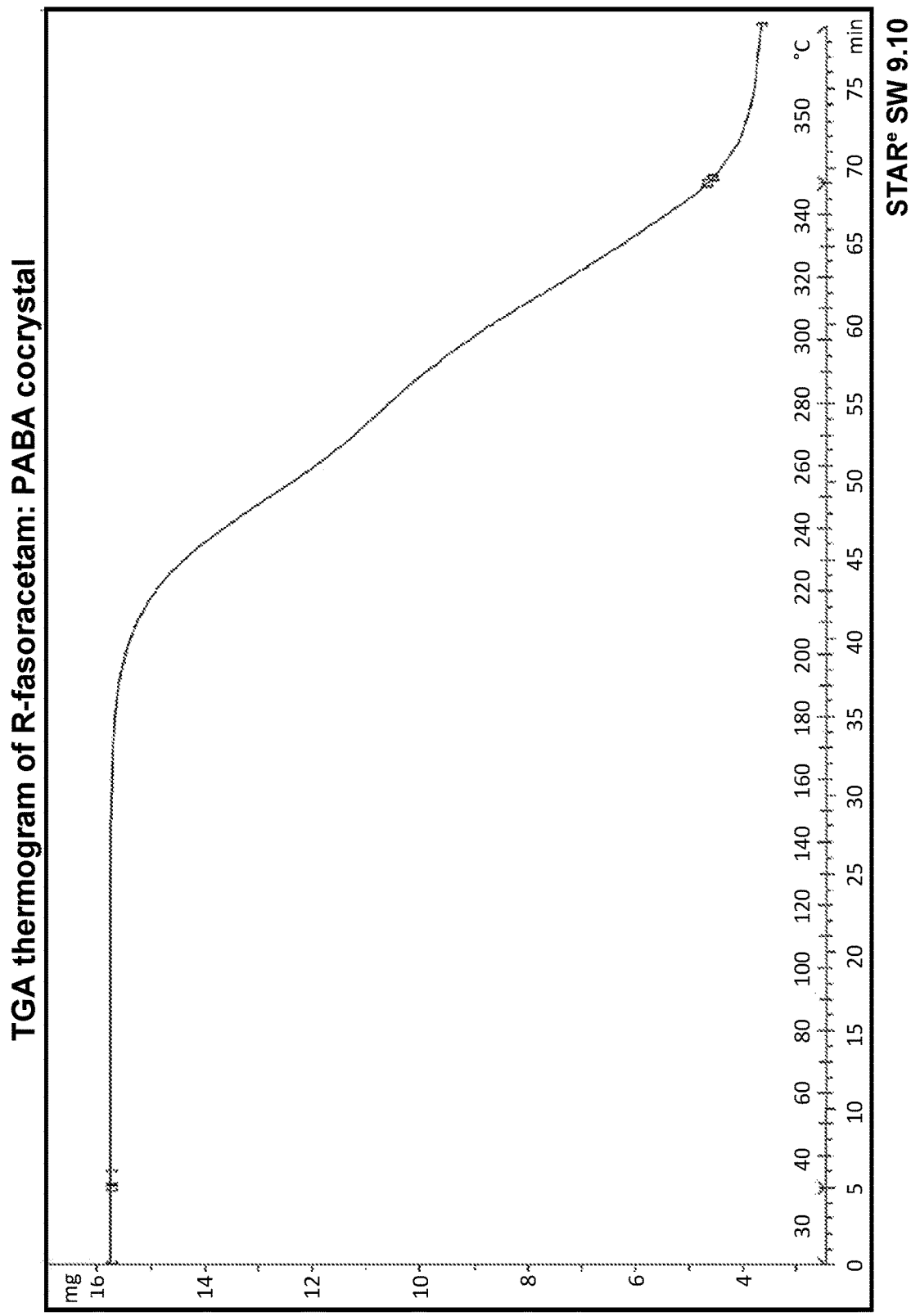
FIG. 6 is a TGA thermogram of R-fasoracetam:PABA cocrystal.

A TGA plot can be found at FIG. 6. The sample was equilibrated at 30.0° C. for five minutes prior to ramping. A heating rate of 5° C. per minute was used from 30.0° C. to 350.0° C. No significant weight loss was observed until temperatures greater than 180° C. were recorded.

Figure 8:
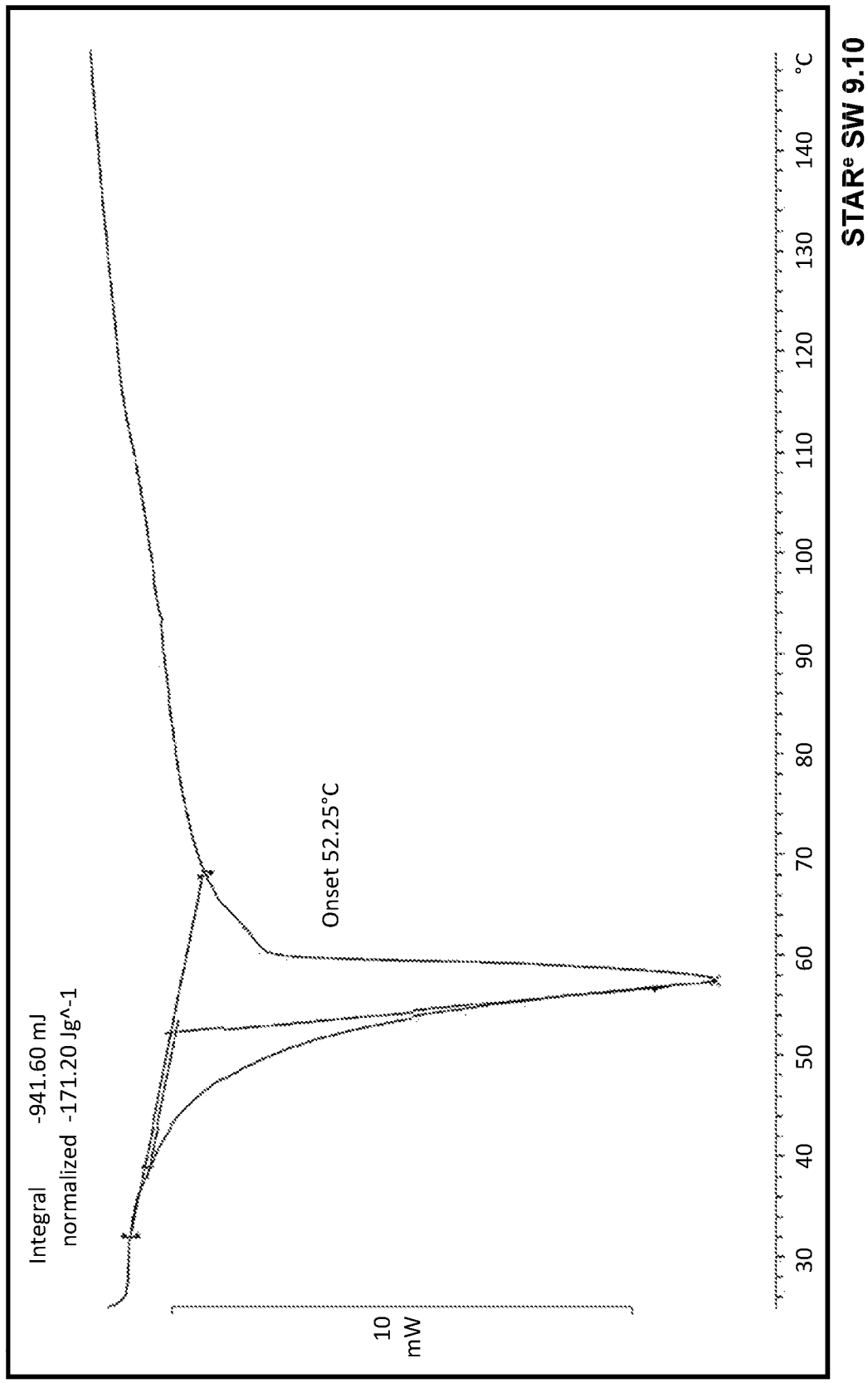
FIG. 8 is a DSC thermogram of R-fasoracetam monohydrate Form I.
Figure 9:
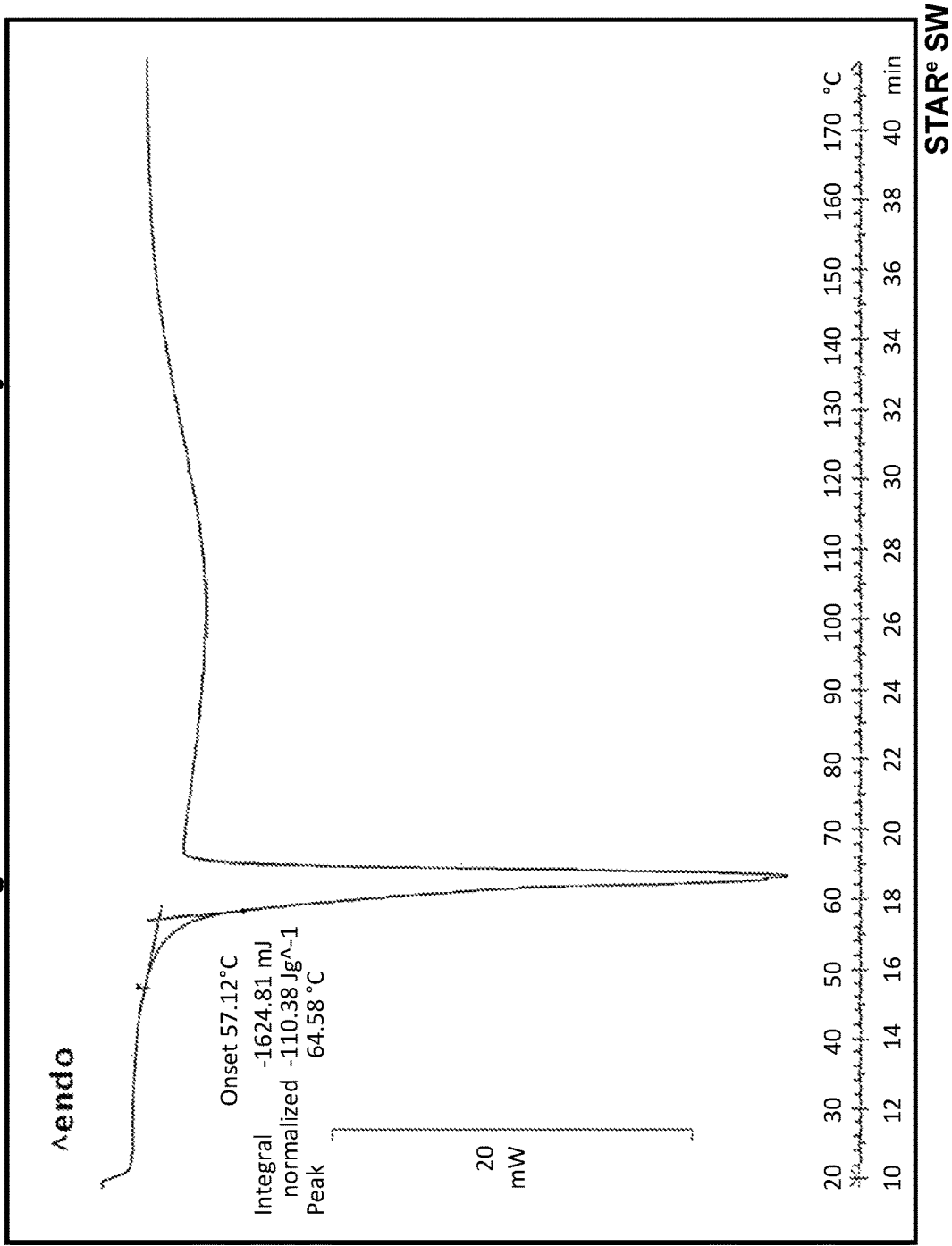
FIG. 9 is a DSC thermogram of R-fasoracetam monohydrate Form I.

FIG. 7 is the x-ray powder diffraction of the R-fasoracetam monohydrate Form I starting material used in this Example 1, and FIG. 8 is the corresponding DSC thermogram of that starting material. A solubility curve was constructed for the cocrystal in ethyl acetate with the results plotted in FIG. 10 (from the data collected in Example 1) using a Crystal16 device from Technobis Crystallization Systems. The samples were created from the cocrystal without adding any additional water or other constituents. The samples were heated at a rate of 1°/15 minutes.

Example 2—Preparation of a Cocrystal of PABA and R-Fasoracetam (Seed)

An equimolar mixture of R-fasoracetam monohydrate Form I (30.63 mg) sourced from Jinan Haohua Industry Co., Ltd. and PABA (21.48 mg) was ground in a RETSCH Mixer Mill MM 400 for 90 min with a beating frequency of 30 Hz and using stainless steel grinding beads. The resulting ground mixture was characterized using x-ray powder diffraction and a diffractogram of the cocrystal seed can be found in FIG. 11.

Figure 12:
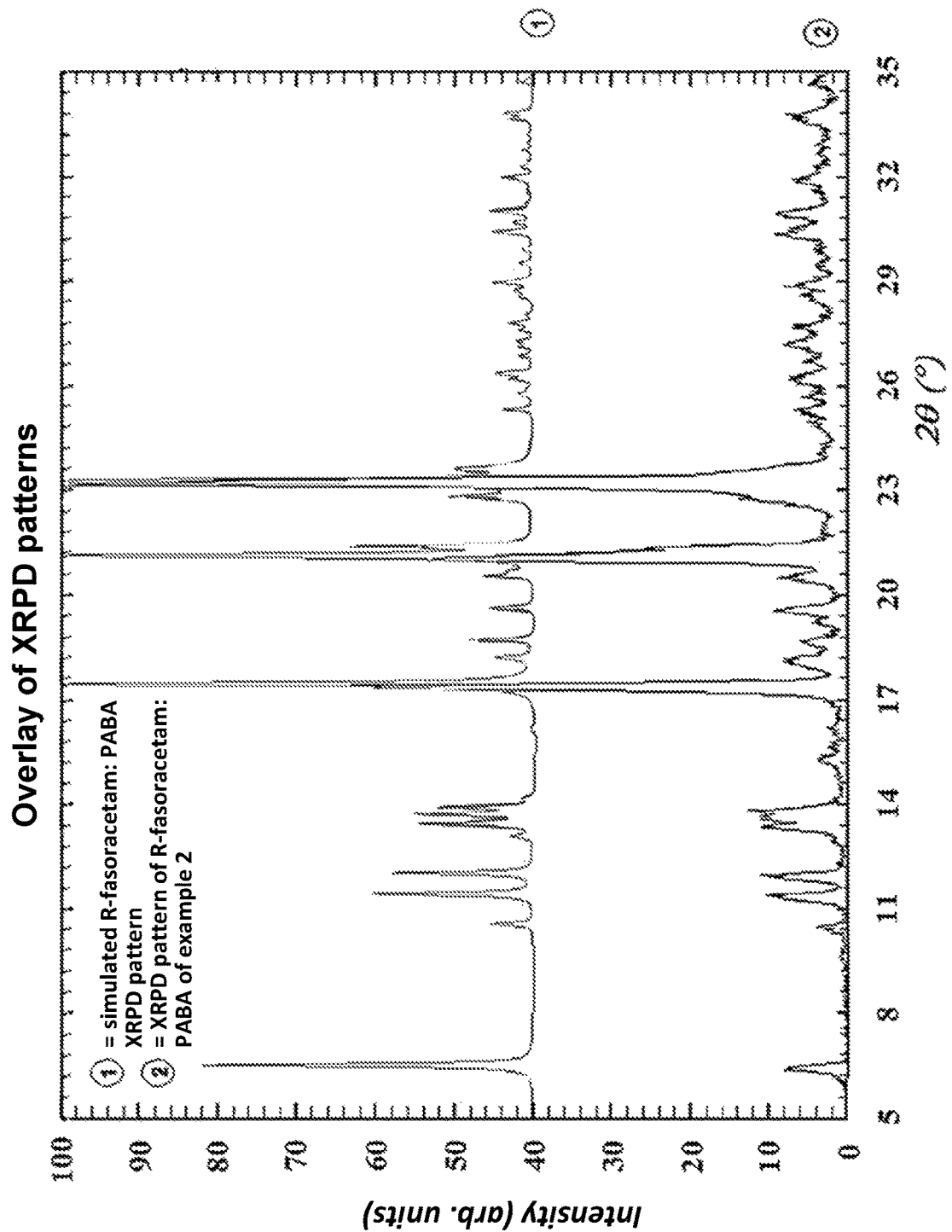
FIG. 12 is an overlay of XRPD patterns: (1) simulated R-fasoractam:PABA XRPD pattern; (2) XRPD pattern of R-fasoractam:PABA of Example 2.
Figure 14:
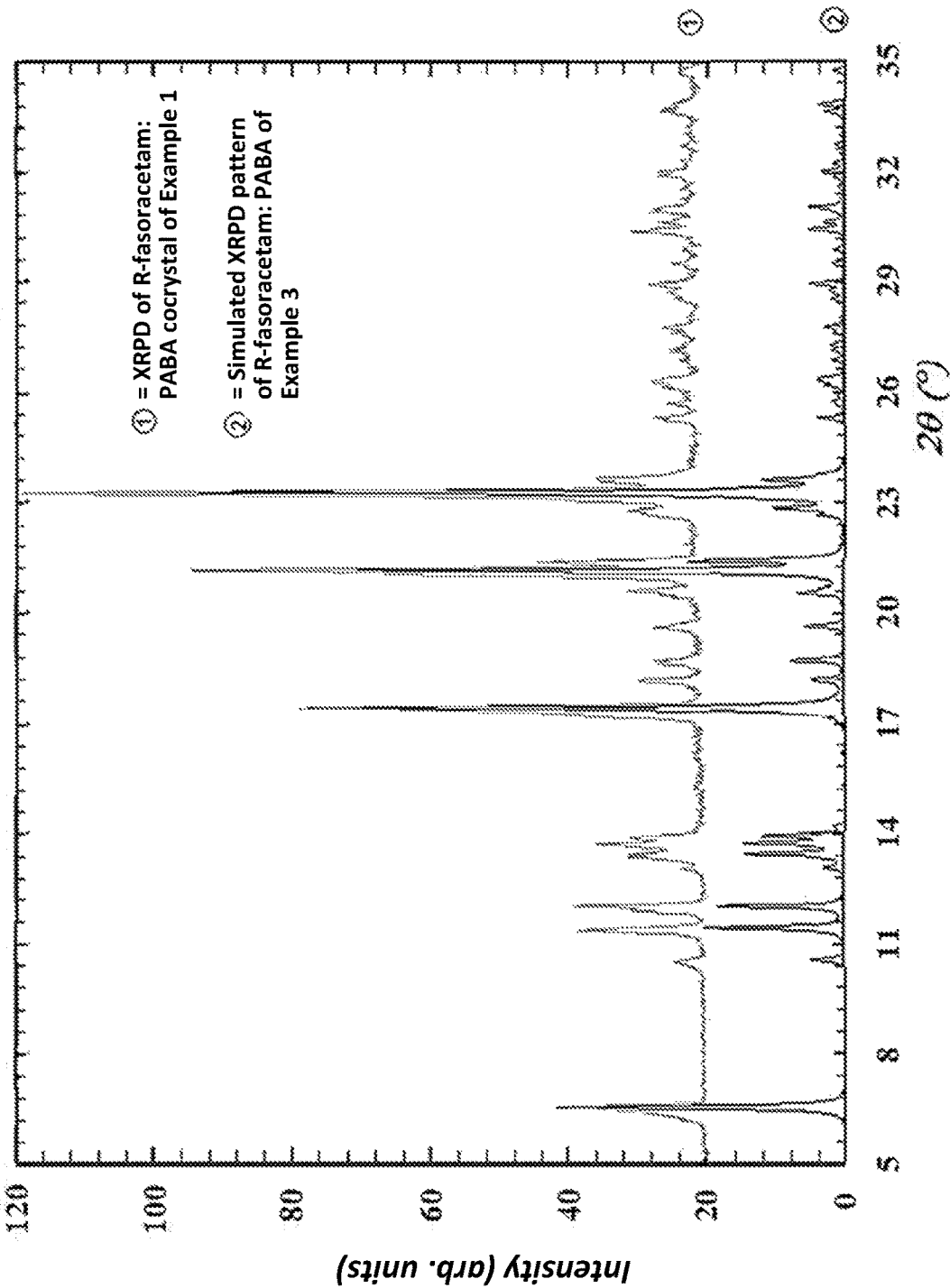
FIG. 14 is an overlay of XRPD Patterns of R-fasoracetam: PABA cocrystal: (1) XRPO of R-fasoracetam: PABA cocrytal of Example 1; (2) Simulated XRPO pattern of R-fasoracetam: PABA cocrystal of Example 3.
Figure 15:
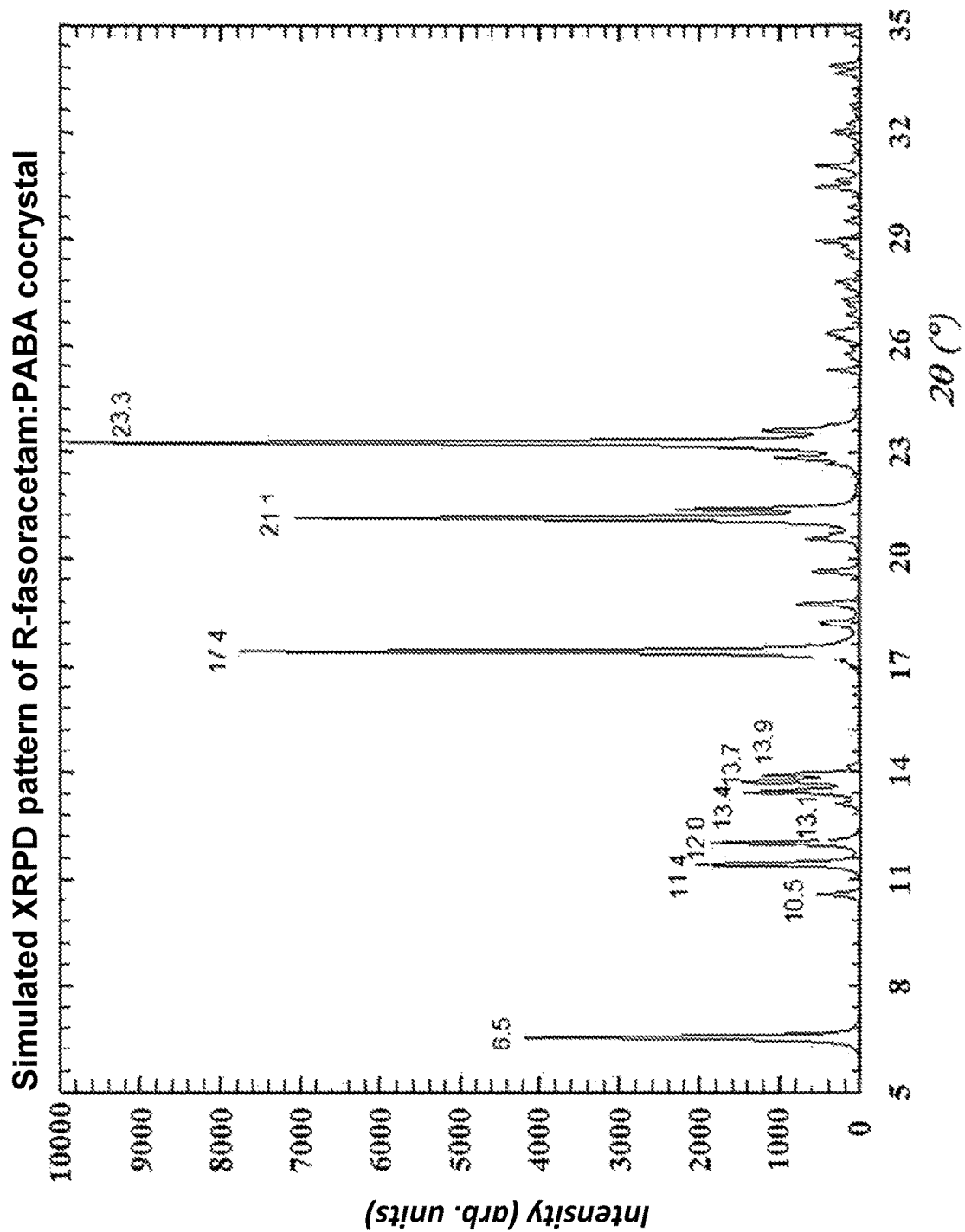
FIG. 15 is a simulated XRPD pattern of R-fasoracetam: PABA cocrystal.

Example 3—Preparation of Cocrystal of PABA and R-Fasoracetam (1:1) for Single Crystal Analysis The single crystal was obtained by dissolving a stoichiometric amount of both PABA (20.98 mg) and R-fasoracetam monohydrate Form I from Jinan Haohua Industry Co., Ltd. (30 mg) in ethyl acetate and then slowly evaporating the solution at room temperature to yield a crystalline material which was analyzed and found to be a 1:1 cocrystal of PABA to R-fasoracetam. The resulting solution can be visualized as an ORTEP drawing in FIG. 13. In addition, Table 4, provides the single crystal solution parameters. A simulated x-ray powder pattern was prepared from the single-crystal data and compared with the experimentally obtained powder pattern and is shown in FIG. 14 as an overlay with the x-ray powder diffraction pattern of Example 1. FIG. 12 is an overlay of the simulated x-ray powder diffraction pattern with that obtained from Example 2. FIG. 15 is the simulated x-ray powder diffraction pattern of the 1:1 R-fasoracetam to PABA cocrystal.

TABLE 4

Crystal data and structure refinement for R-fasoracetam:PABA (1:1) cocrystal

| PARAMETER | RESULTS |
|---|---|
| Empirical formula | C17 H23 N3 O4 |
| Formula weight | 333.38 |
| Temperature | 297(2) K |
| Wavelength | 0.71073 Å |
| Crystal system | Triclinic |
| Space group | P1 |
| Unit cell dimensions | a = 7.6800(5) Å    α = 78.99(2)°. |
|  | b = 8.860(3) Å     β = 84.706(15)°. |
|  | c = 13.806(3) Å    γ = 73.82(2)°. |

TABLE 4-continued

Crystal data and structure refinement for R-fasoracetam:PABA (1:1) cocrystal

| PARAMETER | RESULTS |
|---|---|
| Volume | 884.9(4) Å$^3$ |
| Z | 2 |
| Density (calculated) | 1.251 Mg/m$^3$ |
| Absorption coefficient | 0.090 mm$^{-1}$ |
| F(000) | 365 |
| Crystal size | 0.50 × 0.30 × 0.25 mm$^3$ |
| Theta range for data collection | 3.258 to 25.270°. |
| Index ranges | −9 <= h <= 9, −10 <= k <= 10, −16 <= l <= 16 |
| Reflections collected | 11317 |
| Independent reflections | 6022 [R(int) = 0.0208] |
| Completeness to theta = 25.242° | 98.6% |
| Absorption correction | Semi-empirical from equivalents |
| Max. and min. transmission | 1.00000 and 0.96726 |
| Refinement method | Full-matrix least-squares on F$^2$ |
| Data/restraints/parameters | 6022/56/514 |
| Goodness-of-fit on F$^2$ | 1.087 |
| Final R indices [I > 2sigma(I)] | R1 = 0.0401, wR2 = 0.1085 |
| R indices (all data) | R1 = 0.0435, wR2 = 0.1110 |
| Absolute structure parameter | 0.3(4) |
| Extinction coefficient | n/a |
| Largest diff. peak and hole | 0.134 and −0.094 e · Å$^{-3}$ |

Example 4—Preparation of R-Fasoracetam Monohydrate Form II

Figure 16:
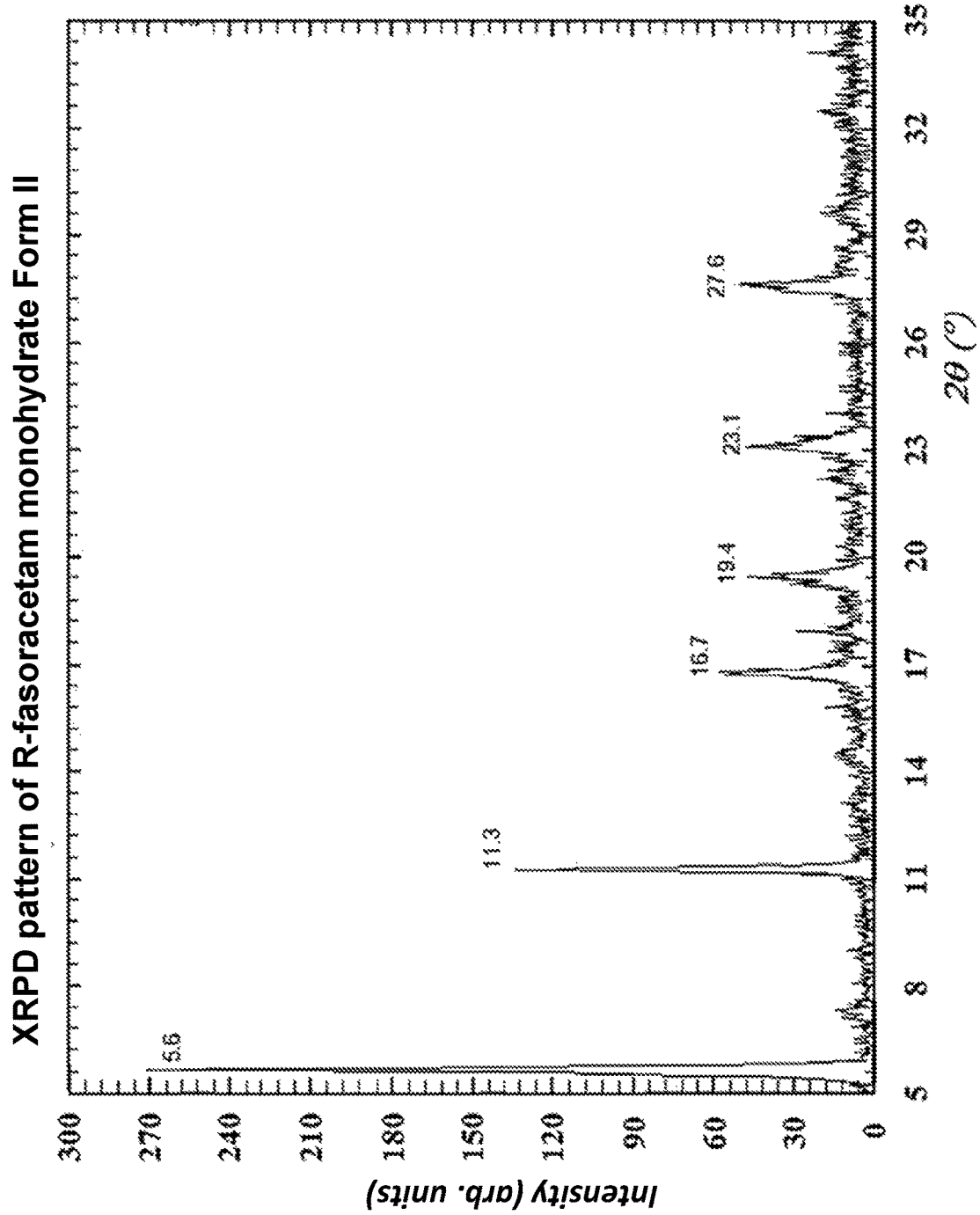
FIG. 16 is an XRPD pattern of R-fasoracetam monohydrate Form II.
Figure 17:
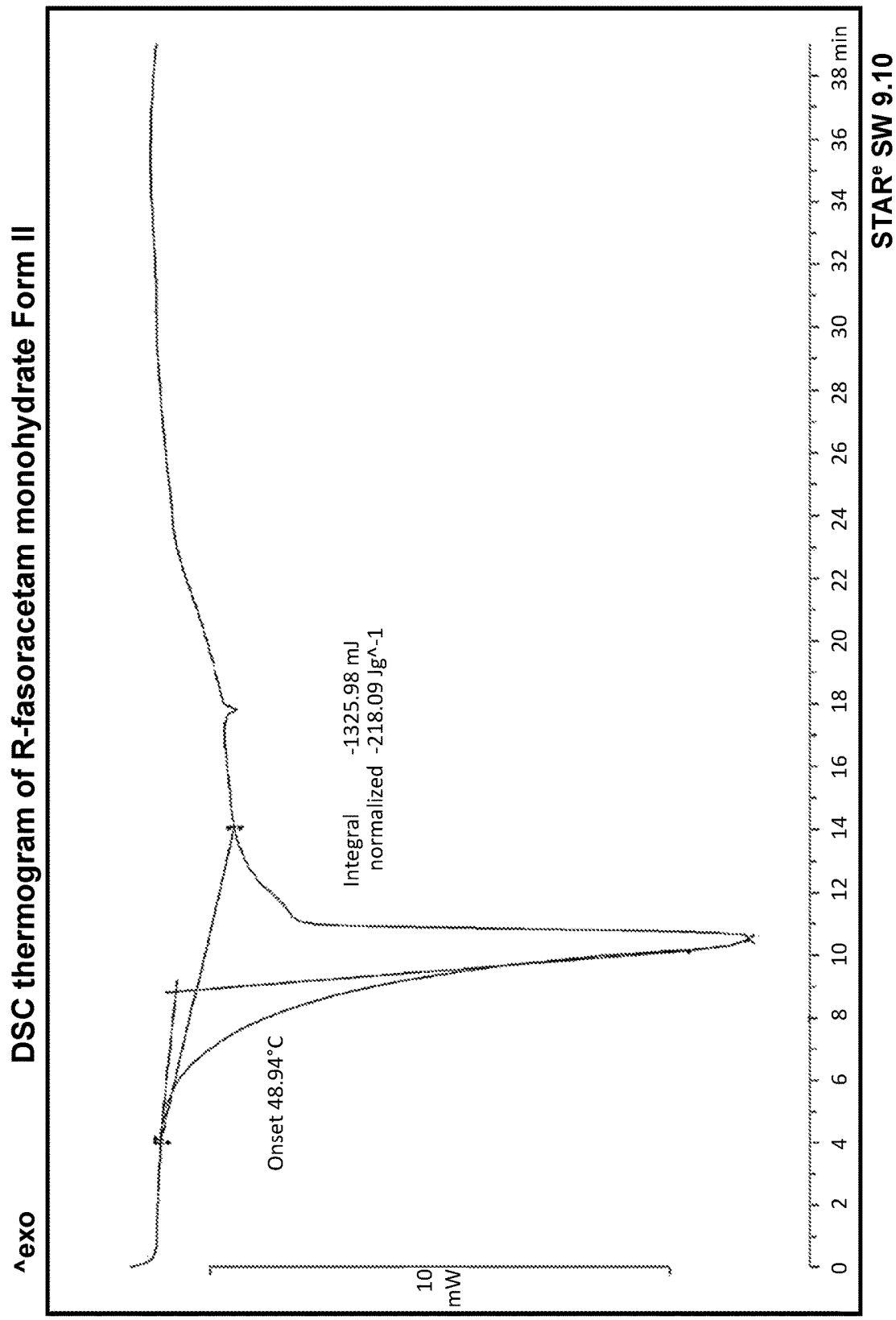
FIG. 17 is a DSC thermogram of R-fasoracetam monohydrate Form II.

R-fasoracetam monohydrate Form II was obtained by adding water to 50.69 mg of R-fasoracetam monohydrate Form I (from Aevi Genomic Medicine) until total dissolution occurred. The solution was then left to evaporate at room temperature for 21 days after which a crystalline powder was obtained, for which the powder pattern is shown in FIG. 16, which is R-fasoracetam monohydrate Form II. FIG. 17 is a DSC thermogram of R-fasoracetam monohydrate Form II.

Example 5—Preparation of R-Fasoracetam Anhydrate

R-fasoracetam monohydrate Form I was sourced from Jinan Haohua Industry Co., Ltd. and was placed in a round bottom flask and rotavapped for 30 min at 65° C. Melting was observed followed by recrystallization. The x-ray powder diffraction pattern of the resulting solid of the dried sample shows a R-Fasoracetam Forms Mixture. FIG. 18 shows an overlay of diffraction patterns of the R-Fasoracetam Forms Mixture based on the simulated patterns from single crystal solutions of the component R-fasoracetam forms compared with the experimental diffraction pattern of the R-Fasoracetam Forms Mixture.

Figure 19:
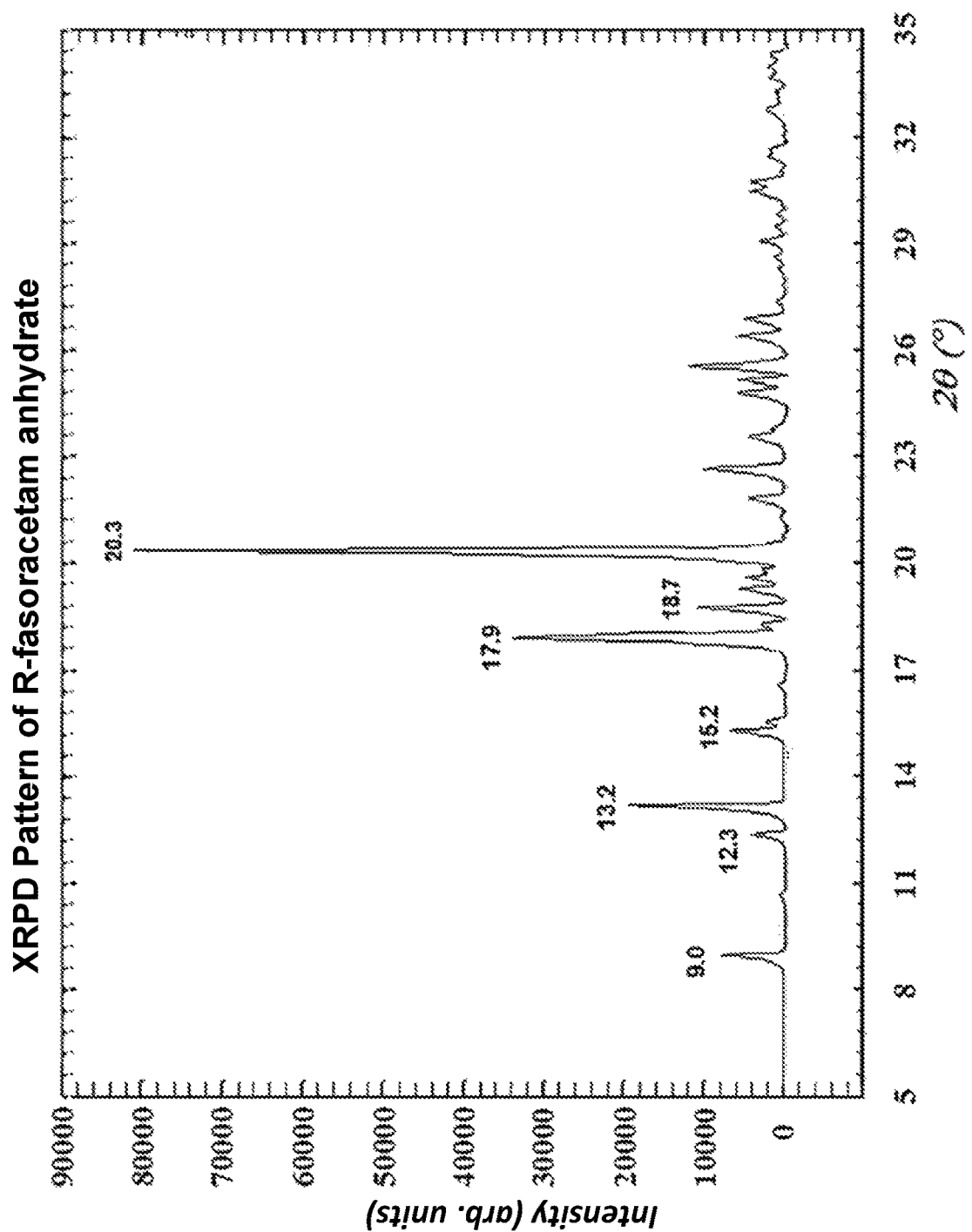
FIG. 19 is an XRPD pattern of R-fasoracetam anhydrate.

To measure the x-ray powder diffractogram of R-fasoracetam anhydrate, the mixture was placed at 80° C. At that temperature, only the pattern of the anhydrate remains, as shown in FIG. 19. FIG. 20 is a DSC thermogram of the mixture of R-fasoracetam monohydrate Form I, R-fasoracetam monohydrate Form II, and R-fasoracetam anhydrate. The thermogram shows an onset temperature of about 93.5° C. The DSC exhibits an additional endotherm onset at about 55° C. which is likely due to the presence R-fasoracetam monohydrate Form I and/or R-fasoracetam monohydrate Form II.

Figure 22:
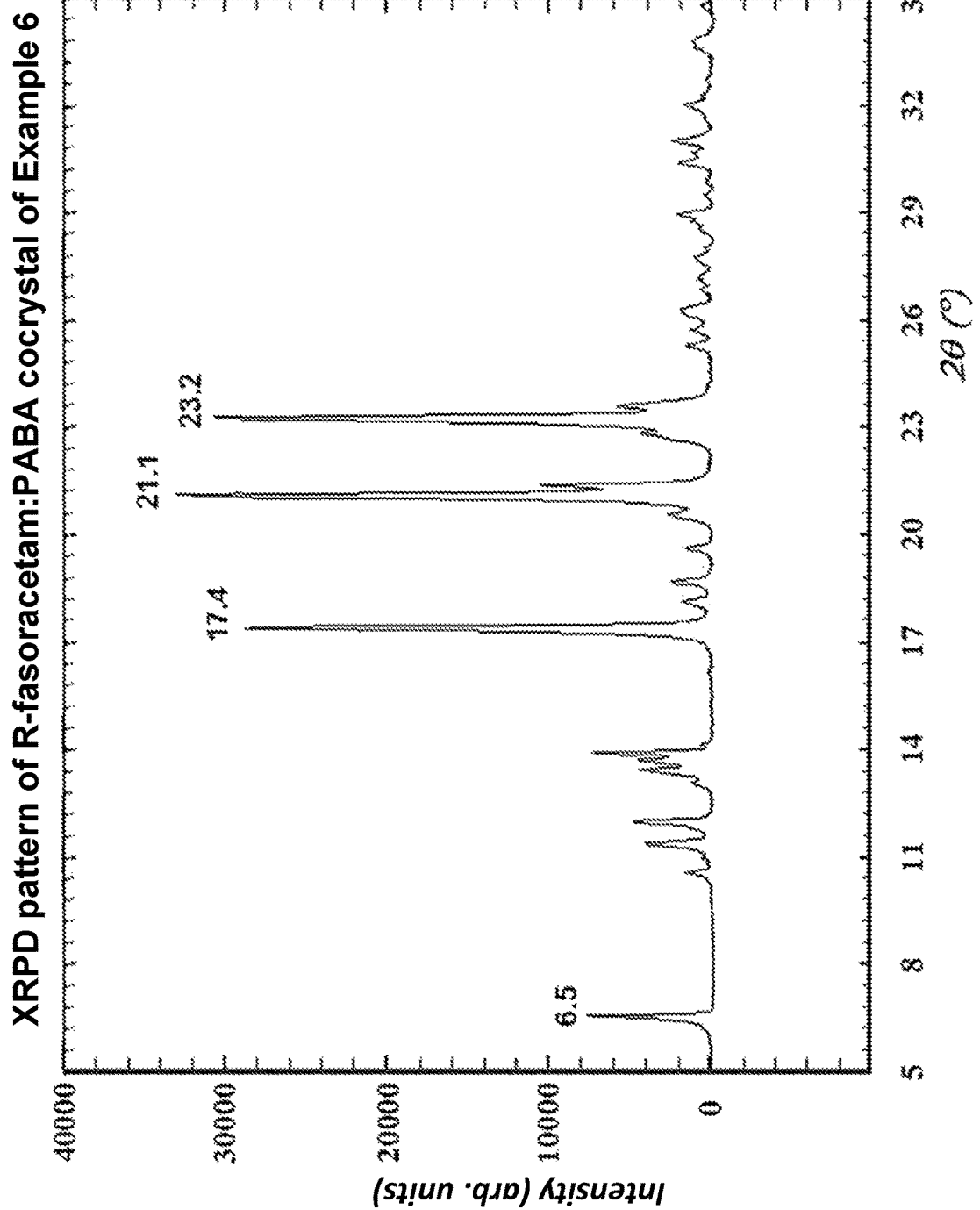
FIG. 22 is an XRPD pattern of R-fasoracetam:PABA cocrystal of Example 6.

Example 6—Scale-Up Preparation of R-Fasoracetam-PABA Cocrystal with R-Fasoracetam Forms Mixture A Mettler Easymax system was used, with a 100 ml reactor with a temperature probe in solution. 19.63 g (0.10 mol, 1 eq.) of a mixture of R-fasoracetam monohydrate Form I (Aevi Genomic Medicine), R-fasoracetam monohydrate Form II, and R-fasoracetam anhydrate (prepared according to the procedure of Example 11) and 75 ml of ethyl acetate were added to the reactor. The stirring was activated at 400 rpm. The reactor was heated to 60° C. The clear solution was left for 30 minutes at 60° C. After the solution was cooled to 25° C. in 30 minutes. At this stage, all fasoracetam remained in solution. Once the 25° C. temperature was reached, 4-Aminobenzoic acid (13.72 g, 0.10 mmol, 1 eq.) was added. The solution took a slight orange color and part of the solid did not dissolve. After 5 minutes, a densification of the solid phase appeared. 30 minutes after addition of 4-aminobenzoic acid, 50.24 mg of R-fasoracetam-PABA seed crystal was added. The seed crystal was prepared by grinding 69.86 mg of R-fasoracetam monohydrate Form I (delivered by Aevi Genomic Medicine) with 44.97 mg of PABA and 3 stainless steel grinding beads at a frequency of 30 Hz for 90 minutes using a Retsch MM400. After seeding, the mixture was left for another 1 hour at 25° C. The mixture was then cooled down to 10° C. with a ramp of 0.3° C./min. The mixture was left at 10° C. for 1 hour, after which it was filtered and the filtrate washed 2 times with 25 ml of cold EtOAc (3° C.). The solid was left to dry for 48 h at room temperature. A mass of 29.84 g was recovered corresponding to a yield of 89%. FIG. 22 is the experimental XRPD pattern of the thus obtained cocrystal and FIG. 23 is an overlay of the experimental pattern and that of the simulated pattern from the single crystal data.

Figure 24:
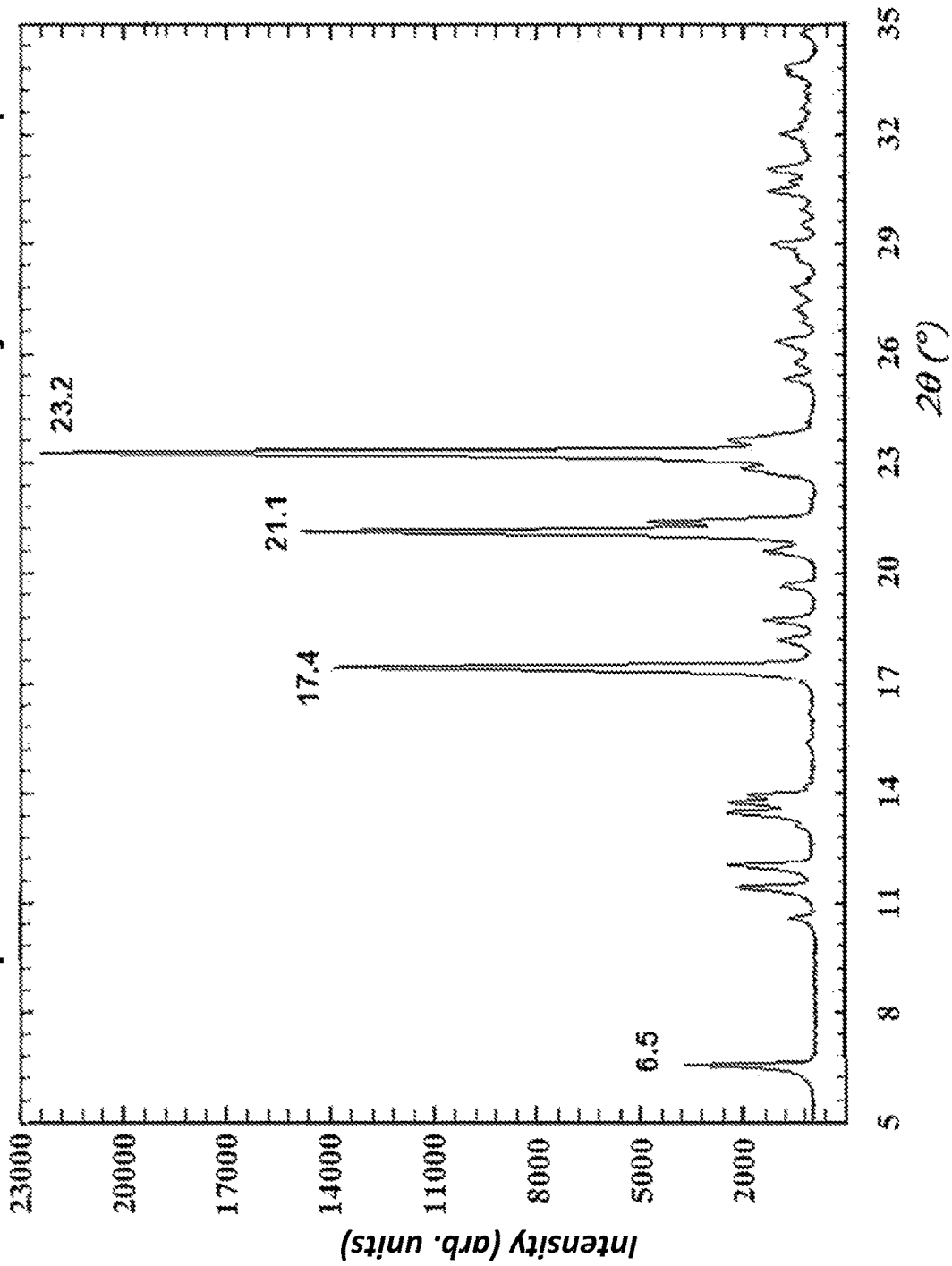
FIG. 24 is an XRPD pattern of R-fasoracetam:PABA cocrystal of Example 7.

Example 7—Scale-Up Preparation of Fasoracetam-PABA Cocrystal with R-Fasoracetam Monohydrate Form I A Mettler Easymax system was used, with a 100 ml reactor with a temperature probe in solution. R-fasoracetam monohydrate Form I (Aevi Genomic Medicine) (9.64 g, 0.045 mol, 1 eq.) and PABA (6.21 g, 0.045 mol, 1 eq.) and 75 ml of ethyl acetate were added to the reactor. The stirring was activated at 400 rpm. The reactor was heated to 70° C. The clear solution was left for 30 min at 70° C. After the solution was cooled to 54° C. in 15 minutes. At this stage, all compounds remained in solution. After 5 minutes at 54° C. 50.34 mg of R-fasoracetam-PABA seed crystal was added. The seed crystal was prepared by grinding 70.77 mg of R-fasoracetam monohydrate Form I (delivered by Aevi Genomic Medicine) with 44.98 mg of PABA and 3 stainless steel grinding beads at a frequency of 30 Hz for 90 minutes using a Retsch MM400. After seeding, the mixture was left for 2 hours at 54° C. The mixture was then cooled down to 10° C. with a ramp of 0.3° C./min. The mixture was left at 10° C. for 1 h, after which it was filtered and the filtrate washed 2 times with 25 ml of cold EtOAc (3° C.). The solid was left to dry for 48 h at room temperature. A mass of 11.18 g was recovered corresponding to a yield of 74%. FIG. 24 is the experimental XRPD pattern of the thus obtained cocrystal and FIG. 25 is an overlay of the experimental pattern and that of the simulated pattern from the single crystal data.

Example 8—Single Crystal Preparation of R-Fasoracetam Monohydrate Form II

Figure 26:
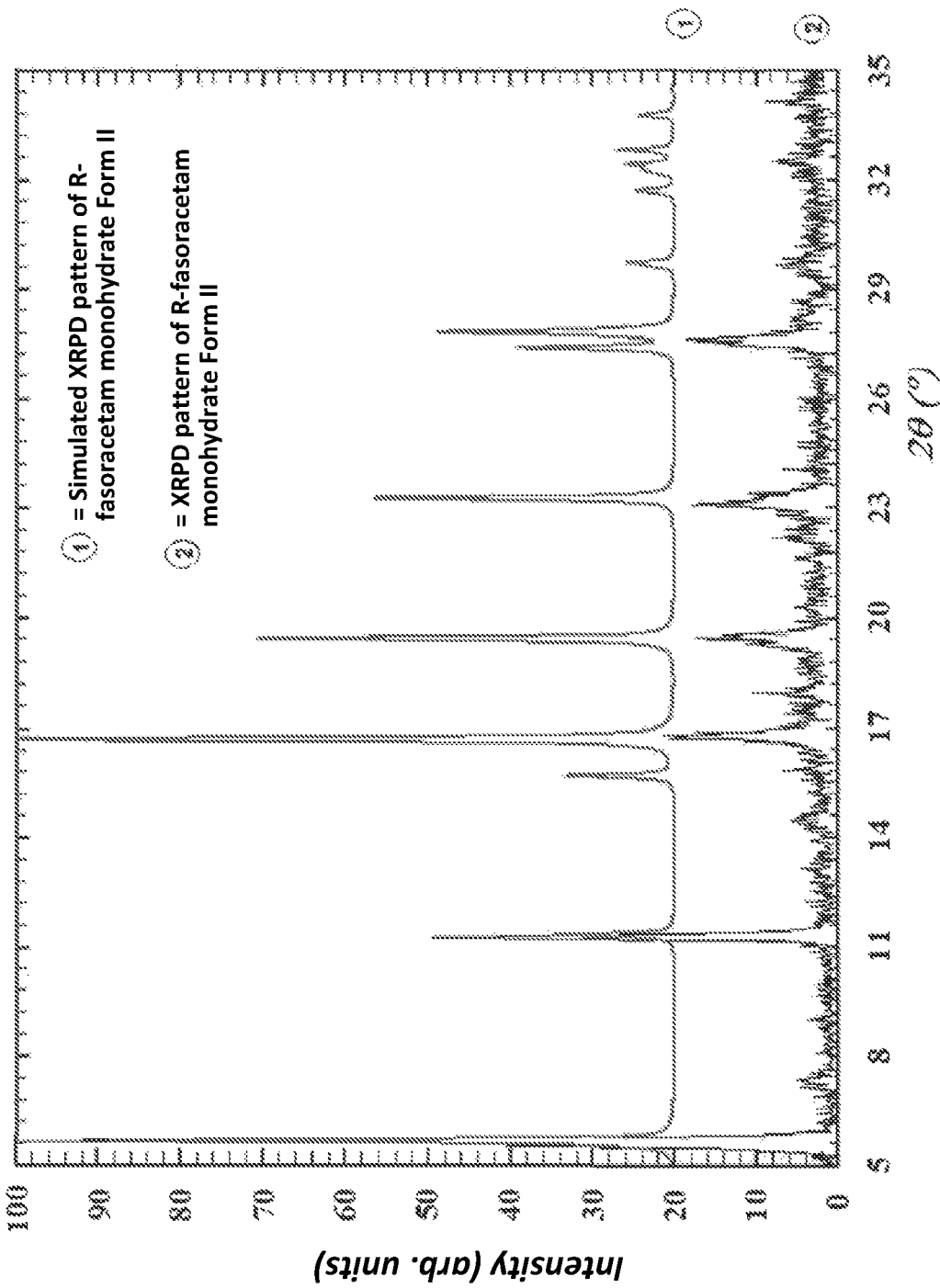
FIG. 26 is an overlay of XRPD patterns: (1) Simulated XRPD pattern of R-fasoracetam monohydrate Form II; (2) XRPD pattern of R-fasoracetam monohydrate Form II.
Figure 27:
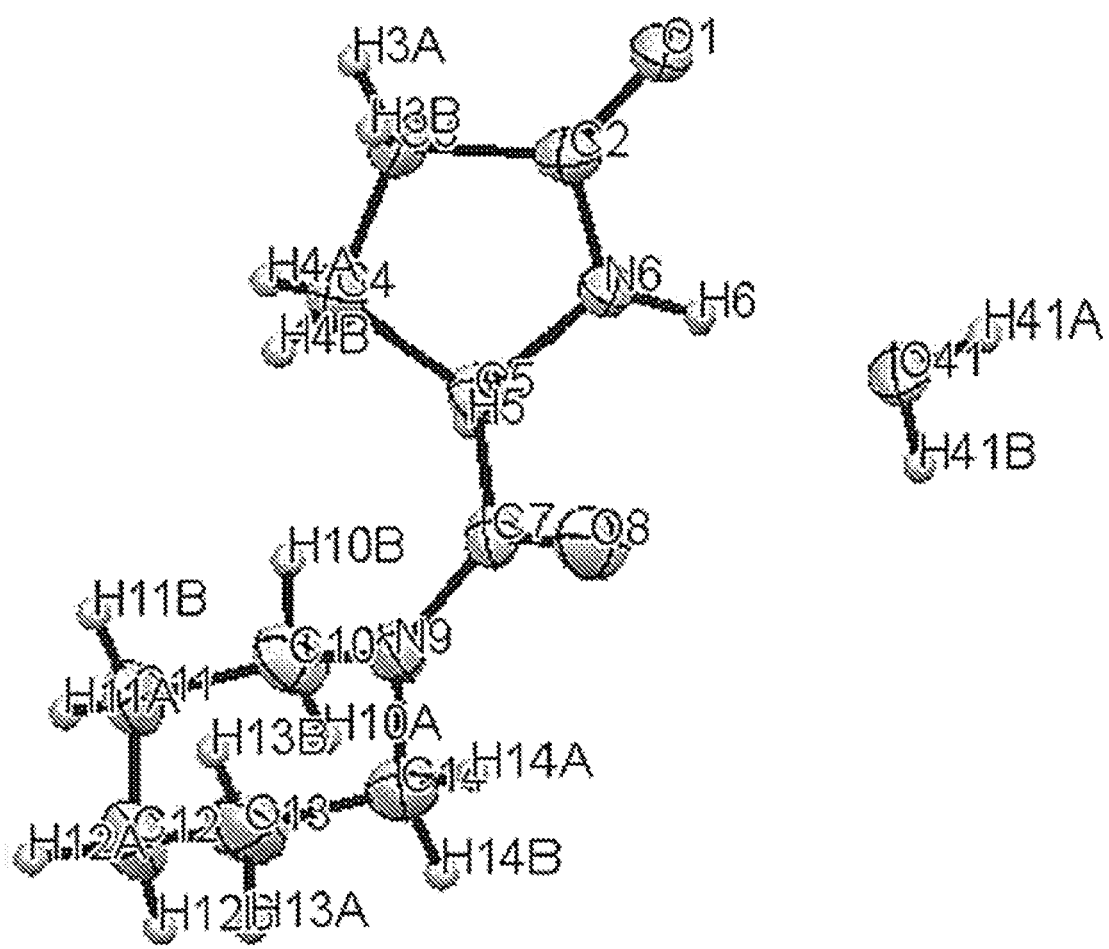
FIG. 27 is an ORTEP drawing of R-fasoracetam monohydrate Form II.
Figure 28:
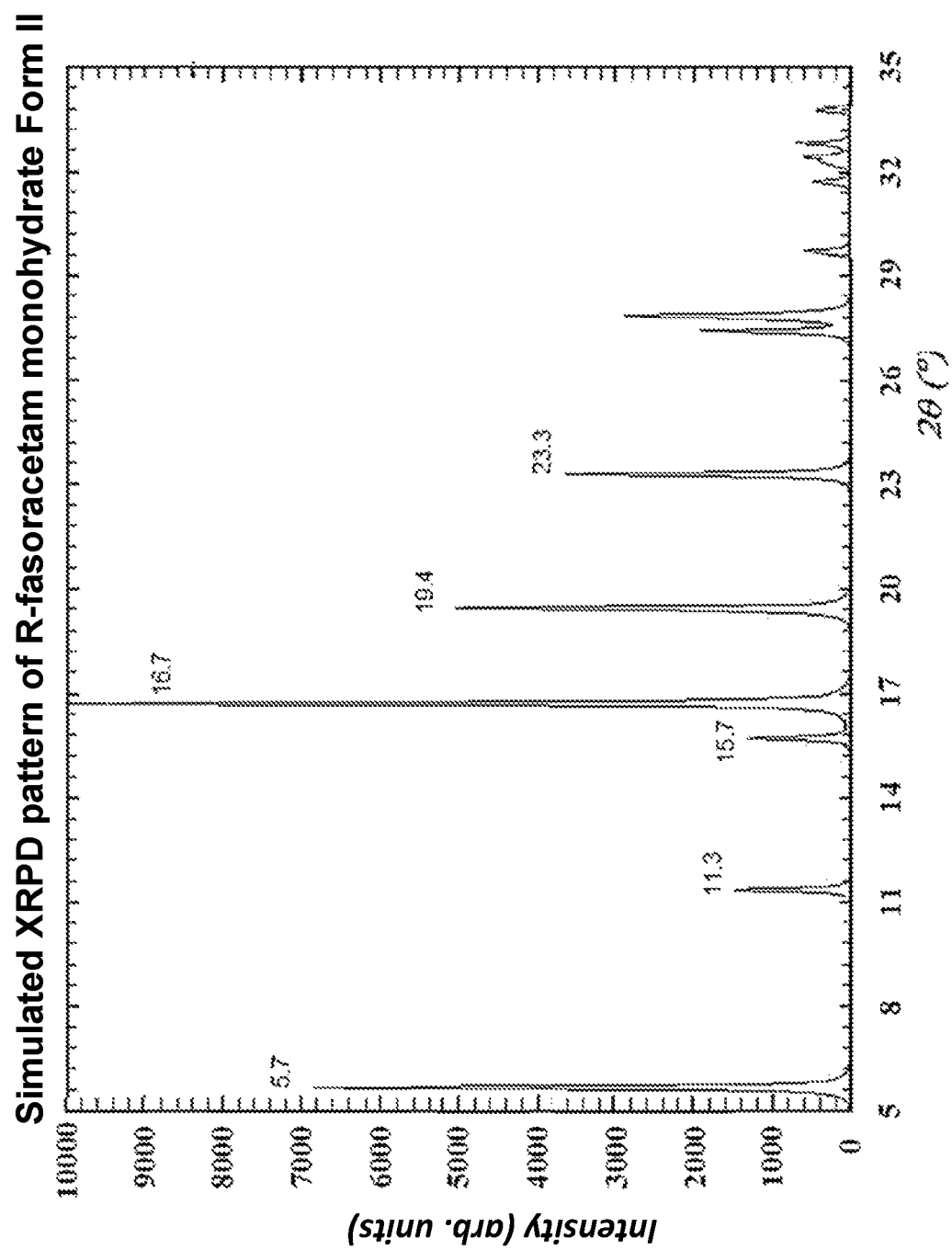
FIG. 28 is a simulated XRPD pattern of R-fasoracetam monohydrate Form II.

R-fasoracetam monohydrate Form I from Jinan Haohua Industry Co., Ltd. was dissolved in methanol. The solution was then left to slowly evaporate at room temperature to yield a crystalline material. A simulated x-ray powder pattern was prepared from the single crystal data solution and compared with the experimentally obtained powder pattern of Example 4 (FIG. 16) and is shown in FIG. 26. An ORTEP drawing is found at FIG. 27 and Table 5 is a list of single crystal data parameters. FIG. 28 is the simulated XRPD pattern.

TABLE 5

Crystal data and structure refinement for R-fasoracetam monohydrate Form II

| PARAMETER | RESULTS | |
|---|---|---|
| Empirical formula | C10 H18 N2 O3 | |
| Formula weight | 214.26 | |
| Temperature | 150(2) K | |
| Wavelength | 0.71073 Å | |
| Crystal system | Monoclinic | |
| Space group | C2 | |
| Unit cell dimensions | a = 11.2982(6) Å | α = 90°. |
| | b = 6.5055(4) Å | β = 90.291(5)°. |
| | c = 15.6050(10) Å | γ = 90°. |
| Volume | 1146.97(12) Å3 | |
| Z | 4 | |
| Density (calculated) | 1.241 Mg/m3 | |
| Absorption coefficient | 0.092 mm−1 | |
| F(000) | 464 | |
| Crystal size | 0.300 × 0.050 × 0.030 mm3 | |
| Theta range for data collection | 3.607 to 25.179°. | |
| Index ranges | −13 <= h <= 13, −7 <= k <= 7, −18 <= l <= 18 | |
| Reflections collected | 4481 | |
| Independent reflections | 2027 [R(int) = 0.0324] | |
| Completeness to theta = 25.179° | 99.5% | |
| Absorption correction | Semi-empirical from equivalents | |
| Max. and min. transmission | 1.00000 and 0.94436 | |
| Refinement method | Full-matrix least-squares on F2 | |
| Data/restraints/parameters | 2027/1/139 | |
| Goodness-of-fit on F2 | 1.080 | |
| Final R indices [I > 2sigma(I)] | R1 = 0.0412, wR2 = 0.0916 | |
| R indices (all data) | R1 = 0.0539, wR2 = 0.0966 | |
| Absolute structure parameter | 0.2(8) | |
| Extinction coefficient | n/a | |
| Largest diff. peak and hole | 0.176 and −0.146 e · Å−3 | |

Example 9—Single Crystal R-Fasoracetam Anhydrate

Figure 29:
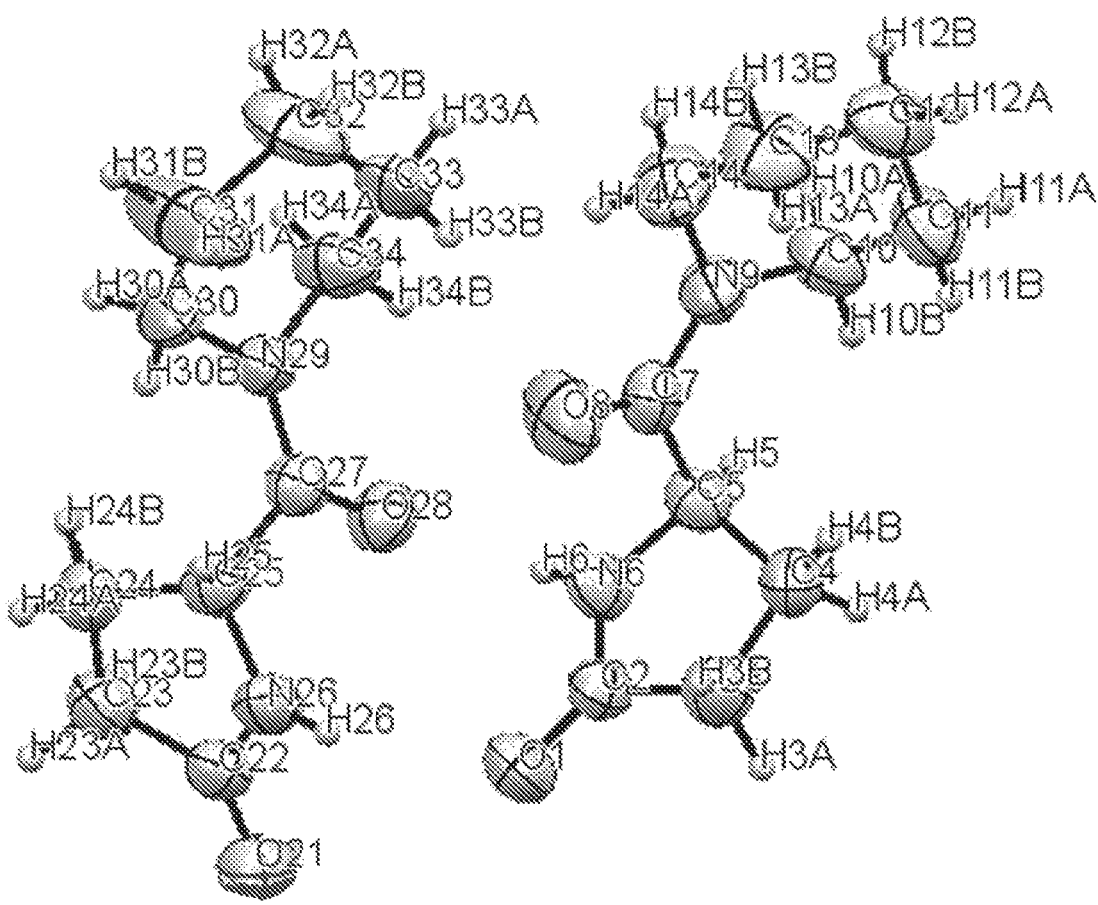
FIG. 29 is an ORTEP drawing of R-fasoracetam anhydrate.
Figure 30:
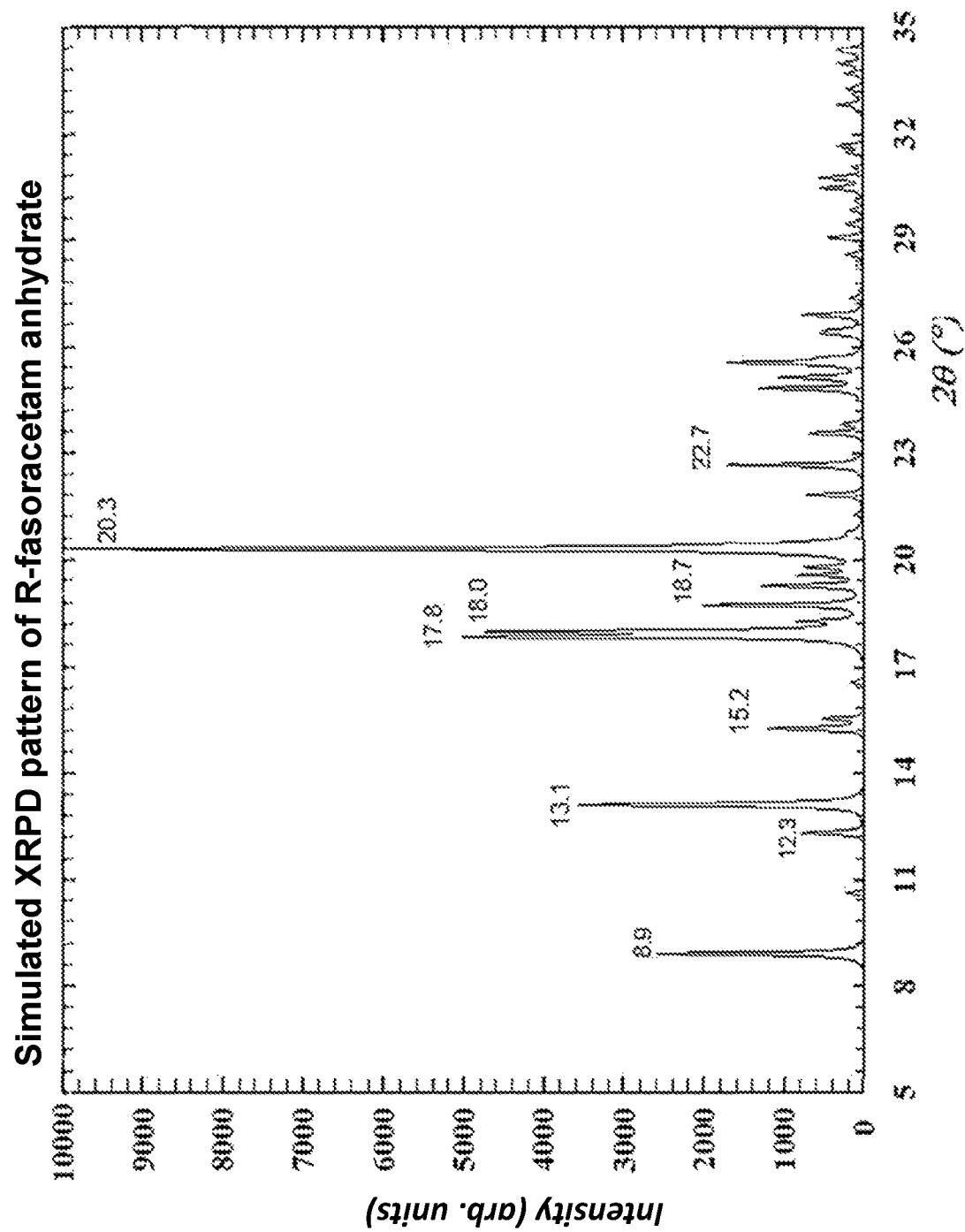
FIG. 30 is a simulated XRPD pattern of R-fasoracetam anhydrate.
Figure 31:
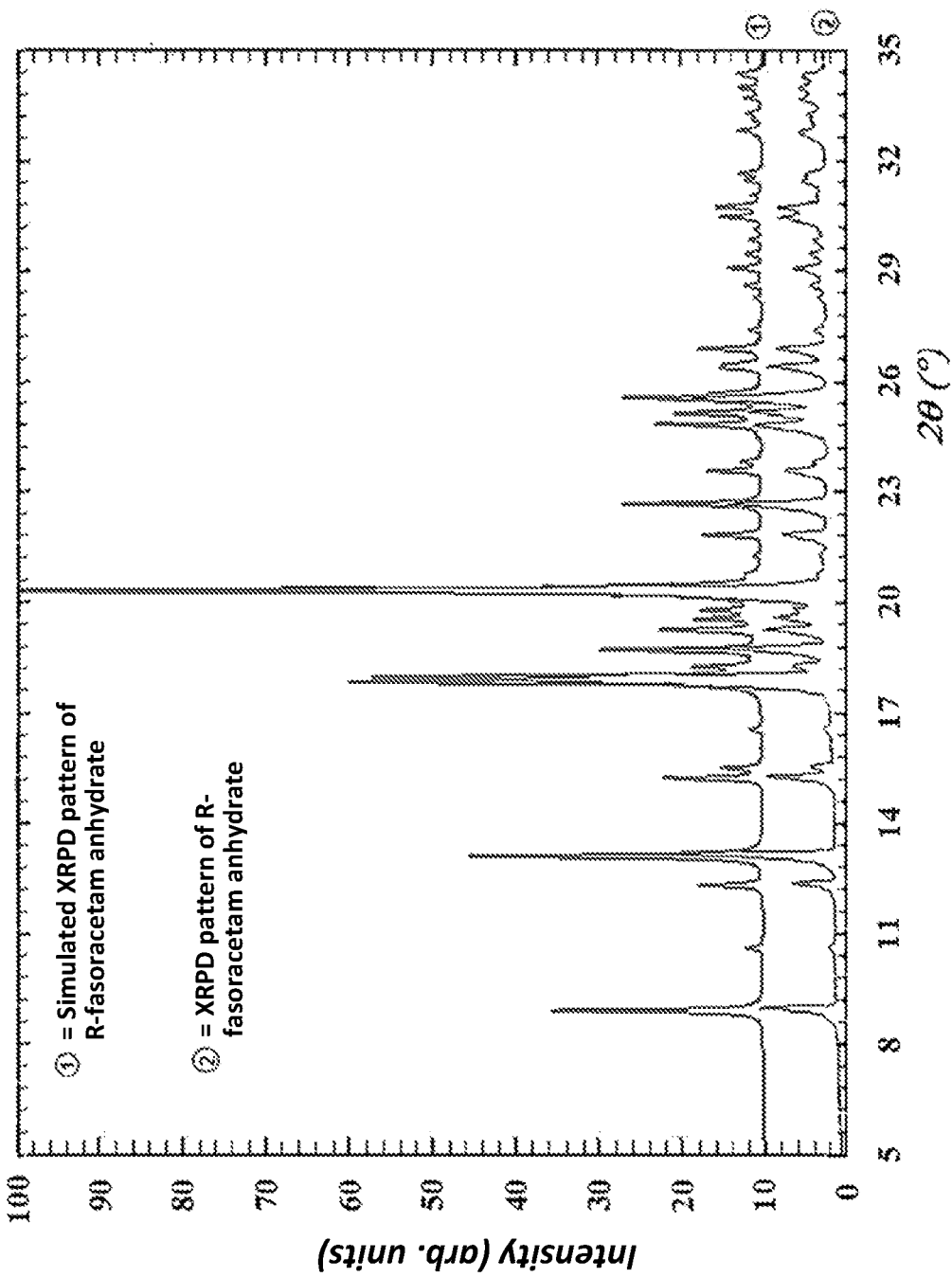
FIG. 31 is an overlay of XRPD patterns: (1) Simulated XRPD pattern of R-fasoracetam anhydrate; (2) XRPD pattern of R-fasoracetam anhydrate.

R-fasoracetam monohydrate Form I from Jinan Haohua Industry Co., Ltd. was placed under vacuum at 60° C. and melting was observed. After one week, the temperature was lowered maintaining vacuum conditions. Crystalline material appeared and was found to be R-fasoracetam anhydrate. An ORTEP drawing is found at FIG. 29, and Table 6 is a list of single crystal data parameters. FIG. 30 is the simulated XRPD pattern and FIG. 31 is an overlay of the simulated pattern and that of R-fasoracetam anhydrate.

TABLE 6

Crystal data and structure refinement for R-fasoracetam anhydrate

| PARAMETER | RESULTS | |
|---|---|---|
| Empirical formula | C10 H16 N2 O2 | |
| Formula weight | 196.25 | |
| Temperature | 297(2) K | |
| Wavelength | 0.71073 Å | |
| Crystal system | Orthorhombic | |
| Space group | P2$_1$2$_1$2$_1$ | |
| Unit cell dimensions | a = 9.2095(5) Å | α = 90°. |
| | b = 11.5104(8) Å | β = 90°. |
| | c = 19.7276(13) Å | γ = 90°. |
| Volume | 2091.2(2) Å3 | |
| Z | 8 | |
| Density (calculated) | 1.247 Mg/m3 | |
| Absorption coefficient | 0.088 mm−1 | |
| F(000) | 848 | |
| Crystal size | 0.5 × 0.4 × 0.4 mm3 | |
| Theta range for data collection | 3.015 to 25.206°. | |
| Index ranges | −10 <= h <= 10, −13 <= k <= 12, −23 <= l <= 23 | |
| Reflections collected | 8790 | |
| Independent reflections | 3731 [R(int) = 0.0335] | |
| Completeness to theta = 25.206° | 99.2% | |
| Absorption correction | Semi-empirical from equivalents | |
| Max. and min. transmission | 1.00000 and 0.42311 | |
| Refinement method | Full-matrix least-squares on F2 | |
| Data/restraints/parameters | 3731/12/308 | |
| Goodness-of-fit on F2 | 1.016 | |
| Final R indices [I > 2sigma(I)] | R1 = 0.0441, wR2 = 0.1139 | |
| R indices (all data) | R1 = 0.0539, wR2 = 0.1218 | |
| Absolute structure parameter | −0.6(7) | |
| Extinction coefficient | n/a | |
| Largest diff. peak and hole | 0.126 and −0.134 e · Å−3 | |

Example 10—Single Crystal of R-Fasoracetam Monohydrate Form I

Figure 32:
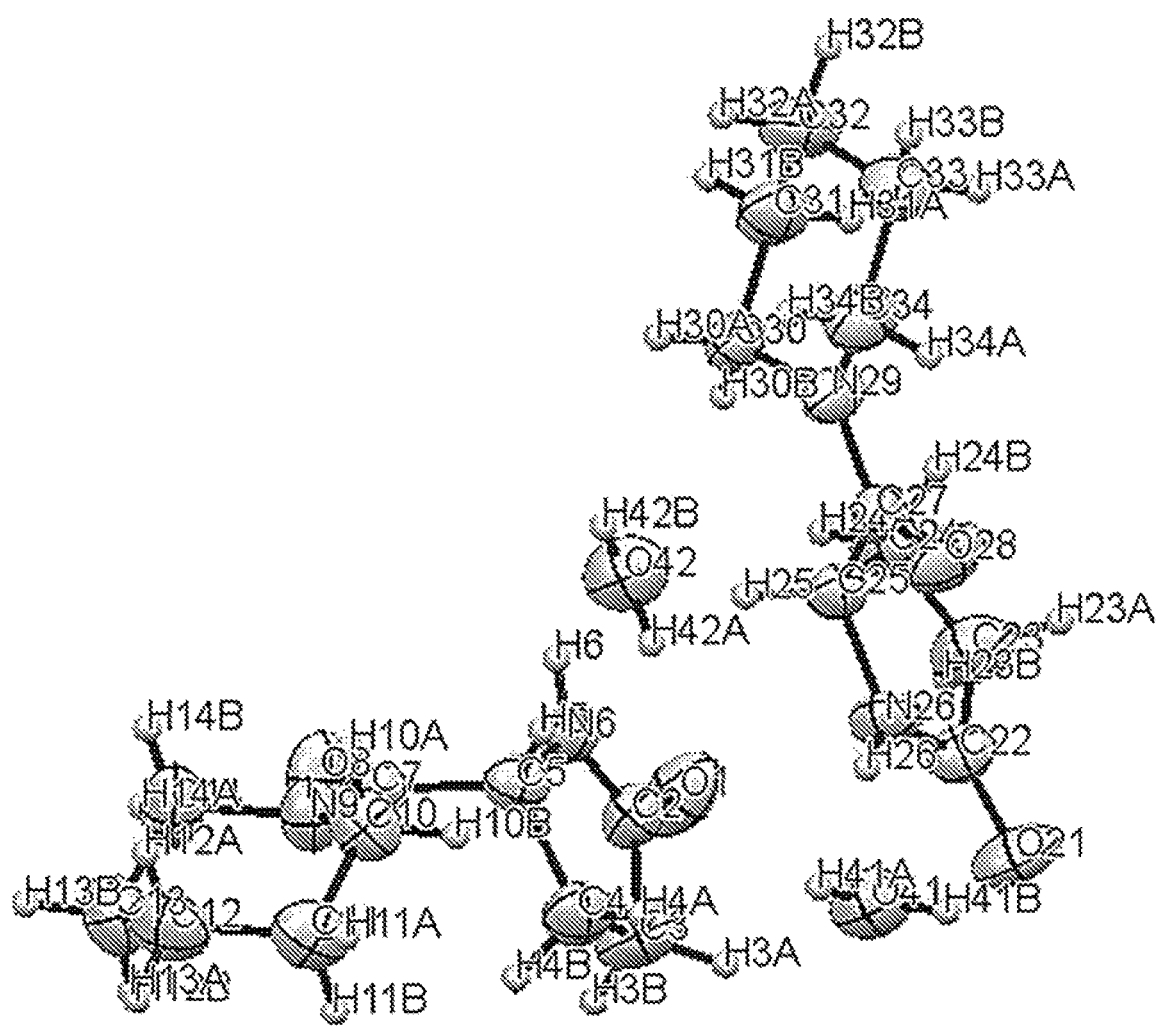
FIG. 32 is an ORTEP drawing of R-fasoracetam monohydrate Form I.
Figure 33:
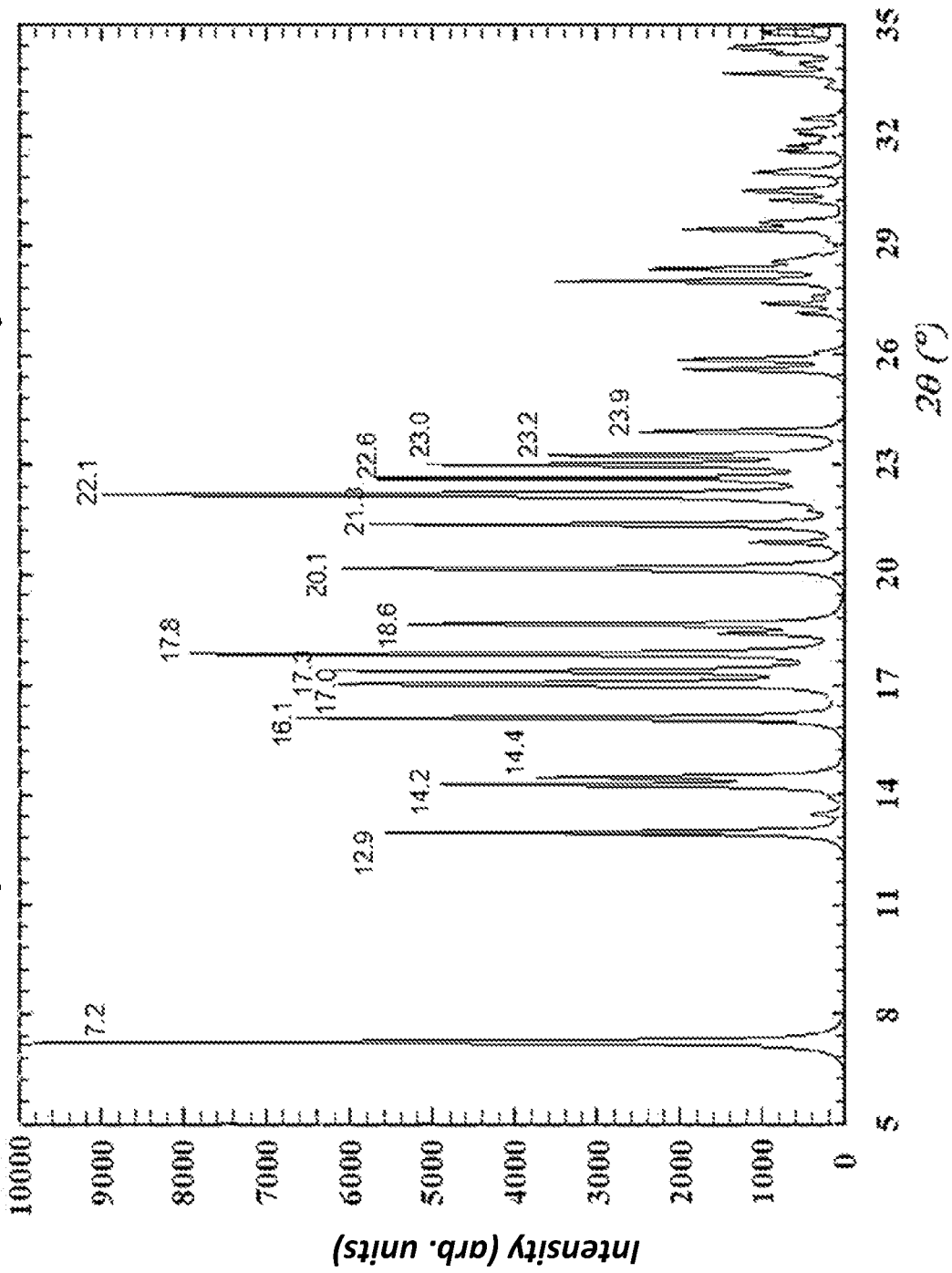
FIG. 33 is a simulated XRPD pattern of R-fasoracetam monohydrate Form I.
Figure 34:
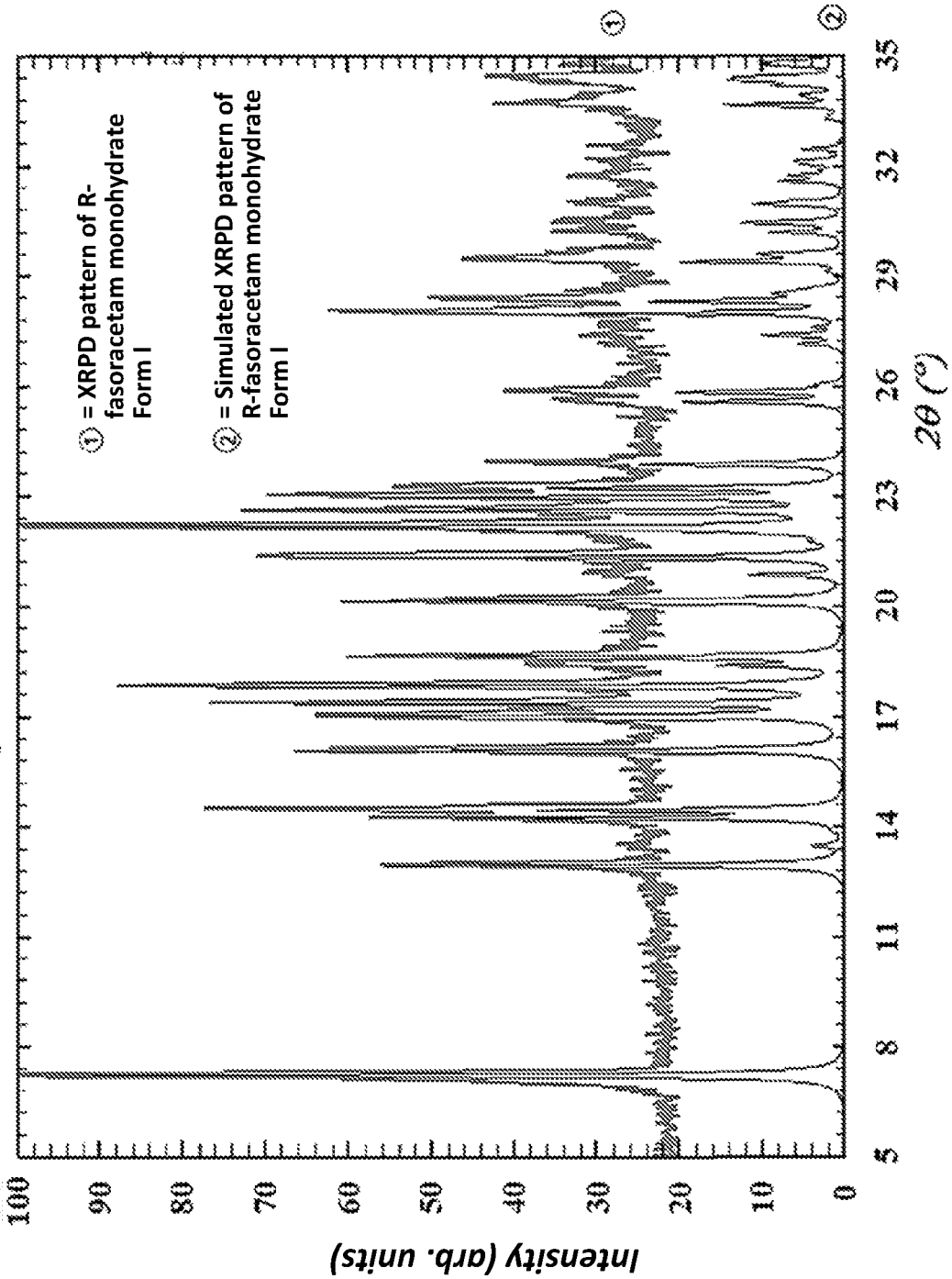
FIG. 34 is an overlay of XRPD patterns: (1) XRPD pattern of R-fasoracetam monohydrate Form I; (2) Simulated XRPD pattern of R-fasoracetam monohydrate Form I.

R-fasoracetam monohydrate Form I from Jinan Haohua Industry Co., Ltd. is dissolved in water. The solution was then left to slowly evaporate at room temperature to yield a crystalline material which was analyzed and found to be R-fasoracetam monohydrate Form I. An ORTEP drawing is found at FIG. 32, and Table 7 is a list of single crystal data parameters. FIG. 33 is a simulated XRPD pattern and FIG. 34 is an overlay of the simulated pattern and that of R-fasoracetam monohydrate Form I indicating a match.

TABLE 7

Crystal data and structure refinement for R-fasoracetam monohydrate Form I

| PARAMETER | RESULTS | |
|---|---|---|
| Empirical formula | C10 H18 N2 O3 | |
| Formula weight | 214.26 | |
| Temperature | 297(2) K | |
| Wavelength | 0.71073 Å | |
| Crystal system | Triclinic | |
| Space group | P1 | |
| Unit cell dimensions | a = 6.6093(7) Å | α = 99.691(10)°. |
| | b = 7.0801(7) Å | β = 100.272(10)°. |
| | c = 12.7221(18) Å | γ = 99.363(9)°. |
| Volume | 565.91(12) Å3 | |
| Z | 2 | |
| Density (calculated) | 1.257 Mg/m3 | |
| Absorption coefficient | 0.093 mm−1 | |
| F(000) | 232 | |
| Crystal size | 0.21 × 0.11 × 0.05 mm3 | |
| Theta range for data collection | 3.102 to 25.525°. | |
| Index ranges | −7 <= h <= 7, −8 <= k <= 8, −15 <= l <= 15 | |
| Reflections collected | 7583 | |
| Independent reflections | 4076 [R(int) = 0.0514] | |
| Completeness to theta = 25.242° | 99.3% | |
| Absorption correction | Semi-empirical from equivalents | |
| Max. and min. transmission | 1.00000 and 0.75526 | |
| Refinement method | Full-matrix least-squares on F2 | |
| Data/restraints/parameters | 4076/3/277 | |
| Goodness-of-fit on F2 | 1.054 | |
| Final R indices [I > 2sigma(I)] | R1 = 0.0455, wR2 = 0.1137 | |
| R indices (all data) | R1 = 0.0567, wR2 = 0.1217 | |
| Absolute structure parameter | −1.4(10) | |
| Extinction coefficient | n/a | |
| Largest diff. peak and hole | 0.131 and −0.121 e · Å−3 | |

Example 11—R-Fasoracetam Forms Mixture

R-fasoracetam monohydrate Form I from Jinan Haohua Industry Co., Ltd. was placed in a round flask, and placed under vacuum in a rotavap device at 65° C. Melting of R-fasoracetam monohydrate Form I was observed. The sample was left for 30 min in the rotavap device under vacuum at 65° C., during which recrystallization occurred. The sample was then left for full recrystallization. FIG. 18 shows the x-ray powder diffraction pattern of the resulting sample compared with simulated x-ray powder diffraction patterns of simulated patterns corresponding to each of R-fasoracetam monohydrate Form I, R-fasoracetam monohydrate Form II, and R-fasoracetam anhydrate.

Example 12—A Single Crystal Cocrystal of Fasoracetam and Urea (1:1) (Form B)

Figure 36:
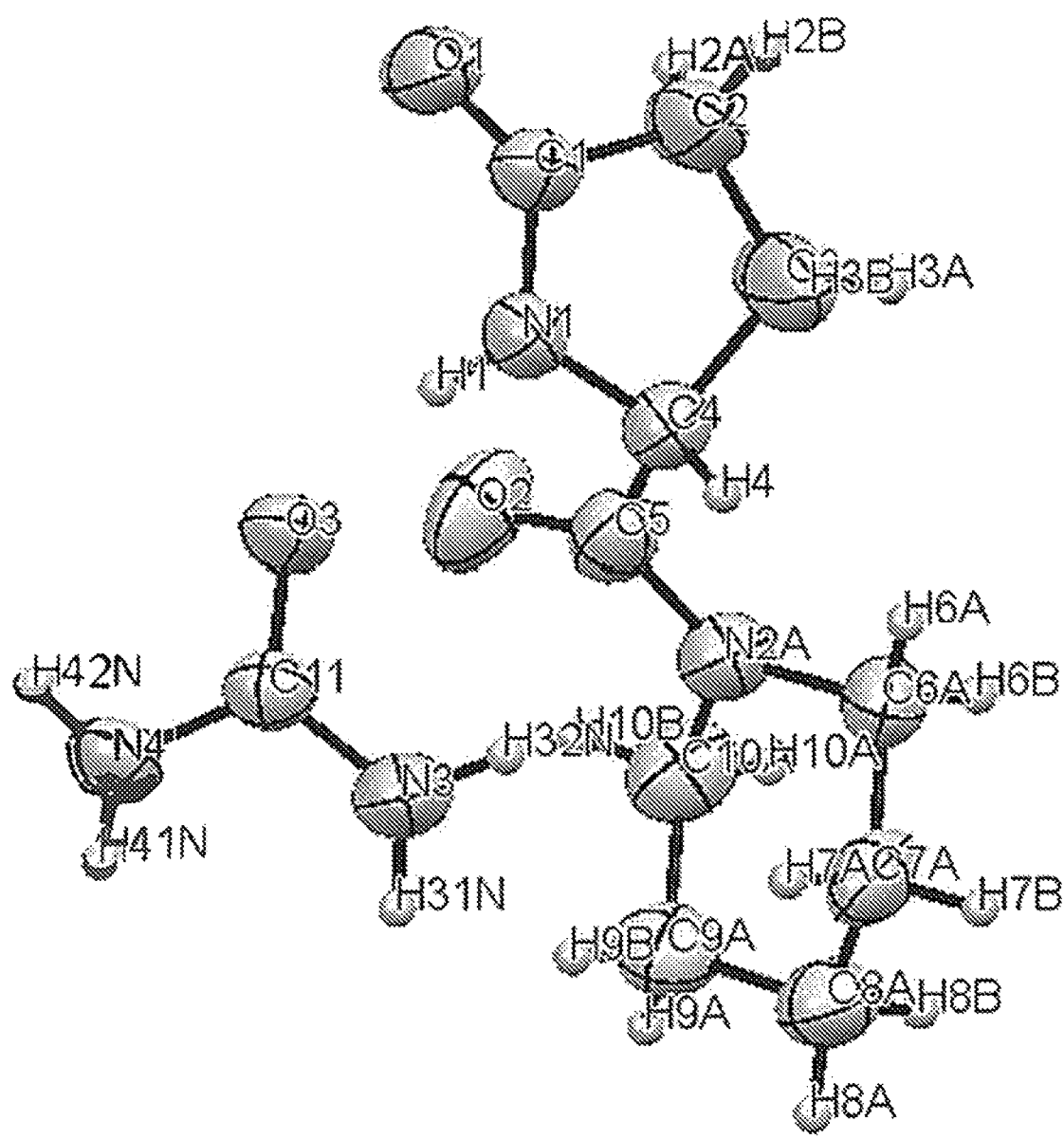
FIG. 36 is an ORTEP drawing of a cocrystal of a R-fasoracetam and urea Form B.

A 1:1 stoichiometric cocrystal of R-fasoracetam and urea was obtained as follows. 201.28 mg of R-fasoracetam monohydrate Form I sourced by Aevi Genomic Medicine were placed under vacuum in a rotavap at 65° C. for 50 minutes. The sample was cooled to room temperature and 55.1 mg of urea added. The mixture was then kept at 120° C. for 10 minutes until a full melt was obtained. The temperature was then left at 90° C. for 24 h, after which single crystals of the R-fasoracetam:urea cocrystal were obtained. FIG. 36 is an ORTEP drawing of the single crystal solution of a cocrystal of R-fasoracetam and urea. Table 7A lists single crystal parameters for the cocrystal of R-fasoracetam and urea. FIG. 37 is a simulated x-ray powder diffraction pattern from a single crystal solution of a cocrystal of R-fasoracetam and urea.

TABLE 7A

Single Crystal parameters for a 1:1 cocrystal of R-fasoracetam and urea.

| PARAMETER | RESULTS |
|---|---|
| Empirical formula | $C_{11}H_{20}N_4O_3$ |
| Formula weight | 256.31 |
| Temperature/K | 295(2) |
| Crystal system | orthorhombic |
| Space group | $P2_12_12_1$ |
| a/Å | 8.77239(9) |
| b/Å | 9.16446(11) |
| c/Å | 16.93396(18) |
| α/° | 90 |
| β/° | 90 |
| γ/° | 90 |
| Volume/Å$^3$ | 1361.39(3) |
| Z | 4 |
| $\rho_{calc}$g/cm$^3$ | 1.251 |
| μ/mm$^{-1}$ | 0.766 |
| F(000) | 552.0 |
| Crystal size/mm$^3$ | 0.41 × 0.4 × 0.072 |
| Radiation | CuKα (λ = 1.54184) |
| 2Θ range for data collection/° | 10.448 to 134.16 |
| Index ranges | −10 ≤ h ≤ 10, −10 ≤ k ≤ 10, −20 ≤ l ≤ 20 |
| Reflections collected | 16430 |
| Independent reflections | 2404 [$R_{int}$ = 0.0203, $R_{sigma}$ = 0.0093] |
| Data/restraints/parameters | 2404/60/231 |
| Goodness-of-fit on F$^2$ | 1.038 |
| Final R indexes [I >= 2σ (I)] | $R_1$ = 0.0334, w$R_2$ = 0.0917 |
| Final R indexes [all data] | $R_1$ = 0.0343, W$R_2$ = 0.0927 |
| Largest diff. peak/hole/e Å$^{-3}$ | 0.14/−0.14 |
| Flack parameter | 0.01(5) |

Example 13—Cocrystal of Fasoracetam and Urea (Form B)

6.49 mg of urea and 20.19 mg (1:1 molar ratio) of an R-Fasoracetam Forms Mixture was prepared in general accordance with Example 16 and was added to an Eppendorf together with 3 stainless steel grinding beads with 10 μL of toluene. The mixture was ground in a RETSCH Mixer Mill MM 400 for 90 min with a beating frequency of 30 Hz to yield ground crystalline material which shows the presence of a cocrystal of R-fasoracetam and urea. FIG. 38 is an overlay of x-ray powder diffraction patterns showing the cocrystal of R-fasoracetam and urea from this Example 13, compared with that of the simulated pattern of the R-fasoracetam:urea cocrystal of FIG. 37. FIG. 39 is an overlay XRPD pattern showing the cocrystal of R-fasoracetam and urea compared with that simulated patterns of the R-fasoracetam:urea cocrystal, R-fasoracetam monohydrate Form I, R-fasoracetam monohydrate Form II and R-fasoracetam anhydrate. FIG. 40 is a differential scanning calorimetry thermogram of a cocrystal of fasoracetam and urea prepared in this example, and indicates a single endotherm with an onset of about 102° C.

Example 14—Cocrystal of Fasoracetam and Urea (Form B)

Figure 42:
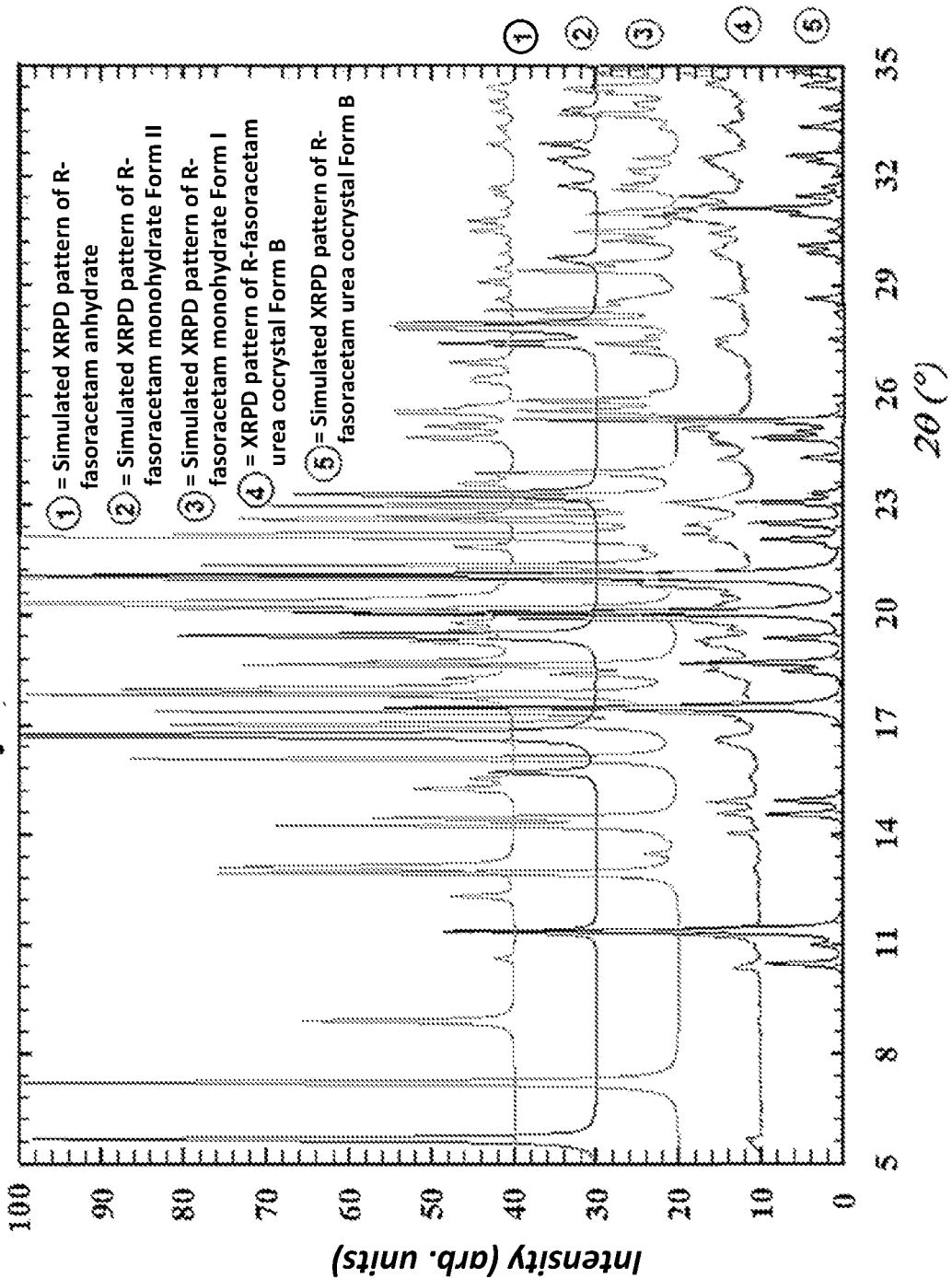
FIG. 42 is an overlay of XRPD patterns: (1) Simulated XRPD pattern of R-fasoracetam anhydrate; (2) Simulated XRPD pattern of R-fasoracetam monohydrate Form II; (3) Simulated XRPD pattern of R-fasoracetam monohydrate Form I; (4) XRPD pattern of R-fasoracetam:urea cocrystal Form B; (5) Simulated XRPD pattern of R-fasoracetam:urea cocrystal Form B.

141.5 mg of urea and 502.3 mg (1:1 molar ratio) of a R-Fasoracetam monohydrate Form I sourced by Aevi Genomic Medicine were placed under vacuum in a rotavap at 65° C. for 1 hour during which crystallization occurred. The sample was then cooled to room temperature. FIG. 41 is an overlay of x-ray powder diffraction patterns showing the cocrystal of R-fasoracetam and urea compared with that of the simulated pattern of the R-fasoracetam:urea cocrystal. FIG. 42 is an overlay XRPD pattern showing the cocrystal of R-fasoracetam and urea compared with that simulated patterns of the R-fasoracetam:urea cocrystal, R-fasoracetam monohydrate Form I, R-fasoracetam monohydrate Form II and R-fasoracetam anhydrate.

Example 15—Cocrystal of R-Fasoracetam and Urea (Form A)

Figure 43:
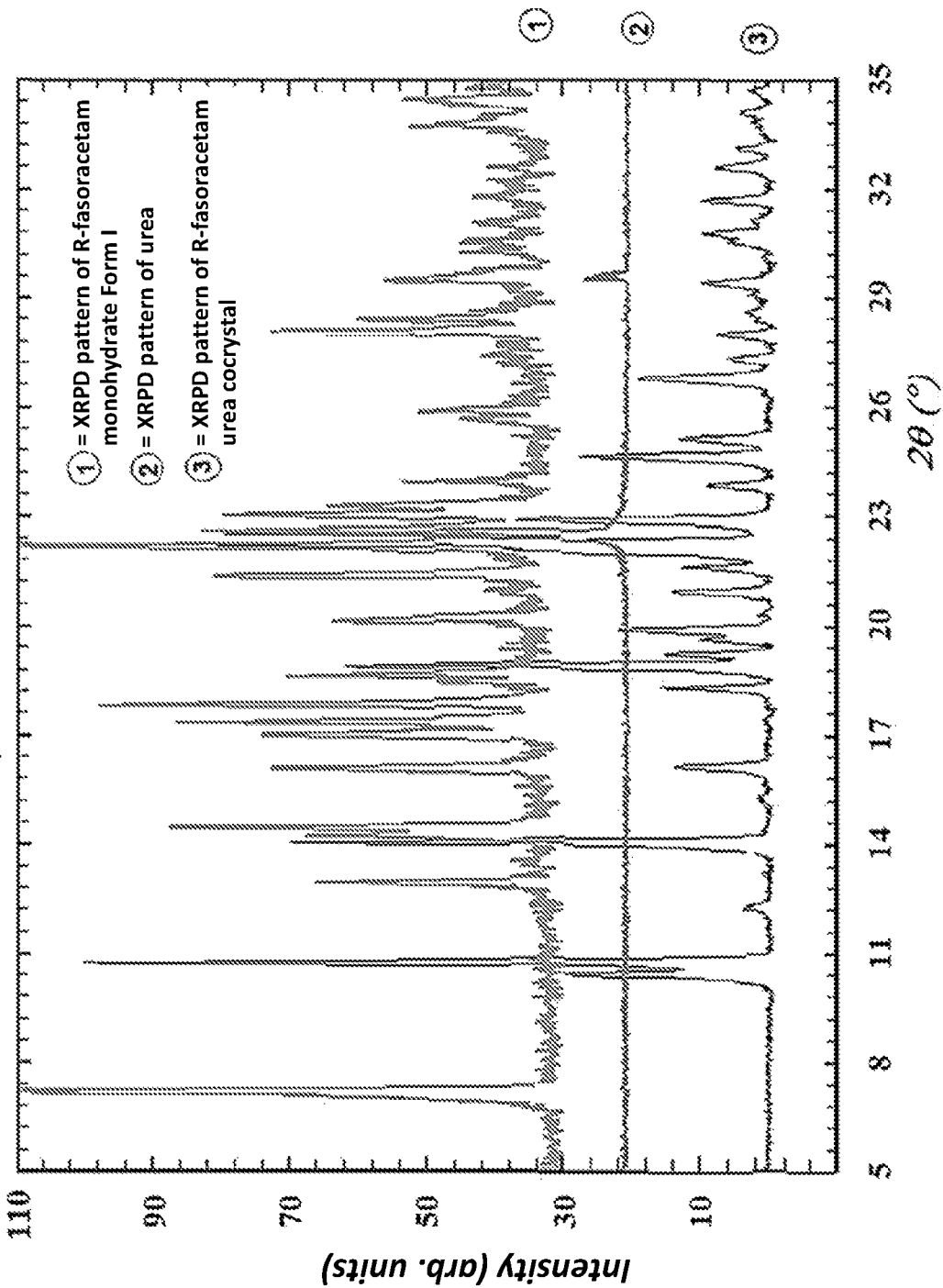
FIG. 43 is an overlay of XRPD patterns: (1) XRPD pattern of R-fasoracetam monohydrate Form I; (2) XRPD pattern of urea; (3) XRPD pattern of R-fasoracetam:urea cocrystal.
Figure 46:
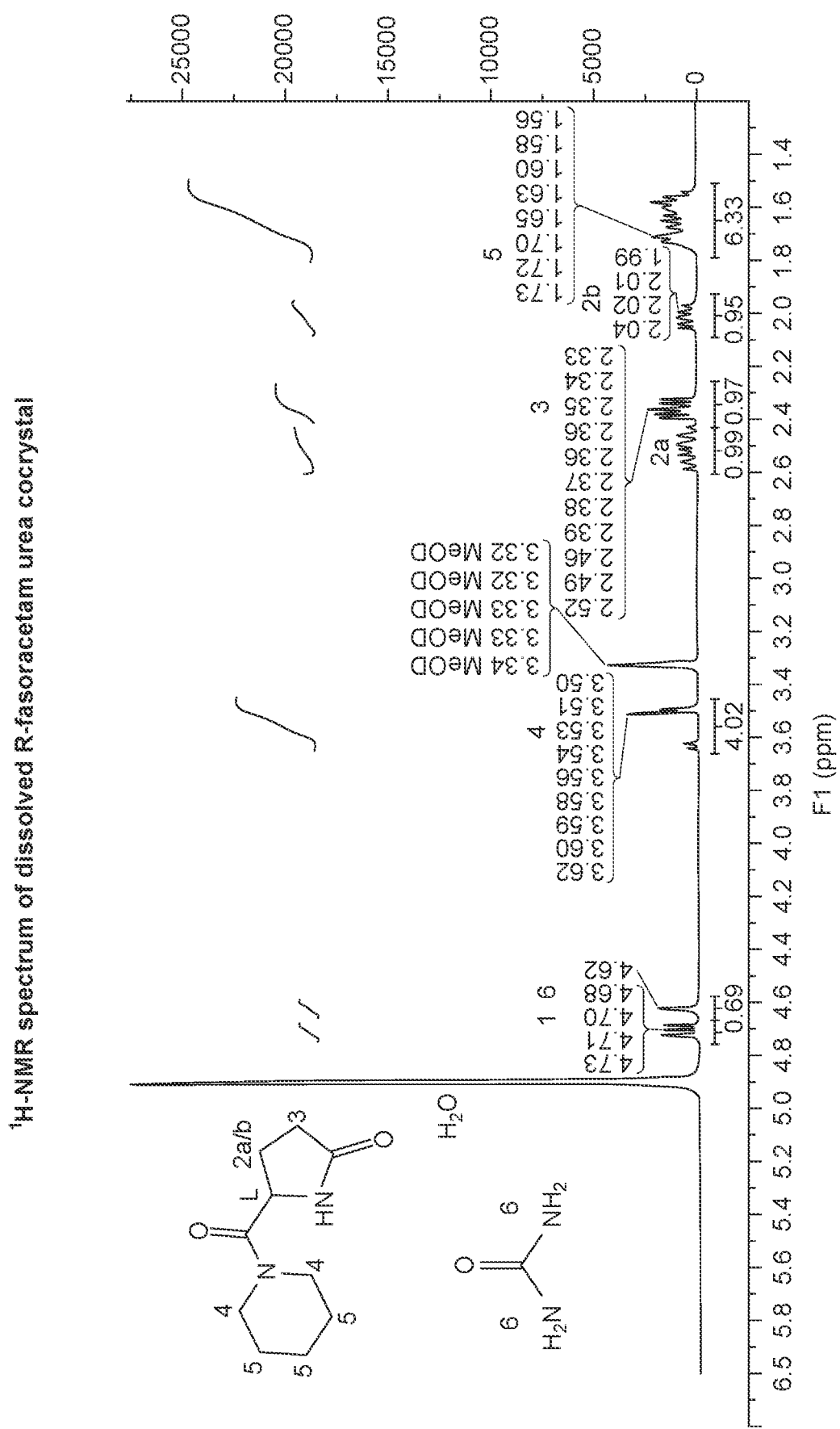
FIG. 46 is a $^1$H-NMR spectrum of a dissolved R-fasoracetam:urea cocrystal.
Figure 47:
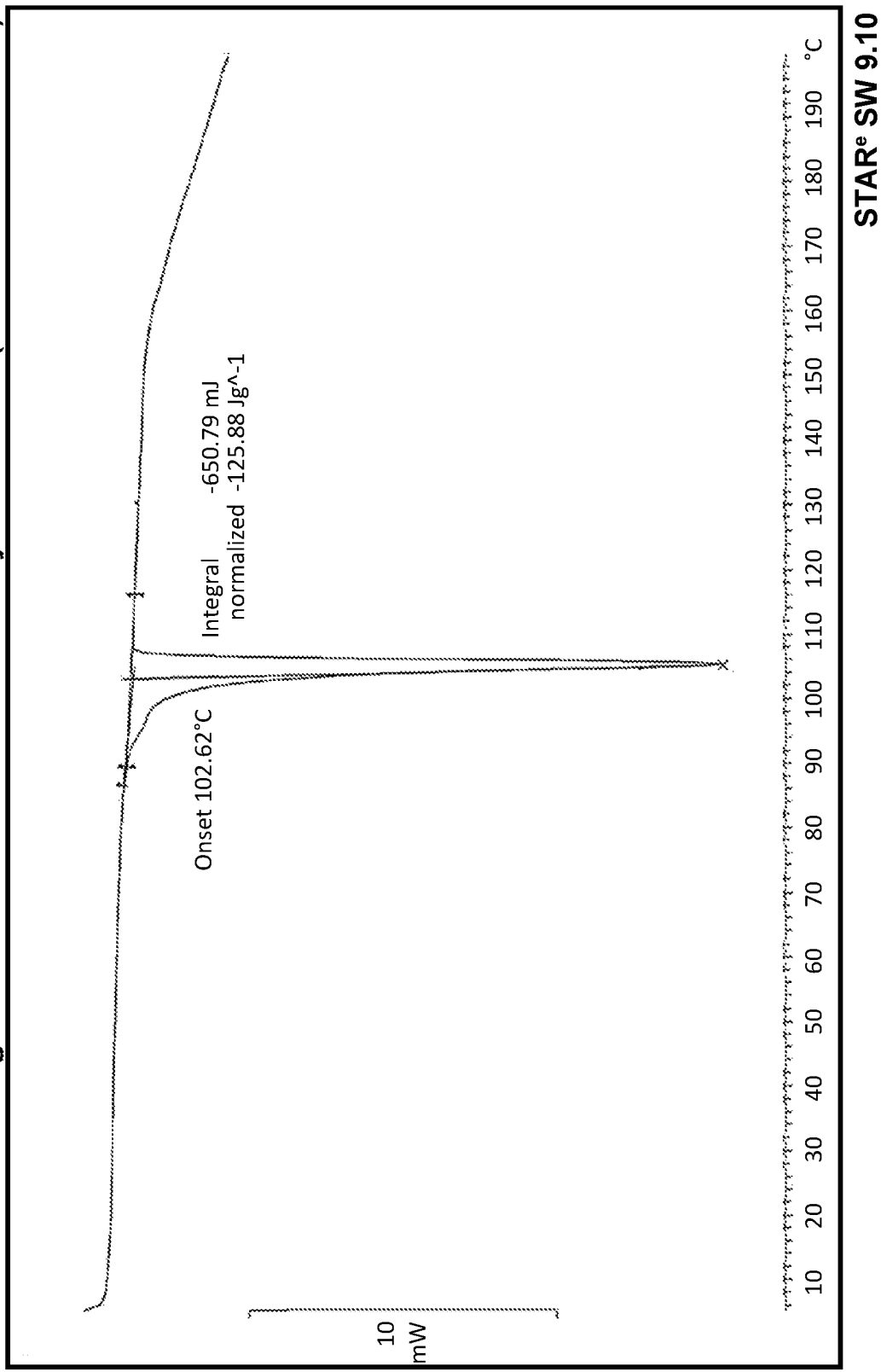
FIG. 47 is a DSC thermogram of a R-fasoracetam:urea cocrystal Form A (converted to Form B).
Figure 48:
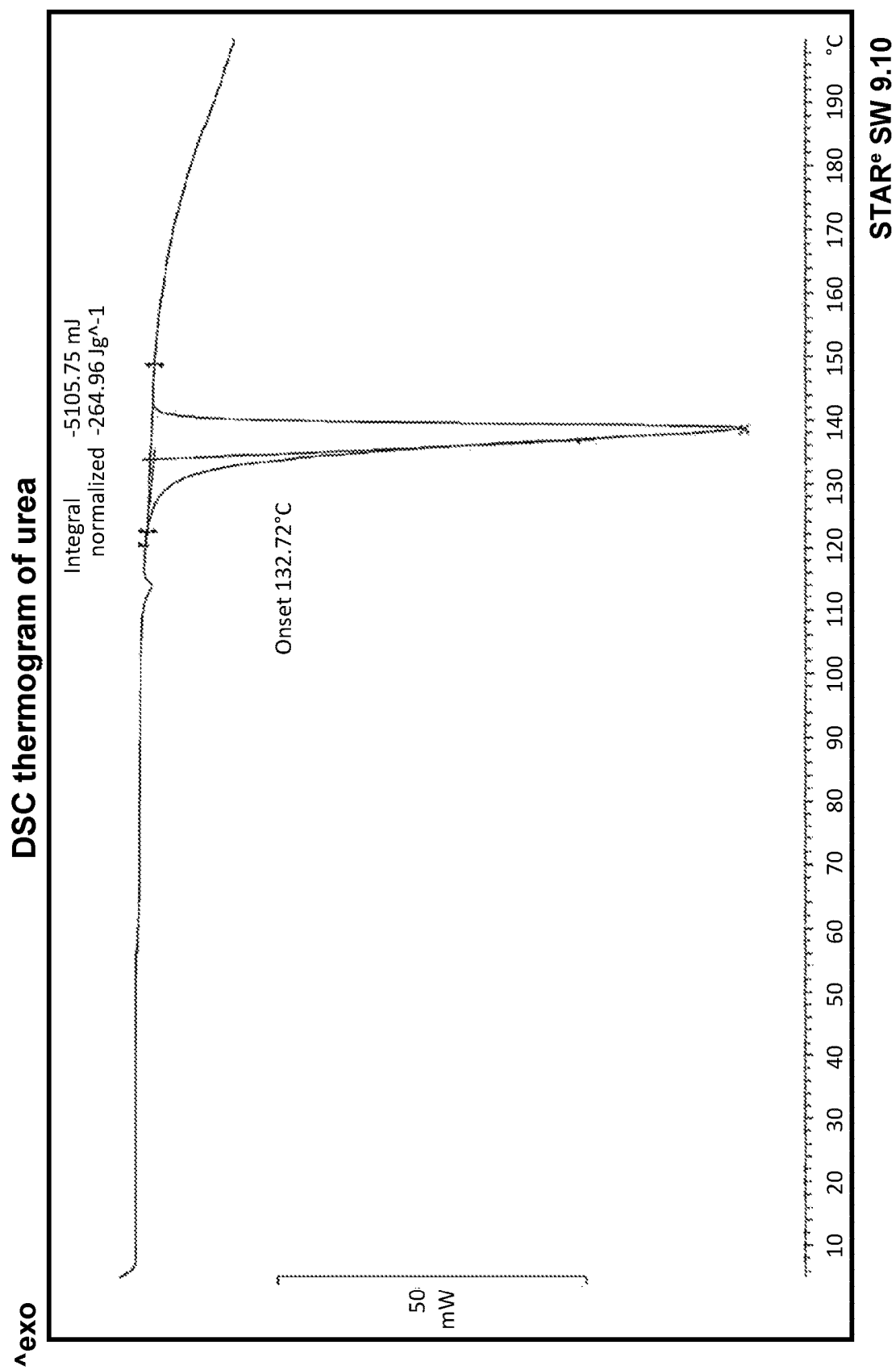
FIG. 48 is a DSC thermogram of urea.

6.32 mg of urea and 19.75 mg (1:1 molar ratio) of an R-Fasoracetam Forms Mixture prepared according to Example 11 and/or Example 16 was added to an Eppendorf together with 3 stainless steel grinding beads. The mixture was ground in a RETSCH Mixer Mill MM 400 for 90 min with a beating frequency of 30 Hz to yield ground crystalline material which shows the presence of a cocrystal of R-fasoracetam and urea. FIG. 35 is an overlay of x-ray powder diffraction patterns showing the cocrystal of R-fasoracetam and urea compared with that of urea and the R-Fasoracetam Forms Mixture. FIG. 43 is an overlay XRPD pattern showing the cocrystal of R-fasoracetam and urea compared with that of urea and Form I. FIG. 44 is a peak-picked x-ray powder diffraction pattern of a cocrystal of R-fasoracetam and urea. FIG. 113 is the x-ray powder diffraction pattern of urea. FIG. 46 is the solution-state $^1$H-NMR spectrum of a dissolved cocrystal of R-fasoracetam and urea showing that all hydrogens are accounted for and there is no degradation. FIG. 47 is a differential scanning calorimetry thermogram of a cocrystal of R-fasoracetam and urea which indicates a single endotherm with a shoulder and FIG. 48 is the differential scanning calorimetry thermogram of urea. The DSC thermogram of the cocrystal shows an onset of about 103° C., however, that is the onset temperature of Form B, which shows that the material had converted to Form B by the time the DSC measurement was completed. FIG. 49 is the XRPD pattern overlay comparing the XPRD pattern of the cocrystal of this Example 15 and the simulated XRPD pattern from the single crystal of Example 12.

Example 16—Fasoracetam Form Mixture

A mixture of R-fasoracetam monohydrate Form I, R-fasoracetam monohydrate Form II, and R-fasoracetam anhydrate was prepared by placing R-fasoracetam monohydrate Form I sourced from Jinan Haohua Industry C., Ltd. under vacuum in a rotavap device at 65° C. When the compound started to melt, water was removed from the melt. After approximately 30 min, the mixture solidified.

Example 17—A Cocrystal of R-Fasoracetam and Trimesic Acid

Figure 52:
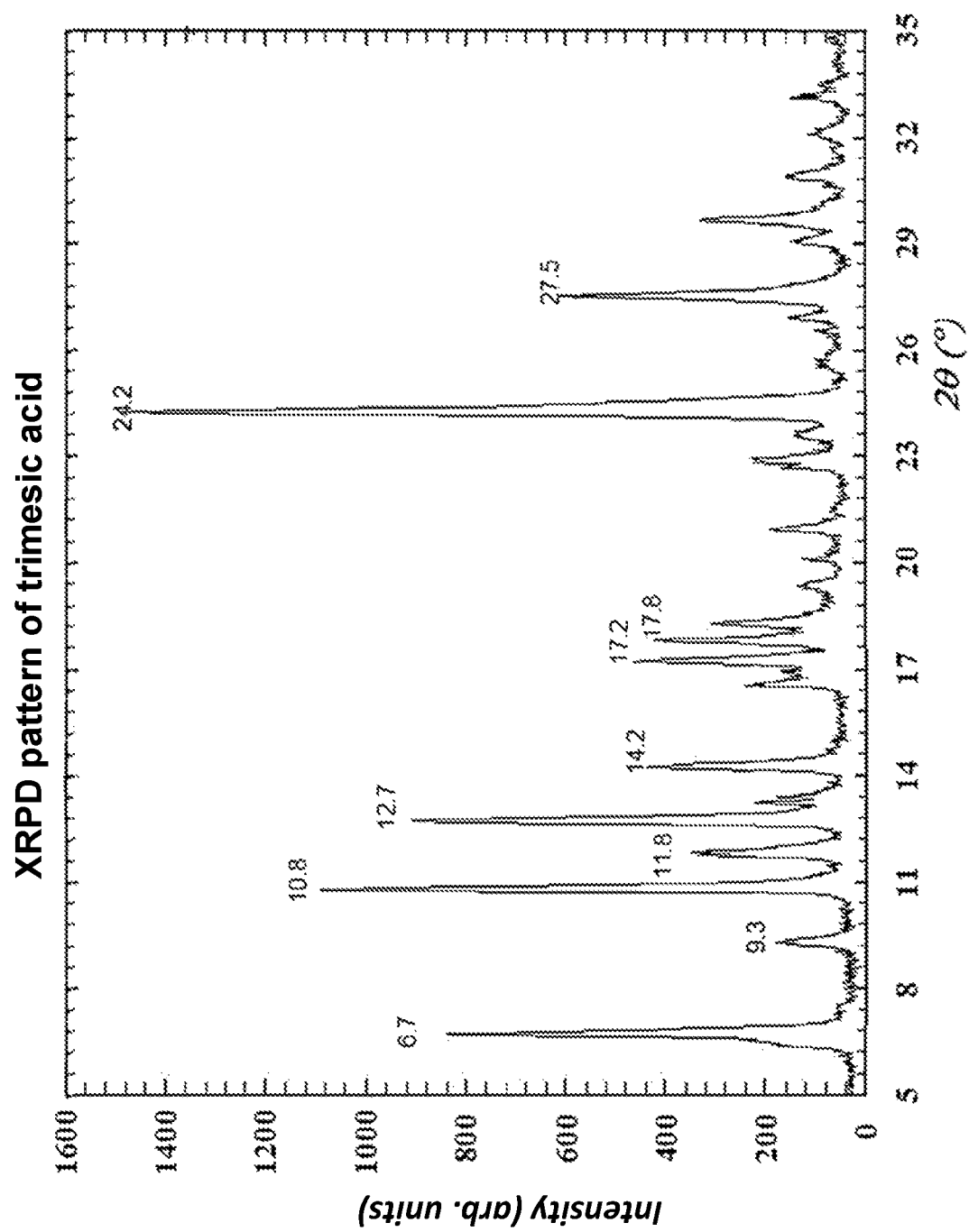
FIG. 52 is an XRPD pattern of trimesic acid.
Figure 53:
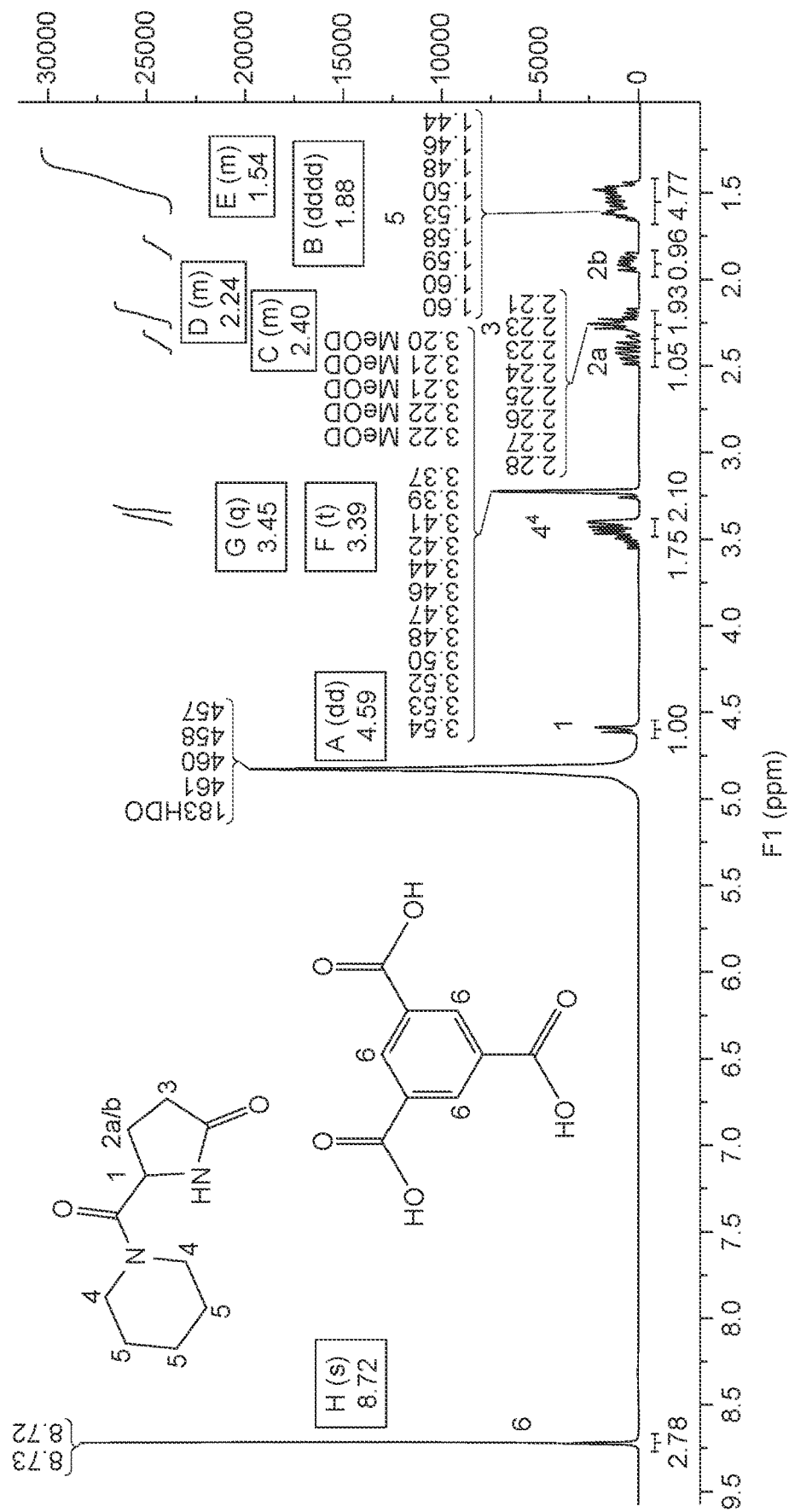
FIG. 53 is a $^1$H-NMR spectrum of dissolved R-fasoracetam:trimesic acid cocrystal.
Figure 55:
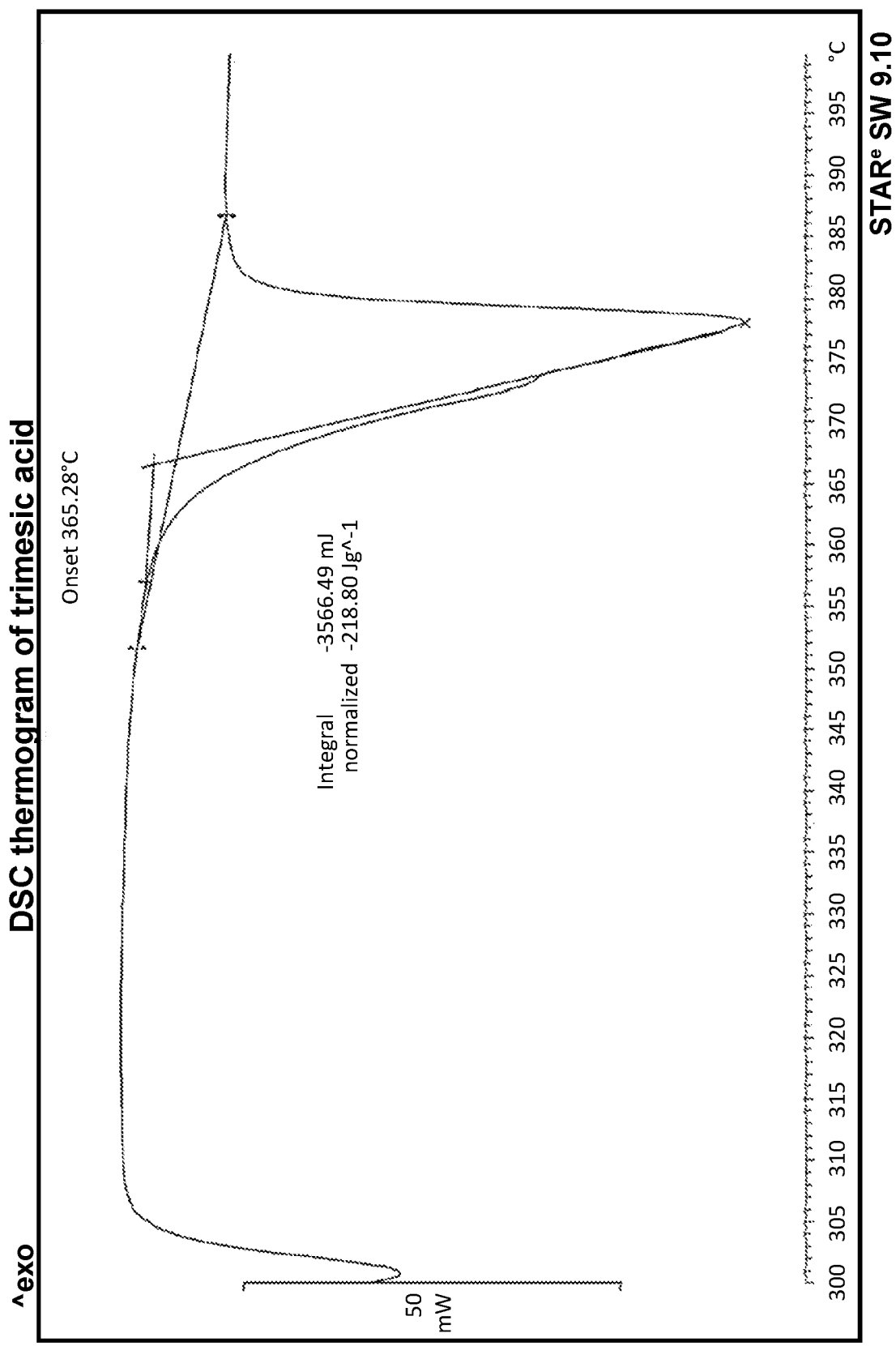
FIG. 55 is a DSC thermogram of trimesic acid.

A cocrystal of R-fasoracetam and trimesic acid was prepared by addition of 32.23 mg of trimesic acid and 30.25 mg of R-fasoracetam monohydrate Form I (1:1 molar ratio) to an Eppendorf together with 3 stainless steel grinding beads. The mixture was ground in a RETSCH Mixer Mill MM 400 for 90 min with a beating frequency of 30 Hz to provide a ground crystalline material. FIG. 50 is an overlay of x-ray powder diffraction patterns of the ground crystalline material compared with that of trimesic acid and R-fasoracetam monohydrate Form I, indicating a cocrystal of R-fasoracetam and trimesic acid. FIG. 51 is an x-ray powder diffraction pattern of a cocrystal of R-fasoracetam and trimesic acid and FIG. 52 is an x-ray powder diffraction pattern of trimesic acid. FIG. 53 is a ¹H-NMR spectrum of a dissolved cocrystal of R-fasoracetam and trimesic acid and all hydrogens are accounted for without evidence of degradation. FIG. 54 is a differential scanning calorimetry thermogram of a cocrystal of R-fasoracetam and trimesic acid showing a single endotherm and FIG. 55 is a differential scanning calorimetry thermogram of trimesic acid.

Example 18—A Single Crystal Cocrystal of Fasoracetam and R-Ibuprofen

Figure 56:
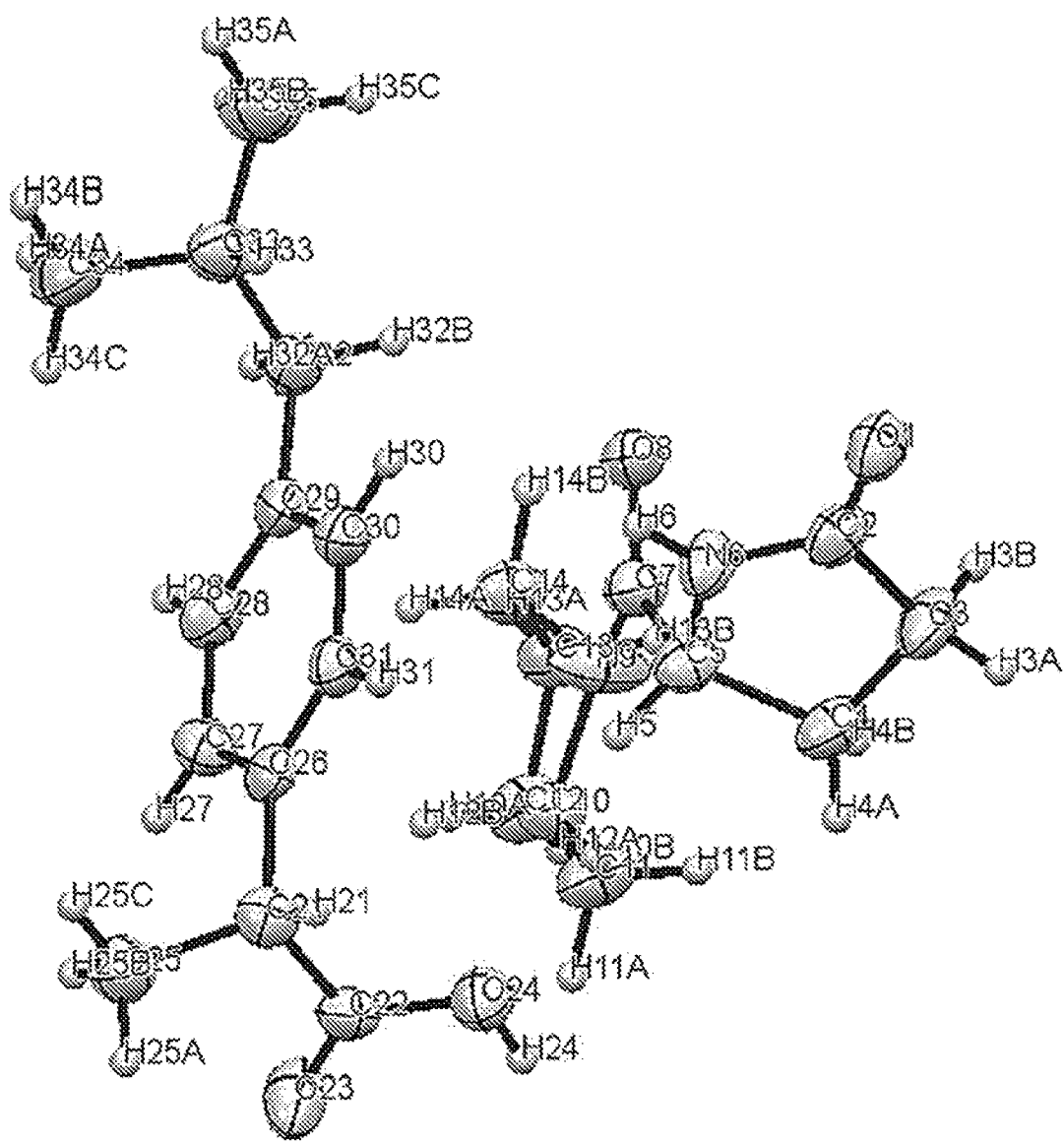
FIG. 56 is an ORTEP drawing of R-fasoracetam:R-ibuprofen cocrystal.

A 1:1 stoichiometric cocrystal of R-fasoracetam and R-ibuprofen may be prepared by slow evaporation in EtOH of an equimolar ratio of R-fasoracetam monohydrate hydrate Form I and RS-Ibuprofen. During evaporation, the solution may be seeded with a seed of the product of Example 19. FIG. 56 is an ORTEP drawing of the single crystal solution of a cocrystal of R-fasoracetam and R-ibuprofen. Table 8 lists single crystal parameters for the cocrystal of R-fasoracetam and R-ibuprofen. FIG. 57 is a simulated x-ray powder diffraction pattern from a single crystal solution of a cocrystal of R-fasoracetam and R-ibuprofen.

TABLE 8

Single Crystal parameters for 1:1 cocrystal of R-fasoracetam and R-ibuprofen

| PARAMETER | RESULTS | |
|---|---|---|
| Empirical formula | C23 H34 N2 O4 | |
| Formula weight | 402.52 | |
| Temperature | 150(2) K | |
| Wavelength | 0.71073 Å | |
| Crystal system | Monoclinic | |
| Space group | P2₁ | |
| Unit cell dimensions | a = 8.782(3) Å | α = 90°. |
| | b = 7.974(2) Å | β = 103.03(3)°. |
| | c = 16.072(4) Å | γ = 90°. |
| Volume | 1096.6(5) Å³ | |
| Z | 2 | |
| Density (calculated) | 1.219 Mg/m³ | |
| F(000) | 436 | |
| Crystal size | 1.20 × 0.25 × 0.10 mm³ | |
| Theta range for data collection | 3.106 to 26.124°. | |
| Index ranges | −10 <= h <= 10, −9 <= k <= 9, −19 <= l <= 19 | |
| Reflections collected | 9972 | |
| Independent reflections | 4256 [R(int) = 0.0560] | |
| Completeness to theta = 25.242° | 99.0% | |
| Absorption correction | Semi-empirical from equivalents | |
| Max. and min. transmission | 1.00000 and 0.18608 | |
| Refinement method | Full-matrix least-squares on F² | |
| Data/restraints/parameters | 4256/1/312 | |
| Goodness-of-fit on F² | 1.050 | |
| Final R indices [I > 2sigma(I)] | R1 = 0.0493, wR2 = 0.1209 | |
| R indices (all data) | R1 = 0.0601, wR2 = 0.1319 | |
| Absolute structure parameter | −0.6(10) | |
| Extinction coefficient | n/a | |
| Largest diff. peak and hole | 0.186 and −0.184 e · Å⁻³ | |

Example 19—Ground Crystalline R-Fasoracetam and R-Ibuprofen

Figure 60:
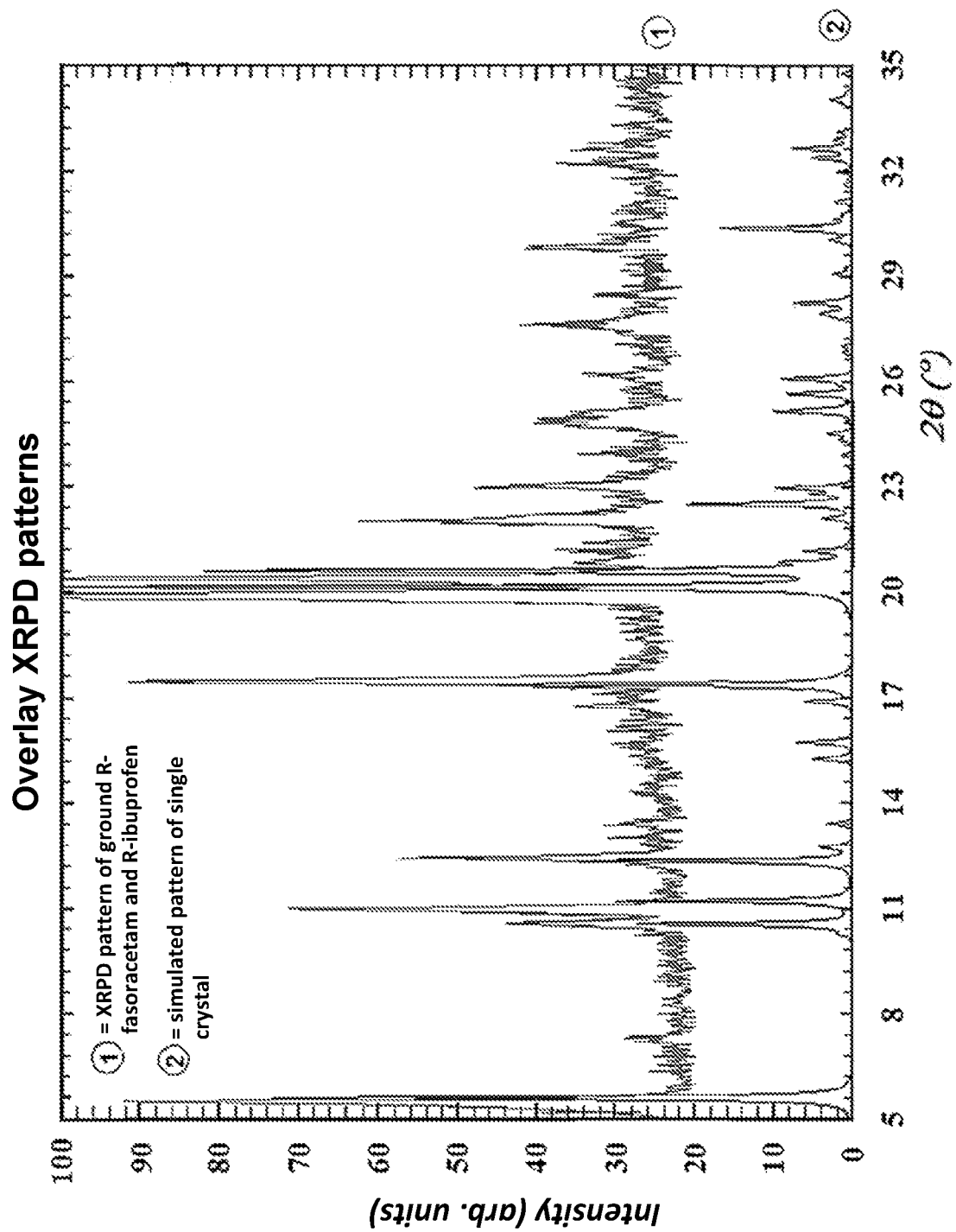
FIG. 60 is an overlay of XRPD patterns: (1) XRPD pattern of ground R-fasoracetam and R-ibuprofen; (2) simulated pattern of a single crystal of R-fasoracetam:R-ibuprofen.
Figure 61:
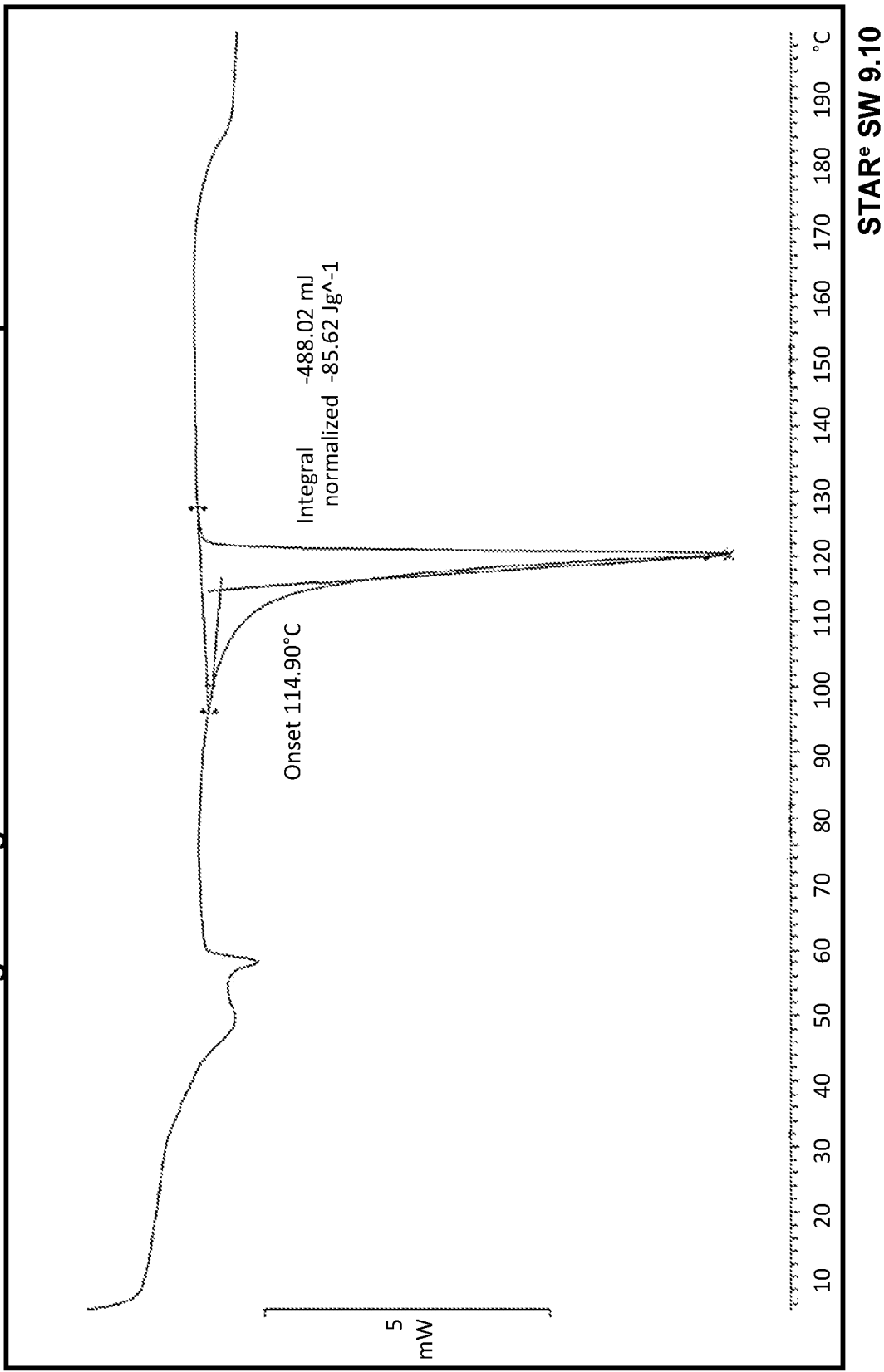
FIG. 61 is a DSC thermogram of ground R-fasoracetam and R-ibuprofen.
Figure 62:
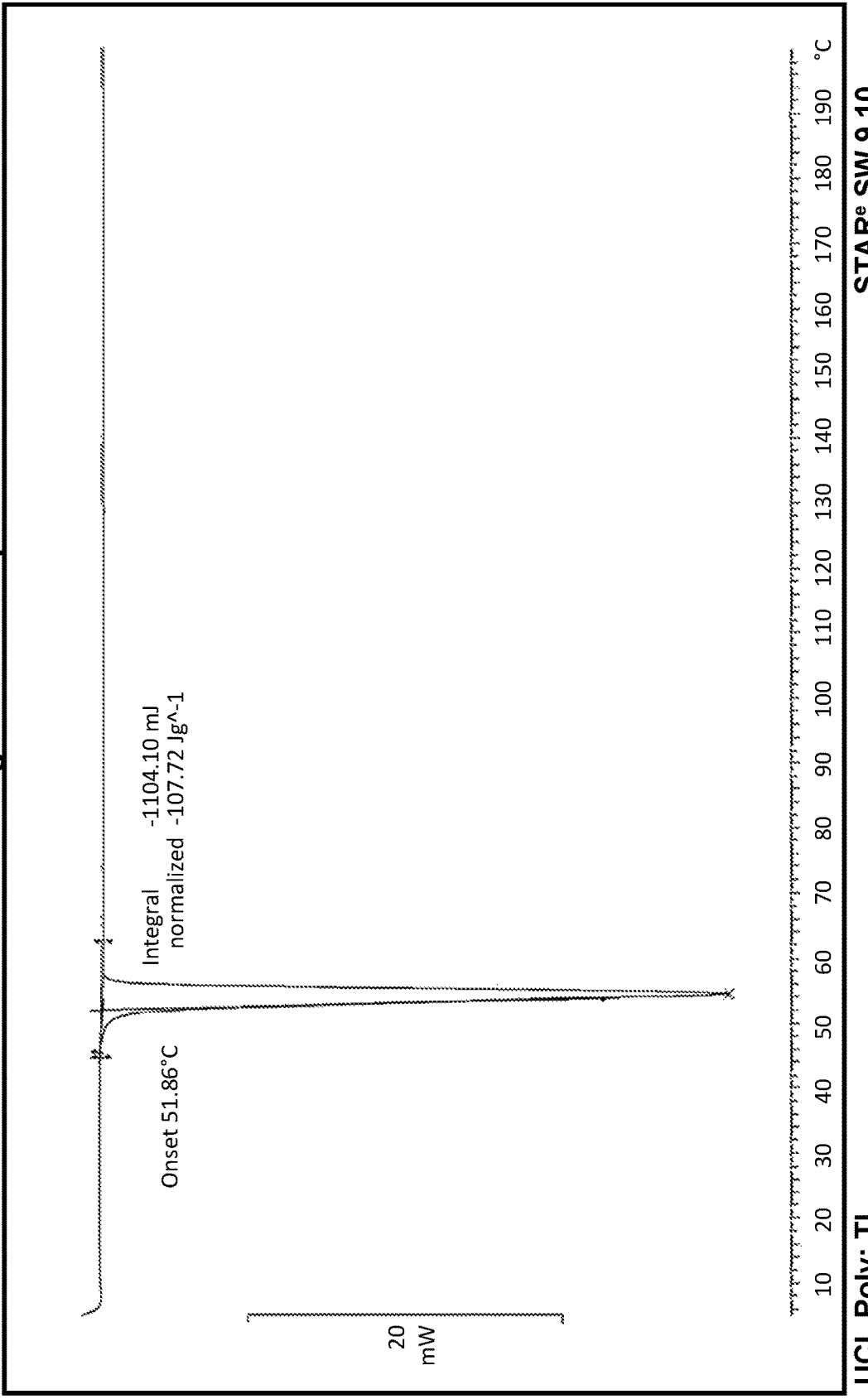
FIG. 62 is a DSC thermogram of R-ibuprofen.

Ground crystalline R-fasoracetam R-ibuprofen material was prepared by addition of 25.3 mg of ibuprofen and 27.9 mg of R-fasoracetam monohydrate Form I sourced from Jinan Haohua Industry Co., Ltd. to an Eppendorf together with 3 stainless steel grinding beads. The mixture was ground in a RETSCH Mixer Mill MM 400 for 90 min with a beating frequency of 30 Hz to create a ground crystalline material of R-fasoracetam and R-ibuprofen to make ground crystalline R-fasoracetam R-ibuprofen. FIG. 58 is an is an x-ray powder diffraction pattern of the ground crystalline R-fasoracetam and R-ibuprofen material. FIG. 59 is an XRPD pattern of R-ibuprofen. FIG. 60 is an overlay of XRPD patterns of ground crystalline R-fasoracetam R-ibuprofen material compared with the simulated XRPD pattern of FIG. 57. FIG. 61 is the DSC thermogram of the ground crystalline R-fasoracetam R-ibuprofen material, and FIG. 62 is a DSC thermogram of R-ibuprofen.

Example 20—A Single Crystal Cocrystal of Fasoracetam and Phthalic Acid (1:1)

Figure 63:
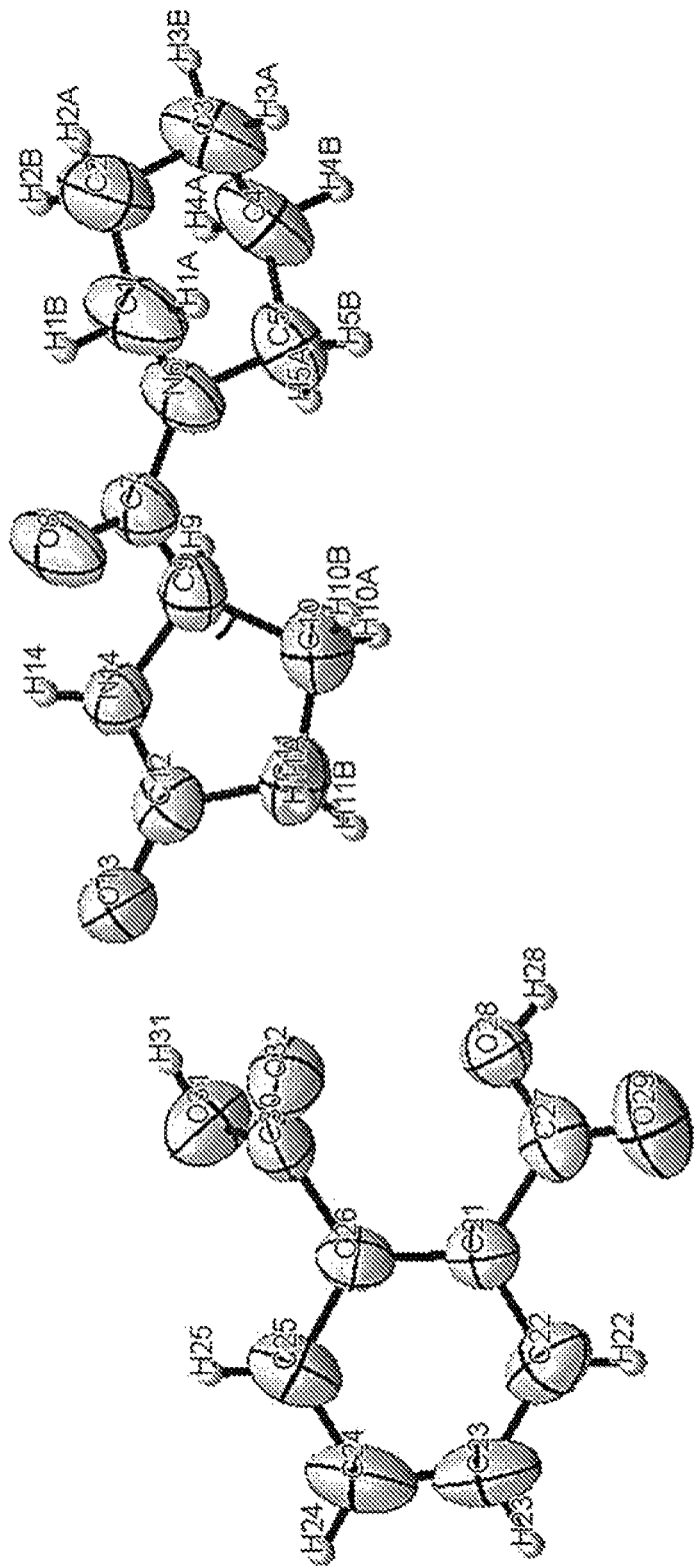
FIG. 63 is an ORTEP drawing of R-fasoracetam:phthalic acid cocrystal.
Figure 64:
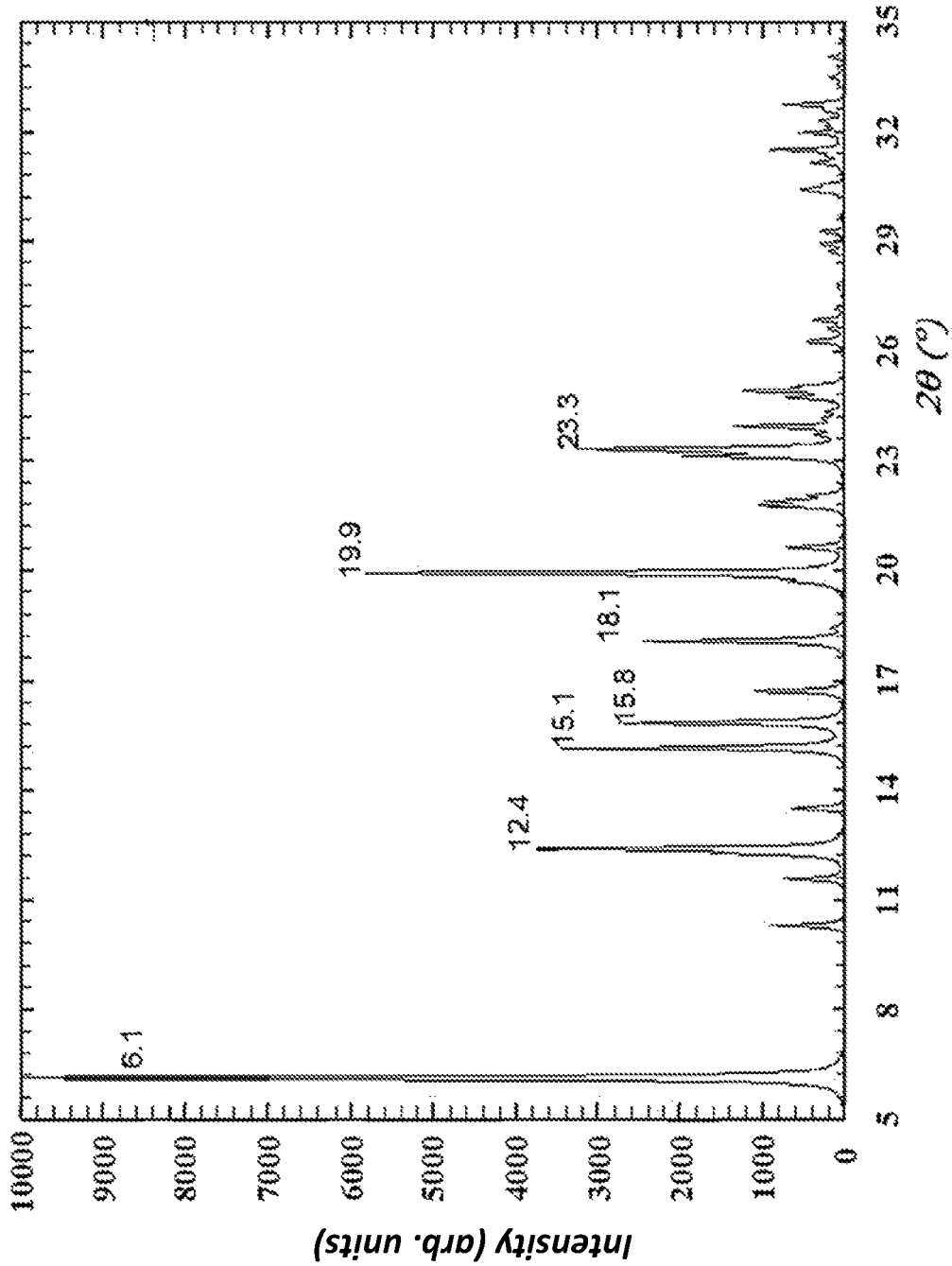
FIG. 64 is a simulated XRPD pattern of R-fasoracetam:phthalic acid cocrystal.
Figure 65:
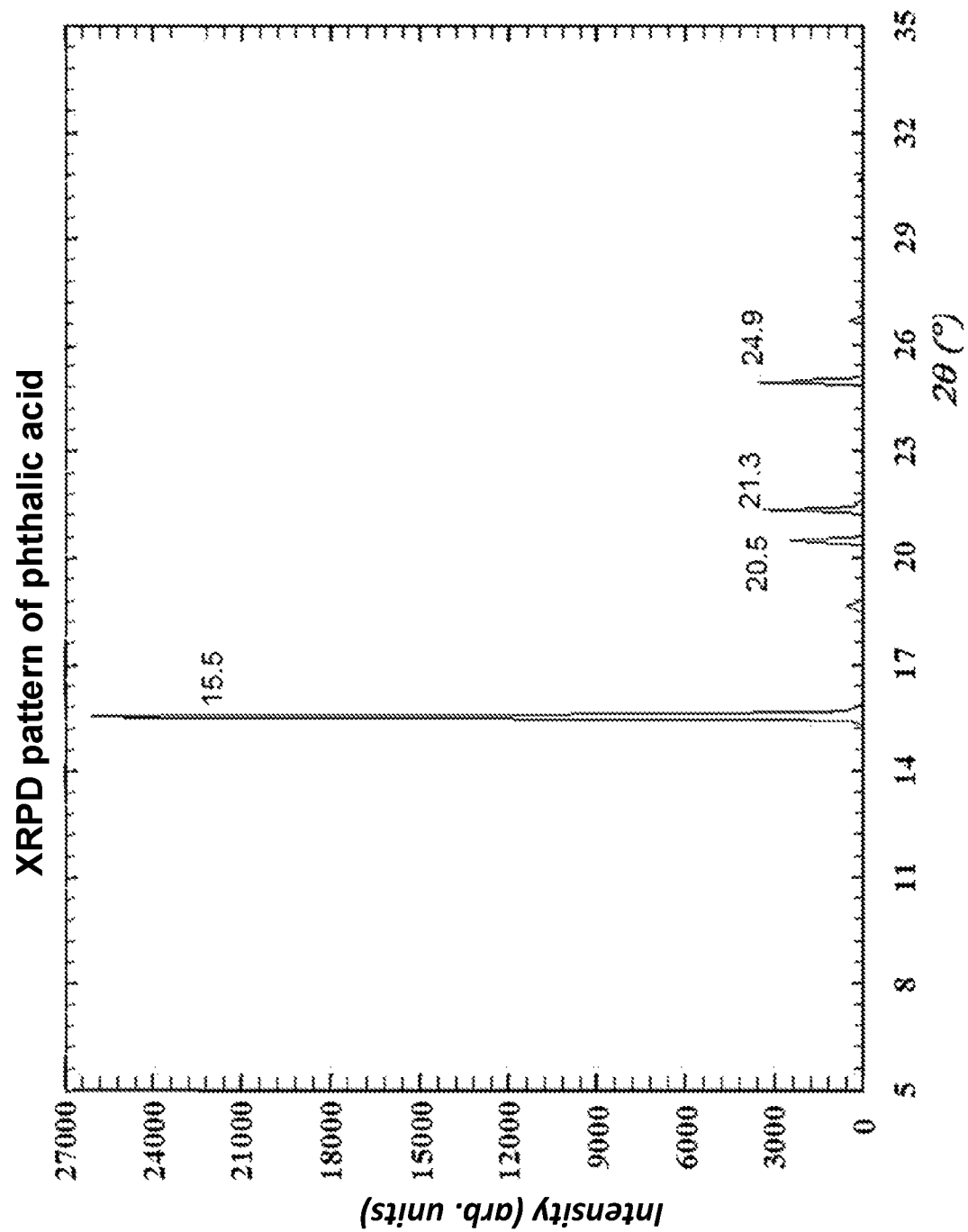
FIG. 65 is an XRPD pattern of phthalic acid.

A single crystal of a 1:1 cocrystal of R-fasoracetam to phthalic acid was obtained dissolving a stoichiometric amount of R-fasoracetam (30 mg of R-fasoracetam monohydrate Form I) and phthalic acid in EtOH and followed by slow evaporation of the ethanol to produce single crystals of the cocrystal. Table 9 provides single crystal data for such a cocrystal and FIG. 63 is an ORTEP drawing of the single crystal data. FIG. 64 is the simulated x-ray powder diffraction pattern of a cocrystal of R-fasoracetam and phthalic acid taken from the single crystal data collected on the single crystal. FIG. 65 is the x-ray powder diffraction pattern of phthalic acid.

TABLE 9

Single Crystal Solution Parameters for a 1:1 cocrystal of R-fasoracetam and phthalic acid

| PARAMETER | RESULTS | |
|---|---|---|
| Empirical formula | C18 H22 N2 O6 | |
| Formula weight | 362.37 | |
| Temperature | 293(2) K | |
| Wavelength | 0.71073 Å | |
| Crystal system | Orthorhombic | |
| Space group | P2₁2₁2₁ | |
| Unit cell dimensions | a = 7.3687(8) Å | α = 90°. |
| | b = 9.0191(9) Å | β = 90°. |
| | c = 28.871(3) Å | γ = 90°. |
| Volume | 1918.7(3) Å³ | |
| Z | 4 | |
| Density (calculated) | 1.254 Mg/m³ | |
| Absorption coefficient | 0.095 mm⁻¹ | |
| F(000) | 768 | |
| Crystal size | 0.40 × 0.10 × 0.10 mm³ | |
| Theta range for data collection | 3.095 to 25.404°. | |
| Index ranges | −8 <= h <= 8, −10 <= k <= 10, −34 <= l <= 34 | |
| Reflections collected | 11979 | |
| Independent reflections | 3388 [R(int) = 0.0684] | |
| Completeness to theta = 25.242° | 98.7% | |
| Absorption correction | Semi-empirical from equivalents | |
| Max. and min. transmission | 1.00000 and 0.87566 | |
| Refinement method | Full-matrix least-squares on F² | |
| Data/restraints/parameters | 3388/128/344 | |
| Goodness-of-fit on F² | 1.054 | |
| Final R indices [I > 2sigma(I)] | R1 = 0.0578, wR2 = 0.1463 | |
| R indices (all data) | R1 = 0.0957, wR2 = 0.1876 | |
| Absolute structure parameter | −1.9(10) | |

TABLE 9-continued

Single Crystal Solution Parameters for a 1:1
cocrystal of R-fasoracetam and phthalic acid

| PARAMETER | RESULTS |
|---|---|
| Extinction coefficient | n/a |
| Largest diff. peak and hole | 0.150 and −0.203 e · Å$^{-3}$ |

Example 21—A Monohydrate Cocrystal of R-Fasoracetam and Phloroglucinol

Figure 66:
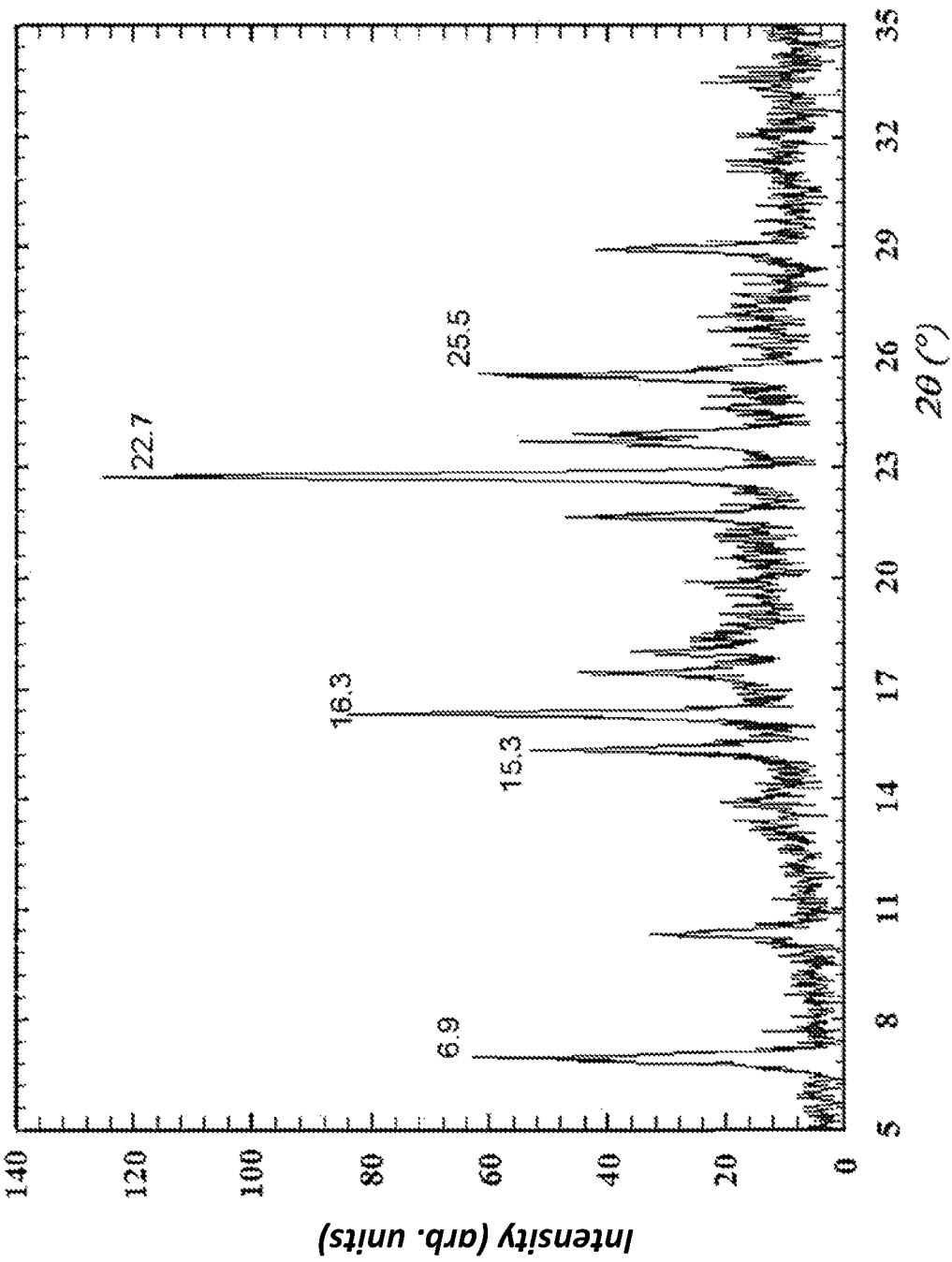
FIG. 66 is an XRPD pattern of a monohydrate cocrystal of R-fasoracetam and phloroglucinol.
Figure 68:
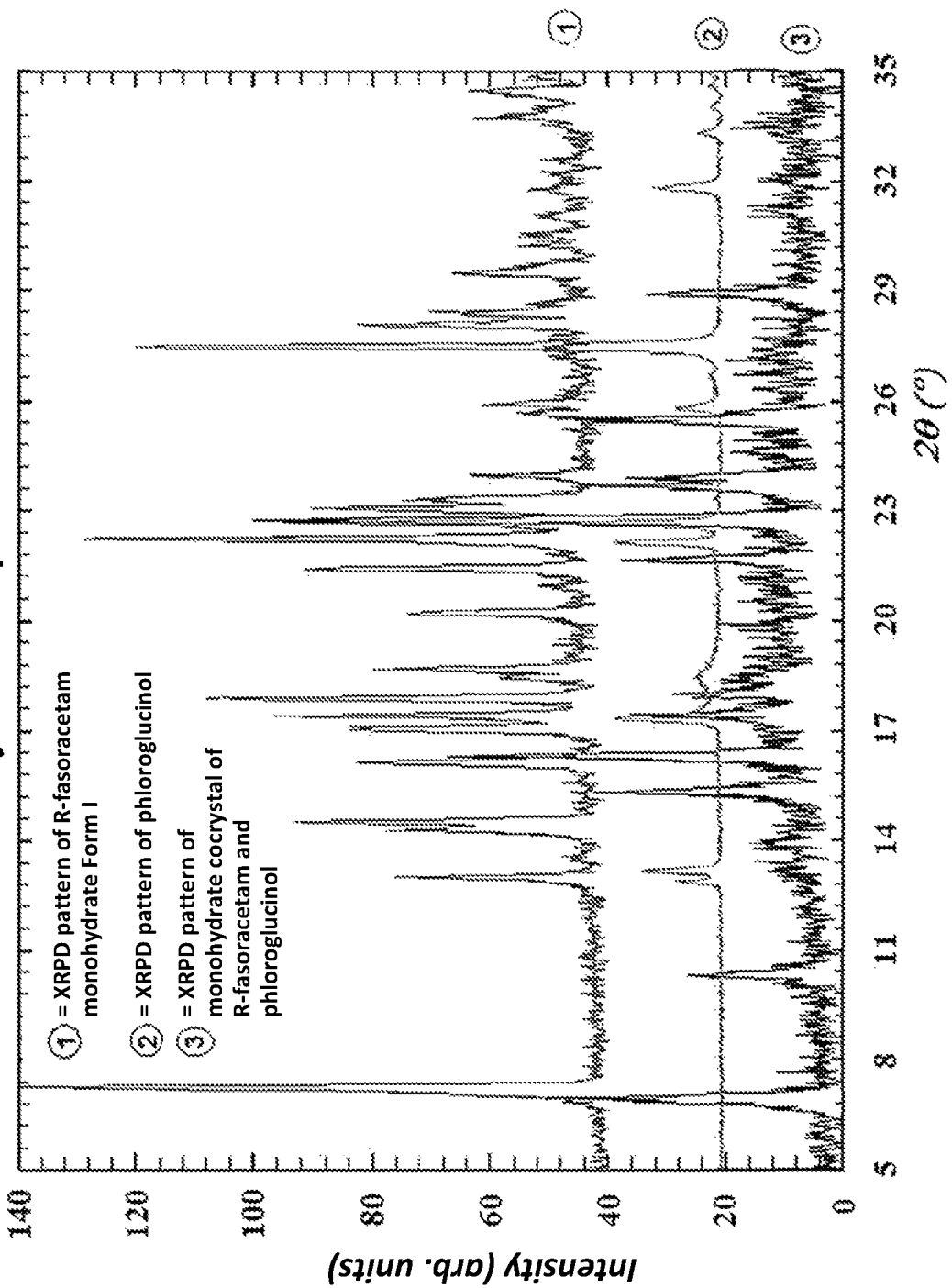
FIG. 68 is an overlay of XRPD patterns: (1) XRPD pattern of R-fasoracetam monohydrate Form I; (2) XRPD pattern of phloroglucinol; (3) XRPD pattern of monohydrate cocrystal of R-fasoracetam and phloroglucinol.
Figure 69:
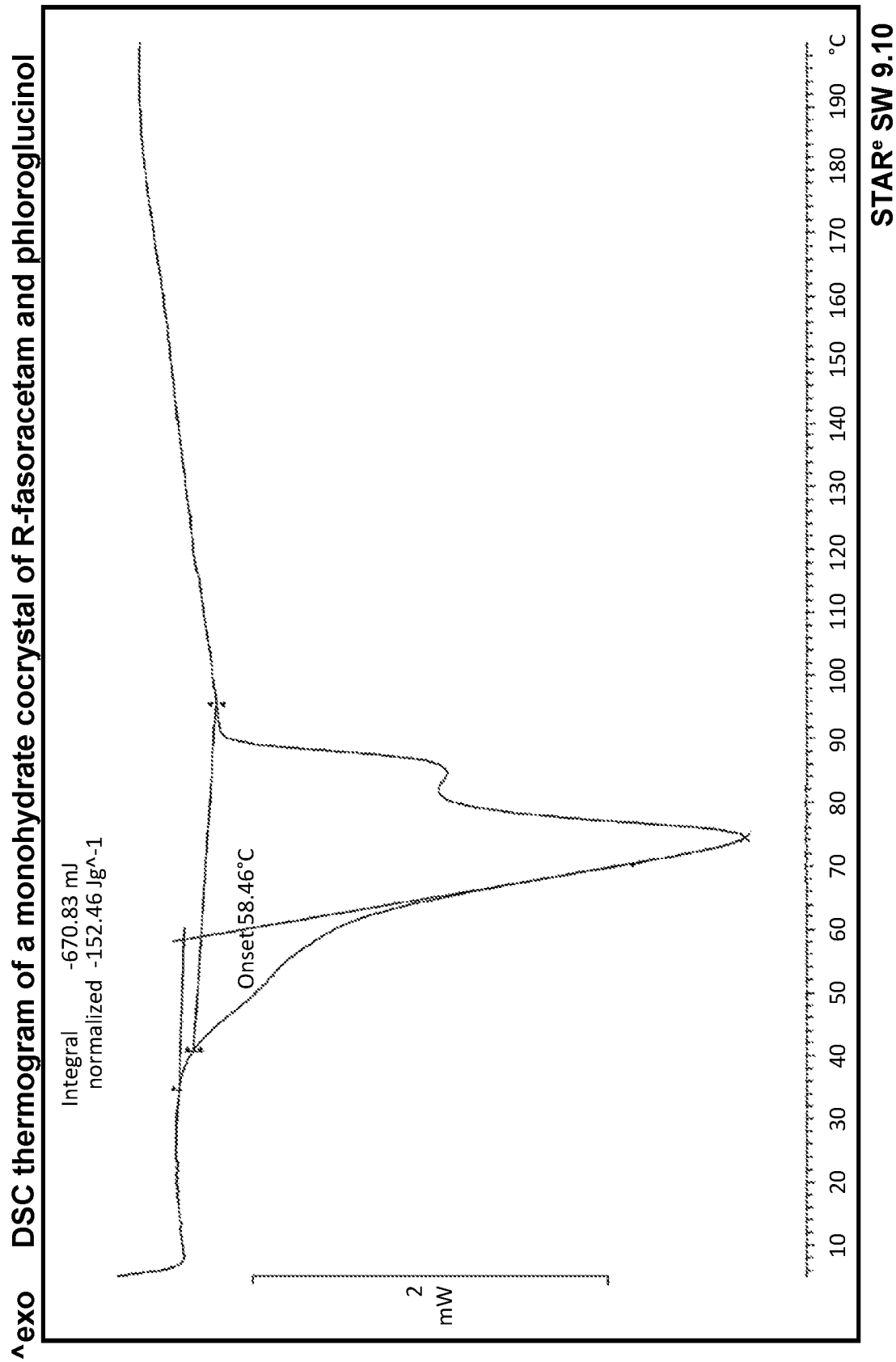
FIG. 69 is a DSC thermogram of a monohydrate cocrystal of R-fasoracetam and phloroglucinol.
Figure 70:
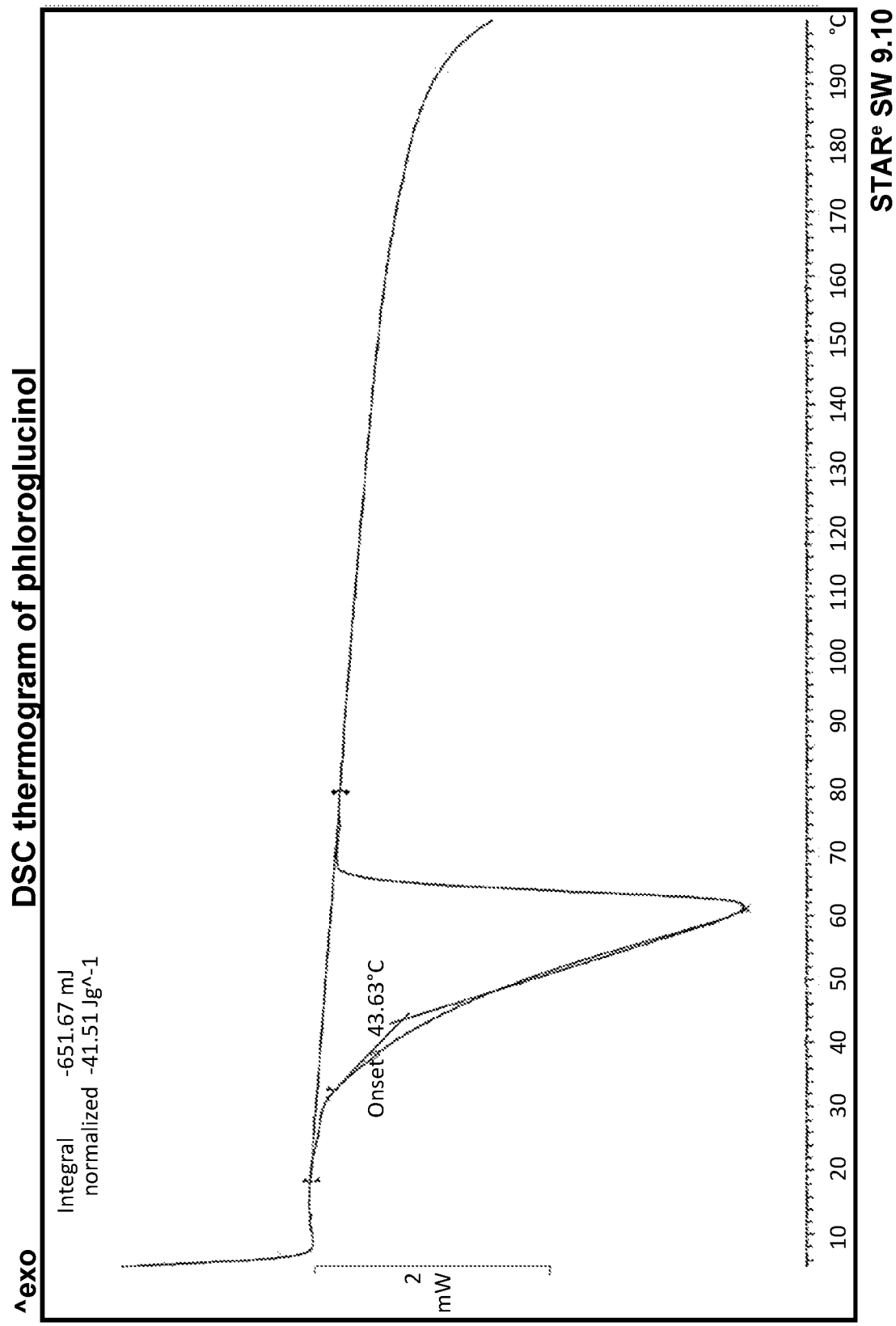
FIG. 70 is a DSC thermogram of phloroglucinol.

A monohydrate cocrystal of R-fasoracetam and phloroglucinol was prepared by addition of 25.7 mg of phloroglucinol and 40 mg of R-fasoracetam monohydrate Form I sourced from Jinan Haohua Industry Co., Ltd to an Eppendorf together with 3 stainless steel grinding beads. The mixture was ground in a RETSCH Mixer Mill MM 400 for 90 min with a beating frequency of 30 Hz to form a ground crystalline material which was a monohydrate of a 1:1 cocrystal of R-fasoracetam to phloroglucinol. FIG. 66 is an x-ray powder diffraction pattern of the monohydrate cocrystal of R-fasoracetam and phloroglucinol. FIG. 67 is an x-ray powder diffraction pattern of phloroglucinol. FIG. 68 is an overlay of x-ray powder diffraction patterns of a monohydrate cocrystal of R-fasoracetam and phloroglucinol, phloroglucinol, and R-fasoracetam monohydrate Form I. FIG. 69 is a differential scanning calorimetry thermogram of a monohydrate cocrystal of R-fasoracetam and phloroglucinol and FIG. 70 is a differential scanning calorimetry thermogram of phloroglucinol.

Example 22—A Monohydrate Cocrystal of R-Fasoracetam and Phloroglucinol

Figure 71:
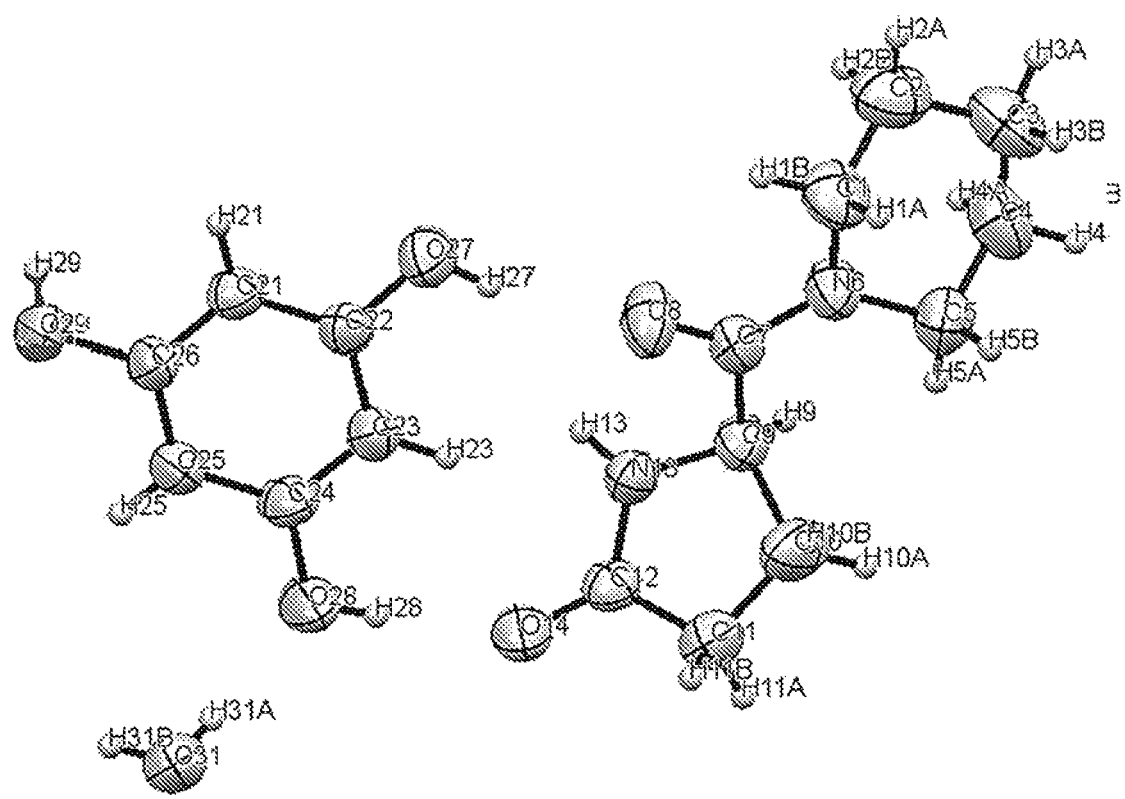
FIG. 71 is an ORTEP drawing of a monohydrate cocrystal of R-fasoracetam and phloroglucinol.
Figure 73:
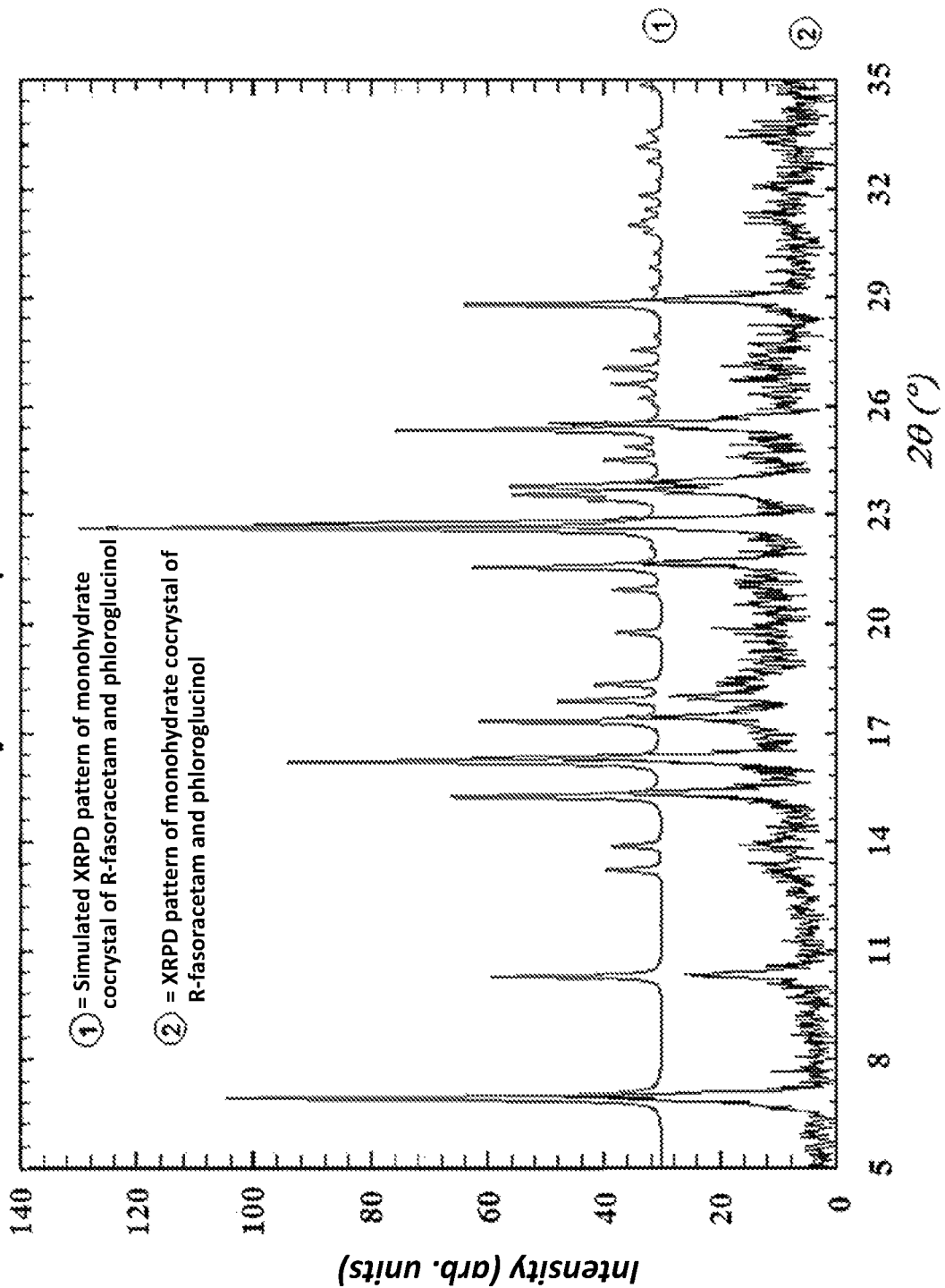
FIG. 73 is an overlay of XRPD patterns: (1) Simulated XRPD pattern of monohydrate cocrystal of R-fasoracetam and phloroglucinol; (2) XRPD pattern of a monohydrate cocrystal of R-fasoracetam and phloroglucinol.

A 1:1:1 cocrystal of R-fasoracetam, phloroglucinol, and water was obtained by dissolving a stoichiometric amount of 30 mg of R-fasoracetam monohydrate Form I sourced from Jinan Haohua Industry Co., Ltd and phloroglucinol in EtOH and through slow solvent evaporation. Table 10 provides single crystal data for the cocrystal and FIG. 71 is an ORTEP drawing of the single crystal data. FIG. 72 is the simulated x-ray powder diffraction pattern of a cocrystal of R-fasoracetam and phloroglucinol taken from the single crystal data collected on the single crystal. FIG. 73 is an overlay of the experimental pattern from Example 21 and the simulated pattern from the single crystal of this Example 22 which matches thus showing that the ground crystalline material of Example 21 is a 1:1:1 cocrystal of R-fasoracetam to phloroglucinol to water.

TABLE 10

Single Crystal Data Parameters of a Monohydrate
Cocrystal of R-fasoracetam and Phloroglucinol

| PARAMETER | RESULTS | |
|---|---|---|
| Empirical formula | C16 H24 N2 O6 | |
| Formula weight | 340.37 | |
| Temperature | 297(2) K | |
| Wavelength | 0.71073 Å | |
| Crystal system | Monoclinic | |
| Space group | P2$_1$ | |
| Unit cell dimensions | a = 8.6696(11) Å | α = 90°. |
| | b = 7.8684(9) Å | β = 97.365(10)°. |
| | c = 12.8601(13) Å | γ = 90°. |
| Volume | 870.03(17) Å$^3$ | |
| Z | 2 | |
| Density (calculated) | 1.299 Mg/m$^3$ | |
| Absorption coefficient | 0.100 mm$^{-1}$ | |
| F(000) | 364 | |
| Crystal size | 0.50 × 0.20 × 0.10 mm$^3$ | |
| Theta range for data collection | 3.042 to 25.240°. | |
| Index ranges | −10 <= h <= 10, −9 <= k <= 9, −15 <= l <= 15 | |
| Reflections collected | 5057 | |
| Independent reflections | 2994 [R(int) = 0.0484] | |
| Completeness to theta = 25.240° | 98.6% | |
| Absorption correction | Semi-empirical from equivalents | |
| Max. and min. transmission | 1.00000 and 0.17960 | |
| Refinement method | Full-matrix least-squares on F$^2$ | |
| Data/restraints/parameters | 2994/1/220 | |
| Goodness-of-fit on F$^2$ | 1.112 | |
| Final R indices [I > 2sigma(I)] | R1 = 0.0471, wR2 = 0.1206 | |
| R indices (all data) | R1 = 0.0660, wR2 = 0.1351 | |
| Absolute structure parameter | 2.2(10) | |
| Extinction coefficient | n/a | |
| Largest diff. peak and hole | 0.159 and −0.172 e · Å$^{-3}$ | |

Figure 74:
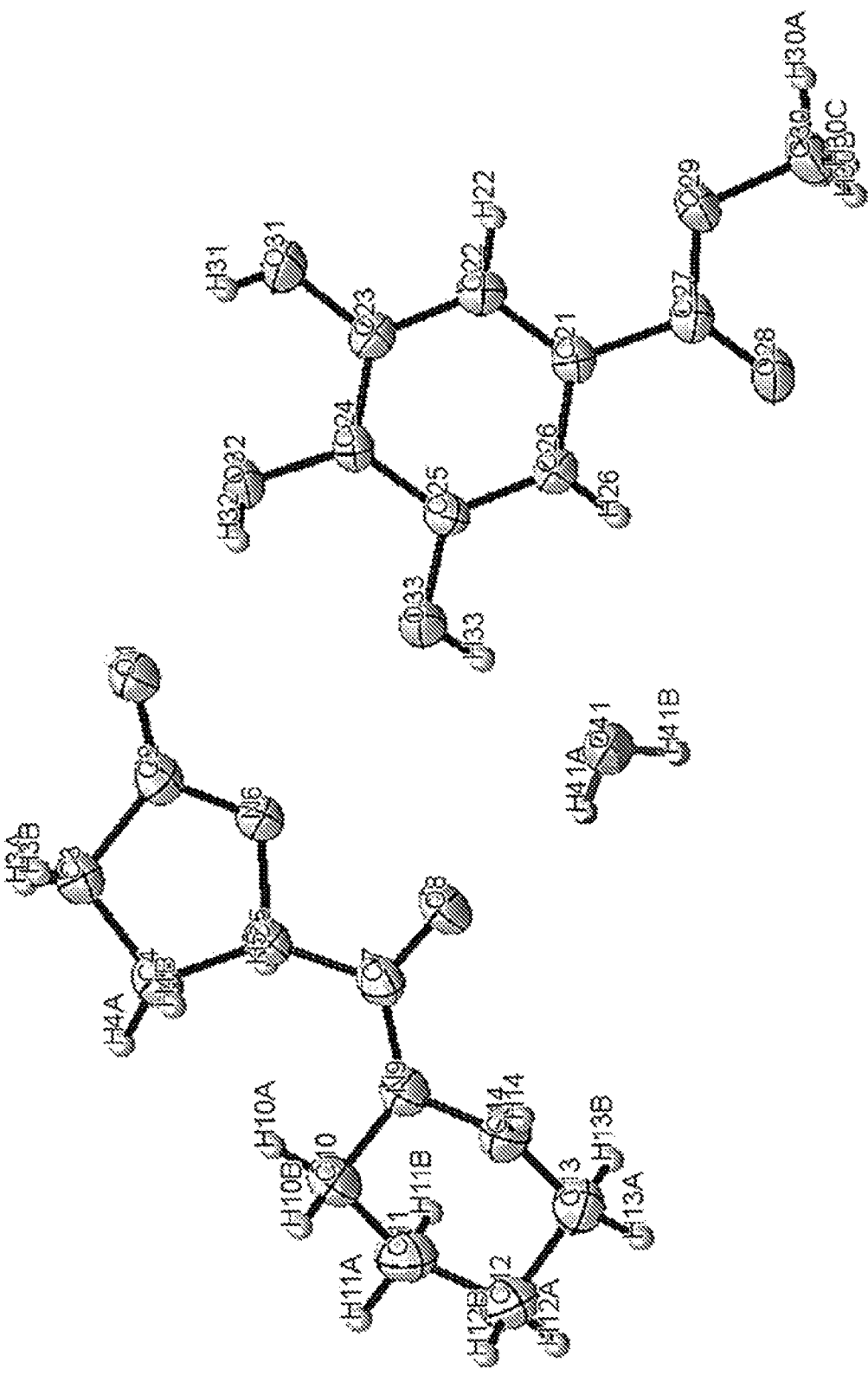
FIG. 74 is an ORTEP drawing of a monohydrate of R-fasoracetam and methyl-3,4,5-trihydroxybenzoate cocrystal.
Figure 76:
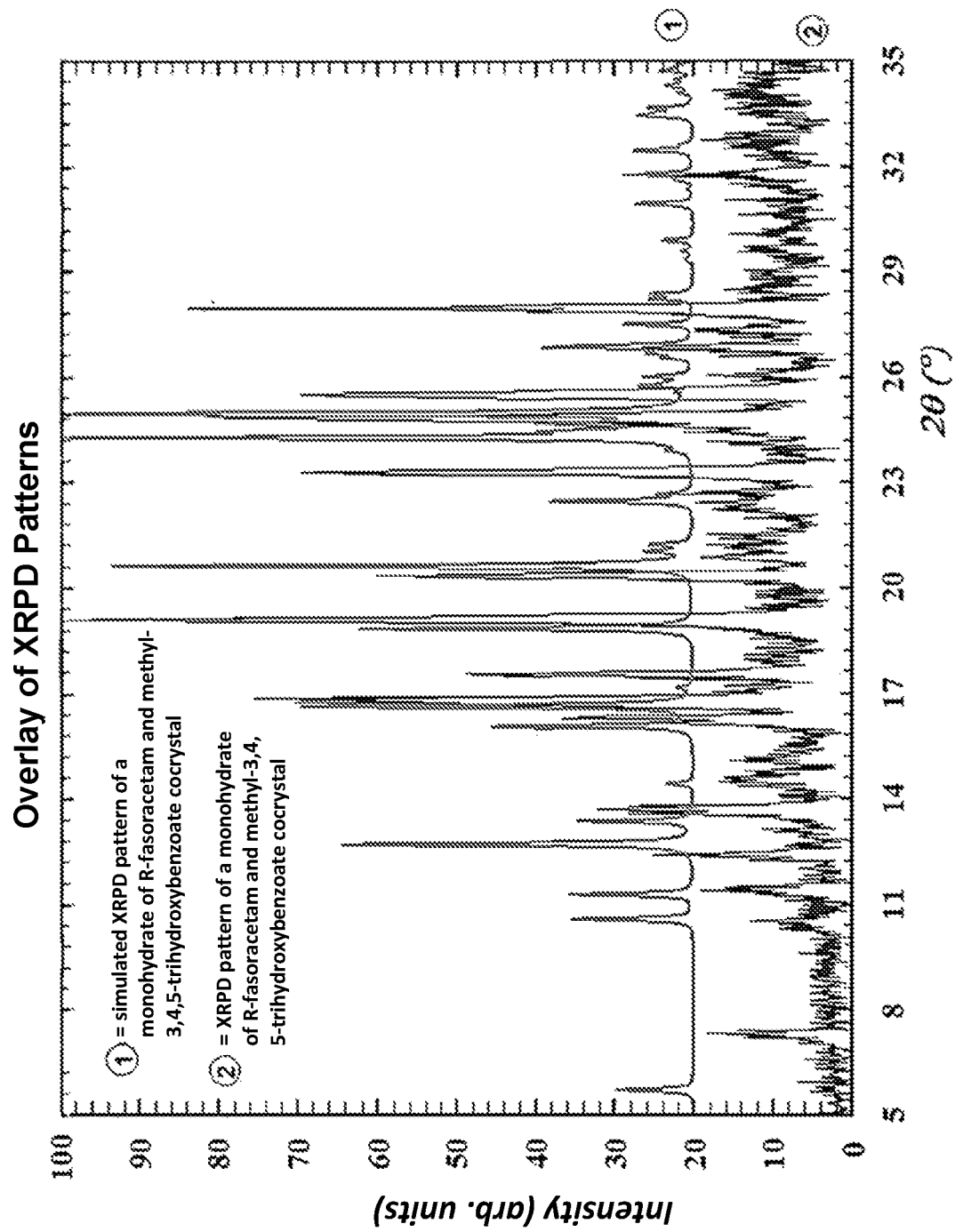
FIG. 76 is an overlay of XRPD patterns: (1) simulated XRPD pattern of a monohydrate of R-fasoracetam and methyl-3,4,5-trihydroxybenzoate cocrystal; (2) XRPD pattern of a monohydrate of R-fasoracetam and methyl-3,4,5-trihydroxybenzoate cocrystal.

Example 23—Single Crystal of a Monohydrate of R-Fasoracetam Methyl-3,4,5-Trihydroxybenzoate Cocrystal A single crystal of a monohydrate of R-fasoracetam and methyl-3,4,5-trihydroxy benzoic acid cocrystal was prepared by dissolving a stoichiometric amount of 30 mg of R-fasoracetam monohydrate Form I sourced from Jinan Haohua Industry Co., Ltd and methyl-3,4,5-trihydroxybenzoate in EtOH and through slow solvent evaporation. Table 11 is data from the single crystal solution of the cocrystal and FIG. 74 is an ORTEP drawing of the single crystal. FIG. 75 is a simulated x-ray powder diffraction pattern of a monohydrate cocrystal of R-fasoracetam and methyl-3,4,5-trihydroxybenzoate. FIG. 76 is an overlay of x-ray powder diffraction patterns of a simulated pattern of a single crystal of a monohydrate of R-fasoracetam methyl-3,4,5-trihydroxybenzoate and an x-ray powder diffraction pattern of ground crystalline R-fasoracetam and methyl-3,4,5-trihydroxybenzoate material. FIG. 77 is an x-ray powder diffraction pattern of methyl-3,4,5-trihydroxybenzoate.

TABLE 11

Single Crystal Data Parameters from a Monohydrate
of R-fasoracetam Methyl-3,4,5-trihydroxy benzoate

| PARAMETER | RESULTS | |
|---|---|---|
| Empirical formula | C18 H24 N2 O8 | |
| Formula weight | 396.39 | |
| Temperature | 296(2) K | |
| Wavelength | 0.71073 Å | |
| Crystal system | Monoclinic | |
| Space group | P2$_1$ | |
| Unit cell dimensions | a = 8.4519(5) Å | α = 90°. |
| | b = 7.3250(4) Å | β = 98.135(5)°. |
| | c = 15.6450(7) Å | γ = 90°. |

TABLE 11-continued

Single Crystal Data Parameters from a Monohydrate
of R-fasoracetam Methyl-3,4,5-trihydroxy benzoate

| PARAMETER | RESULTS |
|---|---|
| Volume | 958.83(9) Å$^3$ |
| Z | 2 |
| Density (calculated) | 1.373 Mg/m$^3$ |
| Absorption coefficient | 0.109 mm$^{-1}$ |
| F(000) | 420 |
| Crystal size | 0.35 × 0.30 × 0.09 mm$^3$ |
| Theta range for data collection | 3.076 to 25.227°. |
| Index ranges | −10 <= h <= 10, −8 <= k <= 8, −18 <= l <= 18 |
| Reflections collected | 5449 |
| Independent reflections | 5449 [R(int) = 0] |
| Completeness to theta = 25.227° | 99.0% |
| Absorption correction | Semi-empirical from equivalents |
| Max. and min. transmission | 1.00000 and 0.76085 |
| Refinement method | Full-matrix least-squares on F$^2$ |
| Data/restraints/parameters | 5449/1/261 |
| Goodness-of-fit on F$^2$ | 1.013 |
| Final R indices [I > 2sigma(I)] | R1 = 0.0622, wR2 = 0.1667 |
| R indices (all data) | R1 = 0.0698, wR2 = 0.1731 |
| Absolute structure parameter | −0.6(10) |
| Extinction coefficient | n/a |
| Largest diff. peak and hole | 0.305 and −0.220 e · Å$^{-3}$ |

Example 24—Single Crystal of a 1:1 Cocrystal of R-Fasoracetam to Ethyl Gallate

Figure 78:
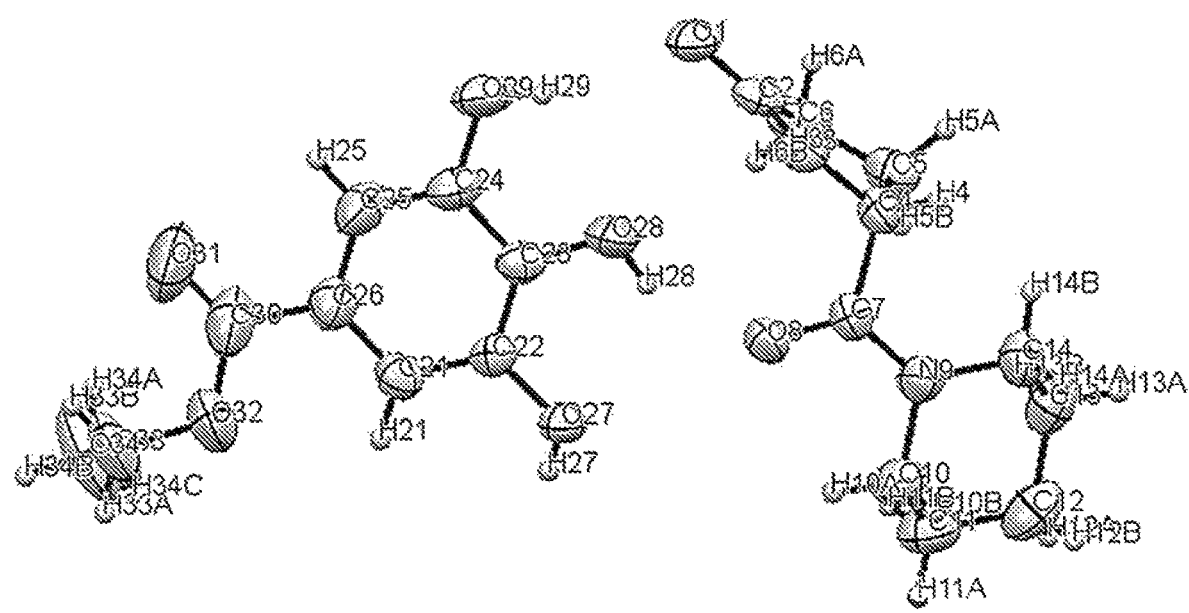
FIG. 78 is an ORTEP drawing of a 1:1 cocrystal of R-fasoracetam:ethyl gallate.

A 1:1 single crystal R-fasoracetam to ethyl gallate was obtained by adding a saturated solution of R-fasoracetam monohydrate Form I in ethanol to a saturated solution of ethyl gallate in EtOH. Equal volumes of both saturated solutions were added together, and the resulting solution left to evaporate which resulted in the cocrystal. Table 12 contains the single crystal solution data parameters and FIG. 78 is an ORTEP drawing of the single crystal. FIG. 79 is a simulated XRPD pattern of the cocrystal.

TABLE 12

Single Crystal Data Parameters for 1:1 Cocrystal
of R-fasoracetam to Ethyl Gallate

| PARAMETER | RESULTS | |
|---|---|---|
| Empirical formula | C19 H26 N2 O7 | |
| Formula weight | 394.42 | |
| Temperature | 293(2) K | |
| Wavelength | 0.71073 Å | |
| Crystal system | Orthorhombic | |
| Space group | P2$_1$2$_1$2$_1$ | |
| Unit cell dimensions | a = 8.0531(2) Å | α = 90°. |
|  | b = 8.0853(2) Å | β = 90°. |
|  | c = 30.6150(8) Å | γ = 90°. |
| Volume | 1993.40(9) Å$^3$ | |
| Z | 4 | |
| Density (calculated) | 1.314 Mg/m$^3$ | |
| Absorption coefficient | 0.100 mm$^{-1}$ | |
| F(000) | 840 | |
| Crystal size | 0.5 × 0.25 × 0.03 mm$^3$ | |
| Theta range for data collection | 3.215 to 26.185°. | |
| Index ranges | −9 <= h <= 10, −10 <= k <= 9, −37 <= l <= 37 | |
| Reflections collected | 14124 | |

TABLE 12-continued

Single Crystal Data Parameters for 1:1 Cocrystal
of R-fasoracetam to Ethyl Gallate

| PARAMETER | RESULTS |
|---|---|
| Independent reflections | 3933 [R(int) = 0.0357] |
| Completeness to theta = 25.242° | 99.1% |
| Absorption correction | Semi-empirical from equivalents |
| Max. and min. transmission | 1.00000 and 0.76047 |
| Refinement method | Full-matrix least-squares on F$^2$ |
| Data/restraints/parameters | 3933/0/268 |
| Goodness-of-fit on F$^2$ | 1.095 |
| Final R indices [I > 2sigma(I)] | R1 = 0.0409, wR2 = 0.1097 |
| R indices (all data) | R1 = 0.0467, wR2 = 0.1138 |
| Absolute structure parameter | −0.5(5) |
| Extinction coefficient | n/a |
| Largest diff. peak and hole | 0.152 and −0.143 e · Å$^{-3}$ |

Example 25—Cocrystal of R-Fasoracetam and Ethyl Gallate (1:1)

Figure 80:
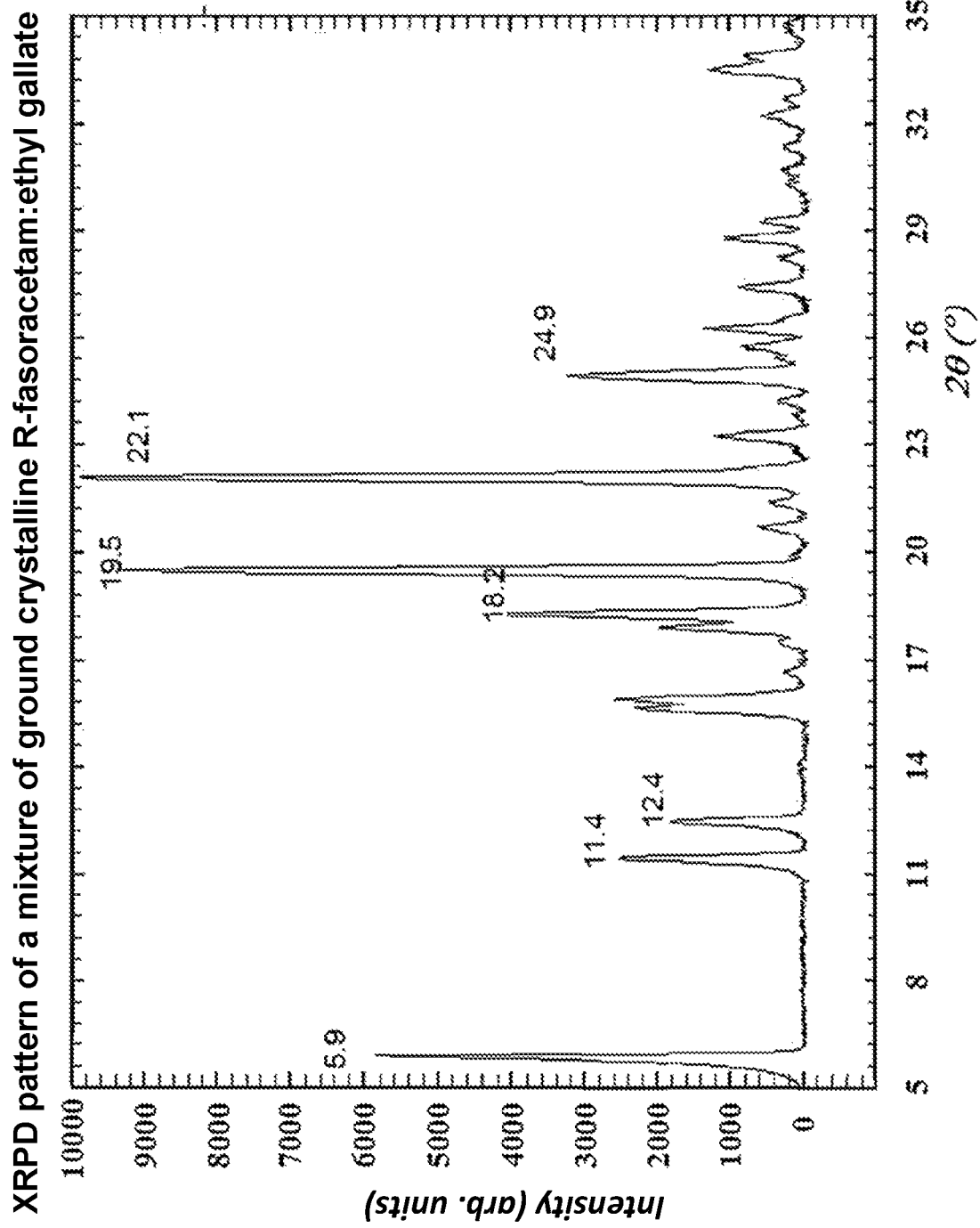
FIG. 80 is an XRPD pattern of a mixture of ground crystalline R-fasoracetam:ethyl gallate.
Figure 84:
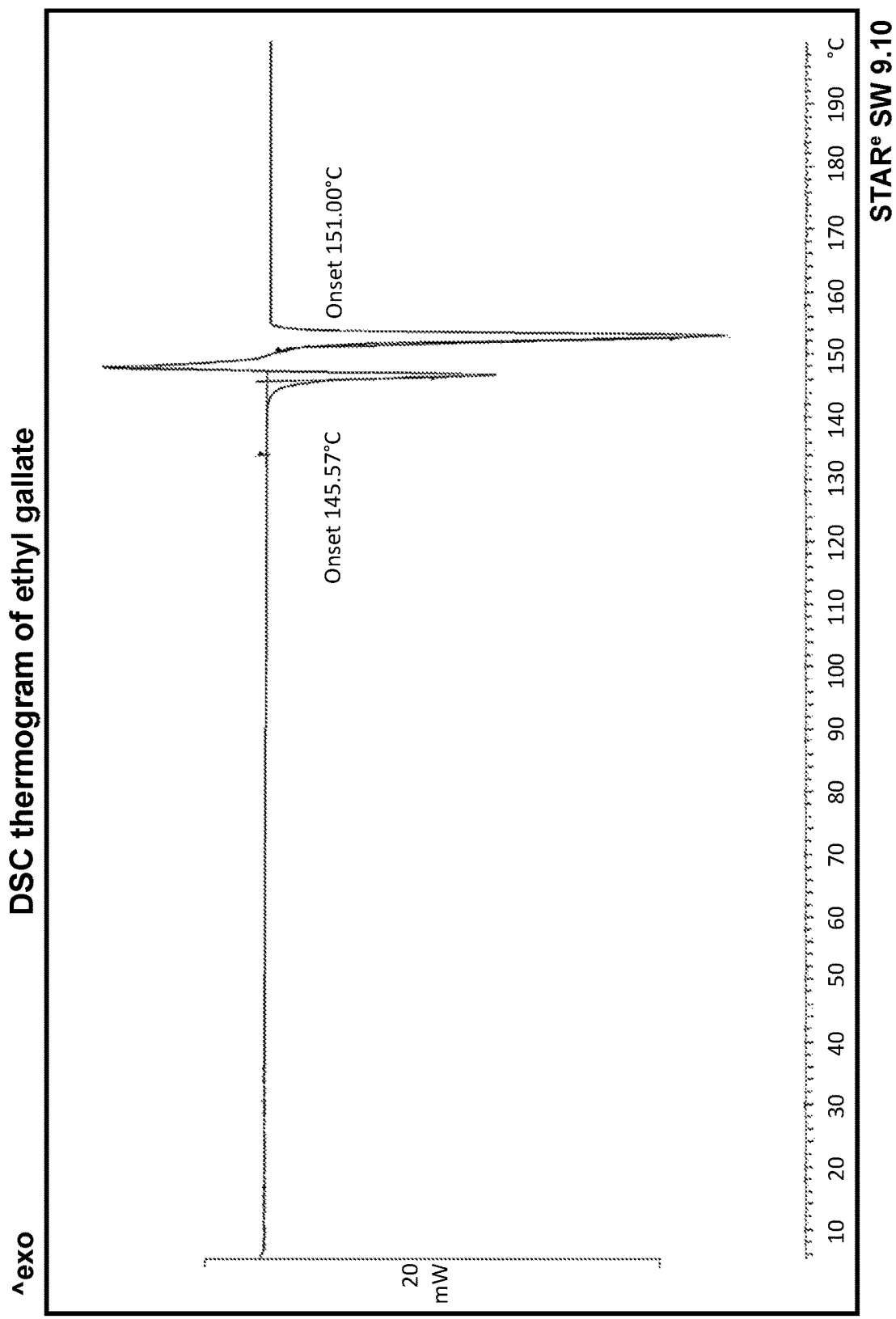
FIG. 84 is a DSC thermogram of ethyl gallate.

Ground crystalline R-fasoracetam and ethyl gallate was prepared by addition of 20.81 mg ethyl gallate and 19.90 mg of the material resulting from Example 26 to an Eppendorf together with 3 stainless steel grinding beads. The resulting combination was ground in a RETSCH Mixer Mill MM 400 for 90 min with a beating frequency of 30 Hz to form a ground crystalline material which was a 1:1 cocrystal of R-fasoracetam to ethyl gallate. FIG. 80 is an XRPD pattern of the ground crystalline material and FIG. 81 is an overlay of that XRPD pattern with that of a simulated pattern made from the single crystal showing a match. FIG. 82 is the XRPD pattern of ethyl gallate. FIG. 83 is a DSC thermogram of the cocrystal of R-fasoracetam and ethyl gallate prepared according to this Example 25 and FIG. 84 is a DSC thermogram of ethyl gallate.

Example 26—Preparation of R-Fasoracetam Forms Mixture

R-fasoracetam monohydrate Form I was placed under vacuum via rotavap at 65° C. The sample started to melt, after which water was removed from the melt by rotavap. After approximately 30 min, an R-Fasoracetam Forms Mixture resulted.

Example 27—Single Crystal of a 1:2 Cocrystal of R-Fasoracetam to Ethyl Gallate

Figure 85:
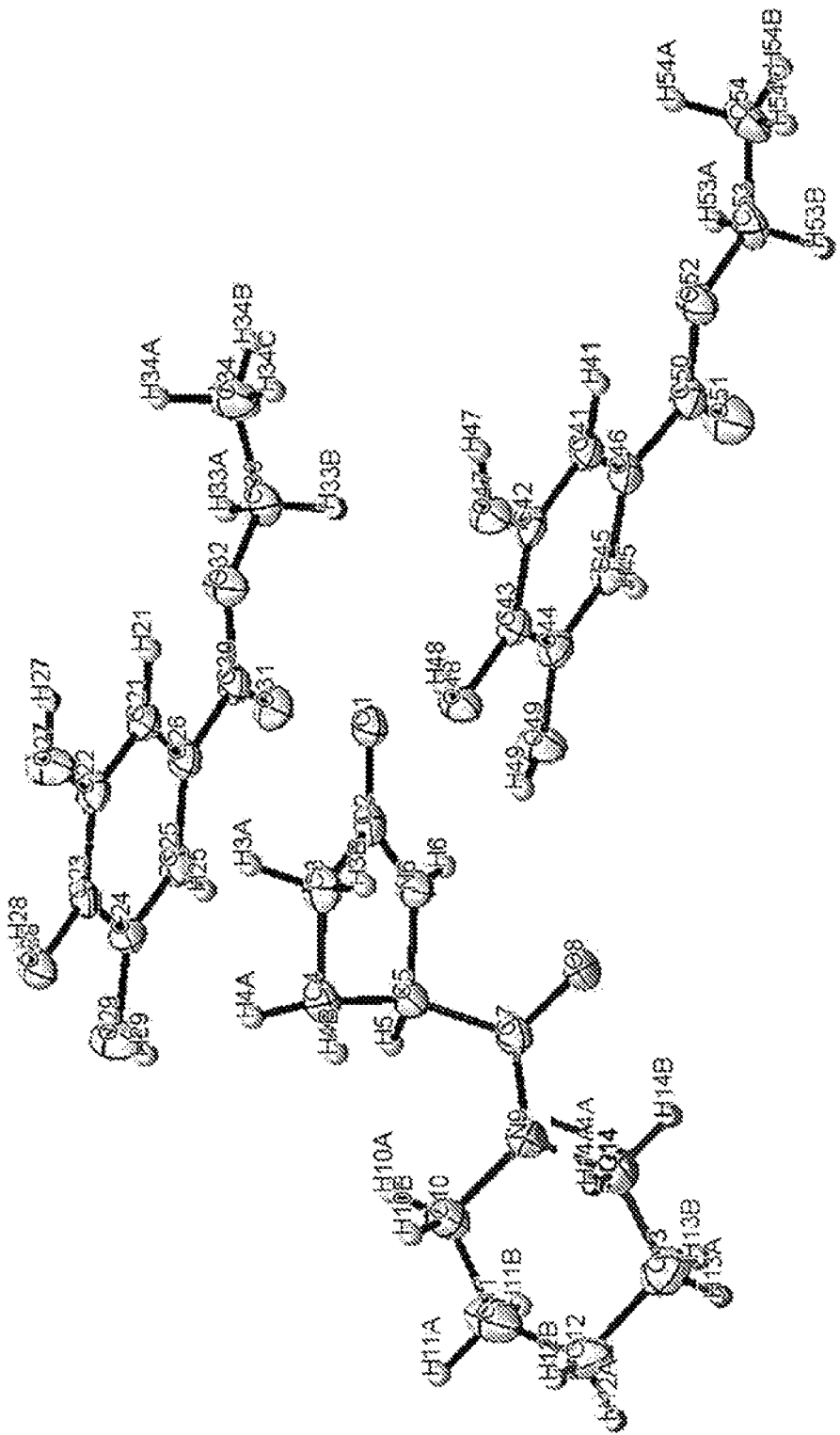
FIG. 85 is an ORTEP drawing of 1:2 R-fasoracetam:ethyl gallate cocrystal.

A 1:2 cocrystal of R-fasoracetam to ethyl gallate may be prepared by dissolving a stoichiometric amount of both components in ethyl acetate and through slow solvent evaporation followed by heating-cooling cycles. Table 13 identifies data parameters from the single crystal solution of the cocrystal and FIG. 85 is an ORTEP drawing obtained from the single crystal. FIG. 86 is the simulated XRPD pattern of the single crystal.

TABLE 13

Single Crystal Data Parameters for a 1:2 cocrystal of R-fasoracetam to ethyl gallate

| PARAMETER | RESULTS | |
|---|---|---|
| Empirical formula | C28 H36 N2 O12 | |
| Formula weight | 592.59 | |
| Temperature | 150(2) K | |
| Wavelength | 0.71073 Å | |
| Crystal system | Orthorhombic | |
| Space group | P$2_1 2_1 2$ | |
| Unit cell dimensions | a = 30.5465(11) Å | α = 90°. |
| | b = 13.4136(4) Å | β = 90°. |
| | c = 6.8752(2) Å | γ = 90°. |
| Volume | 2817.04(15) Å$^3$ | |
| Z | 4 | |
| Density (calculated) | 1.397 Mg/m$^3$ | |
| Absorption coefficient | 0.110 mm$^{-1}$ | |
| F(000) | 1256 | |
| Crystal size | 0.30 × 0.20 × 0.10 mm$^3$ | |
| Theta range for data collection | 2.963 to 25.250°. | |
| Index ranges | −34 <= h <= 36, −16 <= k <= 16, −8 <= l <= 8 | |
| Reflections collected | 14926 | |
| Independent reflections | 5086 [R(int) = 0.0486] | |
| Completeness to theta = 25.242° | 99.7% | |
| Absorption correction | Semi-empirical from equivalents | |
| Max. and min. transmission | 1.00000 and 0.53076 | |
| Refinement method | Full-matrix least-squares on F$^2$ | |
| Data/restraints/parameters | 5086/0/387 | |
| Goodness-of-fit on F$^2$ | 1.032 | |
| Final R indices [I > 2sigma(I)] | R1 = 0.0397, wR2 = 0.0976 | |
| R indices (all data) | R1 = 0.0500, wR2 = 0.1037 | |
| Absolute structure parameter | −0.3(6) | |
| Extinction coefficient | n/a | |
| Largest diff. peak and hole | 0.202 and −0.184 e · Å$^{-3}$ | |

Figure 87:
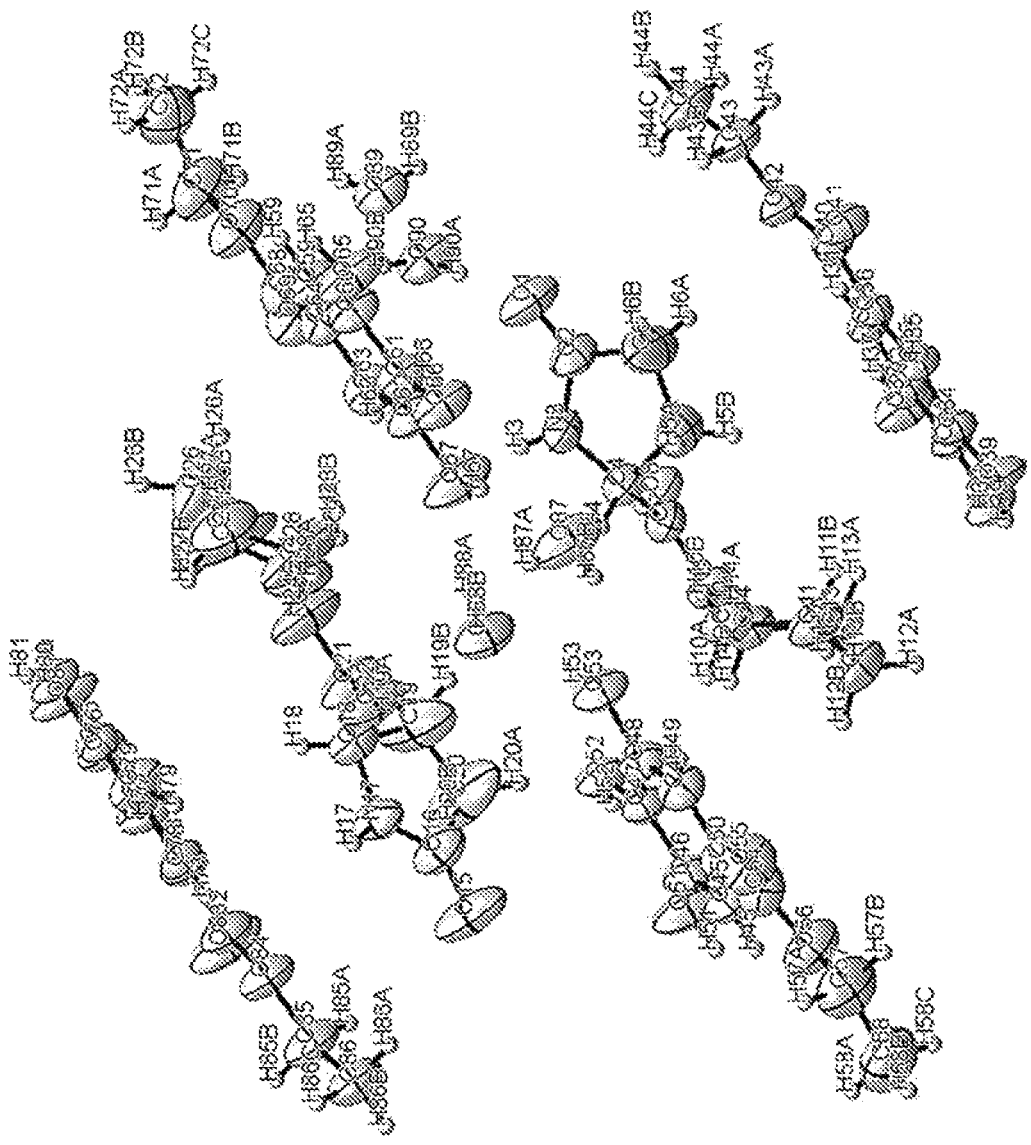
FIG. 87 is an ORTEP drawing of dihydrate 1:2 R-fasoracetam:ethyl gallate cocrystal.

Example 28—Single Crystal of a Dihydrate of a 1:2 Cocrystal of R-Fasoracetam to Ethyl Gallate A single crystal of a dihydrate of a 1:2 cocrystal of R-fasoracetam to ethyl gallate was prepared. The single crystal was obtained adding saturated solution of R-fasoracetam monohydrate Form I in ethyl acetate to a saturated solution of ethyl gallate in ethyl acetate. Equal volumes of both saturated solutions were added together, and the resulting solution left to evaporate which resulted in the cocrystal. Table 14 has data parameters for the single crystal and FIG. 87 is an ORTEP drawing of the single crystal solution. FIG. 88 is a simulated XRPD pattern of the single crystal.

TABLE 14

Single Crystal Data Parameters for a dihydrate of a 1:2 cocrystal of R-fasoracetam to ethyl gallate

| PARAMETER | RESULTS | |
|---|---|---|
| Empirical formula | C28 H40 N2 O14 | |
| Formula weight | 628.62 | |
| Temperature | 293(2) K | |
| Wavelength | 0.71073 Å | |
| Crystal system | Triclinic | |
| Space group | P1 | |
| Unit cell dimensions | a = 9.8997(15) Å | α = 72.643(14)°. |
| | b = 13.004(2) Å | β = 77.179(13)°. |
| | c = 13.824(2) Å | γ = 68.710(15)°. |

TABLE 14-continued

Single Crystal Data Parameters for a dihydrate of a 1:2 cocrystal of R-fasoracetam to ethyl gallate

| PARAMETER | RESULTS |
|---|---|
| Volume | 1569.8(5) Å$^3$ |
| Z | 2 |
| Density (calculated) | 1.330 Mg/m$^3$ |
| Absorption coefficient | 0.107 mm$^{-1}$ |
| F(000) | 668 |
| Crystal size | 0.50 × 0.50 × 0.30 mm$^3$ |
| Theta range for data collection | 2.875 to 25.240°. |
| Index ranges | −11 <= h <= 11, −15 <= k <= 15, −16 <= l <= 16 |
| Reflections collected | 17916 |
| Independent reflections | 10169 [R(int) = 0.0360] |
| Completeness to theta = 25.240° | 95.5% |
| Absorption correction | Semi-empirical from equivalents |
| Max. and min. transmission | 1.00000 and 0.90925 |
| Refinement method | Full-matrix least-squares on F$^2$ |
| Data/restraints/parameters | 10169/184/882 |
| Goodness-of-fit on F$^2$ | 1.015 |
| Final R indices [I > 2sigma(I)] | R1 = 0.0503, wR2 = 0.1415 |
| R indices (all data) | R1 = 0.0527, wR2 = 0.1442 |
| Absolute structure parameter | 0.1(5) |
| Extinction coefficient | n/a |
| Largest diff. peak and hole | 0.189 and −0.155 e · Å$^{-3}$ |

Figure 89:
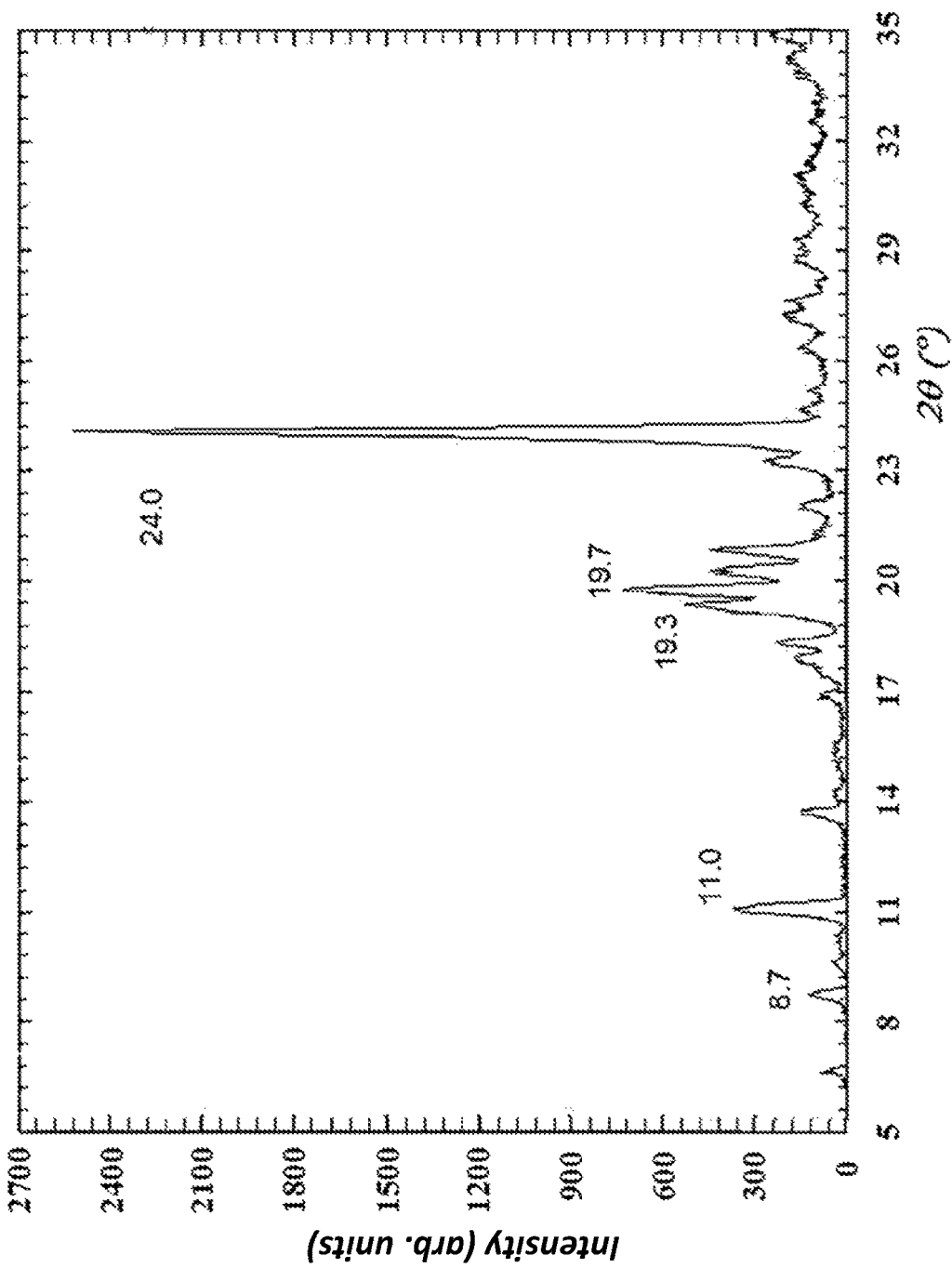
FIG. 89 is an XRPD pattern of dihydrate of 1:2 R-fasoracetam:ethyl gallate cocrystal.
Figure 90:
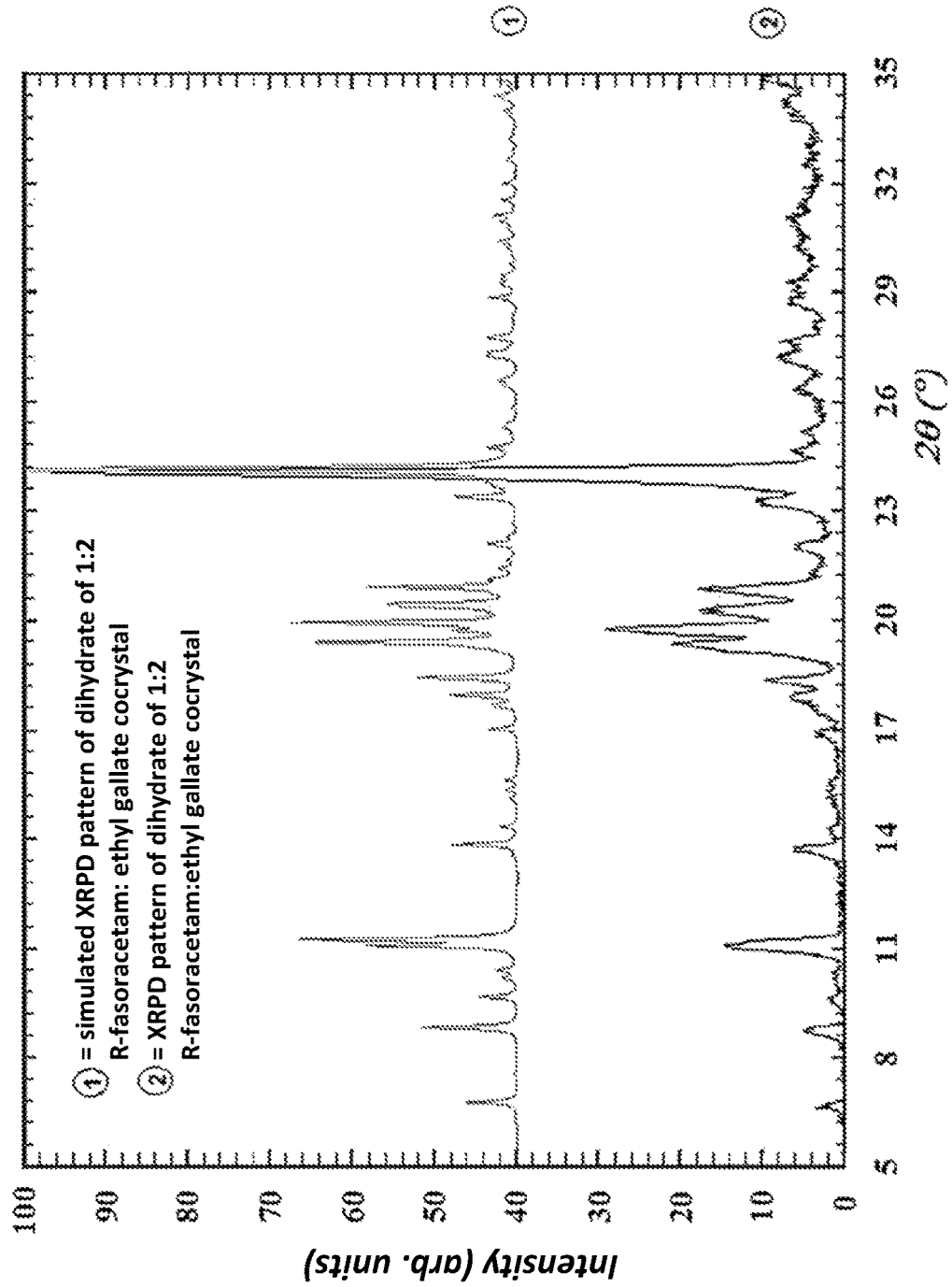
FIG. 90 is an overlay of XRPD patterns: (1) simulated XRPD pattern of dihydrate of 1:2 R-fasoracetam:ethyl gallate cocrystal; (2) XRPD pattern of dihydrate of 1:2 R-fasoracetam:ethyl gallate cocrystal.
Figure 91:
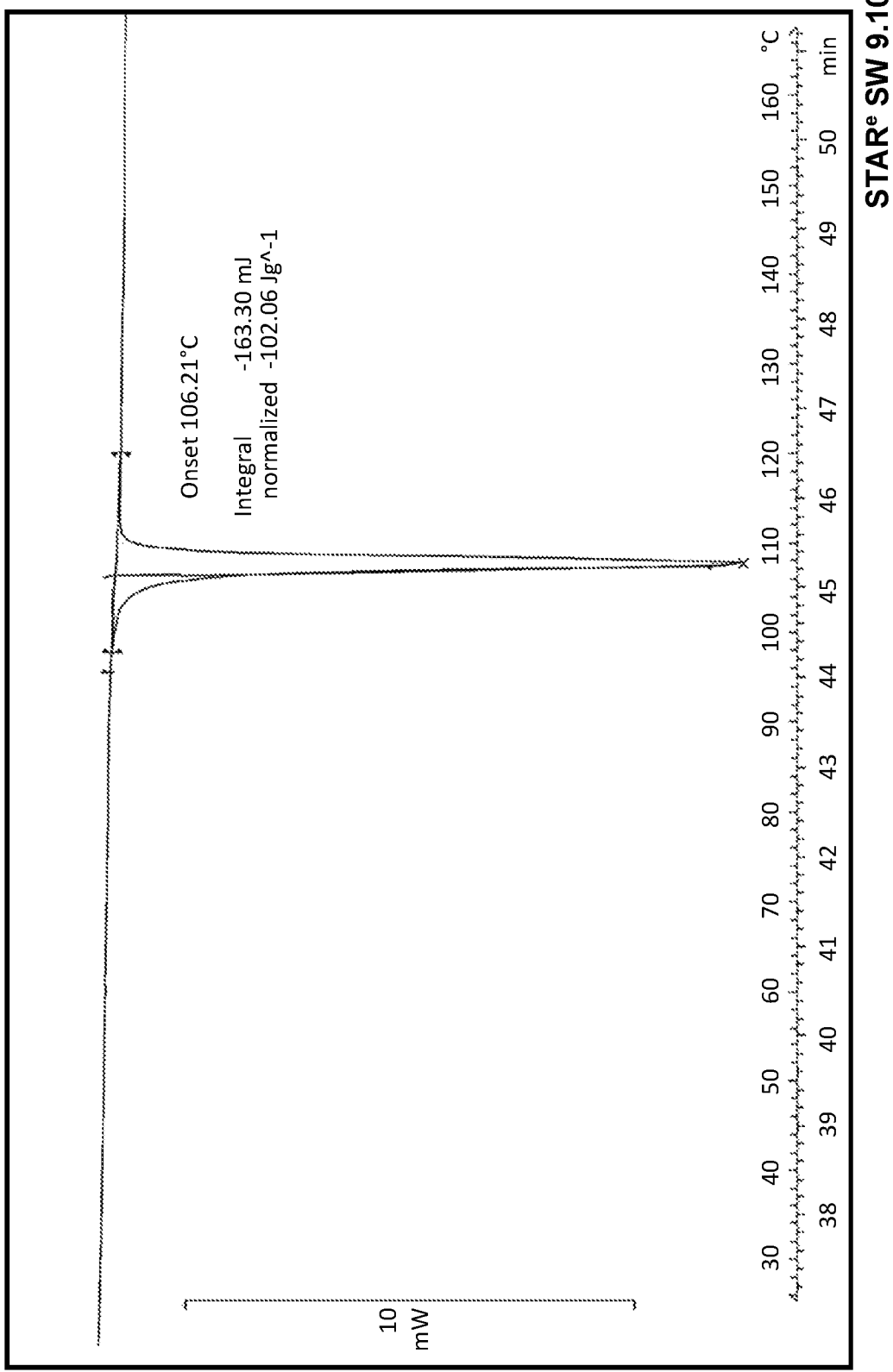
FIG. 91 is a cycled DSC thermogram of dihydrate of 1:2 cocrystal of R-fasoracetam:ethyl gallate.
Figure 92:
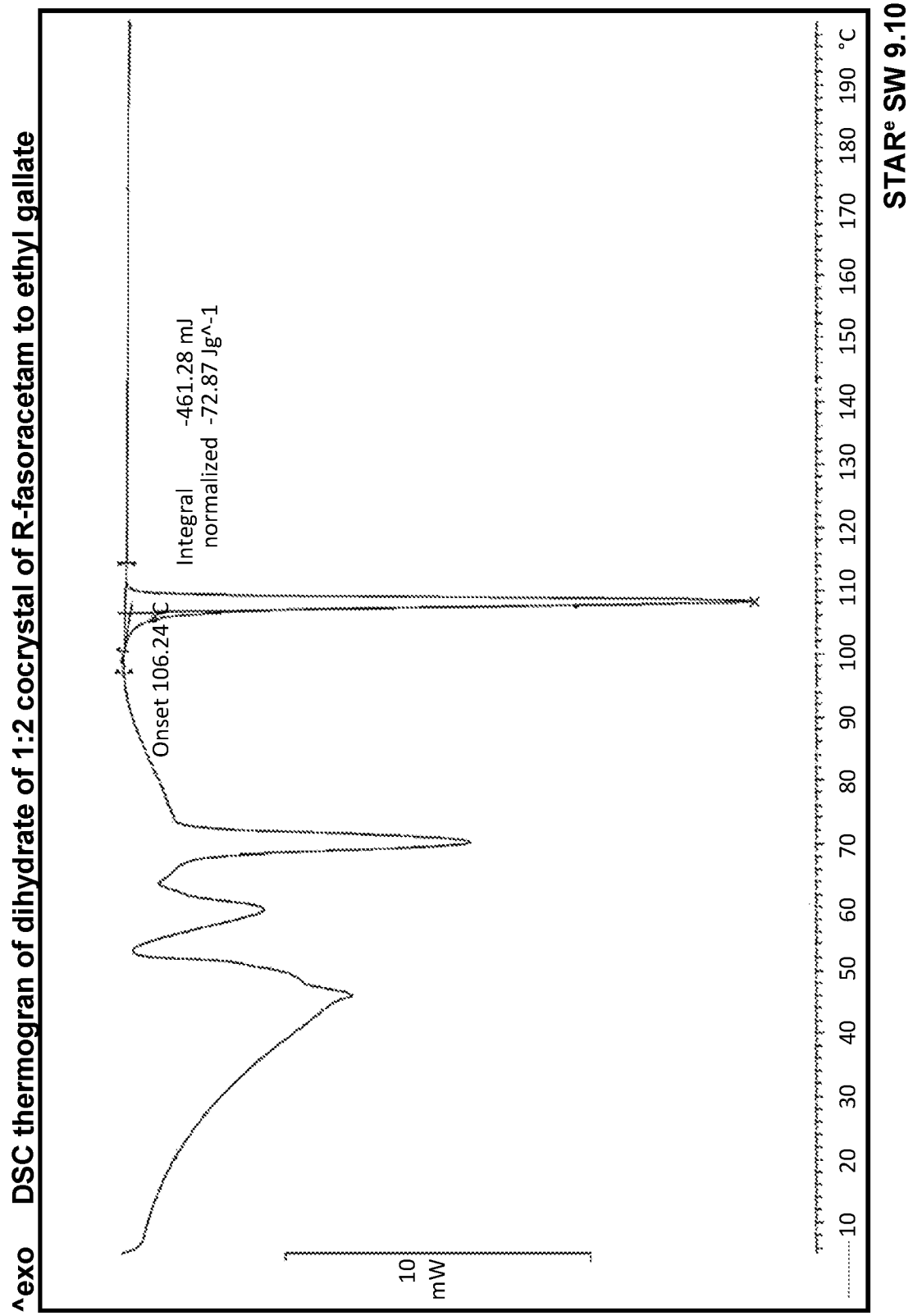
FIG. 92 is a DSC thermogram of dihydrate of 1:2 cocrystal of R-fasoracetam:ethyl gallate.

Example 29—Crystalline Dihydrate of a 1:2 Cocrystal of R-Fasoracetam to Ethyl Gallate A crystalline dihydrate of a 1:2 cocrystal of R-fasoracetam to ethyl gallate was prepared by slurrying 931.8 mg of ethyl gallate (2 equivalents) with 505.00 mg of R-fasoracetam monohydrate Form I sourced from Jinan Haohua Industry Co., Ltd in 5 ml of water under magnetic stirring at room temperature and left overnight. After stirring, the sample was filtered and the solid was left to dry resulting in crystalline dihydrate of a 1:2 cocrystal of R-fasoracetam to ethyl gallate. FIG. 89 is an XRPD pattern of the crystalline material thus obtained. FIG. 90 is an overlay of the simulated XRPD pattern of the dihydrate single cocrystal of 1:2 R-fasoracetam to ethyl gallate and the crystalline material of this Example 29 showing a match. Therefore, the crystalline material of this Example 29 is a dihydrate of a cocrystal of R-fasoracetam and ethyl gallate (1:2). FIG. 91 is a cycled DSC thermogram of the dihydrate of a cocrystal of R-fasoracetam and ethyl gallate (1:2) and FIG. 92 is a DSC thermogram of the dihydrate of a cocrystal of R-fasoracetam and ethyl gallate (1:2).

Example 30—Ground Crystalline R-Fasoracetam and 6-Hydroxy-2-Naphthoic Acid

Figure 96:
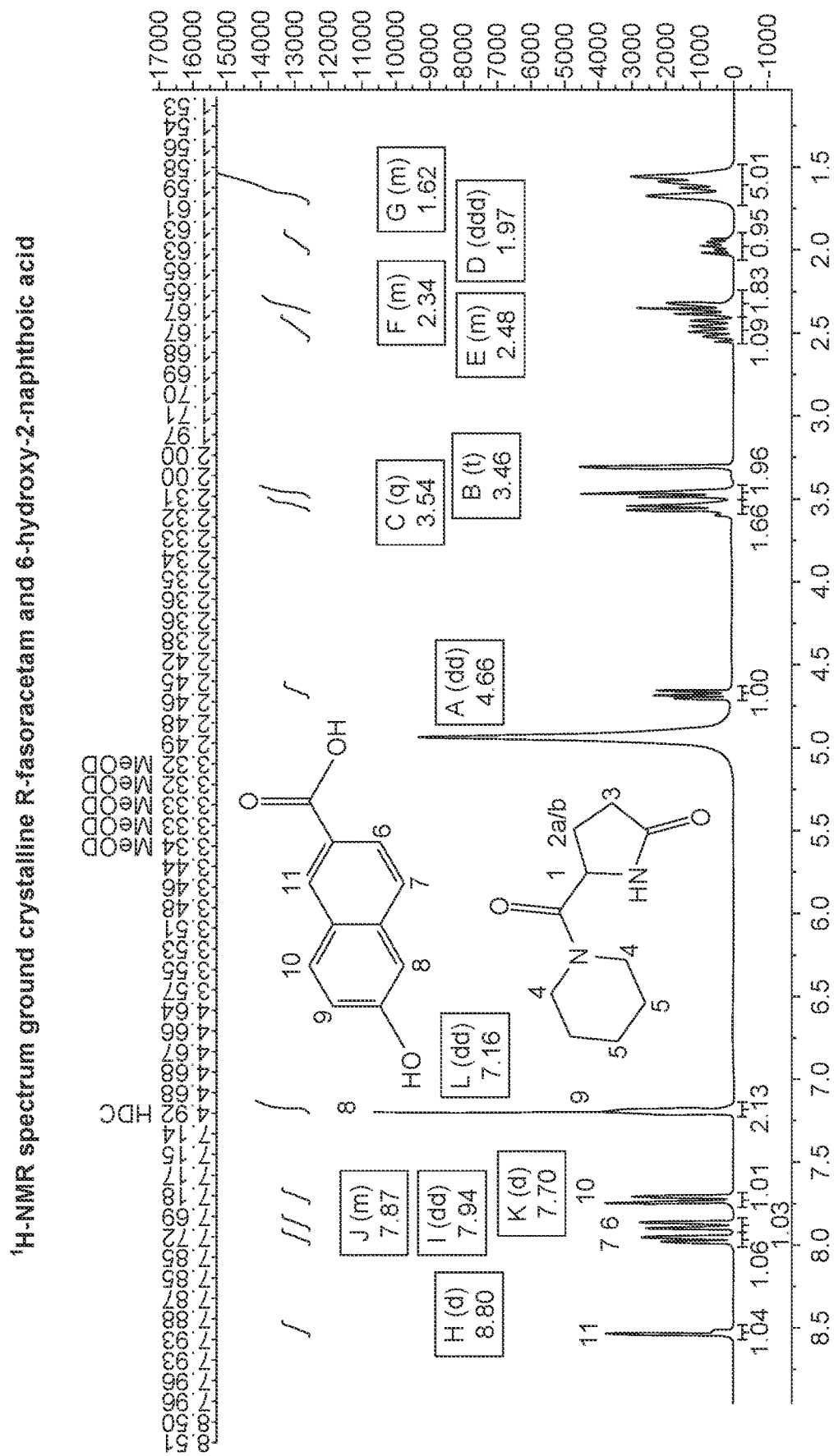
FIG. 96 is a $^1$H-NMR spectrum of ground crystalline R-fasoracetam and 6-hydroxy-2-naphthoic acid.
Figure 98:
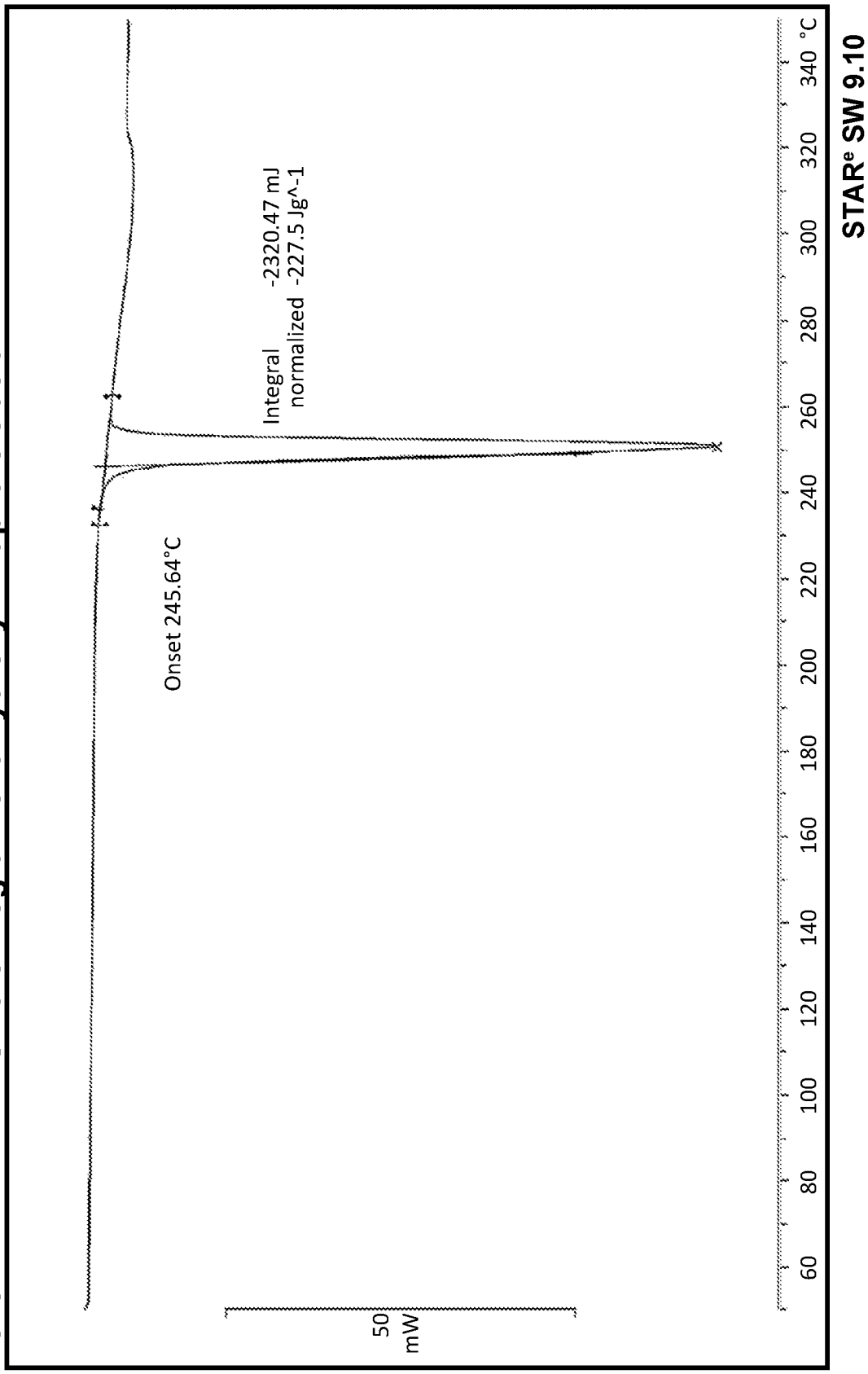
FIG. 98 is a DSC thermogram of 6-hydroxy-2-naphthoic acid.

Ground crystalline R-fasoracetam and 6-hydroxy-2-naphthoic acid was prepared by addition of 28.88 mg of 6-hydroxy-2-naphthoic acid and 30.26 mg of R-fasoracetam monohydrate Form I sourced from Jinan Haohua Industry C., Ltd. to an Eppendorf together with 3 stainless steel grinding beads to form a mixture. The mixture was ground in a RETSCH Mixer Mill MM 400 for 90 min with a beating frequency of 30 Hz to provide ground crystalline material of R-fasoracetam and 6-hydroxy-2-naphthoic acid. FIG. 93 is an XRPD pattern of the ground crystalline R-fasoracetam and 6-hydroxy-2-naphthoic acid material. FIG. 94 is an XRPD pattern of 6-hydroxy-2-naphthoic acid, and FIG. 95 is an overlay of XRPD patterns of R-fasoracetam monohydrate Form I, the ground crystalline R-fasoracetam and 6-hydroxy-2-naphthoic acid material and that of 6-hydroxy-2-naphthoic acid. This preparation was repeated using 38.36 mg of 6-hydroxy-2-naphthoic acid and 40 mg of R-fasoracetam monohydrate Form I. FIG. 96 is a $^1$H-NMR spectrum of dissolved ground crystalline R-fasoracetam and 6-hydroxy-2-naphthoic acid where all hydrogens are accounted for and no degradation is observed. FIG. 97 is a DSC thermogram of ground crystalline fasoracetam and 6-hydroxy-2-naphthoic acid and a single endotherm is observed and FIG. 98 is a DSC thermogram of 6-hydroxy-2-naphthoic acid. Based on the data presented and because the XRPD pattern of the ground crystalline material differs from that of the components in the mixture, the ground crystalline material is a cocrystal of R-fasoracetam to 6-hydroxy-2-naphthoic acid.

Example 31—Single Crystal of R-Fasoracetam and 4-Nitrobenzoic Acid (1:2)

Figure 99:
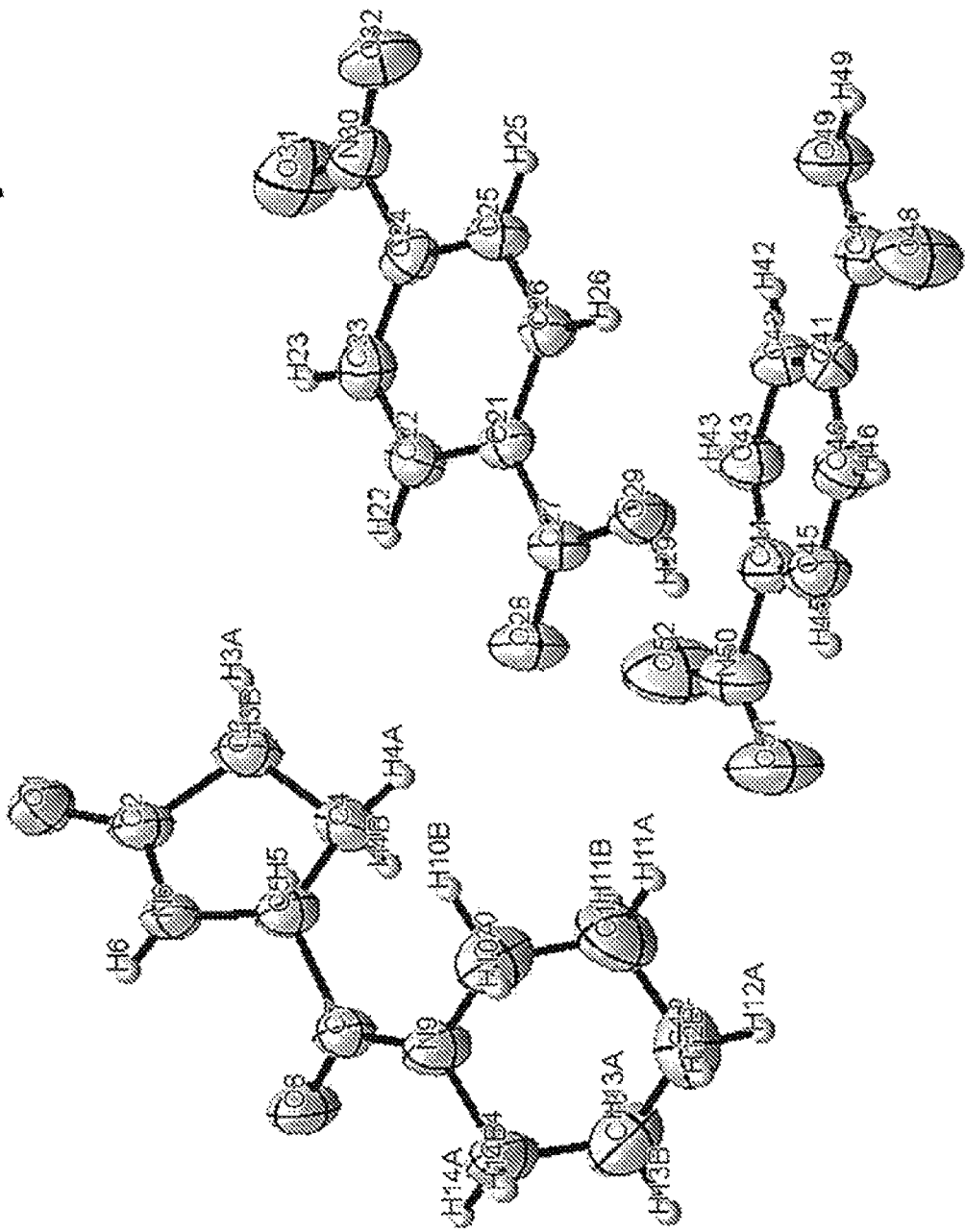
FIG. 99 is an ORTEP drawing of R-fasoracetam:4-nitrobenzoic acid cocrystal.

A 1:2 R-fasoracetam to 4-nitrobenzoic acid cocrystal was obtained dissolving a stoichiometric amount of 30 mg of R-fasoracetam monohydrate Form I sourced from Jinan Haohua Industry Co., Ltd and 4-nitrobenzoic acid in EtOH and through slow solvent evaporation. Table 15 lists parameters from the single crystal x-ray solution and FIG. 99 is an ORTEP drawing of the cocrystal. FIG. 100 is the simulated XRPD pattern of the cocrystal of this Example 31.

TABLE 15

Single Crystal Data Parameters

| PARAMETER | RESULTS |
| --- | --- |
| Empirical formula | C24 H26 N4 O10 |
| Formula weight | 530.49 |
| Temperature | 297(2) K |
| Wavelength | 0.71073 Å |
| Crystal system | Monoclinic |
| Space group | P21 |
| Unit cell dimensions | a = 13.2239(9) Å  α = 90°. |
| | b = 6.8980(5) Å  β = 94.660(7)°. |
| | c = 13.7085(11) Å  γ = 90°. |
| Volume | 1246.34(15) Å$^3$ |
| Z | 2 |
| Density (calculated) | 1.414 Mg/m$^3$ |
| Absorption coefficient | 0.112 mm$^{-1}$ |
| F(000) | 556 |
| Crystal size | 0.500 × 0.300 × 0.300 mm$^3$ |
| Theta range for data collection | 3.245 to 25.243°. |
| Index ranges | −15 <= h <= 15, −8 <= k <= 8, −16 <= l <= 16 |
| Reflections collected | 9341 |
| Independent reflections | 4304 [R(int) = 0.0270] |
| Completeness to theta = 25.242° | 99.2% |
| Absorption correction | Semi-empirical from equivalents |
| Max. and min. transmission | 1.00000 and 0.77939 |
| Refinement method | Full-matrix least-squares on F$^2$ |
| Data/restraints/parameters | 4304/1/346 |
| Goodness-of-fit on F$^2$ | 1.038 |
| Final R indices [I > 2sigma(I)] | R1 = 0.0371, wR2 = 0.0926 |
| R indices (all data) | R1 = 0.0441, wR2 = 0.0975 |
| Absolute structure parameter | 0.2(6) |

TABLE 15-continued

Single Crystal Data Parameters

| PARAMETER | RESULTS |
| --- | --- |
| Extinction coefficient | n/a |
| Largest diff. peak and hole | 0.122 and −0.160 e · Å$^{-3}$ |

Example 32—Ground Crystalline R-Fasoracetam and 4-Nitrobenzoic Acid

Figure 101:
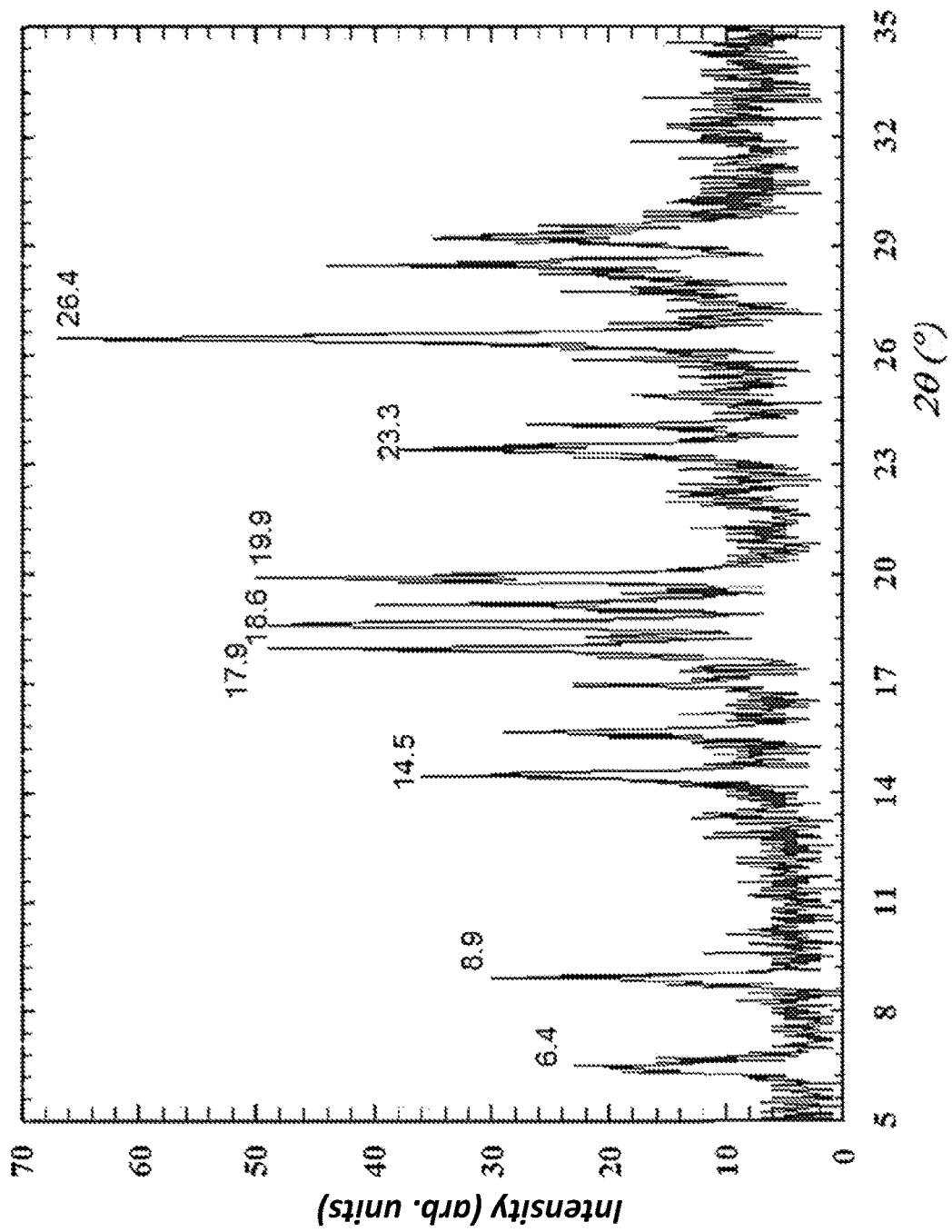
FIG. 101 is an XRPD pattern of ground R-fasoracetam:4-nitrobenzoic acid.
Figure 103:
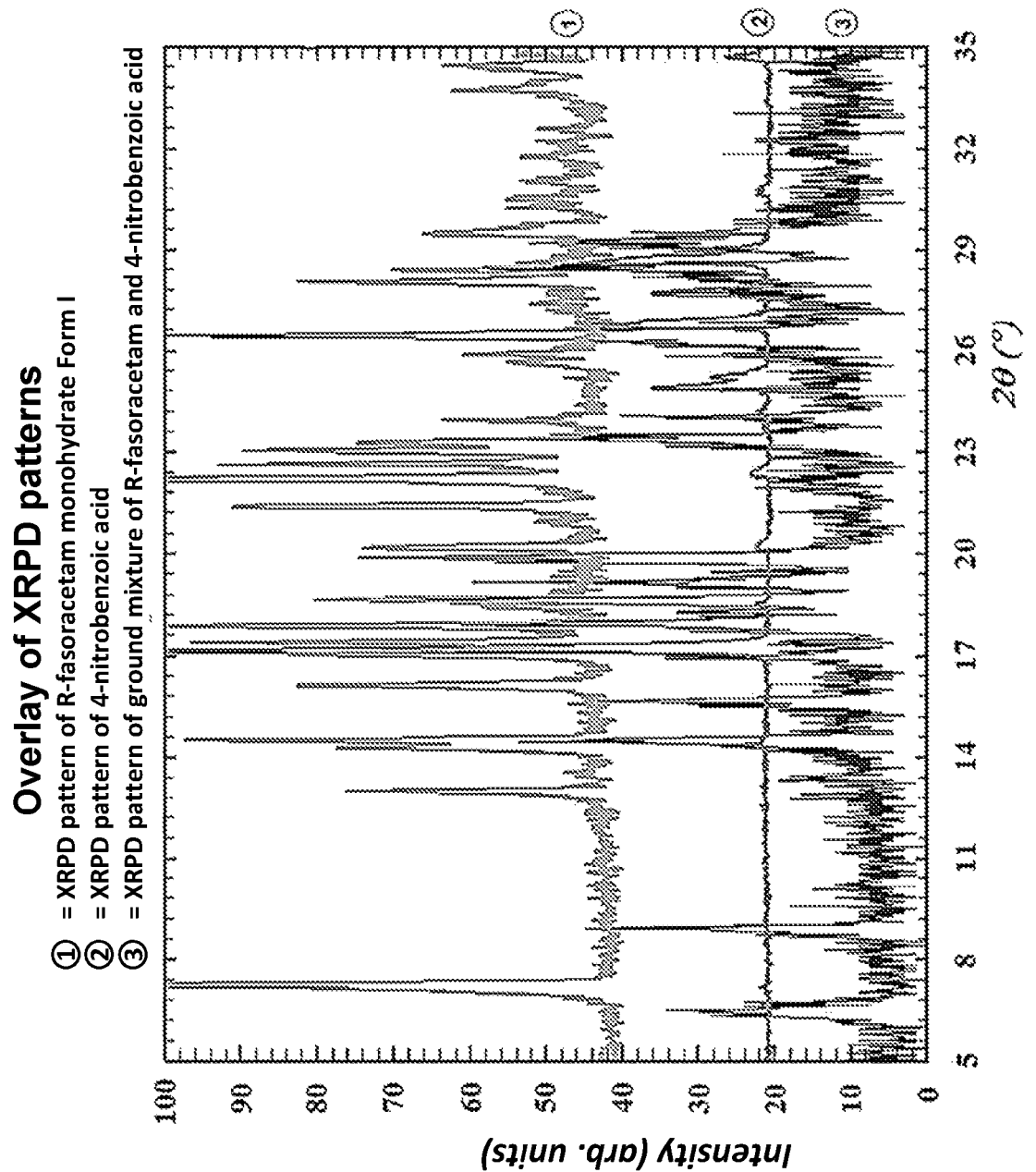
FIG. 103 is an overlay of XRPD patterns: (1) XRPD pattern of R-fasoracetam monohydrate Form I; (2) XRPD pattern of 4-nitrobenzoic acid; (3) XRPD pattern of ground mixture of R-fasoracetam and 4-nitrobenzoic acid.
Figure 104:
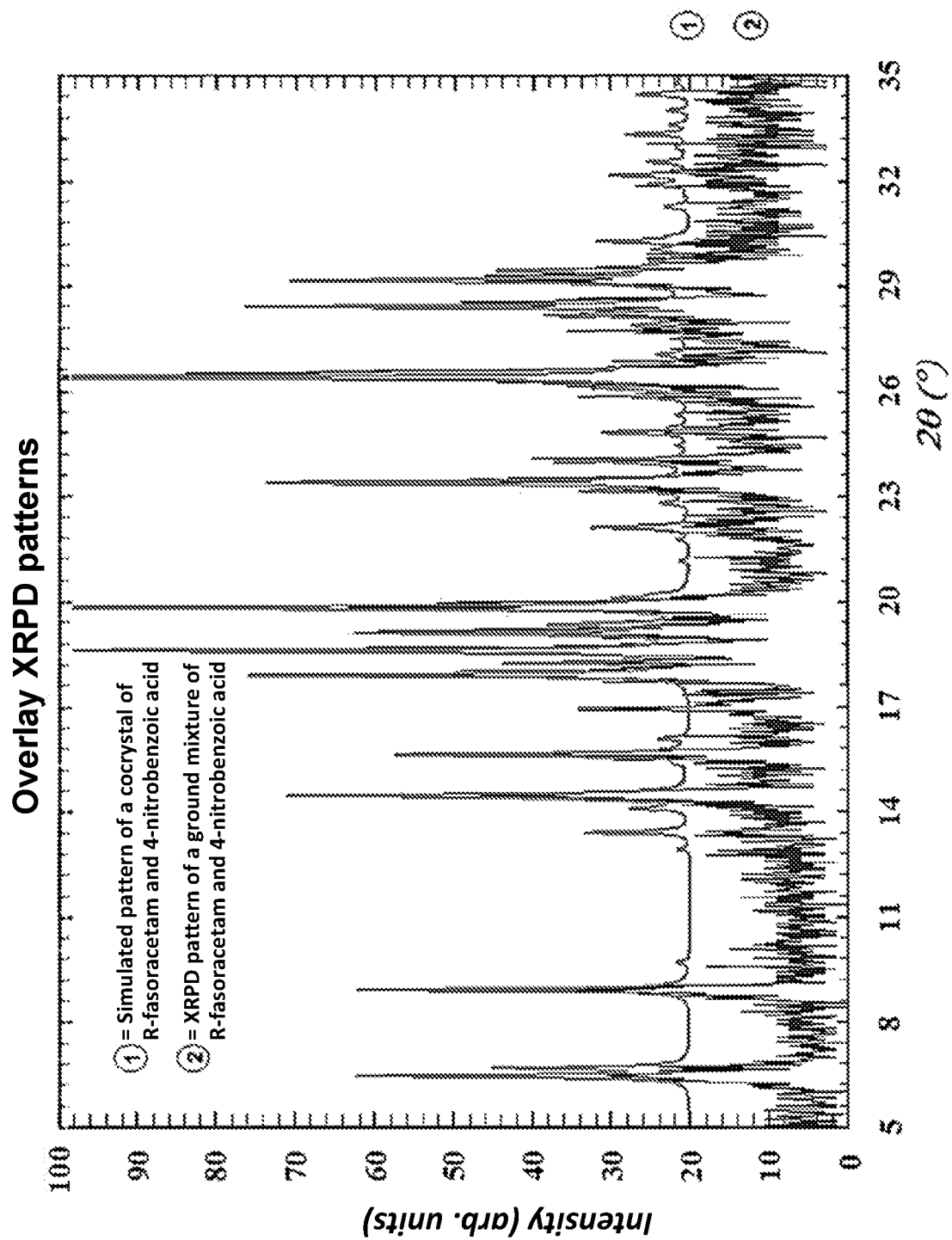
FIG. 104 is an overlay of XRPD patterns: (1) Simulated pattern of a cocrystal of R-fasoracetam and 4-nitrobenzoic acid; (2) XRPD pattern of ground mixture of R-fasoracetam and 4-nitrobenzoic acid.
Figure 105:
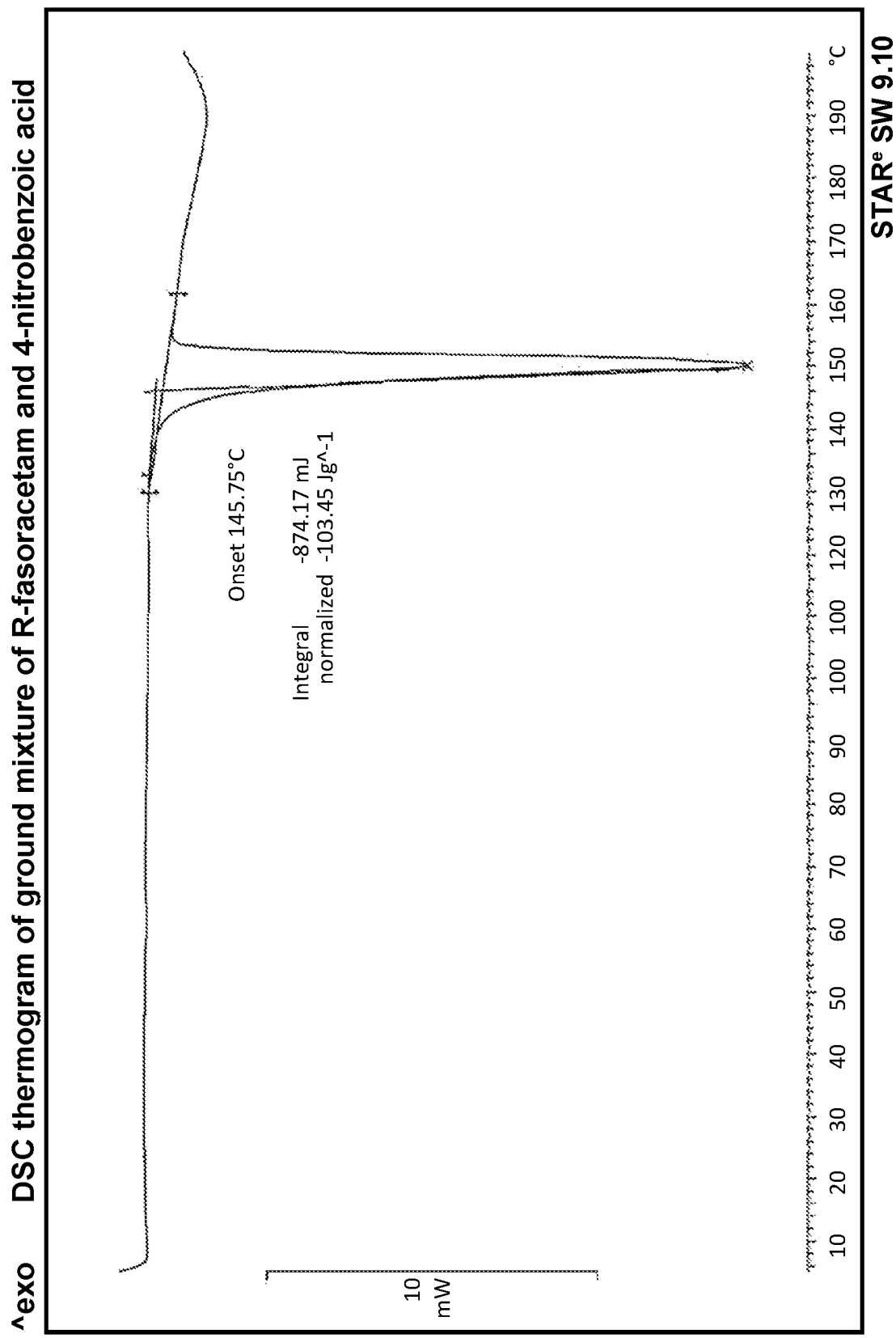
FIG. 105 is a DSC thermogram of ground mixture of R-fasoracetam and 4-nitrobenzoic acid.
Figure 106:
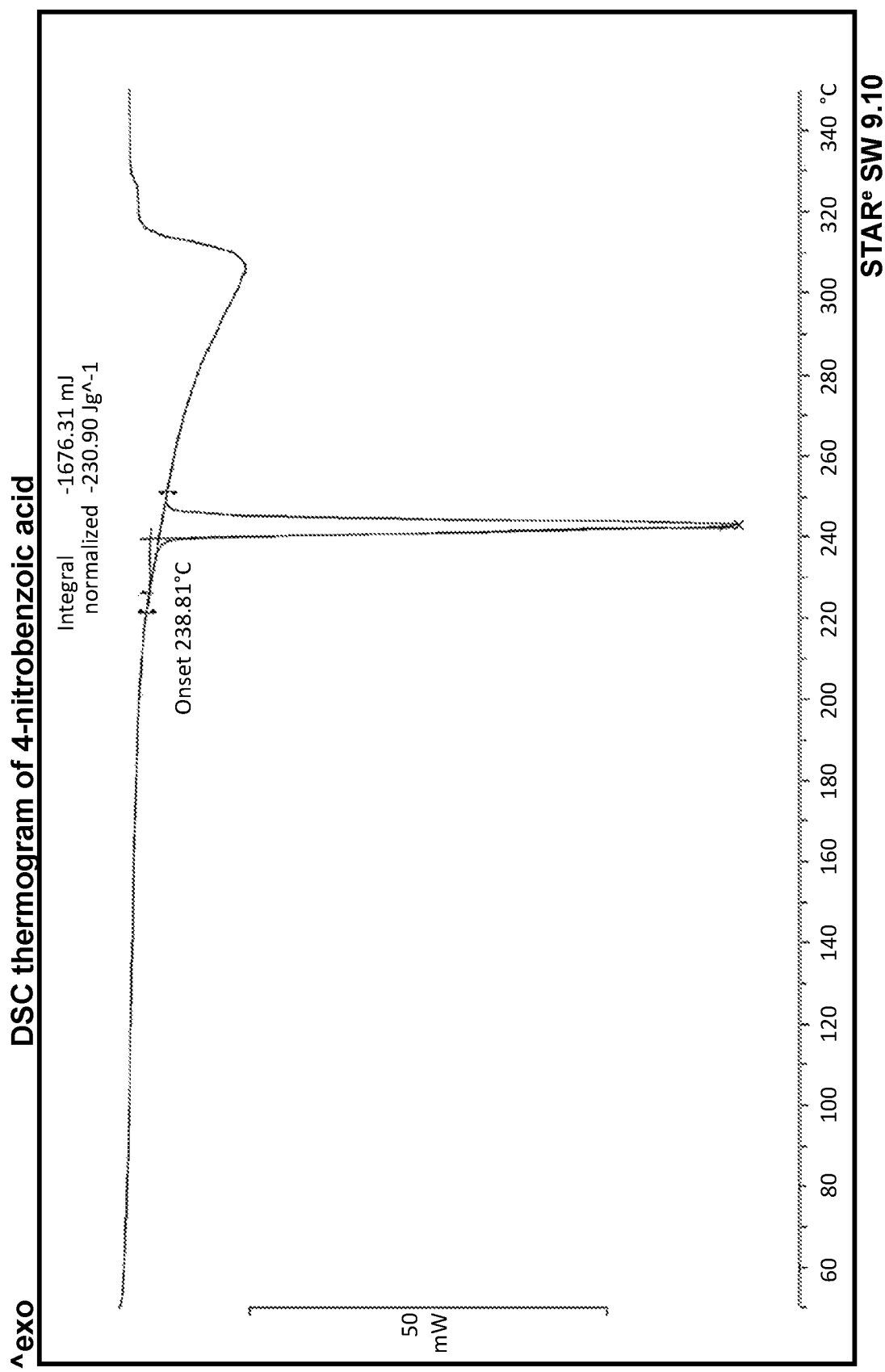
FIG. 106 is a DSC thermogram of 4-nitrobenzoic acid.

Ground crystalline R-fasoracetam and 4-nitrobenzoic acid was prepared by addition of 34.06 mg of 4-nitrobenzoic acid (2 equivalents) and 20.00 mg of R-fasoracetam monohydrate Form I (1 equivalent) sourced from Jinan Haohua Industry Co., Ltd. to an Eppendorf together with 3 stainless steel grinding beads to form a mixture. The mixture was ground in a RETSCH Mixer Mill MM 400 for 90 min with a beating frequency of 30 Hz to form a crystalline ground material of R-fasoracetam and 4-nitrobenzoic acid. FIG. 101 is the XRPD pattern of the ground crystalline material. FIG. 102 is the XRPD pattern of 4-nitrobenzoic acid. FIG. 103 is an overlay of XRPD patterns of the ground crystalline material with respect to the 4-nitrobenzoic acid and R-fasoracetam monohydrate Form I. FIG. 104 is an overlay of XRPD patterns of the simulated XRPD pattern of the cocrystal and the XRPD pattern of the ground crystalline material which match. Thus, the ground crystalline material is a 1:2 cocrystal of R-fasoracetam to 4-nitrobenzoic acid. FIG. 105 is the DSC thermogram of the ground crystalline material and FIG. 106 is the DSC of 4-nitrobenzoic acid.

Example 33—Ground Crystalline R-Fasoracetam and 2-Indole-3-Acetic Acid

Figure 110:
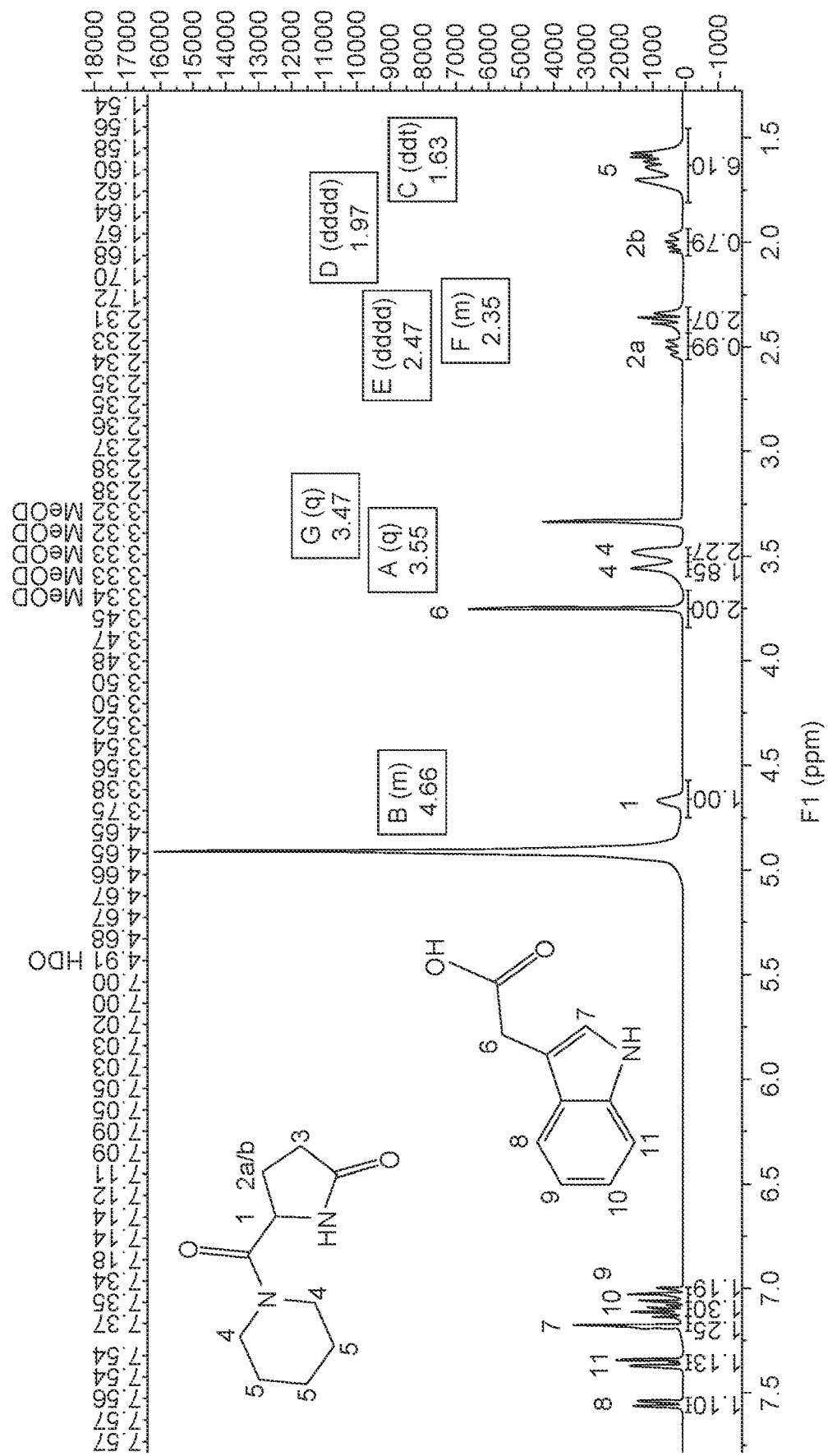
FIG. 110 is a $^1$H-NMR spectrum of ground crystalline R-fasoracetam and 2-indole-3-acetic acid.
Figure 111:
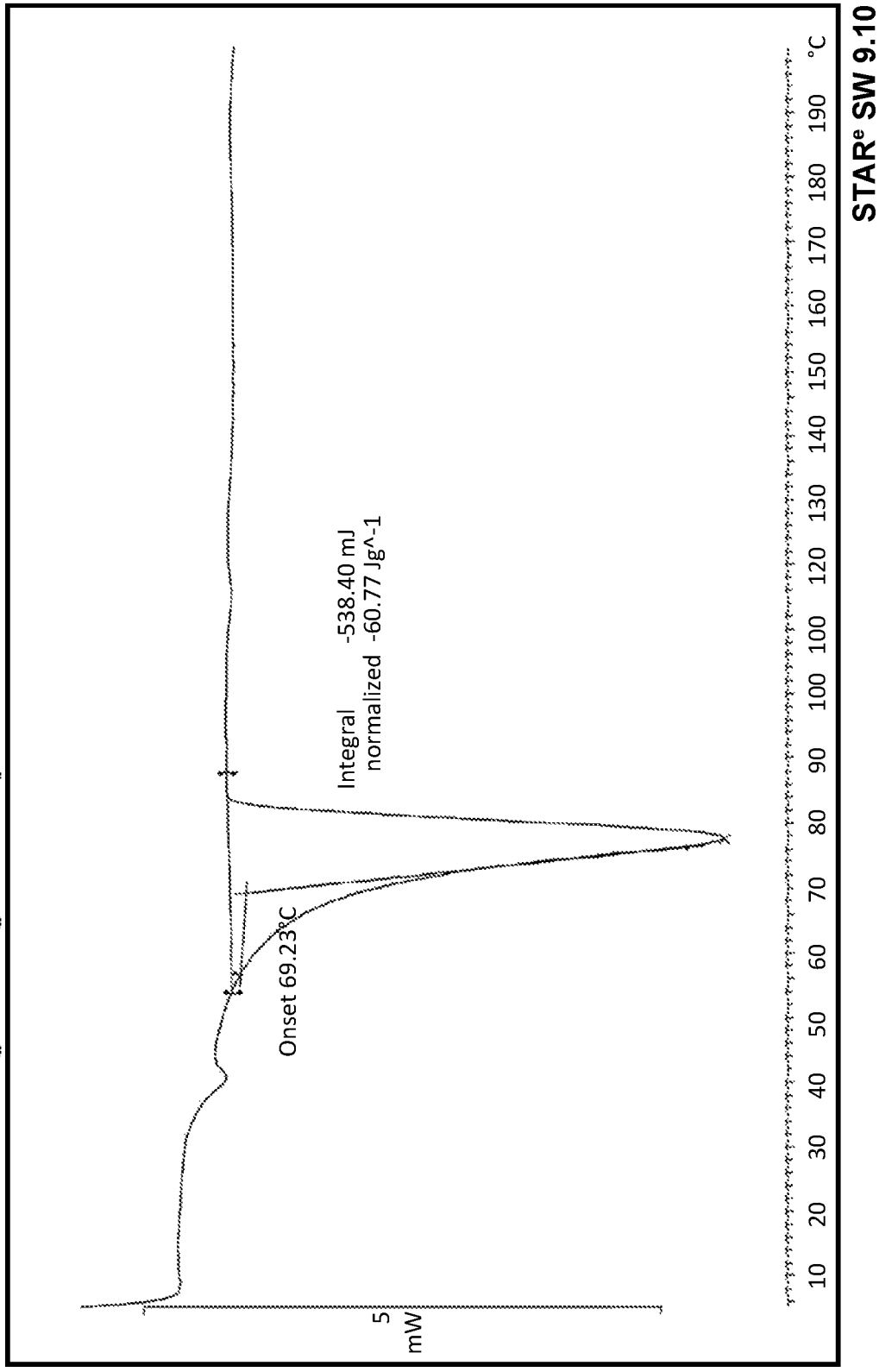
FIG. 111 is a DSC thermogram of ground crystalline R-fasoracetam and 2-indole-3-acetic acid.
Figure 112:
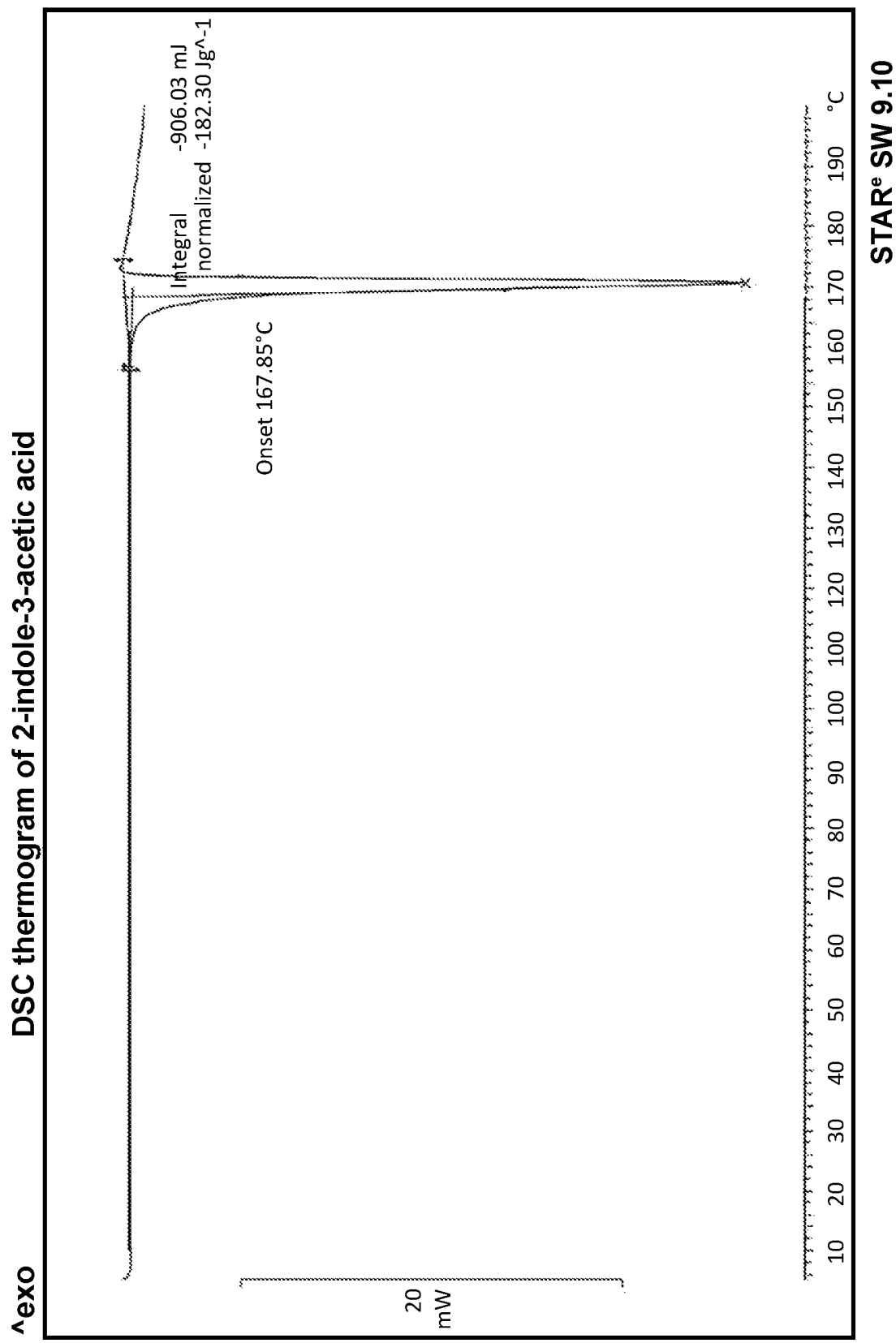
FIG. 112 is a DSC thermogram of 2-indole-3-acetic acid.

Ground crystalline R-fasoracetam and 2-indole-3-acetic acid material was prepared by addition of 17.98 mg of 2-Indole-3-acetic acid and 21.33 mg of the material of Example 26 to an Eppendorf together with 3 stainless steel grinding beads as well as 10 μl of toluene to form a mixture. The mixture was ground in a RETSCH Mixer Mill MM 400 for 90 min with a beating frequency of 30 Hz to give a ground crystalline material. FIG. 107 is an XRPD pattern of the ground crystalline material. FIG. 108 is an XRPD pattern of 2-indole-3-acetic acid. FIG. 109 is an overlay of the XRPD patterns of the ground crystalline, 2-indole-3-acetic acid, and R-fasoracetam monohydrate Form I material. FIG. 110 is a $^1$H-NMR spectrum of a solution of the ground crystalline material, and all hydrogens are accounted for, showing no degradation. FIG. 111 is a DSC thermogram of the ground crystalline material. FIG. 112 is a DSC thermogram of 2-indole-3-acetic acid.

Figure 116:
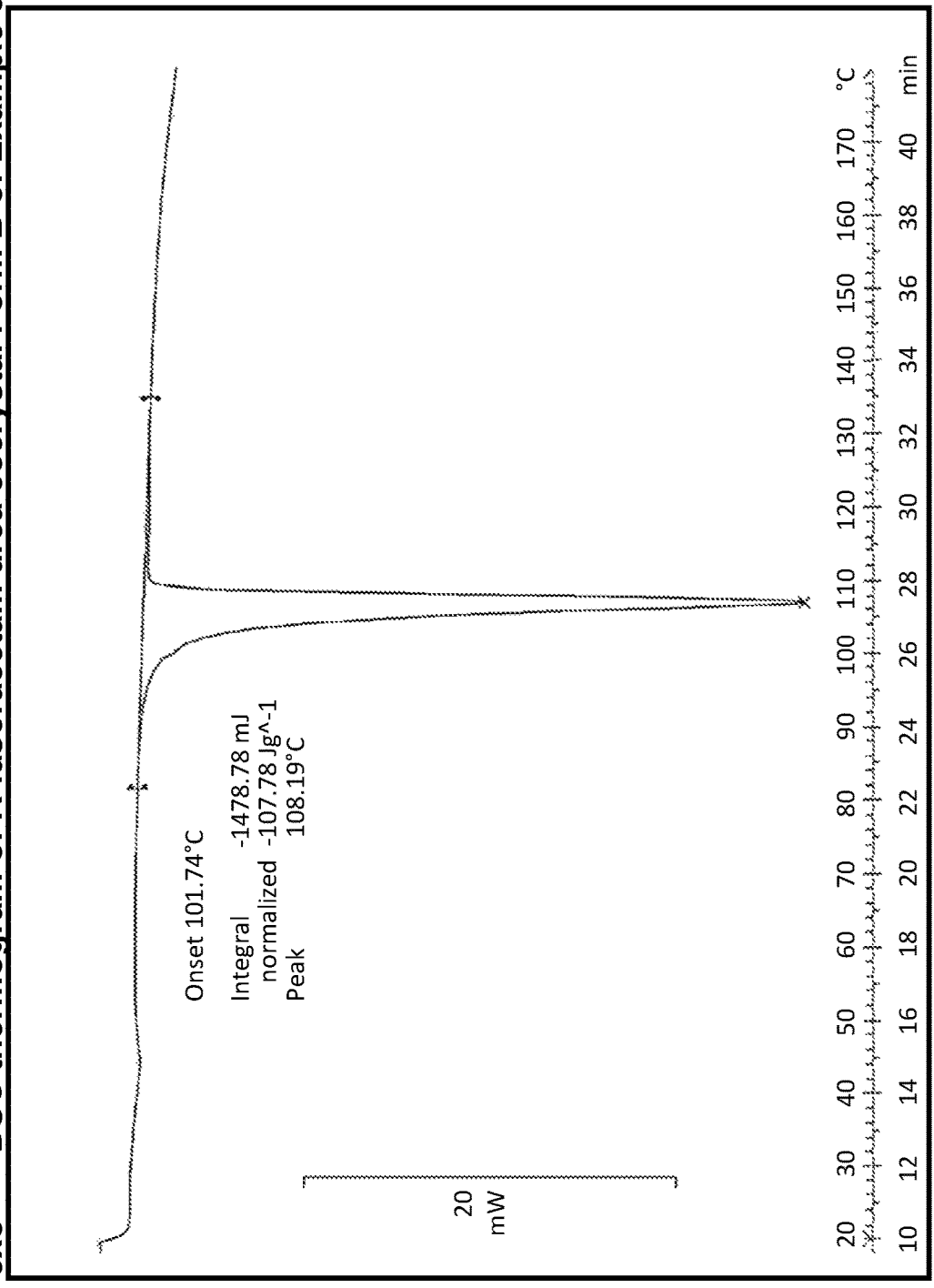
FIG. 116 is a DSC thermogram of a R-fasoracetam:urea cocrystal Form B of Example 34.
Figure 117:
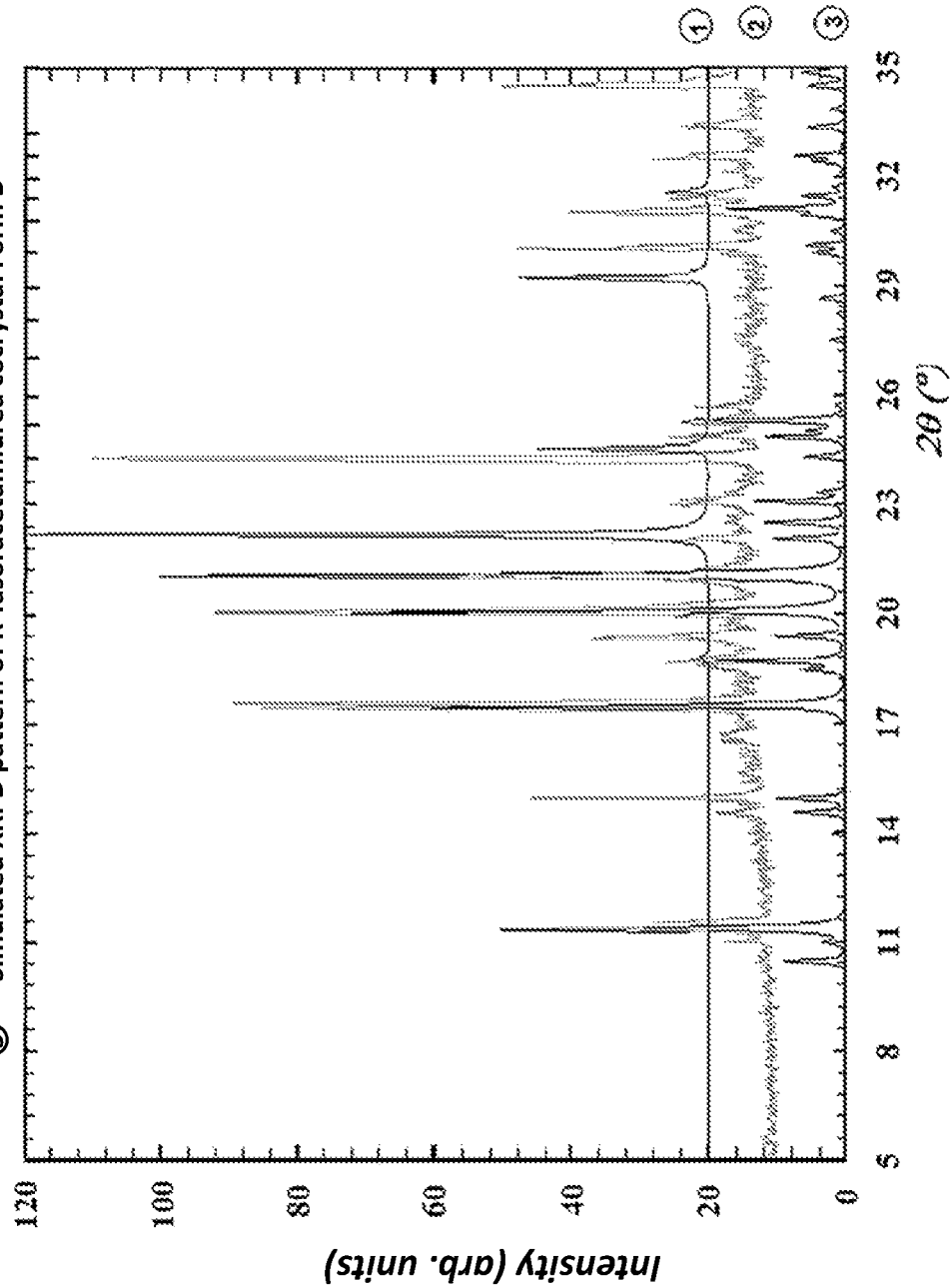
FIG. 117 is an overlay of XRPD patterns: (1) Simulated XRPD pattern of urea; (2) Experimental XRPD pattern of Example 34; (3) Simulated XRPD pattern of R-fasoracetam:urea cocrystal Form B.

Example 34—Scale-Up Preparation of R-Fasoracetam:Urea Cocrystal Form B 13 g of R-fasoracetam monohydrate Form I (sourced from Aevi Genomic Medicine) was added to a 100 ml reactor vessel of the Mettler Toledo Easymax system, equipped with overhead stirrers. 50 ml of Ethylacetate was added, and the suspension heated to 60° C. Dissolution occurs upon heating. After 10 minutes at 60° C., 3.46 g of urea (0.95 eq) was added to the solution, and the suspension was left to stabilize for 2 h. The suspension was then cooled with a cooling rate of 0.3° C./min to −10° C. and left at this temperature for 1.5 h. Filtration was performed after which, the cake was washed with 10 ml of Ethylacetate that was kept at 9° C. The solid was left to dry at room temperature. A mass of 14.12 g was recovered, corresponding to a 91% yield with respect to the amount of R-fasoracetam engaged. FIG. 116 shows the DSC thermogram of the R-fasoracetam:urea cocrystal Form B so prepared, and FIG. 117 is an overlay of the XRPD pattern of the powder recovered and a simulated pattern of the R-fasoracetam:urea cocrystal form B.

Example 35—Estimation of the Solubility of R-Fasoracetam:Urea Cocrystal Form B 5 g of the R-fasoracetam:urea cocrystal Form B as prepared in Example 34 were added to 1 ml of water in a round bottom flask at room temperature. No full dissolution occurred. The suspension was left for 15 minutes under magnetic stirring. 200 µl water was added and another 15 minute hold time installed. Dissolution did not occur. Another 200 water was added and another 15 minute hold time installed. Dissolution did not occur. 200 µl water was added and another 15 minute hold time installed. Dissolution did not occur. 200 µl water was added and another 15 minute hold time installed. Full dissolution occurred. A total of 1.8 ml of water was thus required to dissolve 5 g of the R-fasoracetam:urea cocrystal Form B Example 36—Synthesis of R-Fasoracetam:Urea Cocrystal Form A 25.03 g of R-fasoracetam monohydrate Form I and 116 mL of ethyl acetate were combined and polish filtered hot and held at 60° C. 6.62 g of ground urea sourced by M&P was added (0.94 equivalents). The solids dissolved leading to a biphasic mixture which was held at 60° C. for two hours and then cooled at 18° C. per hour and an oil was observed to solidify at the bottom of the reactor at 23° C. The reactor was heated to 43° C. and the oil reformed. The mixture was then seeded with 128 mg of material of Example 37 and held at 43° C. for 1.5 hours. The mixture was then cooled at 18° C. per hour to 9° C. and held overnight. The obtained suspension was filtered and washed with 17 mL of cold ethyl acetate. The wet cake was then vacuum oven dried for 22 hours at 43° C. yielding 26.47 grams of Cocrystal Form A. Chemical composition was confirmed by solution-state $^1$H and $^{13}$C NMR. Form A was confirmed by XRPD (FIG. 118) and DSC (FIG. 119). A peak list corresponding to FIG. 118 is shown below in Table 16.

TABLE 16

Figure 118:
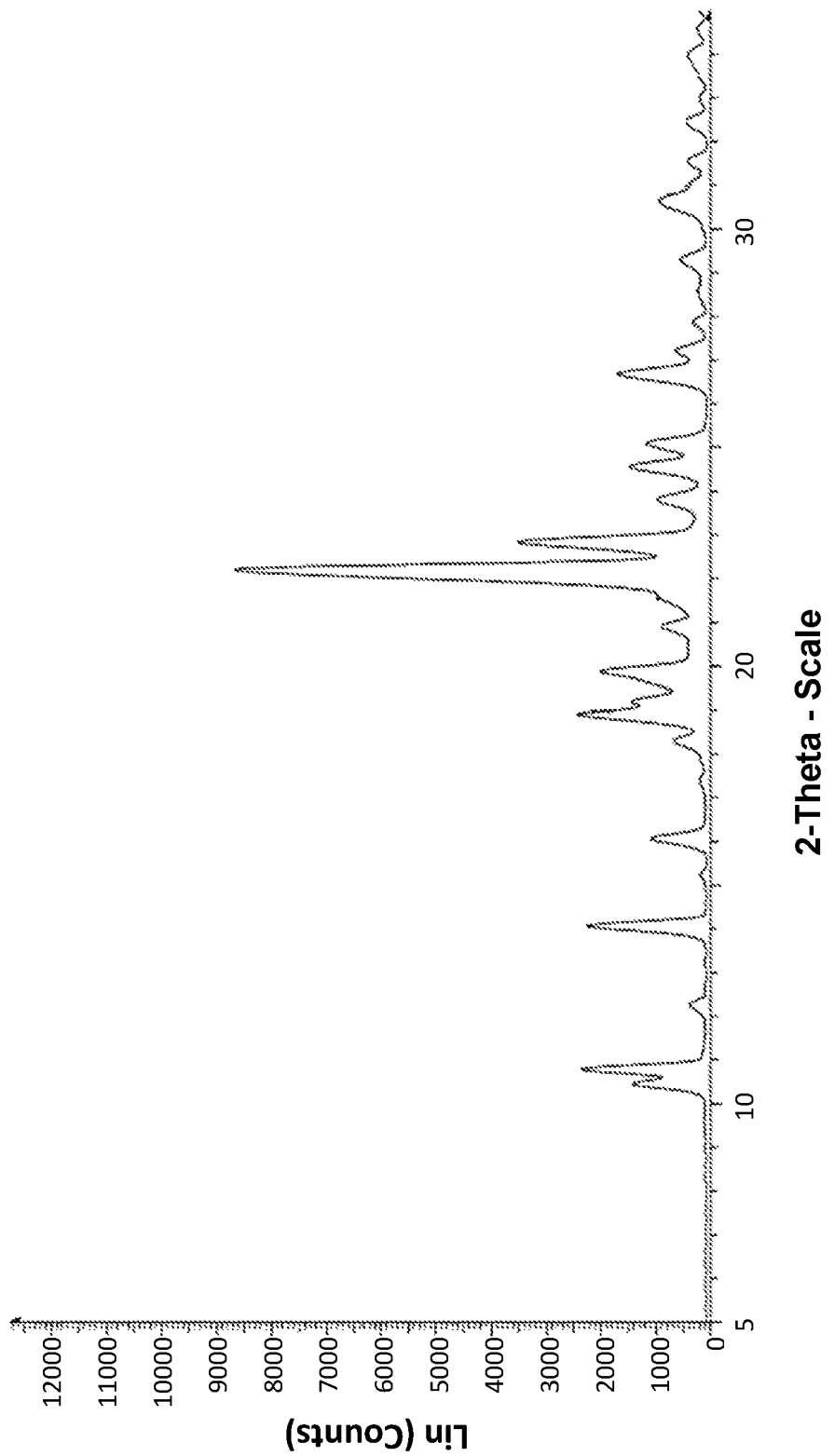
FIG. 118 is an XRPD pattern of R-fasoracetam:urea cocrystal Form A.

Peak Table for FIG. 118

2 theta 10.4
10.8
12.2
13.2
14.1
15.2
16.1
17.4
18.3
18.9
19.2
19.9
20.9
21.6
22.2

TABLE 16-continued

Peak Table for FIG. 118

2 theta 22.8
23.8
24.6
25.1
26.7
27.2
27.9
28.6
29.3
30.7
31.1
31.6
32.5
33.0
33.6
34.0
34.6

Example 37—Preparation of Seed for Example 36

100 grams of D-pyroglutamic acid sourced from Wilshire was reacted with 0.91 equivalents of piperidine in ethyl acetate to yield R-fasoracetam in the ethyl acetate. An aliquot of the solution was brought to 5 relative volumes with ethyl acetate (for a total of 161 grams of solution) and polish filtered hot and cooled to 43° C. 14.1 grams of urea were added to the solution and after 1 hour, the suspension was heated to reflux. A triphasic mixture formed and the mixture was cooled at 20° C. per hour to 20° C. and held overnight. The formed suspension was filtered and washed with 50 mL of ethyl acetate. The wet cake was dried in a vacuum oven for 70 hours at 40° C. yielding 47.0 g. A portion of this resulting solid was used as a seed in Example 36.

Example 38—Stability of R-Fasoracetam Cocrystal Form A

Figure 120:
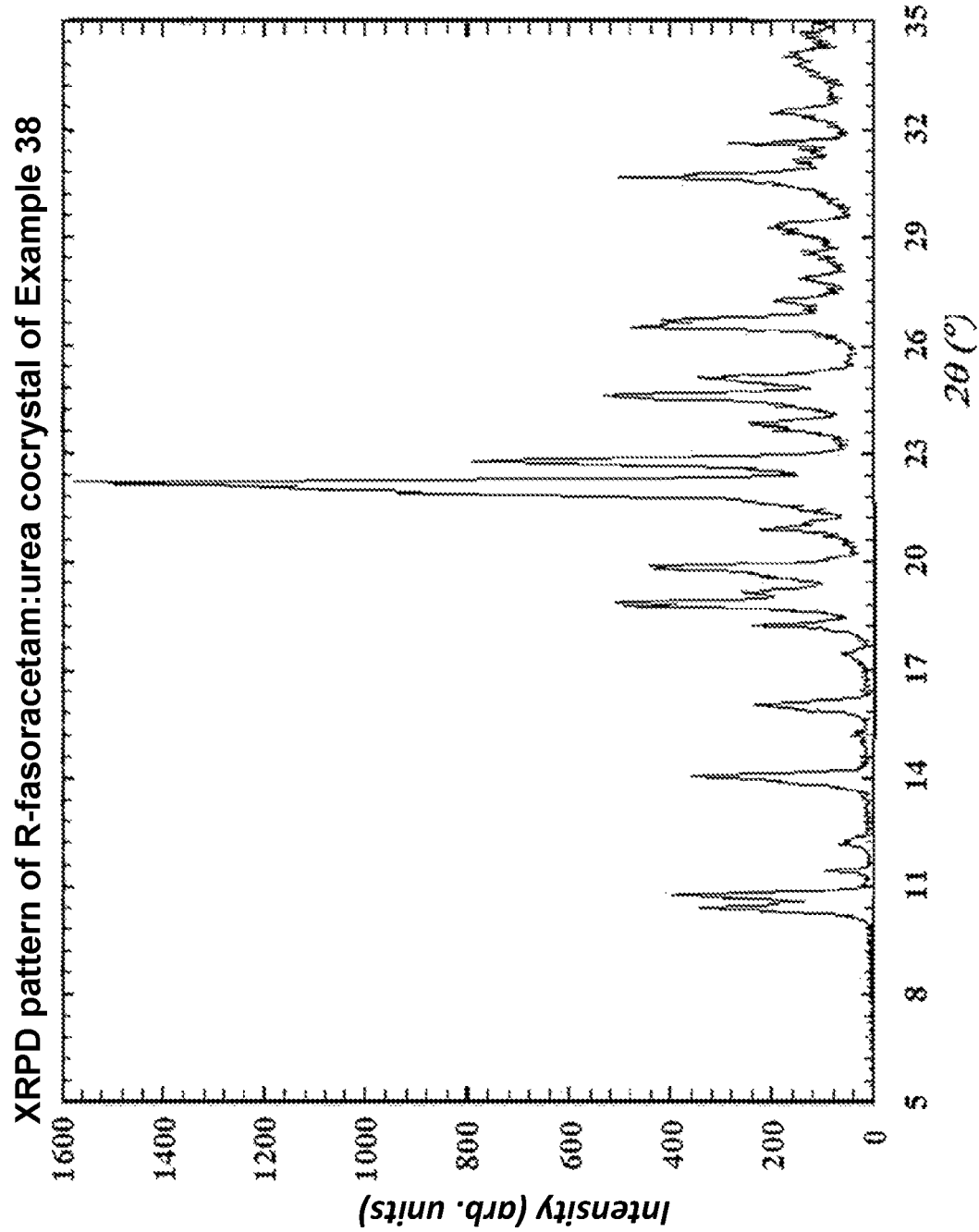
FIG. 120 is an XRPD pattern of R-fasoracetam:urea cocrystal of Example 38.
Figure 121:
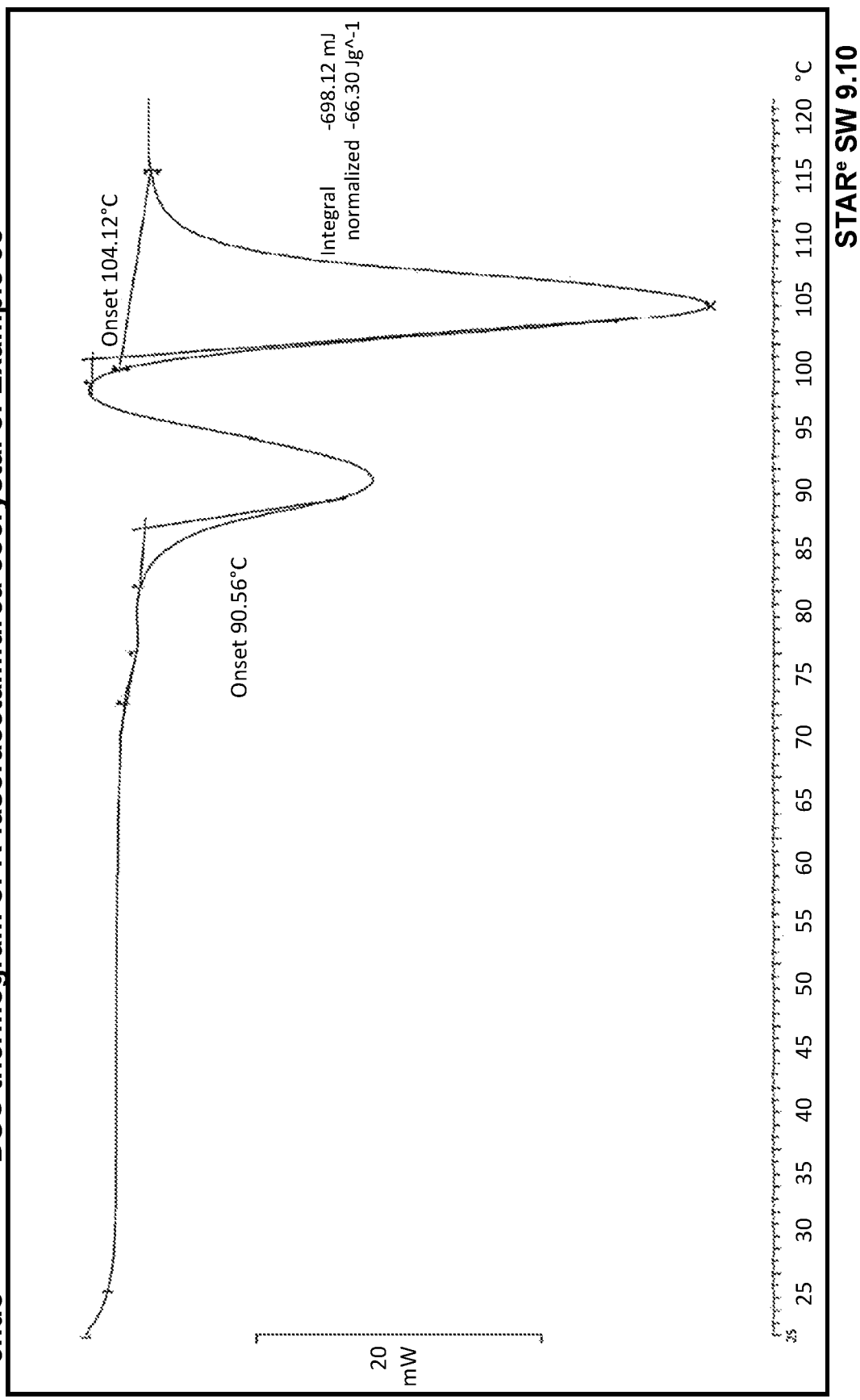
FIG. 121 is a DSC thermogram of R-fasoracetam:urea cocrystal of Example 38.

A vial containing R-fasoracetam:urea cocrystal Form A made in accordance with Example 36 was opened and analyzed by XRPD (FIG. 120) and DSC (FIG. 121—which shows two large endotherms). The XRPD shows the presence of mostly Form A and some Form B, as illustrated by the peak at 11.4°2θ. The vial was then closed and placed at −15° C. Each day, material from the vial was sampled and analyzed by XRPD. In parallel, a sample of this compound was kept open at room temperature and the same sample analyzed each day by XRPD. In the room temperature experiment, FIG. 122 shows that R-fasoracetam:urea cocrystal Form A transforms completely as can be seen by XRPD into Form B in two days. The sample also converted to Form B at −15° C. as seen from FIG. 123. Form A is thus shown to be a meta-stable polymorph of the R-fasoracetam:urea cocrystal as compared to the more stable Form B.

The DSC thermogram of FIG. 121 (above) was performed at 20° C./min. In FIG. 121, Form A shows a melting onset at about 91° C. followed by a recrystallization into Form B which subsequently shows a melting onset at about 104° C. These data confirm Form A to be the meta-stable form, which upon melt recrystallizes into the more stable Form B.

Example 39—A Preparation of Seeds of a R-Fasoracetam:PABA Cocrystal

Cocrystal seeds were obtained by slurrying a 1:1 ratio of R-fasoracetam monohydrate Form I and 4-aminobenzoic acid in 20 mL of ethyl acetate for 4 days at 350 RPM. After 4 days, the slurry was filtered and washed with 2 times 20 mL of cold (−15° C.) ethyl acetate. The presence of the cocrystal was confirmed via XRPD and $^1$H-NMR spectroscopy.

Figure 136:
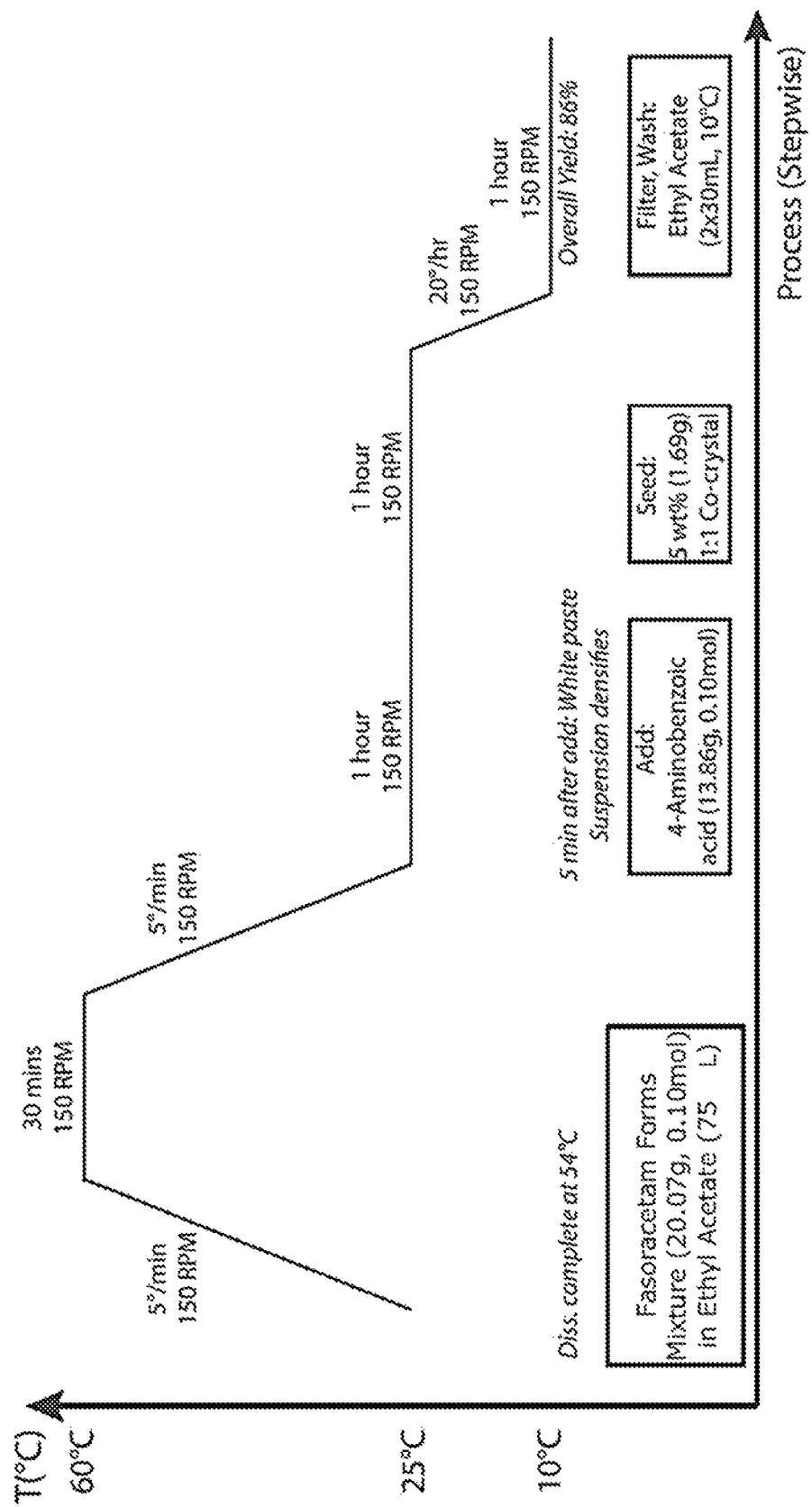

Example 40—Scale-Up of R-Fasoracetam:PABA Cocrystal (FIG. 136)

R-fasoracetam Forms Mixture (20.07 g, 0.10 mol) was dissolved in ethyl acetate (75 mL). The suspension was stirred at 150 RPM and heated up from room temperature to 60° C. with a heating rate of 5° per minute. To assure complete dissolution (although observed to be complete at 54° C.) the solution was left at 60° C. for 30 minutes. The isothermal hold was followed by cooling back to 25° C. with a cooling rate of 5° per minute and subsequently 1 equivalent of 4-aminobenzoic acid (13.86 g, 0.10 mol) was added. 5 minutes after the addition of the co-former, a white paste appeared and the formed suspension densified. This paste was analyzed via XRPD and was confirmed to be the cocrystal. After keeping this suspension at 25° C. for 1 hour, it was seeded with 5 wt % cocrystal (1.69 g) of Example 39 and left for another hour to ensure the only solid formed is the desired cocrystal. Lastly, the suspension was cooled to 10° C., filtered and washed twice via displacement with cold Ethyl Acetate (30 mL, 10° C.), where analysis via XRPD confirmed that only cocrystal was present. The yield recorded for this process was 86%. The crystallization process in this Example was done using a 500 mL Double J Reactor device from Cambridge Reactor Design.

Figure 137:
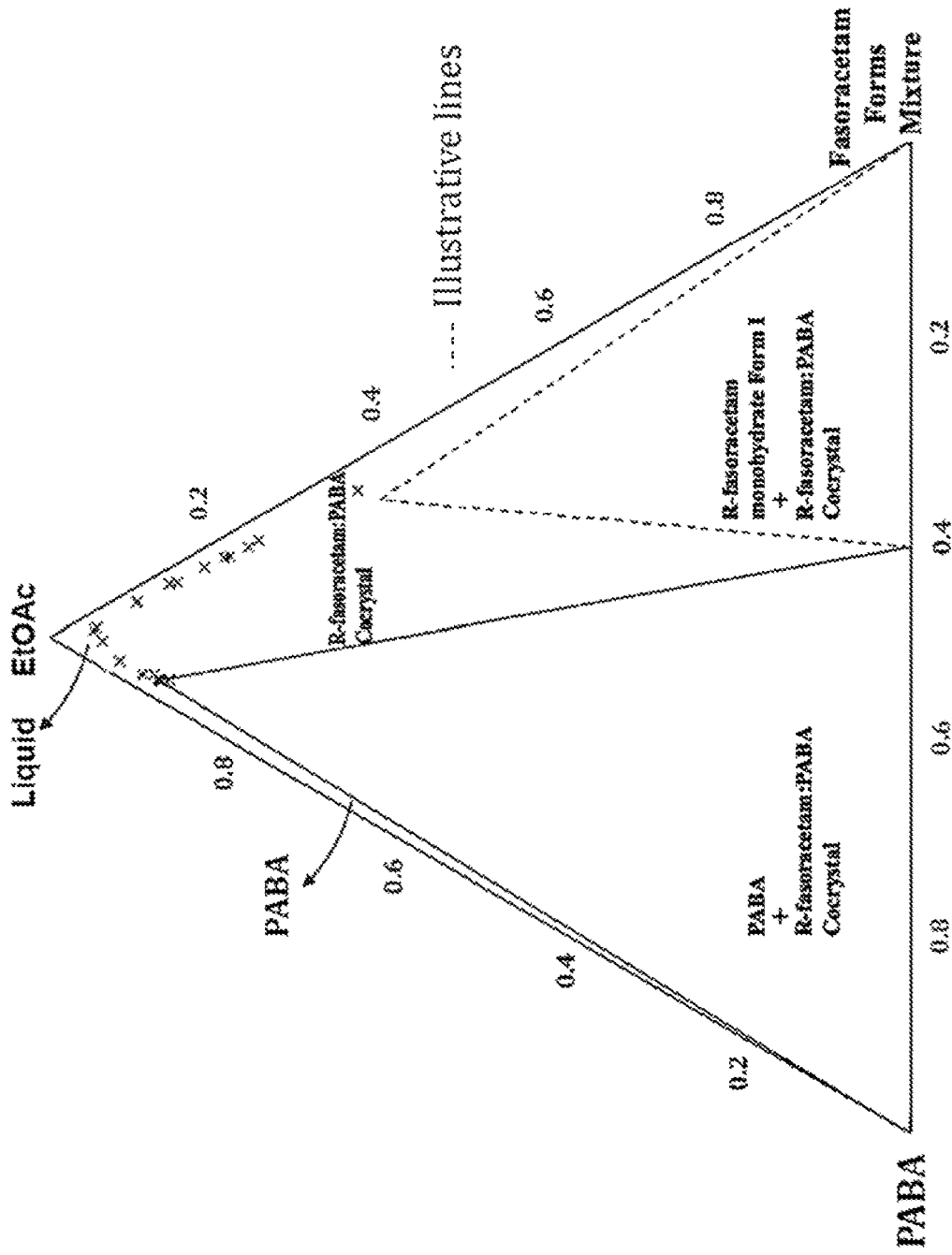

Example 41—Preparation of Phase Diagram on FIG. 137

Different vials were prepared with varying masses of R-fasoracetam Forms Mixture, PABA and ethylacetate. A magnet was placed in each vial, the vial was closed and left for an hour at room temperature. After this one-hour hold, each vial was seeded with cocrystal seeds of R-fasoracetam: PABA made by grinding about 70.01 mg of R-Fasoracetam monohydrate Form I and about 44.95 mg of PABA for 90 minutes at 30 Hz. Vials were also seeded with R-fasoracetam Forms Mixture as well as PABA. The samples were then left under a magnetic stirring for another 48 hours at room temperature. Afterwards, the liquid phase was analyzed using HPLC and the solid phase (obtained after filtering) with XRPD. The data were plotted in the ternary phase diagram of FIG. 137 and the lines in FIG. 137 were drawn as a guideline based on the data.

Example 42—Cocrystal of Fasoracetam and Urea (Form B) Scale-Up 1500.6 g of Form I R-fasoracetam monohydrate was charged into a vessel with 5.26 liters of ethyl acetate (water content of about 0.01%) and heated to about 40° C. to form an orange-tan solution. The solution was polish filtered through one micron filters and the filtrates were vacuum transferred into reactors. The filtrates were combined into a single reactor with 0.60 L of warm ethyl acetate used as a rinse and heated to about 50° C. and the solution was agitated. 204 grams of urea (0.485 equivalents) were charged into the reactor. After about half an hour 204.2 grams of urea were added (0.486 equivalents) and held for 15 minutes. 74.8 grams of seeds of Form B prepared previously were added the reactor held at a temperature ranging from 51° C. to 52° C. for about 2 hours and then cooled to about −14° C. over 14 hours and was held at about −10° C. for 6 hours. Solids were isolated by filtration and washed with ethyl acetate. Following vacuum oven drying, Form B having an orange tint was prepared having a mass of 1749.8 grams. Form B was verified by DSC and XRPD. It is believed that the orange tint is due to a minor impurity. The impurity was not detected by XRPD, which confirmed Form B.

What is claimed is:

1. A crystalline compound or cocrystal comprising fasoracetam and one of:
   (a) 4-aminobenzoic acid;
   (b) trimesic acid;
   (c) R-ibuprofen;
   (d) phloroglucinol;
   (e) methyl-3,4,5-trihydroxybenzoate;
   (f) ethyl gallate;
   (g) phthalic acid;
   (h) 6-hydroxy-2-naphthoic acid;
   (i) 4-nitrobenzoic acid;
   (j) 2-indole-3-acetic acid; and
   (k) urea.

2. The cocrystal of claim 1, wherein the cocrystal is (a) with an x-ray powder diffraction pattern comprising one or more peaks chosen from peaks at about 6.5°2θ, about 10.5°2θ, about 11.3°2θ, about 12.0°2θ, about 13.4°2θ, about 13.7°2θ, about 17.4°2θ, about 18.1°2θ, about 18.7°2θ, about 19.6°2θ, about 20.6°2θ, about 21.1°2θ, about 21.4°2θ, about 22.8°2θ, about 23.2°2θ, and about 23.7°2θ.

3. The cocrystal of claim 1, wherein the cocrystal is (a) and comprises (S)-5-(piperidine-1-carbonyl)pyrrolidin-2-one.

4. The cocrystal of claim 1, wherein the cocrystal is (b) with an x-ray powder diffraction pattern comprising one or more peaks chosen from peaks at about 9.7°2θ, about 10.9°2θ, about 11.4°2θ, about 14.6°2θ, about 16.5°2θ, about 17.5°2θ, about 18.6°2θ, about 19.4°2θ, about 19.8°2θ, about 21.8°2θ, about 23.5°2θ, about 26.7°2θ, and about 27.3°2θ.

5. The cocrystal of claim 1, wherein the cocrystal is (c) with an x-ray powder diffraction pattern comprising one or more peaks chosen from peaks at about 5.6°2θ, about 10.5°2θ, about 11.2°2θ, about 12.3°2θ, about 17.4°2θ, about 20.1°2θ, and about 20.6°2θ.

6. The cocrystal of claim 1, wherein the cocrystal is (d) and is a monohydrate cocrystal.

7. The cocrystal of claim 1, wherein the cocrystal is (d) with an x-ray powder diffraction pattern having one or more peaks chosen from peaks at about 6.9°2θ, about 10.3°2θ, about 15.3°2θ, about 16.2°2θ, about 17.3°2θ, about 21.6°2θ, about 22.6°2θ, and about 25.3°2θ.

8. The cocrystal of claim 1, wherein the cocrystal is (e) and is a monohydrate cocrystal.

9. The cocrystal of claim 1, wherein the cocrystal is (e) with an x-ray powder diffraction pattern comprising one or more peaks chosen from peaks at about 5.7°2θ, about 10.6°2θ, about 11.3°2θ, about 12.7°2θ, about 16.6°2θ, about 18.9°2θ, about 20.6°2θ, about 24.3°2θ, and about 25.0°2θ.

10. The cocrystal of claim 1, wherein the cocrystal is (f) and either of the following applies:
    (a) the cocrystal has an x-ray powder diffraction pattern comprising one or more peaks chosen from peaks at about 5.8°2θ, about 11.3°2θ, about 12.4°2θ, about 15.5°2θ, about 15.8°2θ, about 18.2°2θ, about 19.4°2θ, about 22.0°2θ, and about 24.8°2θ and wherein the molar ratio of fasoracetam to ethyl gallate in a unit cell is 1:1 or wherein the stoichiometric ratio of fasoracetam to ethyl gallate is about 1:1; or (b) the cocrystal has an x-ray powder diffraction pattern comprising one or more peaks chosen from peaks at about 5.8°2θ, about 7.2°2θ, about 14.8°2θ, about 20.4°2θ, about 21.9°2θ, and about 23.5°2θ wherein the stoichiometric ratio of fasoracetam to ethyl gallate is about 1:2.

11. The cocrystal of claim 1, wherein the cocrystal is (g) with an x-ray powder diffraction pattern comprising one or more peaks chosen from peaks at about 6.1°2θ, about 12.4°2θ, about 15.1°2θ, about 15.8°2θ, about 18.1°2θ, about 19.9°2θ, and about 23.3°2θ.

12. The cocrystal of claim 1, wherein the cocrystal is (h) with an x-ray powder diffraction pattern comprising one or more peaks chosen from peaks at about 11.2°2θ, about 14.9°2θ, about 15.7°2θ, about 20.1°2θ, about 21.1°2θ, about 23.6°2θ, about 24.1°2θ, about 25.0°2θ, and about 25.5°2θ.

13. The cocrystal of claim 1, wherein the cocrystal is (i) with an x-ray powder diffraction pattern comprising one or more peaks chosen from peaks at about 6.5°2θ, about 6.7°2θ, about 8.9°2θ, about 14.5°2θ, about 15.6°2θ, about 17.9°2θ, about 18.6°2θ, about 19.8°2θ, about 23.4°2θ, and about 26.4°2θ.

14. The cocrystal of claim 1, wherein the cocrystal is (j) with an x-ray powder diffraction pattern comprising one or more peaks chosen from peaks at about 5.3°2θ, about 7.9°2θ, about 10.7°2θ, about 11.8°2θ, about 14.7°2θ, about 15.8°2θ, about 18.0°2θ, about 21.9°2θ, about 23.1°2θ, and about 23.5°2θ.

15. The cocrystal of claim 1, wherein the cocrystal is (k) and at least one of the following applies:

(a) the cocrystal has an x-ray powder diffraction pattern comprising a peak at about 12.2°θ and one or more peaks chosen from peaks at about 10.4°2θ, about 10.8°2θ, about 14.1°2θ, about 16.1°2θ, about 18.9°2θ, about 22.3°2θ, and about 22.9°2θ; and (b) the cocrystal has an x-ray powder diffraction pattern comprising a peak at about 16.1°2θ, and one or more peaks chosen from peaks at about 10.4°2θ, about 10.8°2θ, about 12.2°2θ, about 14.1°2θ, about 18.9°2θ, about 22.3°2θ, and about 22.9°2θ.

16. A pharmaceutical composition comprising the crystalline compound or cocrystal of claim 1, and one or more pharmaceutically acceptable excipients.

17. A method of treating attention-deficit hyperactive disorder (ADHD) in a human subject in need thereof, the method comprising administering to the subject the crystalline compound or cocrystal of claim 1.

18. The method of claim 17, wherein the subject has at least one copy number variation (CNV) in a metabotropic glutamate receptor (mGluR) network gene.

* * * * *